US005646276A

United States Patent [19]

Robl

[11] Patent Number: 5,646,276
[45] Date of Patent: Jul. 8, 1997

[54] DIAZEPINE CONTAINING DUAL ACTION INHIBITORS

[75] Inventor: Jeffrey A. Robl, Newtown, Pa.

[73] Assignee: Bristol-Myers Squibb Co., Princeton, N.J.

[21] Appl. No.: 666,158

[22] Filed: Jun. 19, 1996

Related U.S. Application Data

[60] Division of Ser. No. 160,540, Dec. 1, 1993, Pat. No. 5,552,397, which is a continuation-in-part of Ser. No. 61,606, May 13, 1993, abandoned.

[51] Int. Cl.$^6$ .................... C07D 487/04; C07D 513/04; A61K 31/55
[52] U.S. Cl. .................... 540/500; 540/489; 540/527; 540/524; 540/488; 540/490; 540/523; 540/492; 544/54; 544/47; 544/90; 546/138
[58] Field of Search .................... 540/500, 489; 514/221, 211

[56] References Cited

U.S. PATENT DOCUMENTS

| | | | |
|---|---|---|---|
| 4,105,776 | 8/1978 | Ondetti et al. | 548/570 |
| 4,192,945 | 3/1980 | Ondetti | 546/245 |
| 4,339,600 | 7/1982 | Ondetti et al. | 562/426 |
| 4,374,829 | 2/1983 | Harris et al. | 514/19 |
| 4,409,146 | 10/1983 | Thorsett | 514/211 |
| 4,410,520 | 10/1983 | Watthey | 514/211 |
| 4,415,496 | 11/1983 | Harris et al. | 514/211 |
| 4,460,579 | 7/1984 | Karanewsky | 544/54 |
| 4,465,679 | 8/1984 | Huang et al. | 544/239 |
| 4,470,988 | 9/1984 | Watthey | 514/211 |
| 4,473,575 | 9/1984 | Watthey | 514/211 |
| 4,477,464 | 10/1984 | Slade et al. | 514/211 |
| 4,512,924 | 4/1985 | Attwood et al. | 540/500 |
| 4,537,885 | 8/1985 | Watthey | 514/183 |
| 4,539,150 | 9/1985 | Katakami et al. | 540/500 |
| 4,548,932 | 10/1985 | Sugihara et al. | 514/211 |
| 4,575,503 | 3/1986 | Watthey | 514/213 |
| 4,584,294 | 4/1986 | Ruyle | 514/214 |
| 4,587,050 | 5/1986 | Harris et al. | 540/500 |
| 4,587,238 | 5/1986 | Harris et al. | 514/183 |
| 4,594,341 | 6/1986 | Cheung et al. | 514/211 |
| 4,617,301 | 10/1986 | Patchett et al. | 514/214 |
| 4,629,787 | 12/1986 | Harris et al. | 540/528 |
| 4,680,392 | 7/1987 | Harris et al. | 540/527 |
| 4,699,905 | 10/1987 | Yangisawa et al. | 514/211 |
| 4,711,884 | 12/1987 | Karanewsky | 514/226 |
| 4,734,410 | 3/1988 | Yanagisawa et al. | 514/212 |
| 4,749,688 | 6/1988 | Haslanger | 514/19 |
| 4,808,713 | 2/1989 | Attwood et al. | 540/487 |
| 4,824,832 | 4/1989 | Flynn et al. | 514/214 |
| 4,873,235 | 10/1989 | Parsons et al. | 514/312 |
| 4,963,539 | 10/1990 | Delaney | 514/119 |
| 4,973,585 | 11/1990 | Flynn et al. | 514/214 |
| 5,075,302 | 12/1991 | Neustadt | 514/211 |
| 5,098,934 | 3/1992 | Vevert et al. | 514/513 |
| 5,190,974 | 3/1993 | Clemence et al. | 514/513 |
| 5,208,236 | 5/1993 | Neustadt | 514/482 |
| 5,223,516 | 6/1993 | Delaney | 514/339 |
| 5,225,401 | 7/1993 | Seymour | 519/19 |
| 5,232,920 | 8/1993 | Neustadt | 514/212 |
| 5,238,924 | 8/1993 | Smith | 514/19 |
| 5,262,436 | 11/1993 | Haslanger et al. | 514/513 |
| 5,362,727 | 11/1994 | Robl | 514/214 |
| 5,366,973 | 11/1994 | Flynn et al. | 514/221 |

FOREIGN PATENT DOCUMENTS

| | | |
|---|---|---|
| 249223 | 12/1987 | European Pat. Off. . |
| 249224 | 12/1987 | European Pat. Off. . |
| 481522 | 4/1992 | European Pat. Off. . |
| 524553 | 1/1993 | European Pat. Off. . |
| 534363 | 3/1993 | European Pat. Off. . |
| 534396 | 3/1993 | European Pat. Off. . |
| 534492 | 3/1993 | European Pat. Off. . |
| 595610 | 5/1994 | European Pat. Off. . |
| 629627 | 12/1994 | European Pat. Off. . |
| 2207351 | 2/1989 | United Kingdom . |
| WO93/16103 | 1/1993 | WIPO . |
| WO94/10193 | 5/1994 | WIPO . |
| WO94/28901 | 12/1994 | WIPO . |

OTHER PUBLICATIONS

Boyer, T.D. "Githosis of the Liver and Its Major Sequelae" in: Wyngaardon, J. O. et al., *Girl Textbook of Medicine*, vol. 1. (Philadelphia, Saunders Co., 1992), pp. 786–789.

Robl, J.A. et al. *Bioorg. Med. Chem. Lett.* 4, 1795–1800 (1994).

Robl et al., Biiorganic & Medicinal Chem. Letters, vol. 4, pp. 1795–1800, 1994 Month of publication not provided.

Dussaule et al., Jour. of Clinical Endocrinology and Metabolism, vol. 72, pp. 653–659, 1991 Month of publication not provided.

Loffi et al., Gastroenterology, vol. 96, pp. 167–177, 1989 Month of publication not provided.

(List continued on next page.)

*Primary Examiner*—Matthew V. Grumbling
*Assistant Examiner*—King Lit Wong
*Attorney, Agent, or Firm*—Stephen B. Davis

[57] ABSTRACT

Compounds of the formula $$R_1-S-(CH_2)_n-\underset{R_{19}}{\overset{}{C}}-\overset{O}{\overset{\|}{C}}-X_1$$
$$\phantom{R_1-S-(CH_2)_n-}\diagdown R_2$$

wherein $X_1$ is

[structure showing a bicyclic diazepine ring system with substituents $Y_3$, $R_{13}$, $R_{10}$, $R_{11}$, and $-N-C-(CH_2)_b-C-OR_{12}$]

are disclosed as possessing inhibotory activity against angiotensin converting enzyme (ACE) and neutral endopeptidase (NEP) and thus being useful as cardiovascular agents.

8 Claims, No Drawings

OTHER PUBLICATIONS

Fyhrquist et al., The Lancet, Dec. 21/28, 1985, p. 1439. Month of publication not provided.

Fernandez-Cruz, The Lancet, Dec. 21/28, 1985, p. 1439–1440. Month of publication not provided.

Naming and Indexing of Chemical Substances for Chemical Abstracts, 1987 Index Guide, Section 203. Month of publication not provided.

Watthey et al., J. Med. Chem., 28, pp. 1511–1516 (1985). Publication month not provided.

Slade et al., J. Med. Chem., 28, pp. 1517–1521 (1985). Publication month not provided.

Thorsett et al., J. Med. Chem., 29, pp. 251–260 (1986). Publication month not provided.

Yanagisawa et al., J. Med. Chem., 30, pp. 1984–1991 (1987). Publication month not provided.

Yanagisawa et al., J. Med. Chem., 31, pp. 422–428 (1988). Publication month not provided.

Parsons et al., Biochem and Biophysical Research Comm. 117, pp. 108–113 (1993). Publication month not provided.

Atwood et al., FEBS Letters, vol. 165, pp. 201–206 (1984). Publication month not provided.

Natoff et al., Drugs Of the Future, vol. 12, pp. 475–483 (1987). Publication month not provided.

Itoh et al., Chem. Pharm. Bull., vol. 34, pp. 1128–1147 and 2078–2089 (1986). Publication month not provided.

Flynn, Tetrahedron Letters, vol. 31, pp. 815–818 (1990). Publication month not provided.

Thorsett, Actual Chim. Ther., vol. 13, pp. 257–268 (1986). Publication month not provided.

Atwood et al., J. Chem. Soc. Perkin Trans I (1986) pp. 1011–1019. Publication month not provided.

Robl, Tetrahedron Letters, vol. 35, pp. 393–396 and 1393–1396, (1994). Publication month not provided.

Delaney et al., Bioorganic & Medicinal Chemistry Letters, vol. 4, pp. 1783–1788 (1994). Publication month not provided.

Robl et al., Bioorganic & Medicinal Chemistry Letters, vol. 4, pp. 1789–1794 (1994). Publication month not provided.

Robl et al., Bioorganic & Medicinal Chemistry letters, vol. 4, pp. 2055–2060 (1994). Publication month not provided.

Das et al., Bioorganic & Medicinal Chemistry Letters, vol. 4, pp. 2193–2198 (1994). Publication month not provided.

Bolos et al., J. Org. Chem., 57, 3535–3539 (1992). Publication month not provided.

Bolos et al., Tetrahedron, vol. 48, pp. 9567–9576 (1992). Publication month not provided.

Adams et al., Synthetic Communications, vol. 18, 2225–2231 (1988). Publication month not provided.

Chackalamannil et al., Bioorganic & Medicinal Chemistry Letters, vol. 2, pp. 1003–1006 (1992). Publication month not provided.

Flynn et al., J. Med. Chem., 36, pp. 2420–2423 (1993). Publication month not provided.

Robl et al., J. Am. Chem. Soc., 116, pp. 2348–2355 (1994). Publication month not provided.

DIAZEPINE CONTAINING DUAL ACTION INHIBITORS

PRIOR APPLICATION

This application is a division of Ser. No. 160,540 filed Dec. 1, 1993, now U.S. Pat. No. 5,552,397 which is a continuation-in-part of Ser. No. 061,606 filed May 13, 1993, now abandoned.

BACKGROUND OF THE INVENTION

Captopril, (S)-1-(3-mercapto-2-methyl-1oxopropyl)-L-proline, having the structural formula $$HS-CH_2-\underset{\underset{H}{|}}{\overset{CH_3}{\overset{|}{C}}}-\overset{O}{\overset{\|}{C}}-N\underset{H}{\overset{}{\diagdown}}\text{COOH (L)}$$

is an orally active angiotensin converting enzyme inhibitor useful for treating hypertension and congestive heart failure. See Ondetti et al. U.S. Pat. No. 4,105,776.

Enalapril, (S)-1-[N-[1-(ethoxycarbonyl)-3-phenypropyl]-L-alanyl]-L-proline, having the structural formula $$\text{(phenyl)}-(CH_2)_2-\underset{\underset{H}{|}}{\overset{COOC_2H_5}{\overset{|}{C}}}-NH-\underset{\underset{H}{|}}{\overset{CH_3}{\overset{|}{C}}}-\overset{O}{\overset{\|}{C}}-N\underset{(H)}{\overset{}{\diagdown}}\text{COOH (L)}$$

is also an orally active angiotensin converting enzyme inhibitor. Enalapril contains the L-alanyl-L-proline dipeptide. A related compound, lisinopril, also possesses oral angiotensin converting enzyme inhibitor activity and contains the L-lysyl-L-proline dipeptide. See Harris et al. U.S. Pat. No. 4,374,829.

Haslanger et al. in U.S. Pat. No. 4,749,688 disclose treating hypertension by administering neutral metalloendopeptidase inhibitors alone or in combination with atrial peptides or angiotensin converting enzyme inhibitors.

Neustadt in U.S. Pat. 5,075,302 disclose that mercaptoacyl aminolactams of the formula $$QS-CH_2-\underset{\underset{\underset{R^1}{|}}{(CH_2)_m}}{\overset{}{\overset{|}{CH}}}-\overset{O}{\overset{\|}{C}}-NH-\diagup\diagdown NR^2$$

wherein Y includes propylene and butylene, $R^1$ is lower alkyl, aryl or heteroaryl, and $R^2$ is hydrogen, lower alkyl, lower alkoxy lower alkyl, aryl-lower alkyl or heteroaryl-lower alkyl are endopeptidase inhibitors. Neustadt disclose employing such compounds alone or in combination with angiotensin converting enzyme inhibitors to treat cardiovascular diseases such as hypertension, congestive heart failure, edema, and renal insufficiency.

Delaney et al. U.K. Patent 2,207,351 disclose that endopeptidase inhibitors produce diuresis and natriuresis and are useful alone or in combination with angiotensin converting enzyme inhibitors for the reduction of blood pressure. Delaney et al. include various mercapto and acylmercapto amino acids and dipeptides among their endopeptidase inhibiting compounds.

Flynn et al. in European Patent Application 481,522 disclose dual inhibitors of enkephalinase and angiotensin converting enzyme of the formulas $$R_3S-\underset{\underset{R_2}{|}}{\overset{}{\overset{|}{CH}}}-\overset{O}{\overset{\|}{C}}-\underset{H}{\overset{}{N}}\text{...}$$

and $$R_3S-\underset{\underset{R_2}{|}}{\overset{}{\overset{|}{CH}}}-\overset{O}{\overset{\|}{C}}-\underset{H}{\overset{}{N}}\text{...}$$

wherein n is zero or one and Z is O, S, $-NR_6-$ or $$-N-\overset{O}{\overset{\|}{C}}-R_7.$$

Additional tricyclic dual inhibitors are disclosed by Warshawsky et al. in European Patent Applications 534,363, 534,396 and 534,492.

SUMMARY OF THE INVENTION

This invention is directed to novel compounds possessing both angiotensin converting enzyme inhibitory activity and neutral endopeptidase inhibitory activity and methods of preparing such compounds. This invention is also directed to pharmaceutical compositions containing such dual inhibiting compounds or pharmaceutically acceptable salts thereof and the method of using such compositions. The dual inhibitory compounds of this invention are those of the formula $$R_1-S-(CH_2)_n-\underset{R_{19}}{\overset{}{\diagup}}\overset{}{\underset{R_2}{\diagdown}}\overset{}{\overset{|}{C}}-\overset{O}{\overset{\|}{C}}-X_1$$

and pharmaceutically acceptable salts thereof wherein:

$R_1$ is hydrogen, $$R_3-\overset{O}{\overset{\|}{C}}-,$$

or $R_{18}-S-$;

$R_2$ and $R_{19}$ are independently selected from hydrogen, alkyl, cycloalkyl $-(CH_2)_m-$, substituted alkyl, aryl $-(CH_2)_m-$, substituted aryl $-(CH_2)_m-$, and heteroaryl —(CH$_2$)$_m$— or R$_2$ and R$_{19}$ taken together with the carbon atom to which they are attached complete a cycloalkyl ring or a benzofused cycloalkyl ring;

n is zero or one;

m is zero or an integer from 1 to 6;

R$_3$ is alkyl, substituted alkyl, cycloalkyl —(CH$_2$)$_m$—, aryl —(CH$_2$)$_m$—, substituted aryl —(CH$_2$)$_m$—, or heteroaryl —(CH$_2$)$_m$—;

R$_{18}$ is alkyl, substituted alkyl, cycloalkyl —(CH$_2$)$_m$—, aryl —(CH$_2$)$_m$—, substituted aryl —(CH$_2$)$_m$—, heteroaryl —(CH$_2$)$_m$— or —S—R$_{18}$ completes a symmetrical disulfide wherein R$_{18}$ is of the formula

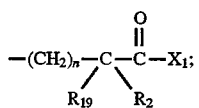
(II)

X$_1$ is of the formula

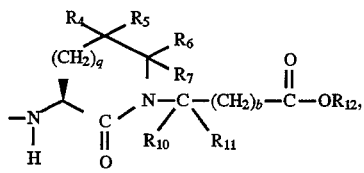
(III)

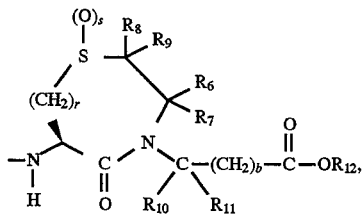
(IV)

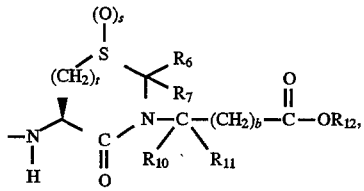
(V)

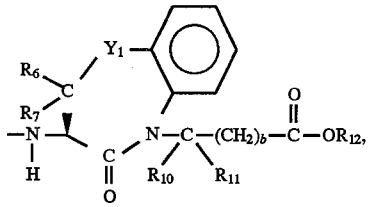
(VI)

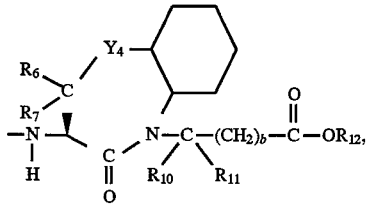
(VII)

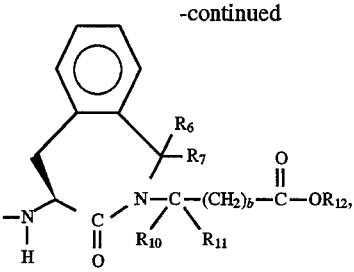
(VIII)

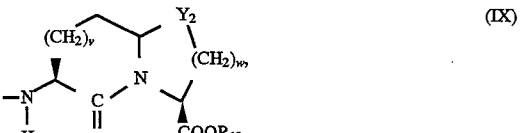
(IX)

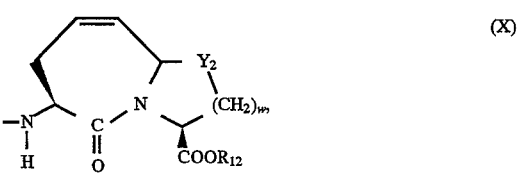
(X)

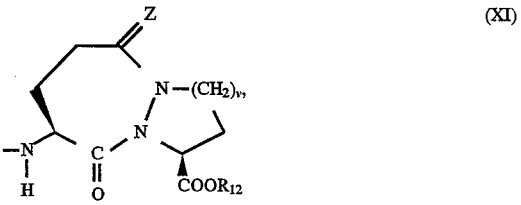
(XI)

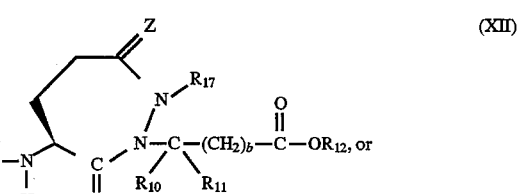
(XII)

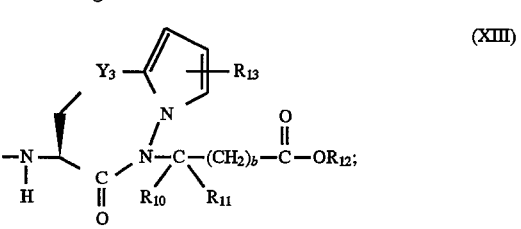
(XIII)

R$_4$ and R$_5$ are independently selected from hydrogen, alkyl, substituted alkyl, alkenyl, substituted alkenyl, cycloalkyl —(CH$_2$)$_m$—, aryl —(CH$_2$)$_m$—, substituted aryl —(CH$_2$)$_m$—, and heteroaryl —(CH$_2$)$_m$—, or one of R$_4$ and R$_5$ is hydroxy and the other is hydrogen, or R$_4$ and R$_5$ taken together with the carbon to which they are attached complete a saturated cycloalkyl ring of 3 to 7 carbons, or R$_4$ and R$_5$ taken together with the carbon to which they are attached complete a keto substituent, i.e.,

C=;

R$_6$, R$_8$ and R$_{10}$ are independently selected from hydrogen, alkyl, substituted alkyl, alkenyl, substituted alkenyl, cycloalkyl —(CH$_2$)$_m$—, aryl —(CH$_2$)$_m$—, substituted aryl —(CH$_2$)$_m$—, and heteroaryl —(CH$_2$)$_m$—;

$R_7$, $R_9$ and $R_{11}$ are independently selected from hydrogen, alkyl, substituted alkyl, alkenyl, substituted alkenyl, cycloalkyl $-(CH_2)_m-$, aryl $-(CH_2)_m$, substituted aryl $-(CH_2)_m-$, and heteroaryl $-(CH_2)_m-$, or $R_6$ and $R_7$ taken together with the carbon to which they are attached complete a saturated cycloalkyl ring of 3 to 7 carbons or $R_8$ and $R_9$ taken together with the carbon to which they are attached complete a saturated cycloalkyl ring of 3 to 7 carbons;

b is zero or one;
q is an integer from 1 to 4;
r is one or two;
s is zero, one or two;
t is one, two, or three;
v is one or two;
w is one or two;
$Y_1$ is $-CH_2-$, $-(CH_2)_2-$, $-(CH_2)_3-$, $-O-$, $$-\overset{(O)_s}{\underset{|}{S}}-, -CH_2-O-, \text{ or } -CH_2-\overset{(O)_s}{\underset{|}{S}}-;$$

$Y_2$ is $-CH_2-$, $$-\overset{(O)_s}{\underset{|}{S}}-,$$

or O;
$Y_3$ is $-CH_2-$ or $$-\overset{(O)_s}{\underset{|}{S}}-;$$

$Y_4$ is $-CH_2-$, $-(CH_2)_2-$, $-(CH_2)_3-$, $-O-$, or $-CH_2-O-$;
Z is O or two hydrogens;
$R_{12}$ is hydrogen, alkyl, substituted alkyl, aryl $-(CH_2)_m-$, substituted aryl $-(CH_2)_m-$, heteroaryl $-(CH_2)_m-$, $$-\underset{\underset{R_{14}}{|}}{CH}-O-\overset{O}{\overset{\|}{C}}-R_{15}, \text{ or } -CH_2\overset{O}{\underset{\diagdown}{\diagup}}\overset{O}{\underset{\diagup}{\diagdown}}R_{16};$$

$R_{13}$ is hydrogen, lower alkyl, or substituted lower alkyl;
$R_{14}$ is hydrogen, lower alkyl, cycloalkyl, or phenyl;
$R_{15}$ is hydrogen, lower alkyl, lower alkoxy or phenyl;
$R_{16}$ is lower alkyl or aryl $-(CH_2)_m-$; and
$R_{17}$ is hydrogen, alkyl, substituted alkyl, alkenyl, substituted alkenyl, cycloalkyl $-(CH_2)_m-$, aryl $-(CH_2)_m-$, substituted aryl $-(CH_2)_m-$, or heteroaryl $-(CH_2)_m-$.

DETAILED DESCRIPTION OF THE INVENTION

The term "alkyl" refers to straight or branched chain radicals having up to seven carbon atoms. The term "lower alkyl" refers to straight or branched radicals having up to four carbon atoms and is a preferred subgrouping for the term alkyl.

The term "substituted alkyl" refers to such straight or branched chain radicals of 1 to 7 carbons wherein one or more, preferably one, two, or three, hydrogens have been replaced by a hydroxy, amino, halo, trifluoromethyl, cyano, —NH(lower alkyl), —N(lower alkyl)$_2$, lower alkoxy, lower alkylthio or carboxy.

The term "substituted lower alkyl" refers to such straight or branched chain radicals of 1 to 4 carbons wherein one hydrogen has been replaced by a hydroxy, amino, halo, trifluoromethyl, cyano, —NH(lower alkyl), —N(lower alkyl)$_2$, lower alkoxy, lower alkylthio, or carboxy.

The term "alkenyl" refers to straight or branched chain radicals of 3 to 7 carbon atoms having one or two double bonds. Preferred "alkenyl" groups are straight chain radicals of 3 to 5 carbons having one double bond.

The term "substituted alkenyl" refers to such straight or branched radicals of 3 to 7 carbons having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio, or carboxy.

The terms "lower alkoxy" and "lower alkylthio" refer to such lower alkyl groups as defined above attached to an oxygen or sulfur.

The term "cycloalkyl" refers to saturated rings of 3 to 7 carbon atoms.

The term "halo" refers to chloro, bromo, fluoro, and iodo.

The term "aryl" refers to phenyl, 1-naphthyl, and 2-naphthyl. The term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), or —N(lower alkyl)$_2$, di- and tri-substituted phenyl, 1-naphthyl, or 2-naphthyl wherein said substituents are selected from methyl, methoxy, methylthio, halo, hydroxy, and amino.

The term "heteroaryl" refers to unsaturated rings of 5 or 6 atoms containing one or two O and S atoms and/or one to four N atoms provided that the total number of hetero atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl. Also, if the mono or bicyclic ring has an available N-atom such N atom can also be substituted by an N-protecting group such as $$-CH_2-O-CH_2-\underset{}{\bigcirc}, -SO_2-\underset{}{\bigcirc}-CH_3,$$

2,4-dinitrophenyl, lower alkyl, benzyl, or benzhydryl.

The compounds of this invention wherein $R_1$ is hydrogen or $$R_3-\overset{O}{\overset{\|}{C}}-$$

and $R_{19}$ is hydrogen can be prepared by coupling the acylmercapto containing sidechain of the formula

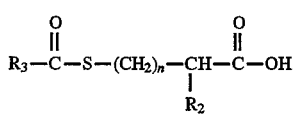

with the intermediate of the formula (XV)

to give the product of the formula

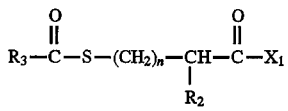

wherein $R_{12}$ in the definition of $X_1$ is preferably an easily removable ester protecting group such as methyl, ethyl, t-butyl or benzyl. The above reaction can be performed in an organic solvent such as dimethyl-formamide and in the presence of a coupling reagent such as benzotriazol-1-yloxytris-(dimethylamino)phosphonium hexafluorophosphate, 1-ethyl-3-(3-dimethylaminopropyl) carbodiimide, dicyclohexylcarbodiimide, or carbonyldiimidazole. Alternatively, the acylmercapto carboxylic acid of formula XIV can be converted to an activated form prior to coupling such as an acid chloride, mixed anhydride, symmetrical anhydride, activated ester, etc.

The product of formula XVI can be converted to the mercaptan product of formula I wherein $R_1$ is hydrogen and $R_{12}$ is hydrogen by methods known in the art. For example when $R_3$ is methyl and $R_{12}$ is methyl or ethyl treatment with methanolic sodium hydroxide yields the product wherein $R_1$ and $R_{12}$ are hydrogen and when $R_3$ is methyl and $R_{12}$ is t-butyl treatment with trifluoroacetic acid followed by ammonia yields the product wherein $R_1$ and $R_{12}$ are hydrogen.

The compounds of this invention wherein both $R_2$ and $R_{19}$ are other than hydrogen and n is zero can be prepared by coupling the substituted mercapto containing sidechain of the formula

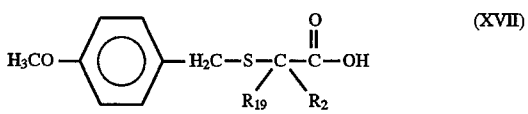

with the intermediate of formula XV as described above to give the compound of the formula

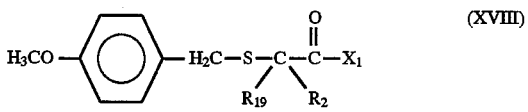

Treatment of the compound of formula XVIII with strong acid such as trifluoromethanesulfonic acid removes the methoxybenzyl protecting group and gives the corresponding product of formula I wherein $R_1$ is hydrogen.

The substituted mercapto containing compounds of formula XVII can be prepared by reacting the disubstituted carboxylic acid of the formula

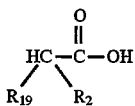

with bis[[(4-methoxy)phenyl]methyl]disulfide in the presence of lithium diisopropylamide.

The compounds of this invention wherein both $R_2$ and $R_{19}$ are other than hydrogen and n is one can be prepared by coupling the acylmercapto containing sidechain of the formula

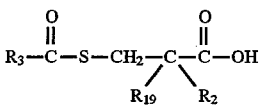

with the intermediate of formula XV as described above to give the product of the formula

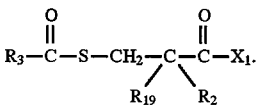

The acylmercapto sidechain compound of formula XX can be prepared by reacting the substituted carboxylic acid of the formula

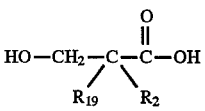

with para-toluenesulfonyl chloride in pyridine to give the lactone of the formula

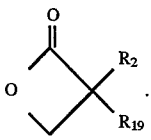

Treatment of the lactone of formula XXIII with a cesium thioacid of the formula

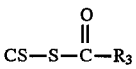

in the presence of dimethylformamide yields the desired acylmercapto sidechain of formula XX.

The products of formula I wherein $X_1$ contains a sulfoxide or sulfone can be prepared by employing the intermediate of XV as the mercaptan, i.e., s is zero, during the coupling reaction. The resulting product of formula XVI, XVIII, or XXI is then oxidized with a known oxidizing reagent such as metachloroperbenzoic acid, peracetic acid, or monoperoxyphthalic acid, magnesium salt hexahydrate, etc. By controlling the amount of oxidizing reagent and the time of the reaction, the products are obtained wherein s is one or two.

The products of formula I wherein $R_1$ is hydrogen can be acylated with an acyl halide of the formula

wherein halo is Cl or Br or acylated with an anhydride of the formula

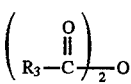

to give other products of formula I wherein $R_1$ is

The products of formula I wherein $R_1$ is —S—$R_{18}$ and $R_{18}$ is alkyl, substituted alkyl, cycloalkyl —$(CH_2)_m$—, aryl —$(CH_2)_m$—, substituted aryl —$(CH_2)_m$— or heteroaryl —$(CH_2)_m$— can be prepared by reacting the products of formula I wherein $R_1$ is hydrogen with a sulfonyl compound of the formula
(XXVII)

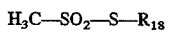

in an aqueous alcohol solvent to yield the desired products. The compounds of formula XXVII are known in the literature or can be prepared by known methods, see for example, Smith et al., Biochemistry, 14, p. 766–771 (1975).

The symmetrical disulfide products of formula I can be prepared by direct oxidation of the product of formula I wherein $R_1$ is hydrogen with iodine as note, for example, Ondetti et al. U.S. Pat. No. 4,105,776.

The ester products of formula I wherein $R_{12}$ is

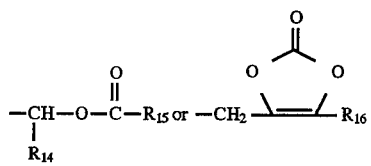

can be prepared by treating the product of formula I wherein $R_{12}$ is hydrogen with a compound of the formula

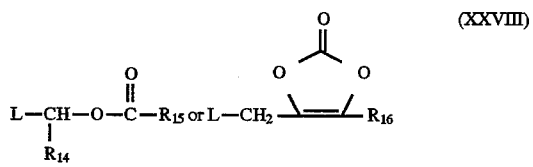

wherein L is a leaving group such as chloro, bromo, or tolylsulfonyloxy.

The acylmercaptoalkanoic acids of formula XIV are described in the literature. See, for example, Ondetti et al. U.S. Pat. Nos. 4,105,776 and 4,339,600, Haslanger et al. U.S. Pat. No. 4,801,609, etc.

The intermediates of formula XV are also described in the literature or are obtained by modifications of known procedures. For example, the intermediates of formula XV wherein $X_1$ is as defined in formula III are disclosed by Thorsett et al., J. Med. Chem., 29, p. 251–260 (1988), Harris et al. in U.S. Pat. Nos. 4,587,050, 4,587,238, 4,629,787 and Yanagisawa et al. in U.S. Pat. No. 4,734,410. The intermediates of formula XV wherein $X_1$ is as defined in formula IV are disclosed by Yanagisawa et al., J., Med. Chem., 30, p. 1984–1991 (1987) and 31, p. 422–428 (1988), Karanewsky in U.S. Pat. No. 4,460,579, Cheung et al. in U.S. Pat. No. 4,594,341, and Yanagisawa et al. in U.S. Pat. No. 4,699,905. The intermediates of formula XV wherein $X_1$ is as defined in formula V are disclosed by Karanewsky in U.S. Pat. Nos. 4,460,579 and 4,711,884. The intermediates of formula XV wherein $X_1$ is as defined in formula VI and $Y_1$ is —$CH_2$—, —$(CH_2)_2$— of —$(CH_2)_3$— are disclosed by Watthey et al., J. Med. Chem., 28, p. 1511–1516 (1985) and Watthey in U.S. Pat. Nos. 4,410,520, 4,470,988, 4,473,575, 4,537,885 and 4,575,503 and also by Parsons et al., Biochemical & Biophysical Research Comm., 117, p. 108–113 (1983) and in U.S. Pat. No. 4,873,235. The intermediates of formula XV wherein $X_1$ is as defined in formula VI and $Y_1$ is S or O are disclosed by Slade et al., J. Med. Chem., 28, p. 1517–1521 (1985) and in U.S. Pat. No. 4,477,464 and Itoh et al., Chem. Pharm. Bull., 34, p. 1128–1147 (1986) and 34, p. 2078–2089 (1986) as well as Sugihara et al. in U.S. Pat. No. 4,548,932 (Y is O) and Katakami et al. in U.S. Pat. No. 4,539,150 (Y is S). The intermediates of formula XV wherein X is as defined in formula VII can be prepared by reduction of the corresponding intermediates wherein $X_1$ is as defined in formula VI. The intermediates of formula XV wherein $X_1$ is as defined in formula VIII are disclosed by Flynn et al. in U.S. Pat. No. 4,973,585. The intermediates of formula XV wherein X is as defined in formula IX and $Y_2$ is S, —SO, or —$SO_2$ are disclosed by Harris et al. and Patchett et al. in U.S. Pat. Nos. 4,415,496 and 4,617,301. The intermediates for formula XV wherein $X_1$ is as defined in formula IX and $Y_2$ is $CH_2$ is disclosed by Thorsett, Actual. Chim. Ther., 13, p. 257–268 (1986). The intermediates of formula XV wherein $X_1$ is as defined in formula XI are disclosed by Attwood et al., Federation of European Biochemical Studies, 165, p. 201–206 (1984) and in U.S. Pat. No. 4,512,994 and Natoff et al., Drugs Of The Future, 12, p. 475–483 (1987). The intermediates of formula XV wherein $X_1$ is as defined in formula XII are disclosed by Huang et al. in U.S. Pat. No. 4,465,679. The intermediates of formula XV wherein $X_1$ is as defined in formula XIII are disclosed by Bolos et al. in Tetrahedron, 48, p. 9567–9576 (1992).

The intermediates of formula XV wherein $X_1$ is as defined in formula III and q is one or two and $R_7$ is hydrogen can be prepared according to the following process which is also part of this invention.

The N-phthalimido α-amino acid of the formula

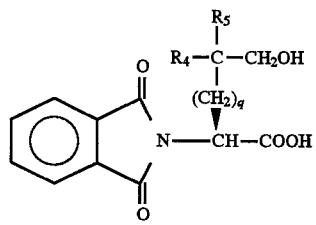

and the amino acid ester of the formula

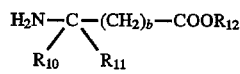

wherein $R_{12}$ is an easily removable ester protecting group such as methyl, ethyl, or benzyl are coupled to give the peptidyl compound of the formula

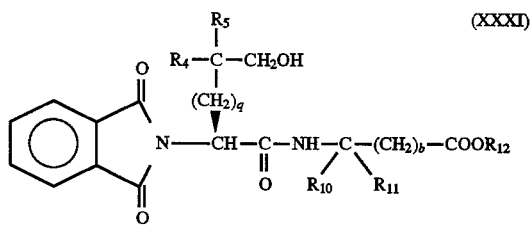

This coupling reaction is preferably carried out in the presence of a coupling reagent such as benzotriazol-1-yloxytris(dimethylamino)phosphonium hexafluorophosphate or ethyl-3-(3-dimethylamino)propyl carbodiimide.

The compound of formula XXXI is oxidized such as by treatment with oxalyl chloride and dimethylsulfoxide or tetra-n-propyl ammonium perruthenate and N-methylmorpholine N-oxide to give the compound of the formula

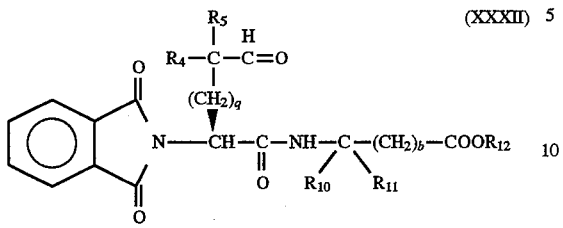

The compound of formula XXXII is cyclized by treatment with a non-aqueous acid such as trifluoroacetic acid, trifluoromethanesulfonic, hydrochloric acid, etc., to give the compound of the formula

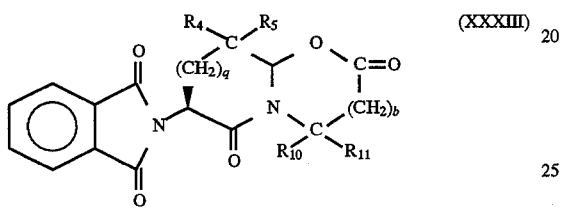

The intermediate of formula XV wherein $X_1$ is as defined in formula III and q is one or two and $R_6$ and $R_7$ are both hydrogen can be prepared by treating the compound of formula XXXIII with a silyl hydride such as triethylsilane, diphenylmethylsilane, phenylmethylsilane, etc., and a Lewis acid catalyst such as stannic chloride, titanium tetrachloride, stannic bromide, boron trifluoride etherate, etc., followed by esterification of the carboxyl group and subsequent treatment with hydrazine hydrate to remove the N-phthaloyl protecting group.

The intermediate of formula XV wherein $X_1$ is as defined in formula III and q is one or two, $R_7$ is hydrogen, and $R_6$ is other than hydrogen can be prepared from the compound of formula XXXIII. For example, when $R_6$ is alkenyl or substituted alkenyl of 3 to 7 carbons, treatment of compound XXXIII with an alkenyl or substituted alkenyl silane in the presence of a Lewis acid catalyst as exemplified above followed by esterification of the carboxyl group and subsequent removal of the N-phthaloyl protecting group as described above gives the desired intermediate. The alkenyl moiety may be hydrogenated to give the desired intermediate wherein $R_6$ is alkyl or substituted alkyl of 3 to 7 carbons. When $R_6$ is other than alkenyl or substituted alkenyl, treatment of compound XXXIII with the corresponding $R_6$ containing organometallic compound in the presence of a Lewis acid catalyst followed by esterification of the carboxyl group and subsequent removal of the N-phthaloyl protecting group gives the desired intermediate.

The intermediates of formula XV wherein $X_1$ is as defined in formula III, q is one, two, or three, $R_7$ is hydrogen, and $R_6$ is other than hydrogen can also be prepared according to the following process which is also part of this invention.

The N-phthalimido α-amino acid of formula XXIX can be converted to an ester such as a benzyl or benzhydryl ester and then oxidized by treating with oxalyl chloride, dimethylsulfoxide, and triethylamine to give the aldehyde of the formula

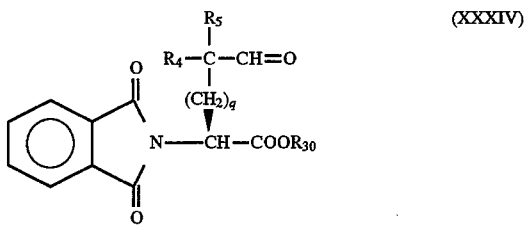

wherein $R_{30}$ is benzyl or benzhydryl.

Treatment of the aldehyde of formula XXXIV with an alkenyl or substituted alkenyl silane in the presence of a Lewis acid catalyst or an organometalic reagent such as trialkylaluminum, alkyl magnesium halide, alkyl lithium, alkyl zinc, or the corresponding reagents for the other definitions of $R_6$ to give the alcohol of the formula

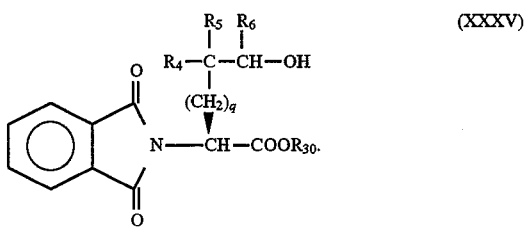

The alcohol of formula XXXV can then be converted to the corresponding azide such as by treatment with carbon tetrabromide and triphenylphosphine followed by lithium or sodium azide or treatment with p-toluenesulfonyl chloride and pyridine followed by lithium or sodium azide. Hydrogenation reduces the azide function to a primary amine and removes the benzyl or benzhydryl ester group. Treatment with ethyl-3-(dimethylamino)propyl carbodiimide and hydroxybenzotriazole gives a mixture of

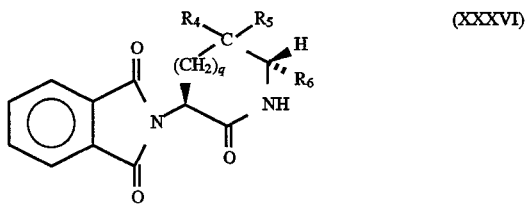

and

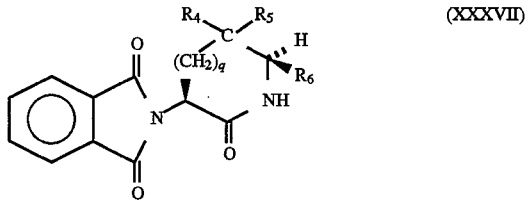

The compound of either formula XXXVI or XXXVII can be treated to remove the N-phthaloyl protecting group and introduce the t-butoxycarbonyl protecting group in its place. Reaction with a compound of the formula

wherein L is a leaving group such as chloro, bromo, or tolylsulfonyloxy in the presence of base followed by removal of the t-butoxycarbonyl protecting group gives the desired intermediates of formula XV wherein $X_1$ is as defined in formula III, q is one, two, or three, $R_7$ is hydrogen and $R_6$ is alkyl or substituted alkyl.

In a modification of this process, the aldehyde of formula XXXIV wherein $R_{30}$ is an alkyl such as methyl can be treated with an alkenyl or substituted alkenyl silane in the presence of a Lewis acid or an organometallic reagent such as trialkylaluminum, alkyl magnesium halide, alkyl lithium, alkyl zinc, or the corresponding reagents for the other definitions of $R_6$ to give the alcohol of formula XXXV wherein $R_6$ is alkyl, substituted alkyl, alkenyl, substituted alkenyl, aryl —$(CH_2)_m$—, substituted aryl —$(CH_2)_m$—, heteroaryl —$(CH_2)_m$—, or cycloalkyl —$(CH_2)_m$— and $R_{30}$ is alkyl.

This alcohol can then be converted to the azide as described above and the N-phthaloyl protecting group removed and replaced by a t-butoxycarbonyl protecting group. Reduction of the azide to a primary amine followed by ring closure gives a mixture of the compounds of the formulas

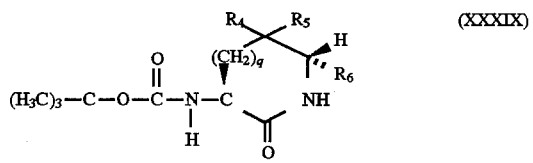

and

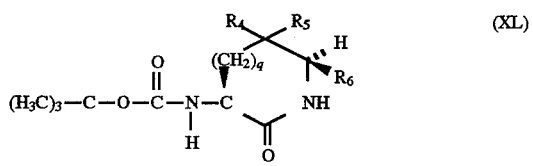

The compound of either formula XXXIX or XL can then be treated with a compound of formula XXXVIII in the presence of base followed by removal of the t-butoxycarbonyl protecting group to give the desired intermediates.

A further modification of these processes can be employed to give the intermediates of formula XV wherein $X_1$ is as defined in formula III, q is one, two, or three, and $R_6$ and $R_7$ are both other than hydrogen.

According to this modification, the alcohol of formula XXXV can be oxidized such as by treatment with oxalyl chloride, dimethylsulfoxide, and triethylamine to give the ketone of the formula

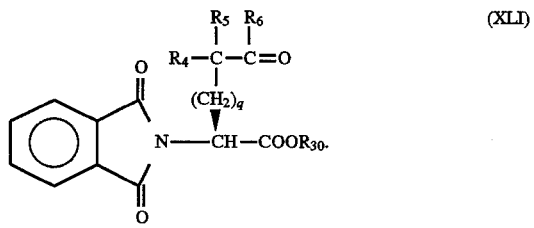

The ketone of formula XLI can then be reacted with an alkenyl or substituted alkenyl silane in the presence of a Lewis acid or with an organometallic reagent such as trialkylaluminum, alkyl magnesium halide, alkyl lithium, alkyl zinc, or the corresponding reagents for the other definitions of $R_7$ to give the alcohol of the formula

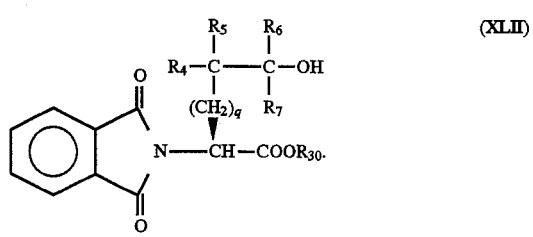

The alcohol of formula XLII can then be converted to the azide, hydrogenated to reduce the azide to an amine, and treated to effect ring closure yielding the compound of the formula

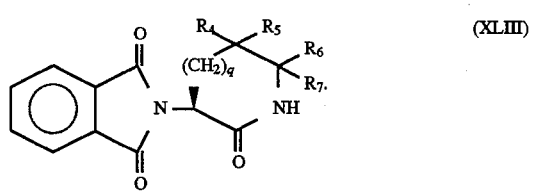

The compound of formula XLIII can be treated to remove the N-phthaloyl protecting group and introduce a t-butoxycarbonyl or triphenylmethyl protecting group in its place followed by reacting with the compound of formula XXXVIII in the presence of base and removal of the t-butoxycarbonyl or triphenylmethyl protecting group.

The intermediates of formula XV wherein $X_1$ is as defined in formula IX or X, $Y_2$ is —$CH_2$— and v is two can be prepared according to the following process which is also part of this invention.

The N-phthalimido α-amino acid of the formula

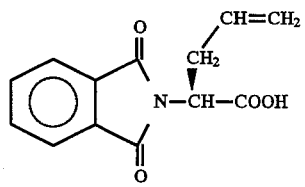

is coupled with the α-amino acid ester of the formula

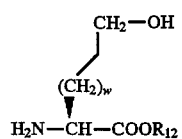

in the presence of a coupling catalyst as described above to give the alcohol of the formula

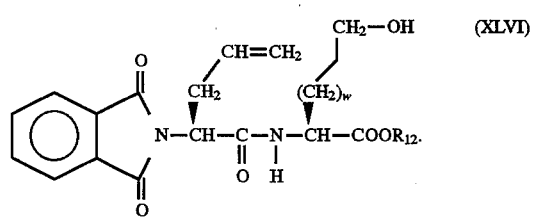

The alcohol of formula XLVI is oxidized such as by treatment with oxalyl chloride, dimethylsulfoxide, and triethylamine to give the corresponding aldehyde which is then treated with an acid such as trifluoroacetic acid or hydrochloric acid to give the carboxylic acid ester of the formula

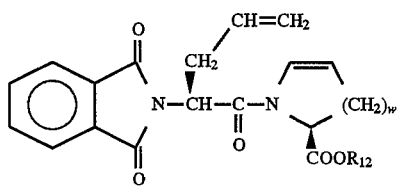

(XLVII)

Cyclization of the compound of formula XLVII with a strong acid such as trifluoromethanesulfonic acid followed by reesterification by conventional means and treatment with sodium iodide gives a mixture of the compounds of the formulas

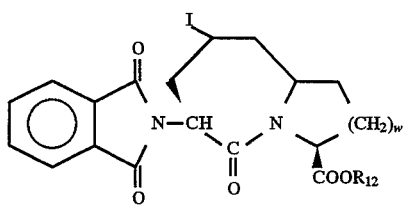

(XLVIII)

and

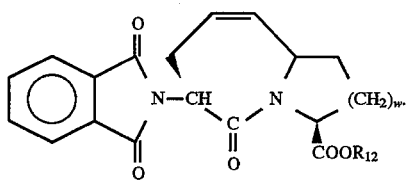

(XLIX)

Removal of the N-phthaloyl protecting group from the intermediate of formula (XLIX) as described above gives the desired compound of formula XV wherein $X_1$ is as defined in formula X and $Y_2$ is —$CH_2$—.

Treatment of the intermediate of formula XLVIII with tris(trimethylsilyl) silane or tri-n-butyltin hydride in the presence of a catalytic amount of azobisisobutyronitrile removes the iodo group. The N-phthaloyl group is subsequently removed as described above to give the desired compound of formula XV wherein $X_1$ is as defined in formula IX, v is two, and $Y_2$ is —$CH_2$—. Similar procedure can be employed to give the corresponding compound of formula XV wherein $X_1$ is as defined in formula IX, v is one, and $Y_2$ is —$CH_2$—.

In a variation of this process, the N-phthalimido α-amino acid of formula XLIV is reacted with the amino acid ester of the formula

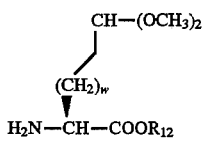

(L)

in the presence of a coupling catalyst as described above to give the dimethoxy compound of the formula

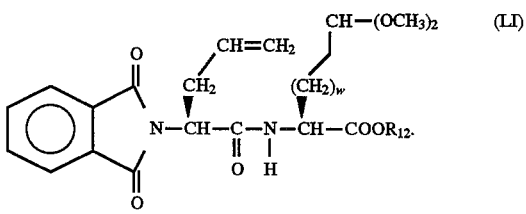

(LI)

The compound of formula LI can then be treated with an acid such as trifluoroacetic acid or hydrochloric acid to give the carboxylic acid ester of formula XLVII.

Other procedures for preparing the intermediates of formula XV appear in the examples.

The compounds of formula I contain one or more asymmetric centers. Thus, these compounds can exist in diastereoisomeric forms or in mixtures thereof and all of such forms are within the scope of this invention. The above described processes can utilize racemates, enantiomers, or diastereomers as starting materials. When diastereomeric compounds are prepared, they can be separated by conventional chromatographic or fractional crystallization methods.

The compounds of formula I wherein $R_{12}$ is hydrogen can be isolated in the form of a pharmaceutically acceptable salt. Suitable salts for this purpose are alkali metal salts such as sodium and potassium, alkaline earth metal salts such as calcium and magnesium, and salts derived from amino acids such as arginine, lysine, etc. These salts are obtained by reacting the acid form of the compound with an equivalent of base supplying the desired ion in a medium in which the salt precipitates or in aqueous medium and then lyophilizing.

The compounds of formula I are dual inhibitors possessing the ability to inhibit both the angiotensin converting enzyme and neutral endopeptidase. Thus, the compounds of formula I including their pharmaceutically acceptable salts are useful in the treatment of physiological conditions in which either angiotensin converting enzyme inhibitors or neutral endopeptidase inhibitors have been shown to be useful. Such conditions include cardiovascular diseases, particularly, hypertension, congestive heart failure, renal failure, and hepatic cirrhosis, as well as analgesic activity. Diuresis, natriuresis, and blood pressure reduction are produced in a mammalian host such as man by the administration of from about 1 mg. to about 100 mg. per kg. of body weight per day, preferably from about 1 mg. to about 50 mg. per kg. of body weight per day, of one or more of the dual inhibitors of formula I or a pharmaceutically acceptable salt thereof. The dual inhibitors of formula I are preferbly administered orally, but parenteral routes such as subcutaneous, intramuscular, and intravenous can also be employed. The daily dose can be administered singly or can be divided into two to four doses administered throughout the day.

The dual inhibitors of formula I can be administered in combination with human ANF 99–126. Such combination would contain the inhibitor of formula I at from about 1 to about 100 mg. per kg. of body weight and the human ANF 99–126 at from about 0.001 to about 0.1 mg. per kg. of body weight.

The dual inhibitors of formula I can be administered in combination with other classes of pharmaceutically active compounds. For example, a calcium channel blocker, a potassium channel activator, a cholesterol reducing agent, etc.

The dual inhibitors of formula I or a pharmaceutically acceptable salt thereof and other pharmaceutically acceptable ingredients can be formulated for the above described pharmacetical uses. Suitable compositions for oral administration include tablets, capsules, and elixirs, and suitable compositions for parenteral administration include sterile solutions and suspensions. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

Preferred compounds of this invention with respect to the mercapto containing sidechain portion of formula I, i.e.

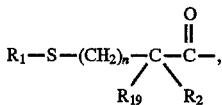

include those wherein:
R₁ is hydrogen,

or R₁₈—S—,
R₃ is lower alkyl of 1 to 4 carbons or phenyl,
R₁₈ is lower alkyl of 1 to 4 carbons,
n is zero or one,
R₂ is aryl —CH₂—, substituted aryl —CH₂—, heteroaryl —CH₂—, or straight or branched chain alkyl of 1 to 7 carbons, and
R₁₉ is hydrogen.

Most preferred are the above mercapto containing sidechains wherein:
R₁ is hydrogen or

especially hydrogen;
n is zero; and
R₂ is benzyl, (2-thienyl)methyl, or straight or branched chain alkyl of 1 to 5 carbons, especially benzyl.

Preferred compounds of this invention with respect to X₁ include those of formula III wherein:
q is one or two;
R₄ is hydrogen, methyl, or phenyl;
R₅ is hydrogen;
R₆ and R₇ are both hydrogen or are both methyl, or R₆ is lower alkyl of 1 to 4 carbons, mono substituted lower alkyl of 1 to 4 carbons, or alkenyl of 3 to 5 carbons having one double bond and R₇ is hydrogen or R₆ and R₇ taken together with the carbon to which they are attached complete a cycloalkyl of 3 to 5 carbons;
R₁₀ and R₁₁ are both hydrogen or one is hydrogen and the other is lower alkyl of 1 to 4 carbons;
b is zero or one; and
R₁₂ is hydrogen or lower alkyl of 1 to 4 carbons.

Most preferred are the above compounds of formula III wherein:
q is two;
R₄ and R₅ are both hydrogen;
R₆ and R₇ are both methyl or R₆ is methyl, propyl, allyl, or 2-hydroxyethyl and R₇ is hydrogen;
b is zero;
R₁₀ and R₁₁ are both hydrogen or one is hydrogen and the other is methyl; and
R₁₂ is hydrogen.

Preferred compounds of this invention with respect to X₁ include those of formula IV wherein:
r is one;
s is zero;
R₈ is hydrogen, phenyl, or lower alkyl of 1 to 4 carbons;
R₉ is hydrogen;
R₆ and R₇ are both hydrogen or are both methyl and R₆ is lower alkyl of 1 to 4 carbons or phenyl and R₇ is hydrogen;
R₁₀ and R₁₁ are both hydrogen or one is hydrogen and the other is lower alkyl of 1 to 4 carbons;
b is zero; and
R₁₂ is hydrogen or lower alkyl of 1 to 4 carbons.

Most preferred are the above compounds of formula IV wherein:
R₈ is hydrogen or phenyl;
R₆ and R₇ are both hydrogen or R₆ is phenyl and R₇ is hydrogen;
R₁₀, R₁₁ and R₁₂ are all hydrogen. Preferred compounds of this invention with respect to X₁ include those of formula V wherein:
s is zero;
t is one or two;
R₆ and R₇ are both hydrogen or are both methyl or R₆ is lower alkyl of 1 to 4 carbons or phenyl and R₇ is hydrogen;
R₁₀ and R₁₁ are both hydrogen or one is hydrogen and the other is lower alkyl of 1 to 4 carbons;
b is zero; and
R₁₂ is hydrogen or lower alkyl of 1 to 4 carbons.

Most preferred are the above compounds of formula V wherein:
t is two;
R₆ is phenyl and R₇ is hydrogen; and
R₁₀, R₁₁, and R₁₂ are all hydrogen.

Preferred compounds of this invention with respect to X₁ include those of formula VI wherein:
Y₁ is O, S, or CH₂;
R₆ and R₇ are both hydrogen or R₆ is lower alkyl of 1 to 4 carbons and R₇ is hydrogen;
R₁₀ and R₁₁ are both hydrogen or one is hydrogen and the other is lower alkyl of 1 to 4 carbons;
b is zero; and
R₁₂ is hydrogen or lower alkyl of 1 to 4 carbons.

Most preferred are those above compounds of formula VI wherein:
Y₁ is CH₂;
R₆ and R₇ are both hydrogen; and
R₁₀, R₁₁, and R₁₂ are all hydrogen.

Preferred compounds of this invention with respect to X₁ include those of formula VII wherein:
Y₄ is —CH₂—;
R₆ and R₇ are both hydrogen;
R₁₀ and R₁₁ are both hydrogen or one is hydrogen and the other is lower alkyl of 1 to 4 carbons, especially where both are hydrogen;
b is zero, and
R₁₂ is hydrogen or lower alkyl of 1 to 4 carbons, especially hydrogen.

Preferred compounds of this invention with respect to X₁ include those of formula VIII wherein:
R₆ and R₇ are both hydrogen or one is hydrogen and the other is lower alkyl of 1 to 4 carbons;
R₁₀ and R₁₁ are both hydrogen or one is hydrogen and the other is lower alkyl of 1 to 4 carbons, especially where both are hydrogen;
b is zero, and
R₁₂ is hydrogen or lower alkyl of 1 to 4 carbons, especially hydrogen.

Preferred compounds of this invention with respect to X₁ include those of formula IX wherein
v is one or two; especially two,
w is one or two;
Y₂ is S or CH₂; and
R₁₂ is hydrogen or lower alkyl of 1 to 4 carbons, especially hydrogen.

Preferred compounds of this invention with respect to X₁ include those of formula X wherein:
Y₂ is CH₂;
w is one or two, especially two; and $R_{12}$ is hydrogen or lower alkyl of 1 to 4 carbons, especially hydrogen.

Preferred compounds of this invention with respect to $X_1$ include those of formula XI wherein:

v is one or two, especially two;

Z is O or two hydrogens, especially two hydrogens; and $R_{12}$ is hydrogen or lower alkyl of 1 to 4 carbons, especially hydrogen.

Preferred compounds of this invention with respect to $X_1$ include those of formula XII wherein:

Z is O or two hydrogens, especially O;

$R_{17}$ is lower alkyl of 1 to 4 carbons, especially methyl;

$R_{10}$ and $R_{11}$ are both hydrogen or one is hydrogen and the other is lower alkyl of 1 to 4 carbons, especially where both are hydrogen;

b is zero; and $R_{12}$ is hydrogen or lower alkyl of 1 to 4 carbons, especially hydrogen.

Preferred compounds of this invention with respect to $X_1$ include those of formula XIII wherein:

$Y_3$ is $CH_2$ or S, especially $CH_2$;

$R_{13}$ is hydrogen;

$R_{10}$ and $R_{11}$ are both hydrogen or one is hydrogen and the other is lower alkyl of 1 to 4 carbons, especially where both are hydrogen;

b is zero; and $R_{12}$ is hydrogen or lower alkyl of 1 to 4 carbons, especially hydrogen.

The following examples are illustrative of the invention. Temperatures are given in degrees centigrade. Thin layer chromatography (TLC) was performed in silica gel unless otherwise stated.

EXAMPLE 1

[3R(S*)]-3,4-Dihydro-3-[[2-mercaptomethyl)-1-oxo-3-phenylpropyl]amino]-4-oxo-1,5-benzothiazepine-5 (2H)-acetic acid a) (S)-2-[(Acetylthio)methyl]benzenepropanoic acid, ephedrine salt A solution of (1R,2S)-(−)-ephedrine (17.3 g., 105 mmol.) in diethyl ether (175 ml.) was added in one portion to a solution of 2-[(acetylthio)methyl]benzenepropanoic acid (50.0 g., 210 mmol.) in diethyl ether (175 ml.). After standing at room temperature for 16 hours, the crystallized ephedrine salt was collected by filtration (19.7 g.); m.p. 114°–125°; [α]D=−40.6° (c=1, methanol). An additional amount of solid [8.9 g., m.p. 121°–126°; $[α]_D$=−47.2°, (c=1, methanol)] separated from the filtrate after remaining at room temperature for 20 hours. The solids were combined and recrystallized from acetonitrile (1500 ml.). After 16 hours at room temperature, 20.8 g. of solid was collected; m.p. 125°–130° C.; $[α]_D$=−47.5° (c=1, methanol). This material was recrystallized in the same manner from acetonitrile (300 ml.) to give 18.74 g., m.p. 128°–130° C; $[α]_D$=−48.9° (c=1, methanol). A third recrystallization from acetonitrile (225 ml.) afforded 17.4 g. of solid (S)-2-[(acetylthio)methyl]benzenepropionic acid, ephedrine salt; m.p. 128°–129°; $[α]_D$=150.1° (c=1, methanol).

Anal. calc'd. for $C_{12}H_{14}O_3S \cdot C_{10}H_{15}NO$:

C,65.48; H,7.24; N,3.47; S,7.95 Found: C,65.46; H,7.34; N,3.21; S,8.00.

b) [3R(S*)]-3,4-Dihydro-3-[[2-[(acetylthio)methyl]-1-oxo-3-phenylpropyl]amino]-4-oxo-1,5-benzothiazepine-5(2H)-acetic acid, ethyl ester (S)-2-[(Acetylthio)methyl]benzenepropanoic acid, ephedrine salt (3.34 mmoles, 1.01 eq.) was suspended in ethyl acetate (65 ml.), washed with dilute HCl (65 ml. water+4.7 ml. 1.0N hydrochloric acid then 31 ml. water+1.6 ml. 1.0N hydrochloric acid), brine (10 ml.), dried (anhydrous magnesium sulfate), filtered and evaporated to dryness. The colorless syrup was dried in vacuo for 1.0 hour to afford a quantitative amount of the free acid (836 mg.).

The free acid was dissolved in dry dimethylformamide (19 ml.), cooled down to 0° (ice-salt bath), treated with 1-hydroxybenztriazole hydrate (470 mg., 3.48 mmoles) and 1-ethyl-3-(3-dimethylaminopropyl)carbodiimide (690 mg., 3.60 mmoles) and stirred at 0° under argon for 1.0 hour. The clear solution was treated with (R)-3,4-dihydro-3-amino-4-oxo-1,5-benzothiazepine-5(2H)-acetic acid, ethyl ester [prepared according to the procedure of Slade et al., J. Med. Chem. 28, p 1517–1521 (1985)] (1.2 g., 3.32 mmoles) and 4-methylmorpholine (0.37 ml., 3.32 mmoles) and stirring was continued at 0° for 1.0 hour and at room temperature for 1.0 hour. The reaction mixture was diluted with ethyl acetate (80 ml.), washed successively with water (12 ml.), 5% potassium bisulfate (12 ml.), water (12 ml.), saturated sodium bicarbonate (12 ml.) and brine (12 ml.), dried (anhydrous magnesium sulfate), filtered, evaporated to dryness and dried in vacuo. The crude product was chromatographed on a silica gel column (Merck), eluting the column with ethyl acetate:hexanes (1:4) to give 1.5 g. of the product as a syrup; $R_f$=0.68 (ethyl acetate:hexanes, 1:1).

c) [3R(S*)]-3,4-Dihydro-3-[[2-(mercaptomethyl)-1-oxo-3-phenylpropyl]amino]]-4-oxo-1,5-benzothiazepine-5(2H)-acetic acid A solution of the ethyl ester product from part (a) (1.5 g., 2.996 mmoles) in dry methanol (15 ml.) was purged with argon for 15 minutes, cooled down to 0° (ice-salt bath) then treated dropwise with a previously purged (argon, 30 minutes) solution of 1.0N sodium hydroxide (12 ml., 4 eq.) maintaining the bubbling of argon throughout the addition and the length of the reaction. The reaction mixture was stirred at 0° for 1.0 hour, acidified at 0° with 5% potassium bisulfate (50 ml.) to pH 1.0 then extracted with ethyl acetate (2×100 ml.). The organic extract was washed with brine (25 ml.), dried (anhydrous sodium sulfate), filtered, evaporated to dryness and dried in vacuo. The crude product was dissolved in a mixture of methylene chloride (10 ml.) and ethyl ether (5.0 ml.) then treated portionwise with hexane (30 ml.), scratching the mixture to form a solid. The precipitates were filtered off, washed with hexane (50 ml.) and evaporated from pentane (4×50 ml.). The solid was then stirred with pentane (50 ml.) for 48 hours at room temperature under argon, filtered and dried in vacuo for 6 hours to give 1.01 g. of the product as an amorphous solid; $R_f$=0.62 (methylene chloride:methanol:acetic acid, 20:1:1); $[α]_D$=−171.4° (c=0.74, methanol).

1H NMR (CDCl$_3$): 2.47–2.90 (m, 6H), 3.84 (dd, 1H), 4.13 (d, 1H, J=17 Hz), 4.71 (m, 1H), 4.85 (d, 1H, J=17 Hz), 6.88–7.67 (m, 9H). Anal. calcd. for $C_{21}H_{22}N_2O_4S_2$: C,58.59; H,5.15; N,6.51; S,14.89; SH,7.68 Found: C,58.55; H,5.35; N,6.20; S,14.56; SH,7.54.

EXAMPLE 2

[R-(R*,S*)]-3,4-Dihydro-3-[(2-mercapto-1-oxo-3-phenyl-propyl)amino]-4-oxo-1,5-benzothiazepine-5(2H)-acetic acid a) (S)-2-(Acetylthio)benzenepropanoic acid, dicyclohexylamine salt Sodium nitrite (10.3 g., 280 mmol.) was added to a solution of D-phenylalanine (30.0 g., 181 mmol.) and potassium bromide (73.5 g.) in sulfuric acid (2.5N, 365 ml.) over a period of one hour while maintaining the temperature of the reaction mixture at 0° C. The mixture was stirred for an additional hour at 0° C. and then for one hour at room temperature. The reaction solution was extracted with ether, the ether was back extracted with water, and the ether layer was dried over sodium sulfate. Ether was removed in vacuo, and distillation of the oily residue afforded 25.7 g. of (R)-2-bromo-3-benzenepropanoic acid; b.p. 141° (0.55 mm of Hg.); $[\alpha]_D$=+14.5° (c=2.4, chloroform).

A mixture of thioacetic acid (7 ml., 97.9 mmol.) and potassium hydroxide (5.48 g., 97.9 mmol.) in acetonitrile (180.5 ml.) was stirred under argon at room temperature for 1¾ hours. The mixture was cooled in an ice-bath, and a solution of (R)-2-bromo-3-benzenepropanoic acid (20.4 g., 89 mmol.) in acetonitrile (20 ml.) was added over a ten minute period. The reaction was stirred under argon at room temperature for 5 hours, filtered, and the acetonitrile was removed in vacuo. The oily residue was redissolved in ethyl acetate and washed with 10% potassium bisulfate and water. Removal of the ethyl acetate in vacuo afforded 19.6 g. of crude product. The crude product was purified via its dicyclohexylamine salt using isopropyl ether as solvent for crystallization. An analytical sample of (S)-2-(acetylthio) benzenepropanoic acid, dicyclohexylamine salt was prepared by recrystallization from ethyl acetate; m.p. 146°–147°; $[\alpha]_D$=–39.6° (c=1.39, chloroform).

Anal. calc'd. for $C_{11}H_{12}O_3S$ . $C_{12}H_{23}N$: C,68.11; H,8.70; N,3.45; S,7.91 Found: C,67.93; H,8.71; N,3.37; S,7.94.

b) [R-(R*,S*)]-3,4-Dihydro-3-[[2-(acetylthio)-1-oxo-3-phenylpropyl]amino]-4-oxo-1,5-benzothiazepine-5(2H)-acetic acid, ethyl ester A suspension of (S)-2-(acetylthio)benzenepropanoic acid, dicyclohexylamine salt (1,76 g., 4.34 mmoles, 1.01 eq.) was suspended in ethyl acetate (123 ml.), washed with 5% potassium bisulfate (5×19 ml.) and brine (25 ml.), dried (anhydrous magnesium sulfate), filtered, evaporated to dryness and dried in vacuo.

The free acid was dissolved in dry methylene chloride (25 ml.), cooled down to 0° (ice-salt bath), treated with 1-hydroxybenztriazole hydrate (611 mg., 4.52 mmoles) and 1-ethyl-3-(3-(dimethylaminopropyl)carbodiimide (897 mg., 4.68 mmoles) and stirred at 0° for 1.0 hour. The solution was treated with (R)-3,4-dihydro-3-amino-4-oxo-1,5-benzothiazepine-5(2H)-acetic acid, ethyl ester [prepared according to the procedure of Slade et al., J. Med. Chem., Vol. 28, p 1517–1521(1985)] (1.55 g., 4.29 mmoles) and 4-methylmorpholine (0.48 ml., 4.37 mmoles) and stirring was continued at 0° for 1.0 hour and at room temperature for 1.0 hour. The reaction mixture was diluted with ethyl acetate (104 ml.) , washed successively with water (16 ml.), 5% potassium bisulfate (2×16 ml.), saturated sodium bicarbonate (16 ml.) and brine (16 ml.), dried (anhydrous magnesium sulfate), filtered, evaporated to dryness and dried in vacuo. The crude product was chromatographed on a silica gel column (Merck), eluting the column with ethyl acetate:hexane (1:4) to give 1.347 g. of product as a syrup; $R_f$=0.80 (ethyl acetate:hexane, 1:1).

c) [R-(R*,S*)]-3,4-Dihydro-3-[(2-mercapto-1-oxo-3-phenylpropyl)amino]-4-oxo-1,5-benzothiazepine-5(2H)-acetic acid A solution of the ethyl ester product of part (b) (1.347 g., 2.768 mmoles) in methanol (14 ml.) was purged with argon for 30 minutes, cooled down to 0° (ice-salt bath) then treated dropwise with a previously purged (argon, 30 minutes) solution of 1.0N sodium hydroxide (11 ml., 4 eq.) maintaining the bubbling of argon throughout the addition and the length of the reaction. The reaction mixture was stirred at 0° for 1.0 hour, acidified at 0° with 5% potassium bisulfate (46 ml.) to pH 2.0 then extracted with ethyl acetate (2×100 ml.). The organic extracts were washed with brine (25 ml.), dried (anhydrous sodium sulfate), filtered, evaporated to dryness and dried in vacuo. The crude product was dissolved in methylene chloride (10 ml.) and treated portionwise with hexane (50 ml.), scratching the mixture to form a solid. The supernatant was decanted and the solids triturated with additional hexane (50 ml.) and pentane (2×100 ml.), stirring with the first 100 ml. of pentane for 4 hours and the next 100 ml. overnight under argon. The product obtained was then dried in vacuo for 12 hours to give 1.048 g. of product as an amorphous solid; $R_f$=0.57 (methylene chloride:methanol: acetic acid, 20:1:1); $[\alpha]_D$=–169.9° (c=0.61, methanol).

1H NMR (CDCl$_3$): 1.99 (d, 1H), 2.76 (t, 1H, J=11 Hz), 3.10 (m, 2H), 3.54 (m, 1H), 3.76 (m, 1H), 4.10 (d, 1H, J=17 Hz) 4.65 (m, 1H), 4.86 (d, 1H, J=17 Hz), 7.12–7.68 (m, 9H). Anal. calcd for $C_{20}H_{22}N_2O_4S$ . 0.17 $C_5H_{12}$ . 0.52 $H_2O$: C,57.15; H,5.30; N,6.40; S,14.64; SH,7.55 Found: C,57.15; H,4.99; N,6.14; S,14.72; SH,8.02.

EXAMPLE 3

(S,S)-1,3,4,5-Tetrahydro-4-[[2-(mercaptomethyl)-1-oxo-3-phenylpropyl]amino]-3-oxo-2H-2-benzazepine-2-acetic acid a) N-(N-Phthaloyl-L-phenylalanyl)glycine, ethyl ester Hydroxybenztriazole hydrate (1.42 g., 10.5 mmol.) and 1-ethyl-3-(3-dimethylaminopropyl)carbodiimide hydrochloride (2.10 g., 11.0 mmol) were added to a solution of N-phthaloyl-L-phenylalaninamide (2.95 g., 10.0 mmol.) in dry methylene chloride (30 ml.) at 0° under argon. After stirring at 0° C. for 30 minutes, the resulting mixture was treated with glycine, ethyl ester, hydrochloride (1.675 g., 12.0 mmol.) and N-methylmorpholine (1.32 ml., 12.0 mmol). After stirring at 0° C. for 1 hour and at room temperature for 3 hours, the mixture was partitioned between ethyl acetate-5% potassium bisulfate. The organic phase was washed successively with 5% potassium bisulfate, saturated sodium bicarbonate and saturated sodium chloride solutions; dried (sodium sulfate) and evaporated to dryness. Trituration of the crude product with ethyl ether gave 3.542 g. of product as a white, crystalline solid; m.p 158°–159° C.; $R_f$=0.33 (acetone:hexane, 2:3); $[\alpha]_D$=–99.7° (c=0.61, chloroform).

b) (S)-1,3,4,5-Tetrahydro-4-phthalimido-3-oxo-2H-2-benzazepine-2-acetic acid, ethyl ester A mixture of phosphorus pentoxide (9.6 g, 68 mmol) and 85% phosphoric acid (6.0 ml) was heated with stirring until all of the phosphorus pentoxide had dissolved. The resulting viscous liquid was taken up in glacial acetic acid (36 ml), treated successively with N-(N-phthaloyl-L-phenylalanyl) glycine, ethyl ester (2.241 g., 5.90 mmol.) and trioxane (0.75 g., 8.3 mmol.), and heated at 80° C. (bath temperature) under an argon atmosphere. After stirring at 80° C. for 6.5 hours the mixture was treated with an additional portion of trioxane (0.75 g, 8.3 mmol). After stirring at 80° C. for an additional 16 hours, the reaction was quenched with an ice-water mixture and extracted with ethyl acetate. The ethyl acetate extract was washed with water (3X), saturated sodium bicarbonate (until washes were basic) and saturated sodium chloride solutions, dried (sodium sulfate) and evaporated to dryness. The crude product was purified by flash chromatography on silica gel (Whatmann LPS-1) eluting with ethyl acetate-hexane (35:65) to give 1.718 g. of product as a colorless foam; $R_f$=0.38 (ethyl acetate:toluene, 3:7).

c) (S)-1,3,4,5-Tetrahydro-4-[[(phenylmethoxy)carbonyl] amino]-3-oxo-2H-2-benzazepine-2-acetic acid, ethyl ester A solution of (S)-1,3,4,5-tetrahydro-4-phthalimido-3-oxo-2H-2-benzazepine-2-acetic acid, ethyl ester (1.67 g., 4.26 mmol.) in 1.0M hydrazine hydrate in ethanol (9.0 ml., 9.0 mmol.) was stirred at room temperature under argon for 36 hours. The mixture was diluted with an equal volume of ethyl acetate, filtered and filtrate evaporated to dryness. The residue was taken up in toluene and again evaporated to dryness. The colorless, semi-solid residue (1.81 g.) was taken up in dry methylene chloride (20 ml.), placed in an ice bath and treated successively with triethylamine (0.80 ml., 5.8 mmol.) and benzylchloroformate (0.77 ml., 5.4 mmol.). After stirring at 0° C. for 2 hours, the mixture was partitioned between ethyl acetate-5% potassium bisulfate. The organic phase was washed successively with 5% potassium bisulfate, saturated sodium bicarbonate and saturated sodium chloride solutions, dried (sodium sulfate), and evaporated to dryness. Purification of the crude product by flash chromatography on silica gel (Whatmann LPS-1) eluting with ethyl acetate:hexane (1:2) gave 1.0747 g. of product as a colorless foam; $R_f$=0.52 (ethyl acetate:toluene, 3:7). A sample crystallized from hexane had m.p. 80°–82° C.; $[\alpha]_D$=+87.2° (c=0.53, chloroform).

d) (S)-1,3,4,5-Tetrahydro-4-amino-3-oxo-2H-2-benzazepine-2-acetic acid, ethyl ester 20% Palladium hydroxide/carbon catalyst was added to a solution of (S)-1,3,4,5-tetrahydro-4-[[(phenylmethoxy)carbonyl]amino]-3-oxo-2H-2 -benzazepine-2-acetic acid, ethyl ester (1.037 g., 2.62 mmole) in absolute ethanol (20 ml.) and the resulting suspension was stirred under a hydrogen atmosphere (balloon) for 2 hours. The mixture was filtered through Celite and filtrate was evaporated to dryness. The semi-solid residue was triturated with hexane to give 0.63 g. of product as a white, crystalline solid; m.p. 71°–73° C.; $R_f$=0.38 (methanol:methylene chloride, 1:9); $[\alpha]_D$=77.5° (c=0.59, chloroform).

e) (S,S)-1,3,4,5-Tetrahydro-4-[[2-[(acetylthio)methyl]-1-oxo-3-phenylpropyl]amino]-3-oxo-2H-2-benzazepine-2-acetic acid, ethyl ester (S)-2-[(Acetylthio)methyl]benzenepropanoic acid, ephedrine salt (0.43 g., 1.07 mmol.) was partitioned between ethyl acetate (20 ml.)-aqueous hydrochloric acid (1.5 ml. 1.0N hydrochloric acid+20 ml water). The organic phase was washed with aqueous hydrochloric acid (0.5 ml. 1.0N hydrochloric acid+10 ml water) and saturated sodium chloride solutions, dried (sodium sulfate) and evaporated to dryness. The resulting free acid (0.260 g., about 1.07 mmol) was taken up in dry dimethylformamide (6.0 ml.), placed in an ice bath and treated with hydroxybenztriazole hydrate (0.150 g, 1.11 mmol) and 1-ethyl-3-(3-dimethylaminopropyl)carbodiimide hydrochloride (0.220 g, 1.15 mmol). After stirring at 0° C. for 1 hour, the resulting mixture was treated with (S)-1,3,4,5-tetrahydro-4-amino-3-oxo-2H-2-benzazepine-2-acetic acid, ethyl ester (0.260 g, 0.992 mmol) in one portion. After stirring at 0° C. for 2 hours and at room temperature for 1 hour, the mixture was partitioned between ethyl acetate-water. The organic phase was washed successively with water, 5% potassium bisulfate, saturated sodium bicarbonate and saturated sodium chloride solutions, dried (sodium sulfate) and evaporated to dryness. Purification of the crude product (0.506 g.) by flash chromatography on silica gel (Whatmann LPS-1) eluting with ethyl acetate-hexane (35:65) gave 0.39 g. as a colorless foam; $R_f$=0.30 (ethyl acetate:hexane; 1:1).

f) (S,S)-1,3,4,5-Tetrahydro-4-[[2-(mercaptomethyl)-1-oxo-3-phenylpropyl]amino]-3-oxo-2H-2-benzazepine-2-acetic acid A degassed solution of 1.0N aqueous sodium hydroxide (3.2 ml., 3.2 mmol.) was added to a degassed solution of the ethyl ester product from part (e) 0.39 g., 0.809 mmol.) in methanol (4 ml.) at 0° C. Throughout the course of the reaction, argon was continously passed into the reaction mixture. After stirring at 0° C. for 45 minutes the reaction was quenched with 5% potassium bisulfate (20 ml.) and extracted with ethyl acetate. The ethyl acetate extract was washed with 5% potassium bisulfate and saturated sodium chloride solutions, dried (sodium sulfate) and evaporated to dryness. The crude product was crystallized with ethyl acetate-hexane, collected by suction and dried in vacuo at 50° C. to give 0.309 g, of product as a white solid, mp 149°–151° C. (decomp). $R_f$=0.47 (methylene chloride:acetic acid:methanol, 20:1:1); $[\alpha]_D$=+112.2° (c=0.58, methanol)

Anal. calc'd for $C_{22}H_{24}N_2O_4S$: C,64.06; H,5.86; N, 6.79; S,7.77; SH,8.02 Found: C,64.20; H,6.09; N,6.43; S,7.68; SH,8.33.

EXAMPLE 4

(S,S)-1,3,4,5-Tetrahydro-4-[(2-mercapto-1-oxo-3-phenylpropyl)amino]-3-oxo-2H-2-benzazepine-2-acetic acid a) (S,S)-1,3,4,5-Tetrahydro-4-[[2-(acetylthio)-1-oxo-3-phenylpropyl]amino]-3-oxo-2H-2-benzazepine-2-acetic acid, ethyl ester (S)-2-(Acetylthio)benzenepropanoic acid, dicyclohexylamine salt (0.532 g., 1.31 mmol.) was partitioned between ethyl acetate-5% potassium bisulfate (25 ml. each). The organic phase was washed with 5% potassium bisulfate (2×15 ml) and saturated sodium chloride solutions, dried (sodium sulfate) and evaporated to dryness. The resulting free acid (colorless oil) was taken up in dry dimethylformamide (6.0 ml.), placed in an ice bath and treated with hydroxybenztriazole hydrate (0.185 g., 1.37 mmol) and 1-ethyl-3-(3-dimethylaminopropyl)carbodiimide hydrochloride (0.270 g, 1.41 mmol). After stirring at 0° C. for 45 minutes, the resulting mixture was treated with (S)-1,3,4,5-tetrahydro-4-amino-3-oxo-2H-2-benzazepine-2-acetic acid, ethyl ester (0.32 g., 1.22 mmol.) in one portion. After stirring at 0° C. for 2 hours and at room temperature for 1 hour, the mixture-was partitioned between ethyl acetate-water. The organic phase was washed successively with water, 5% potassium bisulfate, saturated sodium bicarbonate and saturated sodium chloride solutions; dried (sodium sulfate) and evaporated to dryness. TLC (ethyl acetate-hexane; 1:1) shows two products, $R_f$'s=0.35 (desired) and 0.28 (epimer). Purification by flash chromatography on silica gel (Whatmann LPS-1) eluting with ethyl acetate-hexane (1:2) gave 0.357 g. of product as a colorless foam; $R_f$=0.35 (ethyl acetate:hexane, 1:1).

b) (S,S)-1,3,4,5-Tetrahydro-4-[(2-mercapto-1-oxo-3-phenylpropyl)amino]-3-oxo-2H-2-benzazepine-2-acetic acid A degassed solution of 1.0N aqueous sodium hydroxide (3.1 ml., 3.1 mmol.) was added to a degassed solution of the ethyl ester product from part (a) (0.357 g., 0.763 mmol.) in methanol (4 ml.) at 0° C. Throughout the course of the reaction, argon was continously passed into the reaction mixture. After stirring at 0° C. for 45 minutes, the reaction was quenched with 5% potassium bisulfate (25 ml) and extracted with ethyl acetate. The ethyl acetate extract was washed with 5% potassium bisulfate and saturated sodium chloride solutions, dried (sodium sulfate) and evaporated to dryness. The crude product was triturated with ethyl ether-hexane, collected by suction and dried in vacuo at 50° C. to give 0.290 g. as a white solid; m.p. 181°–183° C. (decomposition); $R_f$=0.49 (methylene chloride:acetic acid:methanol, 20:1:1); $[\alpha]_D$=+103.4° (c=0.57, methanol).

Anal. calc'd for $C_{21}H_{22}N_2O_4S$: C,63.30; H,5.56; N,7.03; S,8.05; SH,8.30; Found C,63.35; H,5.65; N,6.87; S,8.07; SH,9.40.

EXAMPLE 5

[S-(R*,R*)]-2,3,4,5-Tetrahydro-3-[[2-(mercaptomethyl)-1-oxo-3-phenylpropyl]amino]-2-oxo-1H-benzazepine-1-acetic acid a) [S-(R*,R*)]-2,3,4,5-Tetrahydro-3-[[2-[(acetylthio)methyl]-1-oxo-3-phenylpropyl]amino]-2-oxo-1H-benzazepine-1-acetic acid, ethyl ester (S)-2-[(Acetylthio)methyl]benzenepropanoic acid, ephedrine salt (1.547 g., 3.83 mmoles, 1.01 eq.) was suspended in ethyl acetate (72 ml.), washed with dilute hydrochloric acid (72 ml. water+5.4 ml. 1.0N hydrochloric acid then 36 ml. water+1.8 ml. 1.0N hydrochloric acid), brine (12 ml.), dried (anhydrous magnesium sulfate), filtered and evaporated to dryness. The colorless syrup was dried in vacuo for 1.0 hour to give 1.062 g. of (S)-2-[(acetylthio)methyl] benzenepropanoic acid.

The free acid was dissolved in dry dimethylformamide (21.8 ml.), cooled down to 0° (ice-salt bath), treated with 1-hydroxybenztriazole hydrate (540 mg., 3.99 mmoles) and 1-ethyl-3-(3-dimethylaminopropylcarbodiimide (792 mg., 4.13 mmoles) and stirred at 0° under argon for 1.0 hour. The clear solution was treated with (S)-2,3,4,5-tetrahydro-3-amino-2-oxo-1H-benzazepine-1-acetic acid, ethyl ester [prepared as described by Watthey et al., J. Med. Chem., 28, p. 1511–1516 (1985)] (1.0 g., 3.81 mmoles) and stirring was continued at 0° for 1.0 hour and at room temperature for 1.0 hour. The reaction mixture was diluted with ethyl acetate (100 ml.), washed successively with water (15 ml.), 5% potassium bisulfate (2×15 ml.), saturated sodium bicarbonate (15 ml.) and brine (15 ml.), dried (anhydrous magnesium sulfate), filtered, evaporated to dryness and dried in vacuo. The crude product was chromatographed on a silica gel column (Merck), eluting the column with ethyl acetate:hexane mixtures (1:4; 1:2) to give 1.725 g. of product as a syrup; $R_f$=0.42 (ethyl acetate:hexane, 1:1).

b) [S-(R*,R*)]-2,3,4,5-Tetrahydro-3-[[2-(mercaptomethyl)-1-oxo-3-phenylpropyl]amino]-2-oxo-1H-benzazepine-1-acetic acid A solution of the ethyl ester product from part (a) (1.725 g., 3.574 mmoles) in methanol (18.0 ml.) was purged with argon for 30 minutes, cooled down to 0° (ice-salt bath) then treated dropwise with a previously purged (argon, 30 minutes) solution of 1.0N sodium hydroxide (14.3 ml., 4 eq.) maintaining the bubbling of argon throughout the addition and the length of the reaction. The reaction mixture was stirred at 0° for 1.0 hour, acidified at 0° with 5% potassium bisulfate (60 ml.) to pH 1.0 then extracted with ethyl acetate (2×120 ml.). The organic extracts were washed with brine (30 ml.), dried (anhydrous sodium sulfate), filtered, and evaporated to dryness. The crude product was dissolved in methylene chloride (10 ml.) and treated portionwise with hexane (50 ml.), scratching the mixture to form a solid. The supernatant was decanted and the solids triturated with additional hexane (2×50 ml.) and pentane (2×100 ml.), stirring with the first 100 ml. of pentane for 4.0 hours and the next 100 ml. overnight under argon. The product obtained was then dried in vacuo for 12 hours to give 1.438 g. of product as an amorphous solid $R_f$=0.53 (methylene chloride:methanol:acetic acid, 20:1:1);

$[\alpha]_D$=–140.4° (c=0.76, methanol) Anal. calc'd for $C_{22}H_{24}N_2O_4$ S . 0.11 $C_5H_{12}$: C,64.42; H,6.07; N, 6.66; S,7.63; SH,7.87 Found: C,64.07; H,6.13; N,6.34; S,7.25; SH,7.14. 1NMR(CDCl$_3$) 1.42 (t, 1H), 1.95 (m, 1H), 2.44–2.90 (m, 7H), 3.27 (m, 1H), 4.37 (d, 1H, J=17 Hz), 4.52 (m, 1H), 4.67 (d, 1H, J=17 Hz), 6.86–8.00 (m, 9H).

EXAMPLE 6

[S-(R*,R*)]-2,3,4,5-Tetrahydro-3-[(2-mercapto-1-oxo-3-phenylpropyl)amino]-2-oxo-1H-benzazepine-1-acetic acid a) [S-(R*,R*)-2,3,4,5-Tetrahydro-3-[[2-acetylthio)-2-oxo-3-phenylpropyl]amino]-2-oxo-1H-benzazepine-1-acetic acid, ethyl ester A suspension of (S)-2-(acetylthio) benzenepropanoic acid, dicyclohexylamine salt (1.70 g., 4.19 mmoles) was suspended in ethyl acetate (120 ml.), washed with 5% potassium bisulfate (5×20 ml.) and brine (25 ml.), dried (anhydrous magnesium sulfate, filtered, evaporated to dryness and dried in vacuo to give 954 mg. of the free acid as a syrup.

This free acid was dissolved in dry methylene chloride (25 ml.) and cooled down to 0° (ice-salt bath) treated with 1-hydroxybenztriazole hydrate (594 mg., 4.40 mmoles) and 1-ethyl-3-(3-dimethylaminopropyl)carbodidimide (870 mg., 4.54 mmoles) and stirred at 0° for 1.0 hour. The solution was treated with a solution of (S)-2,3,4,5-tetrahydro-3-amino-2-oxo-1H-benzazepine-1-acetic acid, ethyl ester [prepared as described by Watthey et al., J. Med. Chem., 28, p 1511–1516 (1985)] (1.0 g., 3.81 mmoles) in dry methylene chloride (10 ml.) and stirring was continued at 0° for 1.0 hour and at room temperature for 1.5 hours. The reaction mixture was diluted with ethyl acetate (100 ml.), washed successively with water (15 ml.), 5% potassium bisulfate (2×15 ml.), saturated sodium bisulfate (15 ml.) and brine (15 ml.), dried (anhydrous sodium sulfate), filtered, evaporated to dryness and dried in vacuo. The crude product was chromatographed on a silica gel column (Merck), eluting the column with ethyl acetate:hexane mixtures (1:4; 1:2) to give 1.632 g. of product as a syrup. An additional 127 mg. of the isomer mixture (1:1 ratio) was also obtained from the column; $R_f$=0.50 (ethyl acetate:hexane, 1:1).

b) [S-(R*,R*)]-2,3,4,5-Tetrahydro-3-[(2-mercapto-1-oxo-3-phenylpropyl)amino]-2-oxo-1H-benzazepine-1-acetic acid A solution of the ethyl ester product from part (a) (1.57 g., 3.35 mmoles) in methanol (17.0 ml.) was purged with argon for 30 minutes, cooled down to 0° (ice-salt bath) then treated dropwise with a previously purged (argon, 30 minutes) solution of 1.0N sodium hydroxide (13.4 ml., 4.0 eq.) maintaining the bubbling of argon throughout the addition and length of the reaction. The reaction mixture was stirred at 0° for 1.0 hour, acidified at 0° with 5% potassium bisulfate (60 ml.) to pH 1.0 then extracted with ethyl acetate (2×110 ml.). The organic extracts were washed with brine (30 ml.), dried (anhydrous sodium sulfate), filtered, evaporated to dryness and dried in vacuo. The crude product was dissolved in methylene chloride (10 ml.) and treated portionwise with hexane (50 ml.), scratching the mixture to form a solid. The supernatant was decanted and the solids triturated with additional hexane (2×50 ml.) and pentane (2× 100 ml.), stirring with the first 100 ml. of pentane for 4 hours and the next 100 ml. overnight under argon. The product obtained was then dried in vacuo for 12 hours to give 1.237 g. of product; $R_f$=0.58 (methylene chloride:methanol:acetic acid, 20:1:1); $[\alpha]_D$=–155.5° (c=0.73, methanol).

Anal. calc'd. for $C_{21}H_{22}N_2O_4S$ . 0.1 $C_5H_{12}$ . 0.18 $H_2O$: C,63.14; H,5.81; N,6.85; S,7.84; SH,8.09 Found: C,63.14; H,5.85; N,6.58; S,7.50; SH,7.05. 1H-NMR-(CDCl$_3$): 1.88 (m, 1H), 1.97 (d, 1H), 2.62 (m,2H), 3.07 (m, 2H), 3.25 (m, 1H), 3.51 (m, 1H), 4.39 (d, 1H, J=17 Hz), 4.45 (m, 1H), 4.64 (m, 1H, J=17 Hz), 7.07–7.41 (m, 9H).

EXAMPLE 7

[2S-[2α,5α(R*)]]-5,6-Dihydro-5-[(2-mercapto-1-oxo-3-phenylpropyl]amino]-4-oxo-2-phenyl-2H-1,3-thiazine-3(4H)-acetic acid a) (2S-cis)-5,6-Dihydro-5-phthalimido-4-oxo-2-phenyl-2H-1,3-thiazine-3(4H)-acetic acid, ethyl ester Following the procedure of U.S. Pat. No. 4,460,579 Example 1(a) through 1(c), 15.6 g., of the diastereomeric product mixture was obtained. The mixture was refluxed in ether (500 ml.) for 4 hours, cooled in an ice-bath, and filtered to yield 5.9 g. of (2R-trans)-5,6-dihydro-5-phthalimido-4-oxo-2-phenyl-2H-1,3-thiazine-3(4H)-acetic acid, ethyl ester; m.p.,166°–168° C.; $R_f$=0.40 (hexanes:ethyl acetate, 1:1); $[α]_D$=–72.9° (c=1, chloroform).

Anal. calc'd. for $C_{22}H_{20}N_2O_5S$: C,62.25; H,4.75; N, 6.60; S,7.77 Found: C,62.21; H,4.82; N,6.63; S,7.52.

Trituration of the remainder of the product mixture with refluxing ether (125 ml.) afforded a second batch of 0.9 g. of the (2R-trans) isomer product. The residue was triturated again with refluxing ether to give 0.75 g. of insoluble substance [largely (2R-trans) isomer] and 7.1 g. of material enriched in (2S-cis) isomer. 6.0 g. of the enriched (2S-cis) isomer material was chromatographed on two connected Waters Prep L C columns and eluted with hexanes:ethyl acetate (3:1). Pooling of the product containing fractions yielded 4.8 g. of (2S-cis)-5,6-dihydro-5-phthalimido-4-oxo-2-phenyl-2H-1,3-thiazine-3(4H)-acetic acid, ethyl ester, m.p. 66°–68° C.;

$[α]_D$=–101.2°. TLC same as isomer A. Anal. calc'd. for $C_{22}H_{20}N_2O_5S$ . 0.2 $H_2O$: C,61.83; H,4.79; N,6.55; S,7.50 Found: C,61.83; H,5.07; N,6.25; S,7.42.

b) (2S-cis)-5,6-Dihydro-5-amino-4-oxo-2-phenyl-2H-1,3-thiazine-3(4H)-acetic acid, ethyl ester A solution of the (2S-cis) isomer product from part (a) (approximately 85% diastereomerically pure, 3.03 g., 7.1 mmol.) in chloroform (15 ml.) was treated with methyl hydrazine (850 µL, 736 mg., 16.0 mmol.). After stirring at room temperature for 24 hours, the mixture was diluted with ethyl acetate and ethyl ether and filtered. The filtrate was extracted twice with 0.5N hydrochloric acid and the pooled aqueous extracts were made basic with 1N sodium hydroxide. The aqueous mixture was extracted three times with methylene chloride and the pooled methylene chloride extracts were dried (sodium sulfate), filtered, and stripped to give 1.648 g., of product as a pale yellow oil; $R_f$=0.43 ( methylene chloride:acetic acid:methanol, 8:1:1). NMR analysis showed the product was obtained in approximately 84% diastereomeric purity.

c) [2S-[2α,5α(R*)]]-5,6-Dihydro-5-[[2-(acetylthio)-1-oxo-3-phenylpropyl]amino]-4-oxo-2-phenyl-2H-1,3-thiazine-3 (4H) acetic acid, ethyl ester (S)-2-(Acetylthio)benzenepropanoic acid, dicyclohexylamine salt (1.318 g., 3.25 mmol.) was partitioned between ethyl acetate and 5% potassium bisulfate. The ethyl acetate layer was washed with water and brine, then dried (sodium sulfate), filtered and stripped to give the free acid as a colorless oil. A mixture of acid this free acid and the (2S-cis) product from part (b) (84% diastereomeric purity, 960 mg., 3.26 mmol.) was dissolved in methylene chloride (25 ml.) and treated with 1-hydroxybenztriazole hydrate (622 mg., 4.6 mmol.) then cooled to –10° C. The mixture was subsequently treated with 1-ethyl-3-(3-dimethyl-aminopropyl) carbodiimide (687 mg., 3.58 mmol.). After slowly warming to 0° C. over a one hour period, the mixture was subsequently warmed to room temperature. After 4 hours, the solution was diluted with ethyl acetate and washed successively with water, 5% potassium bisulfate, water, saturated sodium bicarbonate, and brine, then dried (sodium sulfate), filtered, and stripped. The residue was flash chromatographed (Merck silica gel, 1:1-ethyl acetate:hexane) to give 804 mg. of product as a colorless foam; $R_f$=0.33 (50% ethyl acetate in hexanes). NMR analysis indicated the material was 91% diastereomerically pure with respect to acetylthio center.

d) [2S-[2α,5α(R*)]]-5,6-Dihydro-5-[(2-mercapto-1-oxo-3-phenylpropyl]amino]-4-oxo-2-phenyl-2H-1,3-thiazine-3 (4H)-acetic acid A solution of the ethyl ester product from part (c) (500 mg., 1.0 mmol.) in methanol (5 ml., deoxygenated via argon bubbling) at 0° C. was treated with ice cold 1N sodium hydroxide (5 ml., deoxygenated via argon bubbling) and the resulting mixture was stirred at 0° C. under argon for 30 minutes. The solution was acidified with 10% potassium bisulfate (15 ml.), diluted with water and extracted with ethyl acetate. The ethyl acetate extract was washed with water and brine, then dried (sodium sulfate), filtered and stripped to afford an oil/foam. This material was flash chromatographed (Merck silica gel, 20:1:1-methylene chloride:methanol:acetic acid). The fractions containing the product were pooled and stripped, and the residue was taken up in ethyl acetate and washed successively with water, 0.5N hydrochloric acid, and brine, then dried (sodium sulfate), filtered and stripped again. The resulting oil was dissolved in a small amount of ethyl acetate and ethyl ether and triturated with hexane. The mixture was stripped to dryness, slurried in hexane, stripped to dryness again, and dried in vacuo to give 392 mg., of product as a white foam; $R_f$=0.24 (methylene chloride:methanol:acetic acid, 20:1:1); $[α]_D$=–13.2° (c=0.5, chloroform).

HPLC: YMC S3 ODS column (6.0×150 mm); eluted with 44% A: 90% water-10% methanol-0.2% phosphoric acid and 56% B: 10% water-90% methanol-0.2% phosphoric acid; flow rate 1.5 ml/min detecting at 220 nm; $t_R$=26.22 min. and $t_R$=24.64 min (9.3% 5α(S*) isomer).

Anal. calc'd. for $C_{21}H_{22}N_2O_4S_2$ . 0.17$H_2O$: C,58.18; H,5.19; N,6.46; S,14.79; SH,7.63 Found: C,58.20; H,5.51; N, 6.44; S,14.46; SH,6.60.

EXAMPLE 8

[2S-[2α,5α(R*)]]-5,6-Dihydro-5-[[2-(mercaptomethyl)-1-oxo-3-phenylpropyl]amino]-4-oxo-2-phenyl-2H-1,3-thiazine-3(4H)-acetic acid a) [2S-[2α,5α(R*)]]-5,6-Dihydro-5-[[-2-[(acetylthio) methyl]-1-oxo-3-phenylpropyl]amino]-4-oxo-3-phenyl-2H-1,3-thiazine-3(4H)-acetic acid, ethyl ester (S)-2-[(Acetylthio)methyl]benzenepropanoic acid, ephedrine salt (1.638 g., 4.04 mmol.) was partitioned between ethyl acetate and water containing 6.0 ml. 1N hydrochloric acid. The ethyl acetate layer was washed with water and brine, then dried (sodium sulfate), filtered, and stripped to give the free acid as a colorless oil. A mixture of this free acid and (2S-cis)-5,6-dihydro-5-amino-4-oxo-2-phenyl-2H-1,3-thiazine-3(4H)-acetic acid, ethyl ester 84% diastereomerically pure, 1.19 g., 4.04 mmol.) was dissolved in methylene chloride (25 ml.) and treated with 1-hydroxybenztriazole hydrate (575 mg, 4.2 mmol.) then cooled to 0° C. The mixture was subsequently treated with 1-ethyl-3-(3-dimethylaminopropyl)carbodiimide (775 mg, 4.04 mmol). The mixture was stirred at 0° C. for 45 minutes, then let warm to room temperature. After an additional 2 hours, the solution was diluted with ethyl acetate and washed successively with water, 5% potassium bisulfate, water, saturated sodium bicarbonate, and brine, then dried (sodium sulfate), filtered, and stripped. The residue was flash chromatographed (Merck silica gel, 40% to 60% ethyl acetate in hexane) to give 1.228 g., of product as a white foam; $R_f$=0.29 (50% ethyl acetate in hexanes). NMR analysis indicated that the product was diastereomerically pure.

b) [2S-[2α,5α(R*)]]-5,6-Dihydro-5-[[2-(mercaptomethyl)-1-oxo-3-phenylpropyl]amino]-4-oxo-2-phenyl-2H-1,3-thiazine-3(4H)-acetic acid A solution of the ethyl ester product from part (a) (705 mg,, 1.37 mmol.) in methanol, (10 ml. deoxygenated via argon bubbling) was treated with 1N sodium hydroxide (10 ml., deoxygenated via argon bubbling) and the resulting mixture was stirred at 0° C. under argon for 15 minutes. The solution was acidified with 1N hydrochloric acid (15 ml.), diluted with water and extracted with ethyl acetate. The ethyl acetate extract was washed with water and brine, then dried (sodium sulfate), filtered and stripped to afford an oil. The material was flash chromatographed (Merck silica gel, 20:1:1-methylene chloride:methanol: acetic acid). The fractions containing the desired product were pooled, and stripped, and the residue was taken up in ethyl acetate and washed successively with water, 0.5N hydrochloric acid, and brine, then dried (sodium sulfate), filtered and stripped again. The resulting oil was dissolved in a small amount of ethyl acetate and ethyl ether and triturated with hexane. The mixture was stripped to dryness, slurried in hexane, stripped to dryness again, and dried in vacuo to give 548 mg. of product as a relatively hard white foam; $R_f$=0.29 (methylene chloride:methanol:acetic acid, 20:1:1); $[\alpha]_D$=+42.9° (c=1.0, chloroform).

HPLC: YMC S3 ODS column (6.0×150 mm); eluted with 44% A: 90% water-10% methanol-0.2% phosphoric acid and 56% B: 10% water-90% methanol-0.2% phosphoric acid; flow rate 1.5 ml/min detecting at 220 nm; $t_R$=33.45 min (99.1%). Anal. calc'd. for $C_{22}H_{24}N_2O_4S_2$: C,59.44; H,5.44; N,6.30; S,14.42; SH,7.44 Found: C,59.63; H,5.84; N,5.99; S,14.54; SH,6.83.

EXAMPLE 9

(S,S)-Hexahydro-3-[[2-(mercaptomethyl)-1-oxo-3-phenylpropyl]amino]-2-oxo-1H-azepine-1-acetic acid a) $N^2$-[(1,1-Dimethylethoxy)carbonyl]-$N^6$-[(phenylmethoxy)carbonyl]-L-lysine, methyl ester Cesium carbonate (4.28 g., 13.1 mmoles) was added to a mixture of $N^2$-[(1,1-dimethylethoxy)carbonyl]-$N^6$-[(phenylmethoxy)carbonyl]-L-lysine (10 g., 26.3 mmoles) and 20% water-methanol (60 ml.). The solution became homogeneous within 5 minutes so the solvent was stripped add the residual water removed azeotropically with acetonitrile (3x). The resulting oil was dried in vacuo, dissolved in dry dimethyl-formamide and treated with methyl iodide (3.2 ml., 2.0 eq.). The reaction mixture was stirred at room temperature for 1.5 hours under argon, diluted with ethyl acetate (200 ml.) and washed successively with water (2×25 ml.), saturated sodium bicarbonate (25 ml.) and brine (25 ml.). The organic phase was dried (anhydrous magnesium sulfate), filtered, evaporated to dryness and dried in vacuo to give 10.11 g., of product as a light yellow syrup; $R_f$=0.30 (ethyl acetate:hexanes, 1:2).

b) (S)-3-[[(1,1-Dimethylethoxy)carbonyl]amino]-hexahydro-2H-azepin-2-one

A solution of the methyl ester product from part (a) (8.532 g., 21.63 moles) in dry methanol (100 ml.) was treated with 10% palladium on carbon catalyst (2.13 g.) and hydrogenated at 50 psi for 2 hours. The mixture was diluted with methanol (100 ml.) and filtered through a celite pad in a millipore unit, washing the pad well with methanol (3×100 ml.). The clear filtrate was evaporated to dryness, dried in vacuo and the resulting oil was dissolved in dry xylene (70 ml.). The solution was refluxed under argon for 20 hours, cooled down to room temperature, diluted with ethyl acetate (425 ml.), and washed successively with 5% potassium bisulfate (85 ml.), saturated sodium bicarbonate (85 ml.) and brine (85 ml.). The organic phase was dried (magnesium sulfate), filtered, evaporated to dryness and dried in vacuo. The crude product was chromatographed on a silica gel column (Merck), eluting the column with ethyl acetate:hexane (1:1) to give 2.76 g. of product as a white solid; m.p. 146°–147°; $R_f$=0.58 (ethyl acetate); $[\alpha]_D$=+4.5° (c=1.0, methanol).

Anal. calc'd. for $C_{11}H_{20}N_2O_3$: C,57.87; H,8.83; N, 12.27 Found: C,58.12; H,8,63; N,12,26.

c) (S)-3-[[(1,1-Dimethylethoxy)carbonyl]amino]-hexahydro-2-oxo-1H-azepine-1-acetic acid, ethyl ester A suspension of the 2H-azepine-2-one product from part (b) (2.966 g., 12.99 mmoles) in dry tetrahydrofuran (21.0 ml.) was treated with 1.0M potassium t-butoxide/tetrahydrofuran (16.9 ml., 1.3 eq.) and stirred under argon at room temperature for 5 minutes. The clear light brown solution was treated dropwise with ethyl bromoacetate (2.34 ml., 1.7 eq.) , stirred at room temperature for 1.0 hour then diluted with ethyl acetate (100 ml.). The mixture was washed with saturated sodium bicarbonate (20 ml.), 5% potassium bisulfate (15 ml.) and brine (15 ml.), dried (anhydrous magnesium sulfate), filtered, evaporated to dryness and dried in vacuo. The crude product was chromatographed on a silica gel column (Merck), eluting the column with hexane and ethyl acetate:hexane mixtures (1:6; 1:3) to give 3.387 g. of product as a syrup; $R_f$=0.55 (ethyl acetate: hexane, 1:1)

d) (S)-3-Amino-hexahydro-2-oxo-1H-azepine-1-acetic acid, ethyl ester, hydrochloride salt A solution of the ethyl ester product from part (c) (3,278 g., 10.13 mmoles) in dry dioxane (80 ml.) was treated with 4.0M hydrochloric acid/dioxane (31 ml., 0.124 mole, 12 eq.) and stirred at room temperature under argon for 20 hours. The reaction mixture was stripped to dryness, evaporating the product several times from ether, then dried in vacuo to give 2.541 g. of product as a white crystalline hygroscopic solid; $R_f$=0.32 (methylene chloride:methanol:acetic acid, 8:1:1).

e) (S,S)-3-[[2-[(Acetylthio)methyl]-1-oxo-3-phenylpropyl]amino]-2-oxo-1H-azepine-1-acetic acid, ethyl ester (S)-2-[(Acetylthio)methyl]benzenepropanoic acid, ephedrine salt (1.625 g., 4.028 mmoles, 1.01 eq.) was suspended in ethyl acetate (75 ml.), washed with dilute hydrochloric acid (75 ml. water+5.7 ml. 1.0N hydrochloric acid then 40 ml. water+1.9 ml. 1.0N hydrochloric acid), brine (15 ml.), dried (anhydrous sodium sulfate), filtered and evaporated to dryness. The colorless syrup was dried in vacuo for 1.0 hour to afford 1.05 g. of the free acid.

This free acid was dissolved in dry dimethylformamide (25 ml.), cooled down to 0° (ice-salt bath), treated with 1-hydroxybenztriazole hydrate (567 mg.,4.20 mmoles) and 1-ethyl-3-(3-dimethylaminopropylcarbodiimide (832 mg., 4.34 mmoles) and stirred at 0° under argon for 1.0 hour. The clear solution was treated with a solution of the ethyl ester hydrochloride salt product of part (d) (1.0 g., 3.988 mmoles)

in dry dimethylformamide (3.0 ml.) and 4-methylmorpholine (0.45 ml., 1.0 eq.) and stirring was continued at 0° for 1.0 hour and at room temperature for 2.0 hours. The reaction mixture was diluted with ethyl acetate (100 ml.), washed successively with water (15 ml.), 5 % potassium bisulfate (2×15 ml.), saturated sodium bicarbonate (15 ml.) and brine (15 ml.), dried (anhydrous sodium sulfate), filtered, evaporated to dryness and dried in vacuo. The crude product was chromatographed on a silica gel column (Merck), eluting the column with ethyl acetate:hexane mixtures (1:4; 1:2) to give 1.618 g., of product as a syrup; $R_f$=0.030 (ethyl acetate:hexane, 1:1).

f) (S,S)-Hexahydro-3-[[2-(mercaptomethyl)-1-oxo-3-phenylpropyl]amino]-2-oxo-1H-azepine-1-acetic acid A solution of the ethyl ester product from part (e) (1.537, 3.53 moles) in methanol (18 ml.) was purged with argon for 30 minutes, cooled down to 0° (ice-salt bath) then treated dropwise with a previously purged (argon, 30 minutes) solution of 1.0N sodium hydroxide (14.2 ml., 4 eq.) maintaining the bubbling of argon throughout the addition and the length of the reaction. The reaction mixture was stirred at 0° for 1.0 hour, acidified at 0° with 5% potassium bisulfate (60 ml.) to pH 2.0 then extracted with ethyl acetate (2×100 ml.). The organic extracts were washed with brine (25 ml.), dried (anhydrous sodium sulfate), filtered. evaporated to dryness and dried in vacuo. The crude product was dissolved in methylene chloride (5 ml.) and treated portionwise with hexane (50 ml.), scratching the mixture to form a solid. The supernatant was decanted and the solids were triturated with more hexane (3×50 ml.) and the solids were evaporated from pentane (4×40 ml.). The resulting product was dried in vacuo 12 hours to give 1.261 g., of product as an amorphous solid; $R_f$=0.43 (methylene chloride:methanol:acetic acid, 20:1:1);

$[\alpha]_D$=+20.2° (c=0.61, methanol). 1H-NMR (400 MHz, CDCl$_3$): 1.46 (t,3H), 1.81, (m,6H), 2.60 (m,2H), 2.87 (m,3H), 3,21 (m, 1H), 3.71 (m, 1H), 4.17(s,2H), 4.68 (m, 1H), 7.13–7.27 (m, 5H). Anal. calc'd. for C$_{18}$H$_{24}$N$_2$O$_4$S . 0.2C$_5$H$_{12}$ . 0,45 H$_2$O: C,58.96; H,7.11; N,7.24; S,8.28; SH,8.54; Found: C,58.96; H, 6.86; N,7.07; S,8.31; SH,8.43.

EXAMPLE 10

(S,S)-Hexahydro-3-[(2-mercapto-1-oxo-3-phenylpropyl)amino]-2-oxo-1H-azepine-1-acetic acid a) (S,S)-3-[[2-(Acetylthio)-1-oxo-3-phenylpropyl]amino]-2-oxo-1H-azepine-1-acetic acid, ethyl ester A suspension of (S)-2-(acetylthio)benzenepropanoic acid, dicyclohexylamine salt (2.81 g., 6.93 moles or 1.01 eq.) was suspended in ethyl acetate (200 ml.), washed with 5% potassium bisulfate (5×30 ml) and brine (40 ml.), dried (anhydrous magnesium sulfate), filtered, evaporated to dryness and dried in vacuo to give 1.737 g. of the free acid as a clear syrup.

This free acid was dissolved in dry methylene chloride (30 ml.) and cooled down to 0° (ice-salt bath) treated with 1-hydroxybenztriazole hydrate (978 mg., 7.23 mmoles) and 1-ethyl-3-(3-dimethylaminopropyl)carbodiimide (1.435 mg., 7.49 mmoles) and stirred at 0° for 1.0 hour. The solution was treated with a solution of (S)-3-amino-hexahydro-2-oxo-1H-azepine- 1-acetic acid, ethyl ester, hydrochloride salt (1.58 g., 6.30 mmoles) in dry methylene chloride (10 ml) and 4-methylmorpholine (0.77 ml., 7.01 mmoles) and stirring was continued at 0° for 1.0 hour and at room temperature for 1.5 hours. The reaction mixture was diluted with ethyl acetate (170 ml.), washed successively with water (25 ml.), 5% potassium bisulfate (2×25ml.), saturated sodium bicarbonate (25 ml.) and brine (25 ml.), dried (anhydrous magnesium sulfate), filtered, evaporated to dryness and dried in vacuo. The crude product was chromatographed on a silica gel column (Merck), eluting the column with ethyl acetate:hexanes (3:7) to give 2.045 g. of product as a syrup. An additional 261 mg. of the isomer mixture (1:1 ratio) was obtained from the column; $R_f$=0.45 (ethyl acetate:hexane, 1:1).

b) (S,S)-Hexahydro-3-[(2-mercapto-1-oxo-3-phenylpropyl)amino]-2-oxo-1H-azepine-1-acetic acid A solution of the ethyl ester product from part (a) (2.044 g., 4.86 mmoles) in methanol (25 ml.) was purged with argon for 30 minutes, cooled down to 0° (ice-salt bath) then treated dropwise with a previously purged (argon, 30 minutes) solution of 1.0N sodium hydroxide (19.55 ml., 4 eq.) maintaining the bubbling of argon throughout the addition and the length of the reaction. The reaction mixture was stirred at 0° for 1.0 hour, acidified at 0° with 5% potassium bisulfate (85 ml.) to pH 2.0 then extracted with ethyl acetate (2×140 ml.). The organic extracts were washed with brine (35 ml.), dried (anhydrous sodium sulfate), filtered, evaporated to dryness and dried in vacuo The crude product was dissolved in methylene chloride (10 ml.) and treated portionwise with hexane (50 ml.), scratching the mixture to form a solid. The supernatant was decanted and the solids triturated with more hexane (2×50 ml.) and pentane (2×100 ml.), stirring with the first 100 ml. of pentane for 4 hours and the next 100 ml. overnight under argon. The product obtained was then dried in vacuo for 12 hours to give 1.618 g. of product as an amorphous solid; $R_f$=0.53 (methylene chloride:methanol:acetic acid, 10:1:1);

$[\alpha]_D$=+8.04° (c=0.56, methanol). 1HNMR (400 MHz, CDCl$_3$): 1.71 (m,6H), 2.02 (d, 1H), 3.16 (m,3H), 3.61 (m, 1H), 3.70 (m, 1H), 4.17 (s,2H), 4.65 (m, 1H), 7.18–7.72 (m,5H). Anal. calc'd. for C$_{17}$H$_{22}$N$_2$O$_4$S: C,58.27; H,6.33; N,7.99; S,9.15; SH,9.44 Found: C,58.43; H,6.56; N, 7.85; S,8.96; SH,10.27.

EXAMPLE 11

[3R-[3α,6α(S*),9aβ]]-Octahydro-6-[(2-mercapto-1-oxo-3-phenylpropyl)amino]-5-oxothiazolo[3,2-a]] azepine-3-carboxylic acid a) N$^2$-Phthaloyl-L-lysine A mixture of N$^6$-[(1,1-dimethylethoxy)carbonyl]-L-lysine (10.827 g., 43.9 mmol.) and sodium carbonate (4.665 g., 44.0 mmol.) was stirred in 170 ml of ethanol:water (1:3) for 2.5 hours. The ethanol was removed by rotary evaporation and the aqueous solution was treated with N-carbethoxy phthalimide (9.66 g, 44.0 mmol). After stirring at room temperature for 1.5 hours, the solution was filtered, treated with methylene chloride (200 ml), and the aqueous layer was acidified with 6N hydrochloric acid (to pH 2.8). The layers were shaken and separated. The aqueous layer was extracted again with ethyl acetate and the pooled organic layers were dried (magnesium sulfate), filtered, and stripped to give a near colorless oil/glass (19.510 g).

The residue was cooled to 0° C., treated with trifluoroacetic acid (150 ml.), and the mixture was let stir at room temperature for 3 hours. The trifluoroacetic acid was removed by rotary evaporation and the residue was azeotroped twice with toluene. The crude product was taken up in water and run on a Dowex AG 50-X2 (100–200 mesh, 300 ml, acidic form) column eluting in succession with 1:1 methanol:water (600 ml.), water (500 ml.), and finally 5:95 pyridine:water (1000 ml.). The desired fractions were pooled, stripped, taken up in water and lyophilized to give 7.850 g. of product as a white solid; $R_f$=0.57 (n-butanol:water:acetic acid:ethyl acetate, 1:1:1:1)

b) [2(S),4R]-4-(Methoxycarbonyl)-α-phthalimido-2-thiazolidinepentanoic acid

A slurry of $N^2$-phthaloyl-L-lysine (7.710 g., 27.9 mmol.) in dry dimethylformamide (135 ml.) was treated with 4-formyl-1-methylpyridinium benzenesulfonate (7.320 g, 26.2 mmol). The resulting dark mixture gradually became homogeneous. After stirring at room temperature for 1 hour, the mixture was treated with 1,8-diazobicyclo[5.4.0]undec-7-ene (8.15 ml, 8.30 g, 54.5 mmol.) followed 5 minutes later with L-cysteine, methyl ester, hydrochloride (4.53 g, 26.3 mmol). The dark solution was stirred for 2.5 hours, then diluted with aqueous hydrochloric acid (pH 1.7, 300 ml.) and chloroform (150 ml.). The aqueous layer was adjusted to pH 4.3–4.4 with 0.5N hydrochloric acid and subsequently extracted five times with chloroform. The pooled chloroform extracts were washed with water (50 ml.), dried (sodium sulfate), filtered and stripped. The residue was taken up in ethyl acetate, filtered through Celite, and concentated to give 1.84 g. of crude product as a dark orange-red oil. $R_f$=0.58 major spot (acetic acid:ethyl acetate, 15:85). NMR shows a 2:1 ratio of isomers.

c) [3R-(3α,6α)]-Octahydro-6-phthalimido-5-oxothiazolo[3,2-a]azepine-3-carboxylic acid, methyl ester A solution of the product from part (b) (1.84 g., 4.7 mmol) in tetrahydrofuran (70 ml.) was treated with 2-ethoxy-1-ethoxycarbonyl-1,2-dihydroquinoline (1.400 g., 5.67 mmol.) and the mixture was stirred at room temperature for 3 days. The tetrahydrofuran was removed by rotary evaporation and the residue was taken up in ethyl acetate and washed in succession with 0.5N hydrochloric acid (2X), 50% saturated sodium bicarbonate, water, and brine, then dried (sodium sulfate), flitered, and stripped. The resulting orange oil was flash chromatographed (Merck silica gel, 40–50% ethyl acetate in hexanes) to give 1.126 g. of product as a 1:1 mixture of diastereomers; $R_f$=0.22 and 0.20 (40% ethyl acetate in hexane).

d) [3R-(3α,6α,9aβ)]-Octahydro-6-phthalimido-5-oxothiazolo[3,2-a]azepine-3-carboxylic acid, methyl ester A mixture of the methyl ester product from part (c) (1.110 g.) and p-toluenesulfonic acid hydrate (2.33 g) in benzene (20 ml.) was refluxed with removal of water (Dean-Stark trap) for 2.5 hours. The cooled mixture was diluted with ethyl acetate and washed with 50% saturated sodium bisulfate, water, and brine, then dried (sodium sulfate), filtered, and stripped. The residue was flash chromatographed (Merck silica gel, 10–20% ethyl acetate in methylene chloride) to give nearly pure product as an off-white foam. The foam was dissolved in hot ethyl acetate/hexanes, cooled and seeded to give fine white needles (845 mg). An additional 50 mg of solid product was obtained from the mother liquor bringing the total amount of pure product to 895 mg; m.p. 154°–155° C.; $[\alpha]_D$=−31.8° (c=0.52, chloroform); $R_f$=0.22 (40% ethyl acetate in hexane).

e) [3R-(3α,6α,9aβ)]-6-Amino-octahydro-5-oxothiazolo-[3,2-a]azepine-3-carboxylic acid, methyl ester, hydrochloride salt A slurry of the methyl ester product from part (d) (875 mg., 2.34 mmol.) in absolute ethanol (50 ml.) was treated with hydrazine hydrate (115 μl, 118 mg., 2.37 mmol) and the solution was periodically warmed for the first two hours to effect solubilization. After stirring at room temperature for 3 days, additional hydrazine hydrate (80 μl., 82.6 mg., 1.65 mmol) was added and the mixture was stirred for one more day. The reaction was stripped to dryness and the white residual solid was stirred in cold (0° C.) 0.5N hydrochloric acid (60 ml.) for 3.5 hours. The solid was removed by filtration and the filtrate was made basic with 1N sodium hydroxide to pH 11–12 and extracted with methylene chloride (3X) and ethyl acetate. The pooled organic extracts were dried (sodium sulfate), filtered and stripped to yield a near colorless oil (approx. 600 mg). The oil was treated with water (10 ml.) and 1.0N hydrochloric acid (3.0 ml.), swirled until no more oil was present and the mixture was lyophilized to give 674 mg. of product as a light yellow solid; $R_f$=0.64 major spot (n-butanol: water: acetic acid:ethyl acetate, 1:1:1:1).

f) [3R-[3α,6α(S*),9aβ]]-Octahydro-6[[2-(acetylthio)-1-oxo-3-phenylpropyl]amino]-5-oxothiazolo[3,2-a]azepine-3-carboxylic acid, methyl ester The methyl ester, hydrochloride salt product from part (e) (374 mg., 1.33 mmol.) was partitioned between saturated sodium bicarbonate and methylene chloride. The methylene chloride extract was dried (sodium sulfate), filtered and stripped to give the free amine as a pale yellow oil (302 mg., 1.16 mmol.). Additionally, (S)-2-(acetylthio)benzenepropanoic acid, dicyclohexylamine salt-(648 mg., 1.60 mmol) was partitioned between ethyl acetate and 5% potassium bisulfate. The ethyl acetate layer was washed with water and brine, then dried (sodium sulfate), filtered and stripped to give the free acid as a colorless oil. A mixture of the free amine and the free acid in methylene chloride (9 ml.) was treated with hydroxybenztriazole hydrate (550 mg., 4.07 mmol.), cooled to 0° C., and subsequently treated with 1-ethyl-3-(3-dimethylaminopropyl)carbodiimide (313 mg, 1.63 mmol.). The mixture was stirred at 0° C. for 1 hour, then at room temperature for 3 hours. Additional 1-ethyl-3-(3-dimethylaminopropyl)carbodiimide (100 mg) was added and stirring continued overnight. The solution was diluted with ethyl acetate and washed successively with water, 5% potassium bisulfate, water, 50% saturated sodium bicarbonate, and brine, then dried (sodium sulfate), filtered and stripped. The resulting yellow oil was flashed chromatographed (Merck silica gel, 30% acetone in hexane) to give 396 mg. of product as a 87:13 mixture of side chain diastereomers. This mixture was again flash chromatographed (Merck silica gel, 35–40% ethyl acetate in hexane) to afford 318 mg., of product as a white foam (94–95% diastereomerically pure); $R_f$=0.29 major and 0.26 minor, [6α(R*) isomer]; $[\alpha]_D$=−84.4° (c=0.36, chloroform).

g) [3R-{3α,6α(S*),9aβ}]-Octahydro-6-[(2-mercapto-1-oxo-3-phenylpropyl)amino]-5-oxothiazolo[3,2-a]-azepine-3-carboxylic acid A solution of the methyl ester product from part (f) (308 mg., 0.68 mmol.) in methanol (4 ml., deoxygenated via argon bubbling) was treated with 1N sodium hydroxide (3.5 ml., deoxygenated via argon bubbling) and the homogeneous mixture was stirred under argon for 2 hours. The mixture was acidified with 10% potassium bisulfate (15 ml.), diluted with water, and extracted with ethyl acetate. The ethyl acetate extract was washed with brine, dried (sodium sulfate), filtered, and stripped to give a solid. The solid was dissolved in dimethylformamide (1 ml.), diluted with ethyl acetate, and flash chromatographed (Merck silica gel, 5% acetic acid in ethyl acetate) to give the desired product as a white solid which was triturated with ethyl acetate/ethyl ether, collected by fitration, and dried to give 144 mg., of product; m.p. 217°–220° C.; $R_f$=0.52 (5% acetic acid in ethyl acetate); $[\alpha]_D$=−64.3° (c=0.36, dimethylformamide). NMR analysis indicated the product was 93% diastereomerically pure with 7% of the corresponding 6α(R*) isomer.

HPLC: YMC S3 ODS column (6.0×150 mm); eluted with 44% A: 90% water-10% methanol-0.2% phosporic acid and 56% B: 10% water-90% methanol-0.2% phosporic acid; flow rate 1.5 ml/min dectecting at 220 nm; $t_R$=12.27 min indicates a purity of >95% (no separation of 6α(S*) and 6α(R*) isomers dectected by HPLC)

Anal. calc'd. $C_{18}H_{22}N_2O_4S_2 \cdot 0 \cdot 4 H_2O$: C,53.82; H,5.72; N,6.97; S,15.96; SH,8.21 Found: C,53.88; H,5.67; N,6.78; S,15.37; SH,4.91.

EXAMPLE 12

[3R-[3α,6α(S*)-9aβ]]-Octahydro-6-[[2-(mercaptomethyl)-1-oxo-3-phenylpropyl]amino]-5-oxo-thiazolo[3,2-a]azepine-3-carboxylic acid a) [3R-[3α,6α(S*),9aβ]]-Oxahydro-6-[[2-[(acetylthio)methyl]-1-oxo-3-phenylpropyl]amino]-5-oxo-thiazolo[3,2-a]azepine-3-carboxylic acid, ethyl ester (S)-2-[(Acetylthio)methyl]benzenepropanoic acid, ephedrine salt (481 mg., 1.20 mmol.) was partitioned between ethyl acetate and water containing 2.0 ml. 1N hydrochloric acid. The ethyl acetate layer was washed with water and brine, then dried (sodium sulfate), filtered, and stripped to give the free acid as a colorless oil. This free acid was dissolved in methylene chloride (7 ml.) and treated with [3R-(3α,6α,9aβ)]-6-amino-octahydro-5-oxothiazolo[3,2-a]azepine-3-carboxylic acid, ethyl ester, hydrochloride salt (293 mg., 1.04 mmol.) followed in succession by 4-methyl morpholine (154 μl., 142 mg, 1.4 mmol), dimethylformamide (2.5 ml.), 1-hydroxybenztriazole hydrate (147 mg, 1.08 mmol), and 1-ethyl-3-(3-dimethylaminopropyl) carbodiimide (226 mg, 1.18 mmol). After stirring at room temperature for 2 hours, the mixture was diluted with ethyl acetate and washed successively with water, 0.5N hydrochloric acid, water, 50% saturated sodium bicarbonate, and brine, then dried (sodium sulfate), filtered, and stripped. The residue was flash chromatographed (Merck silica gel, 30% acetone in hexanes) to give 357 mg. of product as a white foam. $R_f$=0.44 (acetone:hexanes, 1:1); $[\alpha]_D$=−77.2° (c=0.50, chloroform). NMR analysis indicated the product was homogeneous.

b) [3R-[3α,6α(S*), 9aβ]]-Octahydro-6-[[2-(mercaptomethyl)-1-oxo-3-phenylpropyl]amino]-5-oxothiazolo[3,2-a]azepine-3-carboxylic acid The ethyl ester product from part (a) (343 mg., 0.74 mmol.) in methanol (2 ml., deoxygenated via argon bubbling) was treated with 1N sodium hydroxide (3.5 ml., deoxygenated via argon bubbling) and the resulting mixture was stirred under argon for 1.5 hours. The solution was acidified with 5% potassium bisulfate (20 ml.), diluted with water and extracted with ethyl acetate. The ethyl acetate extract was washed with water and brine, then dried (sodium sulfate), filtered and stripped to afford a white solid. The solid was dissolved in hot methanol/ethyl acetate, filtered again, and concentrated to precipitate the desired product. The solid was collected by filtration, washed with ethyl acetate and ethyl ether, and dried in vacuo at 50° C. for 2 hours to give 221 mg. of product as a white solid. An additional 20 mg. of product was obtained from the mother liquor; m.p. 212°–213° C.; $R_f$=0.55 (5% acetic acid in ethyl acetate); $[\alpha]_D$=−36.5° (c=0.36, dimethylformamide).

HPLC: YMC S3ODS column (6.0×150 mm); eluted with 44% A: 90% water-10% methanol-0.2% phosphoric acid and 56% B: 10% water-90% methanol-0.2% phosphoric acid flow rate at 1.5 ml./min detecting at 220 nm; tR=15.96 indicates a purity of 99.2%.

Anal. calc'd. for $C_{19}H_{24}N_2O_4S_2$: C,55.86; H,5.92; N,6.86; S,15.70; SH,8.09 Found: C,55.99; H, 6.01; N,6.75; S,15.70; SH,7.81.

EXAMPLE 13

[S-(R*,R*)-3,4-Dihydro-3-[[2-(mercaptomethyl)-1-oxo-3-phenylpropyl]amino]-4-oxo-1,5-benzoxazepine-5(2H)-acetic acid a) N-[(1,1-Dimethylethoxy)carbonyl]-O-(2-nitrophenyl)-L-serine A solution of N-[(1,1-dimethylethoxy)carbonyl]-L-serine (24.3 g., 0.118 mole) in dry dimethylformamide (25 ml.) was added dropwise over a period of 1.0 hour to a cooled (0°, ice-salt bath) suspension of 60% sodium hydride (10.1 g., 0.25 mole) in dry dimethylformamide (200 ml.) and stirring was continued at 0° until the frothing subsided (about 2.0 hours). The reaction mixture was treated dropwise with 1-fluoro-2-nitrobenzene (14.3 ml., 0.13 mole) over a period of 20 minutes, stirred at 0° under argon for 4.0 hours then poured into ice-water (750 ml.) and extracted with ethyl acetate (2×100 ml.). The aqueous phase was brought to pH 1.0 with 6N hydrochloric acid (70 ml.), extracted with ethyl acetate (3×500 ml.) and the combined organic extracts were washed with brine (100 ml.), dried (anhydrous sodium sulfate), filtered, evaporated to dryness and dried in vacuo. The crude product mixture was chromatographed on a silica gel column (Merck), eluting the column with methylene chloride:methanol:acetic acid (100:5:0.2) to give 27.22 g. of product as a thick yellow syrup; $R_f$=0.27 (methylene chloride:methanol:acetic acid, 100:5:0.5).

b) N-[(1,1-Dimethylethoxy)carbonyl]-O-(2-aminophenyl)-L-serine

A solution of the product from part (a) (27.1 g., 83 mmoles) in dry methanol (500 ml.) was treated with 10% palladium on carbon catalyst (900 mg.) and hydrogenated at 40 psi for 2.0 hours. The reaction mixture was filtered through a celite pad in a millipore unit, washing the pad well with methanol (5×100 ml.). The dark filtrate was evaporated to dryness and dried in vacuo to give a dark solid. The crude product was triturated with methylene chloride:hexane (1:4) to give 17.69 g. of product as a light tan solid; $R_f$=0.15 (methylene chloride: methanol:acetic acid, 20:1:1).

c) (S)-3-[[(Dimethylethoxy)carbonyl]amino]-2,3-dihydro-1,5-benzoxazepin-4(5H)-one A solution of the product from part (b) (16.69 g., 56.3 mmoles) in dry dimethyformamide (121 ml.) was treated with 1-ethyl-3-(3-dimethylaminopropyl)carbodiimide (10.64 g., 55.5 mmoles) and stirred at room temperature for 3.0 hours. The reaction mixture was partitioned between ethyl acetate (2×492 ml.) and 1.0N sodium bicarbonate (492 ml.), and the combined organic extracts were washed with water (3×492 ml.), brine (492 ml.), dried (anhydrous magnesium sulfate), filtered, evaporated to dryness and dried in vacuo. The crude product was chromatographed on a silica gel column (Merck), eluting the column with ethyl acetate:hexane mixtures (1:4; 1:2; 1:1) to give 10.5 g. of product as off-white crystals; $R_f$=0.40 (ethyl acetate:hexane, 1:4).

d) (S)-3-[[(Dimethylethoxy)carbonyl]amino]-3,4-dihydro-4-oxo-1,5-benzoxazepine-5(2H)-acetic acid, ethyl ester A solution of the product from part (c) (1.0 g., 3.59 mmoles) in dry tetrahydrofuran (10 ml.) was cooled down to 0° (ice-salt bath) under argon, treated with powdered potassium hydroxide (259 mg., 4.6 mmoles) and tetrabutylammonium bromide (172 mg., 0.53 mmole), stirred for 5 minutes then treated with ethyl 2-bromoacetate (0.50 ml., 1.2 eq.). The reaction mixture was stirred at room temperature under argon for 19.0 hours, partitioned betweeen methylene chloride (2×25 ml.) and water (13 ml.) and the combined organic extracts were washed with water (2×13 ml.), brine (10 ml.), dried (anhydrous sodium sulfate), filtered, evaporated to dryness and dried in vacuo. The crude product mixture was chromatographed on a silica gel (Merck), eluting the column with ethyl acetate:hexane mixtures (1:9; 1:4) to give 860 mg. as a syrup; $R_f$=0.67 (ethyl acetate:hexanes, 1:1).

e) (S)-3-Amino-3,4-dihydro-4-oxo-1,5-benzoxazepine-5 (2H)-acetic acid, ethyl ester, hydrochloride salt A solution of the product from part (d) (4.0 g., 11 mmoles) in dry dioxane (85 ml.) was treated with 4.0M hydrochloric acid/dioxane (33.6 ml., 0.134 mole or 12.2 eq.) and stirred at room temperature for 20 hours. The reaction mixture was evaporated to dryness, evaporating the resulting syrup from toluene (2x) and ethanol (1x) then dried in vacuo to give 3.466 g. of product as a light gold-colored syrup; $R_f$=0.48 (methylene chloride:methanol, 9:1).

f) [S,(R*,R*)]-3-[[2-[(Acetylthio)methyl]-1-oxo-3-phenylpropyl]amino]-3,4-dihydro-4-oxo-1,5-benzoxazepine-5(2H)-acetic acid, ethyl ester (S)-2-[(Acetylthio)methyl]benzenepropanoic acid, ephedrine salt (1.547 g., 3.83 moles, 1.01 eq.) was suspended in ethyl acetate (70 ml.), washed with dilute hydrochloric acid (70 ml. water+5.4 ml. 1.0 N hydrochloric acid then 35 ml. water+1.8 ml. 1.0N hydrochloric acid), brine (15 ml.), dried (anhydrous magnesium sulfate), filtered and evaporated to dryness. The colorless syrup was dried in vacuo for 1.0 hour to afford 1.02 g. of the free acid.

This free acid was dissolved in dry dimethylformamide (22 ml.), cooled down to 0° (ice-salt bath), treated with 1-hydroxybenztriazole hydrate (541 mg., 3.99 mmoles) and 1-ethyl-3-(3-dimethylaminopropyl)carbodiimide (792.5 mg., 4.13 mmoles) and stirred at 0° under argon for 1.0 hour. The clear solution was treated with the product from part (e) (1.147 g., 3.81 mmoles) followed by 4-methylmorpholine (0.47 ml., 4.23 mmoles) and stirring was continued at 0° for 1.0 hour and at room temperature for 1.0 hour. The reaction mixture was diluted with ethyl acetate (92 ml.), washed successively with water (14 ml.), 5% potassium bisulfate (2×14 ml.), water (14 ml.), saturated sodium bicarbonate (14 ml.) and brine (14 ml.), dried (anhydrous sodium sulfate), filtered, evaporated to dryness and dried in vacuo. The crude product was chromatographed on a silica gel column (Merck), eluting the column with ethyl acetate:hexane (1:4) to give 1.516 g. of the product as a white syrupy foam; $R_f$=0.62 (ethyl acetate:hexanes, 1:1).

g) [S-(R*,R*)]-3,4-Dihydro-3-[[2-(mercaptomethyl)-1-oxo-3-phenylpropyl]amino]-4-oxo-1,5-benzazepine-5(2H)-acetic acid A solution of the ethyl ester product from part (f) (1.481 g., 3.056 mmoles) in methanol (15.5 ml.) was purged with argon for 30 minutes, cooled down to 0° (ice-salt bath) then treated dropwise with a previously purged (argon, 30 minutes) solution of 1.0 N sodium hydroxide (12.2 ml., 4.0 eq.) maintaining the bubbling of argon throughout the addition and the length of the reaction. The reaction mixture was stirred at 0° for 1.0 hour, acidified at 0° with 5% potassium bisulfate (53 ml.) to pH 1.0 then extracted with ethyl acetate (2×100 ml.). The organic extracts were washed with brine (25 ml.), dried (anydrous sodium sulfate), filtered, evaporated to dryness and dried in vacuo. The crude product was dissolved in methylene chloride (10 ml.) and treated portionwise with hexane (100 ml.), scratching the mixture to form a solid. The supernatant was decanted and the solids triturated with more hexane (50 ml.) and pentane (2×100 ml.), stirring with the first 100 ml. of pentane for 4.0 hours and the next 100 ml. overnight under argon. The product obtained was then dried in vacuo for 6.0 hours to give 1.273 g. of product as an amorphous solid; $R_f$=0.62 (methylene chloride:methanol:acetic acid, 20:1:1:1);

$[\alpha]_D$=−140.2° (c=0.61, methanol). 1H NMR (400 MHz, CDCl$_3$): 1.43 (t,1H), 2.51–2.90 (m, 5H), 4.17, (t,1H, J=10 Hz), 4.29 (d,1H, J=17 Hz), 4.69 (t, 1H, J=7 Hz), 4.71 (d, 1H, J=17 Hz), 6.76 (d, 1H), 7.05–7.26 (m,9H). Anal. calc'd. for C$_{21}$H$_{22}$N$_2$O$_5$S: C,60.86; H,5.35; N,6.76; S,7.74; SH,7.98 Found: C,60.85; H,5.54; N,6.74; S,7.66; SH,6.29.

EXAMPLE 14

[S,(R*,R*)]-3,4-Dihydro-3-[(2-mercapto-1-oxo-3-phenylpropyl)amino]-4-oxo-1,5-benzoxazepine-5 (2H)-acetic acid a) [S, (R*,R*) -3-[[2-(Acetylthio)-1-oxo-3-phenylpropyl] amino]-3,4-dihydro-4-oxo-1,5-benzoxazepine-5(2H)-acetic acid, ethyl ester (S)-2-(Acetylthio)benzenepropanoic acid, dicyclohexylamine salt (1.35 g., 3.81 moles) was suspended in ethyl acetate (120 ml.), washed with 5% potassium bisulfate (5×20 ml.) and brine (25 ml.), dried (anhydrous magnesium sulfate), filtered, evaporated to dryness and dried in vacuo to give the free acid.

This free acid was dissolved in dry methylene chloride (25 ml.), cooled down to 0° (ice-salt bath), treated with 1-hydroxybenztriazole hydrate (541 mg., 4.0 mmoles) and 1-ethyl-3-(3-dimethylaminopropyl)carbodiimide (792 mg., 4.13 mmoles) and stirred at 0° for 1.0 hour under argon. The solution was treated with (S)-3-amino-3,4-dihydro-4-oxo-1, 5-benzoxazepine-5(2H)-acetic acid, ethyl ester (1.147 g., 3.81 mmoles) and 4-methylmorpholine (0.47 ml., 4.2 moles) and stirring was continued at 0° for 1.0 hour and at room temperature for 1.0 hour. The reaction mixture was diluted with ethyl acetate (100 ml.), washed successively with water (15 ml.), 5% potassium bisulfate (2×15 ml.), water (15 ml.), saturated sodium bicarbonate (15 ml.) and brine (15 ml.), dried (anhydrous sodium sulfate), filtered, evaporated to dryness and dried in vacuo. The crude product was chromatographed on a silica gel column (Merck), eluting the column with ethyl acetate:hexane (1:4) to give 1.21 g. of the product as a syrup. An additional 409.6 mg. of product (isomer mixture 1:1 ratio) was also obtained; $R_f$=0.67 (ethyl acetate:hexanes, 1:4 then 1:1).

b) [S,(R*,R*)]-3,4-dihydro-3-[(2-mercapto-1-oxo-3-phenylpropyl)amino]-4-oxo-1,5-benzoxazepine-5(2H)-acetic acid A solution of the ethyl ester product from part (a) (1.81 g., 2.51 moles) in methanol (13 ml.) was purged with argon for 30 minutes, cooled down to 0° (ice-salt bath) then treated dropwise with a previously purged (argon, 30 minutes) solution of 1.0 sodium hydroxide (10 ml., 4.0 eq.) maintaining the bubbling of argon throughout the addition and length of the reaction. The reaction mixture was stirred at 0° for 1.0 hour, acidified at 0° with 5% potassium bisulfate (45 ml.) to pH 1.0 and extracted with ethyl acetate (2×80 ml.). The combined organic extracts were washed with brine (20 ml.), dried (anhydrous sodium sulfate), filtered, evaporated to dryness and dried in vacuo. The crude product was dissolved in methylene chloride (10 ml.) and treated portionwise with hexane (100 ml.), scratching the mixture to form a solid. The supernatant was decanted and the solids triturated with hexane (50 ml.) and pentane (2×100 ml.), stirring with the first 100 ml. of pentane for 4.0 hours and the next 100 ml. overnight under argon. The product was then dried in vacuo for 6.0 hours to give 969.7 mg. as an amormphous solid;

$R_f$=0.47 (methylene chloride:methanol:acetic acid, 20:1:1); $[\alpha]_D$=−143.3° (c=0.54, methanol). 1H NMR (400

MHz, CDCl$_3$): 2.02 (d, 1H), 3.07 (m,2H), 3.59 (m, 1H), 4.09 (t, 1H, J=10 Hz), 4.24 (d, 1H, J=17 Hz), 4,63 (t, 1H, J=8 Hz), 4.73 (d, 1H, J=17 Hz), 4.93 (m, 1H,) 7.04–7.26 (m, 9H), 7.42 (d, 1H). Anal. calc'd. for C$_{20}$H$_{20}$N$_2$O$_5$S . 0.147 C$_5$H$_{12}$ . 0.43 H$_2$O: C,59.46; H,5.44; N,6.69; S,7.65; SH,7.89 Found: C,59.46; H,5.25; N,6.65; S,7.88; SH,7.84

EXAMPLE 15

[3S-[1(R*),3α(R*)]]-3-[(2-Mercapto-1-oxo-3-phenylpropyl)amino]-α-methyl-2-oxohexahydro-1H-azepine-1-acetic acid a) [3S-[1(R*),3α(R*)]]-3-[[2-(acetylthio)-1-oxo-3-phenylpropyl]amino]-α-methyl-2-oxohexahydro-1H-azepine-1-acetic acid, methyl ester A cold (0°) solution of [S-(R*,R*)]-3-aminohexahydro-α-methyl-2-oxo-1H-azepine-1-acetic acid, methyl ester (374 mg., 1.75 mmol) [prepared as described by Thorsett et al., "Peptides:Structure and Function", Proceeding 8th American Peptide Symposium, p 555 (1983)] and (S)-2-(acetylthio)benzenepropanoic acid (393 mg., 1.75 mmol) in methylene chloride (10 ml.) was treated with triethylamine (245 μl, 178 mg., 1.76 mmol) followed by benzotriazol-1-yloxy-tris(dimethylamino)phosphonium hexafluorophosphate (775 mg, 1.75 mmol). The clear, nearly colorless solution was stirred at 0° C. for one hour and then at room temperature for 3 hours. The mixture was partitioned between ethyl acetate and 0.5N hydrochloric acid and the ethyl acetate extract was washed successively with water, half saturated sodium bicarbonate and brine. The solution was dried (sodium sulfate), filtered and stripped. The residue was flash chromatographed (Merck silica gel, 70:30 ethyl acetate:hexanes) to give 590 mg. of pure product as a colorless oil/foam; R$_f$=0.43 (ethyl acetate:hexanes, 75:25).

b) [3S-[1(R*),3α(R*)]]-3-[(2-Mercapto-1-oxo-3-phenylpropyl)amino]-α-methyl-2-oxohexahydro-1H-azepine-1-acetic acid An ice cold solution of the product from part (a) (570 mg., 1.36 mmol) in methanol (7 ml., deoxygenated via argon bubbling) was treated with 1N sodium hydroxide (5.5 ml., deoxygenated via argon bubbling). After stirring at 0° C. for 1.25 hours, the solution was acidified with 1N hydrochloric acid (9 ml) and extracted with ethyl acetate. The ethyl acetate extract was washed with water and brine, then dried (sodium sulfate), filtered and stripped to afford an oil. The material was flash chromatographed (Merck silica gel, 2% acetic acid in ethyl acetate). The product containing fractions were pooled and stripped, and the residue was taken up in ethyl acetate and washed successively with water and brine, then dried (sodium sulfate), filtered and stripped again. The resulting oil/foam was triturated first with ethyl ether and then with hexane to produce a white oil/foam. The mixture was stripped to dryness, slurried in hexane, stripped to dryness again, and dried in vacuo to give 470 mg. of product as a white foam; (>98% diastereomeric purity as determined by NMR analysis); R$_f$=0.49 (5% acetic acid in ethyl acetate); [α]$_D$=–37.1° (c=0.6, chloroform). HPLC: YMC S3 ODS column (6.0×150 mm); eluted with 44% A: 90% water-10% methanol-0.2% phosphoric acid and 56% B: 10% water-90% methanol-0.2% phosphoric acid; flow rate 1.5 ml/min detecting at 220 nm; t$_R$=11.02 min (98.0%).

Anal. calc'd. for C$_{21}$H$_{22}$N$_2$O$_4$S$_2$: C,59.32; H,6.64; N,7.69; S,8.80; SH,9.07 Found C,59.27; H,6.92; N,7.37; S,8.36; SH,8.75.

EXAMPLE 16

[6R(S*)-2,3,6,7-Tetrahydro-6-[[2-(mercaptomethyl)-1-oxo-3-phenylpropyl]amino]-5-oxo-1,4-thiazepine-4(5H)-acetic acid a) [2-[(Methylsulfonyl)oxy]ethyl]carbamic acid, 1,1-dimethylethyl ester Di-tert-butyldicarbonate (21.8 g., 100 mmol) was added in portions to a stirred solution of ethanolamine (6.1 g., 100 mmol) in dichloromethane (100 ml.) at 0°–5° C. After addition was complete, the cooling bath was removed and the solution was stirred at room temperature for five hours. The solvent was removed in vacuo and the resulting material was dissolved in dichloromethane (100 ml.) and triethylamine (21 ml., 150 mmol), cooled to −10° C. and treated dropwise, over a period of 10 minutes, with methanesulfonyl chloride (9.25 g., 150 mmol). The mixture was diluted with ethyl acetate (200 ml.) and washed with 1N hydrochloric acid and water. The ethyl acetate layer was dried (magnesium sulfate), filtered, and freed of solvent in vacuo to give the product as a viscous oil which was used without purification.

b) S-[2-[[1,1-Dimethylethoxy)carbonyl]amino]ethyl]-N-[(phenylmethoxy)carbonyl]-L-cysteine, diphenylmethyl ester A solution of N-[(phenylmethoxy)carbonyl]-L-cysteine, diphenylmethyl ester (12.7 g., 30.1 mmol.) and the product from part (a) (7.20 g., 30.1 mmol) in dimethylformamide (190 ml.) was treated with spray dried potassium fluoride (25 g., 430 mmol) and stirred at 70°–75° C., under an atmosphere of argon, for 20 hours. After cooling, the mixture was partitioned between ethyl acetate (800 ml.) and water (400 ml.). The organic layer was washed with brine (300 ml.), dried (magnesium sulfate), filtered, and freed of solvent in vacuo leaving an oil. This was chromatographed on silica gel (Merck, ~1000 ml.), eluting with mixtures of ethyl acetate and hexane (1:4, 1:3 and 1:2), to give 9.13 g. of product; R$_f$=0.35, (ethyl acetate:hexanes, 1:2).

c) (R)-Tetrahydro-6-[[(phenylmethoxy)carbonyl]-amino]-1,4-thiazepin-5(4H)-one

A solution of the product from part (b) (6.13 g., 10.86 mmol) in anisole (30 ml.) and trifluoroacetic acid (45 ml.) was stirred at room temperature for two hours and then concentrated in vacuo. The residual oil was diluted with isopropyl ether (40 ml.), stirred, and the isopropyl ether layer was decanted. This process was repeated once more and the residue was dried in vacuo. A mixture this material and diphenylphosphoryl azide (4.4 g., 16 mmol) in dry dimethylformamide (75 ml.) under an argon atmosphere was cooled in an ice bath and, while stirring, 4-methylmorpholine (4.45, 44 mmol) was added dropwise. After addition was complete, the mixture was allowed to warm to room temperature and left stirring for 20 hours. The mixture was partitioned between ethyl acetate (150 ml. and water (100 ml.). The layers were separated and the aqueous layer was reextracted with ethyl acetate (50 ml.). The combined organic layers were washed with saturated potassium bisulfate solution (30 ml.), saturated sodium bicarbonate solution (50 ml.), and brine (50 ml.), dried (magnesium sulfate), and freed of solvent in vacuo. The remaining material was triturated with isopropyl ether to give 2.45 g. of white solid product. R$_f$=0.27, (ethyl acetate: hexanes, 1:1).

d) (R)-Tetrahydro-5-oxo-6-[[(phenylmethoxy)carbonyl]amino]-1,4-thiazepine-4(5H)-acetic acid, ethyl ester A solution of the product from part (c) (3.55 g., 12.68 mmol) in distilled tetrahydrofuran (40 ml.), under an atmosphere of argon, was cooled to 0° C. and treated with powdered potassium hydroxide (2.16 g., 40 mmol) and tetrabutylammonium bromide (420 mg., 1.3 mmol). Ethyl bromoacetate (2.58 g., 15.43 mmol) was added dropwise. The mixture was stirred cold for two hours and then diluted with ethyl acetate (50 ml.), and anhydrous magnesium sulfate was added. The reaction mixture was filtered through a magnesium sulfate pad and the pad was washed several times with ethyl acetate. The filtrate was treated with 1N hydrochloric acid solution (50 ml.) and the layers were separated. The organic layer was dried (magnesium sulfate), filtered and freed of solvent in vacuo leaving an oil which was purified by chromatography on silica gel, eluting with 10–30% ethyl acetate in hexane to give 3.22 g. of product as a viscous oil; $R_f$=0.60 (ethyl acetate:hexanes, 1:1).

e) (R)-6-Aminotetrahydro-5-oxo-1,4-thiazepine-4(5H)-acetic acid, ethyl ester, hydrobromide salt The product from part (d) (3.17 g., 8.65 mmol) was treated with 30% hydrogen bromide in acetic acid (14 ml.). The mixture was stirred at room temperature for one hour and then diethyl ether (200 ml.) was added. After stirring at room temperature for one hour, the precipitated salt was harvested by filtration and washed several times with ether. The slightly gummy material was dissolved in hot ethanol and the solvent was removed in vacuo. This process was repeated once. Diethyl ether was added to the remaining material and the hydrobromide salt product (2.52 g.) was harvested by filtration as a yellow solid.

f) [6R(S*)]-2,3,6,7-Tetrahydro-6-[[2-[(acetylthio)methyl]-1-oxo-3-phenylpropyl]amino]-5-oxo-1,4-thiazepine-4(5H)-acetic acid, ethyl ester A suspension of the ephredine salt of (S)-2-[(acetylthio) methyl]benzenepropanoic acid (1.74 g., 4.31 mmole) in ethyl acetate was washed twice with 0.1N hydrochloric acid (75 ml., 30 ml.), once with brine (25 ml.), dried (magnesium sulfate), filtered and freed of solvent in vacuo leaving the free acid as an oil. This was dissolved in dichloromethane (25 ml.) under an atmosphere of argon and cooled to 0° C. 1-Hydroxybenzotriazole hydrate (642 mg., 4.75 mmol) and 1-ethyl-3-(3-dimethylaminopropyl)carbodiimide (949 mg., 5.0 mmol) were added. The mixture was stirred cold one hour before the hydrobromide salt product of part (e) (1.259 g., 4.03 mmol) was added followed by 4-methylmorpholine (530 µl, 4.75 mmol). The mixture was stirred cold one hour and one hour at room temperature, then diluted with dichloromethane (100 ml.). The solution was washed with water (30 ml.), 5% potassium bisulfate solution (30 ml.), sodium bicarbonate solution (30 ml.), and water (30 ml.). The dichloromethane solution was dried (magnesium sulfate), filtered and freed of solvent in vacuo. The remaining material was chromatographed on silica gel (Merck, 350 ml.), eluting with mixtures of ethyl acetate and hexane (1:3 followed by 1:2, 2:3 and 1:1) to give 991 mg., of product; $R_f$=0.40 (ethyl acetate:hexanes, 1:1).

g) [6R(S*)]-2,3,6,7-Tetrahydro-6-[[2-(mercaptomethyl)-1-oxo-3-phenylpropyl]amino]-5-oxo-1,4-thiazepine-4(5H)-acetic acid A solution of the product from part (f) (991 mg., 2.19 mmol) in methanol (18 ml.) was purged with argon for 15 minutes, cooled in an ice-salt bath and, while stirring and continuing the argon purge, treated dropwise with 1N sodium hydroxide solution (8.8 ml.) which had been purged with argon for 30 minutes just before use. The mixture was stirred cold one hour and then acidified to pH 2 with 5% potassium bisulfate solution. The product was extracted into ethyl acetate (2×50 ml., 1×20 ml.). The combined organic extracts were washed with brine, dried (magnesium sulfate), filtered and freed of solvent in vacuo leaving a white solid foam. This was dissolved in warm ethyl acetate, filtered, and freed of solvent in vacuo. The remaining material was dissolved in dichloromethane and hexane was added. Removal of the solvent in vacuo gave 836 mg. of product as a white solid foam; m.p.85°–101° C.; $R_f$=0.35 (8% methanol in dichloromethane plus 2 drops acetic acid/5 ml.); $[\alpha]_D$=–9.5° (C=0.6, methanol). HPLC:$R_T$=13.2 min., 50% aqueous methanol containing 0.2% phosphoric acid, 1.5 ml./min., detected at 220 mm, YMC S-3 (ODS), 6.0×150 mm., 3 micron spherical end capped column. H.I.=>95%.

Anal. calc'd. for $C_{17}H_{22}N_2O_4S_2 \cdot 0.15 H_2O \cdot 0.15 C_6H_{14}$: C,60.24; H,5.71; N,6.11; S,13.98 Found: C,60.01; H,5.77; N,5.94; S,13.64.

EXAMPLE 17

[6R(S*)]-2,3,6,7-Tetrahydro-6-[(2-mercapto-1-oxo-3-phenylpropyl)amino]-5-oxo-1,4-thiazepine-4(5H)-acetic acid a) [6R(S*)]-2,3,6,7-Tetrahydro-6-[[2-(acetylthio)-1-oxo-3-phenylpropyl]amino]-5-oxo-1,4-thiazepine-4(5H)-acetic acid, ethyl ester A suspension of the dicyclohexylamine salt of (S)-2-(acetylthio)benzenepropanoic acid (1.74 g., 4.29 mmol) in ethyl acetate (75 ml.) was washed twice with 0.1N hydrochloric acid (75 ml., 30 ml.), once with brine (30 ml.), dried (magnesium sulfate), filtered and freed of solvent in vacuo leaving the free acid as an oil. This was dissolved in dichloromethane (25 ml.) under an atmosphere of argon and cooled to 0° C. 1-Hydroxybenzotriazole hydrate (642 mg, 4.75 mmol) and 1-ethyl-3-(3-dimethylaminopropyl) carbodiimide (959 mg., 5.0 mmol) were added. The mixture was stirred cold one hour before the hydrobromide salt product of Example 16(e) (1.259 g., 4.03 mmol) was added followed by 4-methylmorpholine (530 µl, 4.75 mmol). The mixture was stirred cold 1 hour and 1.5 hours at room temperature, then diluted with dichloromethane (100 ml.). The solution was washed with water (30 ml.), 5% potassium bisulfate solution (30 ml.), sodium bicarbonate solution (30 ml.), and water (30 ml.). The dichloromethane solution was dried (magnesium sulfate), filtered and freed of solvent in vacuo. The remaining foam was chromatographed on silica gel (Merck, 350 ml.), eluting with 30–40% ethyl acetate in hexane to give 636 mg. of product; $R_f$=0.29 (ethyl acetate:hexane, 1:1).

b) [6R(S*)]-2,3,6,7-Tetrahydro-6-[(2-mercapto-1-oxo-3-phenylpropyl)amino]-5-oxo-1,4-thiazepine-4(5H)-acetic acid A solution of the product from part (a) (636 mg., 1.45 mmol) in methanol (15 ml.) was purged with argon for 15 minutes, cooled in an ice-salt bath and, while stirring and continuing the argon purge, treated dropwise with 1N sodium hydroxide solution (5.8 ml.) which had been purged with argon for 30 minutes just prior to use. The mixture was stirred cold one hour and then acidified to pH 1 with 5% potassium bisulfate solution. The product was extracted into ethyl acetate (2×50 ml.). The combined organic extracts were washed with brine, dried (magnesium sulfate), filtered and freed of solvent in vacuo leaving a viscous oil. This was dissolved in dichloromethane and freed of solvent in vacuo to give 532 mg. of product as a solid foam; m.p. 69°–76° C. $R_f$=0.29, (8% methanol in dichloromethane plus 2 drops acetic acid/5 ml.). HPLC: $R_T$=9.6 min., 50% aqueous methanol containing 0.2% phosphoric acid, 1.5 ml. min., detected at 220 mm, YMC S-3 (ODS), 6.0×150 mm, 3 micron spherical end capped column. H.I.=98%. The NMR indicates approximately 0.1M of trapped ethyl acetate.

Anal. calc'd. for $C_{22}H_{24}N_2O_4S_2 \cdot 0.1 C_4H_8O_2$: C,52.21; H,5.56; N,7.43; S,17.00 Found: C,52.27; H,5.54; N,7.35; S,16.98.

EXAMPLE 18

[3R-[3α,6α(S*)]]-Tetrahydro-6-[(2-mercapto-1-oxo-3-phenylpropyl)amino]-5-oxo-3-phenyl-1,4-thiazepine-4(5H)-acetic acid a) (3R-cis)-Tetrahydro-5-oxo-3-phenyl-6-[[(phenylmethoxy)carbonyl]amino]-1,4-thiazepine-4(5H)-acetic acid, ethyl ester A solution of (3R-cis)-tetrahydro-3-phenyl-6-[[(phenylmethoxy)carbonyl]amino]-1,4-thiazepin-5(4H)-one (1.16 g., 3.25 mmol) [prepared as described by Yanagisawa et al., J. Med. Chem., Vol. 30, p. 1984–1991 (1987)] in distilled tetrahydrofuran (30 ml.), under an atmosphere of argon, was cooled to 0° C. and treated with powdered potassium hydroxide (540 mg., 10 mmol) and tetrabutylammonium bromide (97 mg, 0.3 mmol). Ethyl bromoacetate (501 mg., 3 mmol) was added dropwise with stirring. The mixture was stirred cold for two hours and then additional ethyl bromoacetate (501 mg., 3 mmol) was added. The mixture was stirred cold for an additional two hours and then diluted with ethyl acetate (50 ml) and anhydrous magnesium sulfate was added. The reaction mixture was filtered through a magnesium sulfate pad and the pad was washed several times with ethyl acetate. The filtrate was poured into cold 1N hydrochloric acid solution (40 ml) and the layers were separated. The organic layer was dried (magnesium sulfate), filtered and freed of solvent in vacuo leaving an oil which was purified by chromatography on silica gel, eluting with 10–30% ethyl acetate in hexane to give 730 mg. of product; $R_f$=0.32 (ethyl acetate:hexanes, 1:2).

b) (3R-cis)-6-Aminotetrahydro-5-oxo-3-phenyl-1,4-thiazepine-4(5H)-acetic acid, ethyl ester, hydrobromide salt The product from part (a) (1.43 g., 3.23 mmol) was treated with 30% hydrogen bromide in acetic acid (5.5 ml.). The mixture was stirred at room temperature for two hours and then diethyl ether (100 ml.) was added. After stirring at room temperature for one hour, the precipitated salt was harvested by filtration and washed several times with ether to give 1.08 g. of the hydrobromide salt product as a beige solid.

c) [3R-[3α,6α(S*)]]-6-[[2-(Acetylthio)-1-oxo-3-phenylpropyl]amino]-tetrahydro-5-oxo-3-phenyl-1,4-thiazepine-4(5H)-acetic acid, ethyl ester A suspension of the dicyclohexylamine salt of (S)-2-(acetylthio)benzenepropanoic acid (736 mg., 1.81 mmol) in ethyl acetate (30 ml.) was washed twice with 0.1N hydrochloric acid (40 ml., 20 ml.) and once with brine (20 ml.), dried (magnesium sulfate), filtered, and freed of solvent in vacuo leaving the free acid as an oil.

The hydrobromide salt product from part (b) (640 mg., 1.65 mmol) was dissolved in dichloromethane (30 ml.), washed with sodium bicarbonate solution (2×20 ml.), then brine (20 ml.), dried (magnesium sulfate), filtered, and freed of solvent in vacuo leaving the free amine as a viscous oil (495 mg.). This and the free acid above were dissolved in dichloromethane (20 ml.) under an atmosphere of argon and cooled to 0° C. 1-Hydroxybenzotriazole hydrate (256 mg., 1.90 mmol) and 1-ethyl-3-(3-dimethylaminopropyl)carbodiimide (362.5 mg., 1.90 mmol) were added. The mixture was stirred cold for three hours and then diluted with dichloromethane (30 ml.). The solution was washed with water (15 ml.), 5% potassium bisulfate solution (15 ml.), sodium bicarbonate solution (15 ml.), and water (15 ml.). The dichloromethane solution was dried (magnesium sulfate), filtered and freed of solvent in vacuo. The remaining material was chromatographed on silica gel (Merck, approximately 150 ml.), eluting with 25% ethyl acetate in hexane to give 610 mg. of product; $R_f$=0.53 (ethyl acetate:hexanes, 1:1).

d) [3R-[[3α,6α(S*)]]-Tetrahydro-6-[(2-mercapto-1-oxo-3-phenylpropyl)amino]-5-oxo-3-phenyl-1,4-thiazepine-4(5H)-acetic acid, mixture of methyl and ethyl esters A solution of the product from part (c) (610 mg., 1.185 mmol) in methanol (12 ml.) was purged with argon for 15 minutes, cooled in an ice-salt bath and, while stirring and continuing the argon purge, treated dropwise with 1N sodium hydroxide solution (4.75 ml.) which had been purged with argon for 30 minutes just before use. The mixture was stirred cold for 75 minutes and then acidified to pH 1 with 5% potassium bisulfate solution. The product was extracted into ethyl acetate (2×40 ml.). The combined organic extracts were washed with brine, dried (magnesium sulfate), filtered and freed of solvent in vacuo leaving 533 mg. of product that slowly crystallized. The NMR and mass spectra of this material indicated it was a mixture of methyl and ethyl esters. $R_f$=0.76 (5% methanol in methylene chloride plus 2 drops acetic acid/5 ml.)

e) [3R-[3α,6α(S*)]]-Tetrahydro-6-[(2-mercapto-1-oxo-3-phenylpropyl)amino]-5-oxo-3-phenyl-1,4-thiazepine-4(5H)-acetic acid The product from part (d) (480 mg., approximately 1.03 mmol) was added to methanol (12 ml.). The material crystallized out. Distilled tetrahydrofuran (5 ml.) was added and the mixture became a clear solution which was purged with argon for 15 minutes, cooled in an ice-salt bath and, while stirring and continuing the argon purge, treated dropwise with 1N sodium hydroxide solution (4 ml.) which had been purged with argon for 30 minutes just before use. The mixture was kept cold and under argon for 27 hours. At this time TLC indicated that the hydrolysis of the ester was complete. The mixture was acidified to pH 1 with 5% potassium bisulfate solution. The product was extracted into dichloromethane (2×30 ml.). The combined organic extracts were washed with brine, dried (magnesium sulfate), filtered and freed of solvent in vacuo leaving a white solid foam. This was dissolved in dichloromethane and hexane was added to turbidity. The mixture was freed of solvent in vacuo leaving a solid. This was triturated with 20% hexane in ether. White solid was harvested by filtration, washed with cold 50% hexane in ether to give 350 mg. of product; m.p.175°–182° C.; $R_f$=0.42 (5% methanol in methylene chloride plus 2 drops acetic acid/5 ml.); $[α]_D$=+26.7° (c=0.8, methanol). HPLC: $R_t$=8.0 min., 66.8% aqueous methanol containing 0.2% phosphoric acid, 1.5 ml./min., detected at 220 nm, YMC S-3 (ODS), 6.0×150 mm, 3 micron spherical end capped column. H.I.=>95%.

Anal. calc'd. for $C_{22}H_{24}N_2O_4S_2$: C,59.44; H, 5.44, N,6.30; S,14.42 Found: C,59.52; H,5.54; N, 6.08; S,14.14.

EXAMPLE 19

[3R-[3α,6α(S*)]]-Tetrahydro-6-[[2-(mercaptomethyl)-1-oxo-3-phenylpropyl]amino]-5-oxo-3-phenyl-1,4-thiazepine-4(5H)-acetic acid a) [3R-[3α,6α(S*))]]-Tetrahydro-6-[[2-[(acetylthio)methyl]-1-oxo-3-phenylpropyl]amino]-5-oxo-3-phenyl-1,4-thiazepine-4(5H)-acetic acid, mixture of methyl and ethyl esters A suspension of the ephredrine salt of (S)-2-[(acetylthio)methyl]benzenepropanoic acid (853 mg., 2.11 mmol.) in ethyl acetate (40 ml.) was washed twice with 0.1N hydrochloric acid (40 ml., 20 ml.), once with brine (20 ml.), dried (magnesium sulfate), filtered, and freed of solvent in vacuo leaving the free acid as an oil.

(3R-cis)-6-Aminotetrahydro-5-oxo-3-phenyl-1,4-thiazepine-4(5H)-acetic acid, mixture of methyl and ethyl esters, hydrobromide salt (320 mg. of ethyl ester, 0.82 mmol. and 410 mg. of methyl ester, 1.09 mmol) [prepared as described in Example 18(b)] were dissolved in dichloromethane (30 ml.), washed with sodium bicarbonate solution (2×20 ml.), brine (20 ml.), dried (magnesium sulfate), filtered and freed of solvent in vacuo leaving the free amine as a viscous oil (495 mg., 98%). This and the free acid described above were dissolved in dichloromethane (20 ml.) under an atmosphere of argon and cooled to 1-Hydroxybenzotriazole hydrate (285 mg., 2.11 mmol) and 1-ethyl-3-(3-dimethylaminopropyl)carbodiimide (403 mg., 2.11 mmol) were added. The mixture was stirred cold 3.5 hours and then diluted with dichloromethane (30 ml.). The solution was washed with water (15 ml.), 5% potassium bisulfate solution (15 ml.), sodium bicarbonate solution (15 ml.), and water (15 ml.). The dichloromethane solution was dried (magnesium sulfate), filtered and freed of solvent in vacuo. The remaining material was chromatographed on silica gel (Merck, 170 ml.), eluting with 25% ethyl acetate in hexane to give 535 mg. of product; $R_f$=0.68 and 0.63, (ethyl acetate: hexanes, 1:1).

b) [3R-[3α,6α(S*)]]-Tetrahydro-6-[[2-(mercaotomethyl)-1-oxo-3-phenylpropyl]amino]-5-oxo-3-phenyl-1,4-thiazeoine-4(5H)-acetic acid The product from part (a) (493 mg., approximately 0.98 mmol) was dissolved in methanol (12 ml.) and purged with argon for 15 minutes, cooled in an ice-salt bath and, while stirring and continuing the argon purge, treated dropwise with 1N sodium hydroxide solution (4 ml.) which had been purged with argon for 30 minutes just before use. The mixture was kept cold and under argon for 48 hours. At this time TLC indicated that the hydrolysis of the ester was complete. The mixture was acidified to pH 1 with 5% potassium bisulfate solution. The product was extracted into dichloromethane (2×30 ml.). The combined organic extracts were washed with brine (20 ml.), dried (magnesium sulfate), filtered and freed of solvent in vacuo leaving a white glassy foam. 25% Hexane in ether (20 ml.) was added and, on stirring, a white solid formed. This was harvested by filtration and washed with 50% hexane in ether to give 342 mg. of product; m.p. 170°–174° C., $R_f$=0.43, (5% methanol in methylene chloride plus 2 drops acetic acid/5 ml.); $[α]_D$=+32.8° (c=0.9, methanol). HPLC: $R_T$=8.6 min., 66.8% aqueous methanol containing 0.2% phosphoric acid, 1.5 ml./min., detected at 220 min. YMC S-3 (ODS), 6.0×150 mm, 3 micron spherical end capped column. H.I. =>95%.

Anal. calc'd. for $C_{23}H_{26}N_2O_4S_2$: C,60.24; H,5.71, N,6.11; S,13,98 Found: C,60.25; H,5.77; N,6.06; S,13.85.

EXAMPLE 20

[2R-{2α,6β(S*)}]-Tetrahydro-6-[[2-(mercaptomethyl)-1-oxo-3-phenylpropyl]amino]-5-oxo-2-phenyl-1,4-thiazepine-4(5H)-acetic acid a) (2R-trans))-Tetrahydro-2-phenyl-6-[[(phenylmethoxy)carbonyl]amino]-1,4-thiazepin-5(4H)-one A suspension of (2R-trans)-6-aminotetrahydro-1,4-thiazepin-5(4H)-one (5.82 g.) [prepared as described by Yanagisawa et al., J. Med Chem., Vol. 30, p. 1984–1991 (1987)] in a mixture of dichloromethane (125 ml.) and triethylamine (11 ml.) was treated with di-tert- butyl dicarbonate (6 g.) and stirred at room temperature four hours. The mixture was diluted with dichloromethane (100 ml.) and washed with water. The dichloromethane solution was dried (magnesium sulfate), filtered and freed of solvent in vacuo leaving a pale yellow solid. This was chromatographed on silica gel, eluting the product with ethyl acetate:hexane (1:1) followed by ethyl acetate to give 2.01 g. of product as a white solid.

b) (2R-trans)-Tetrahydro-5-oxo-2-phenyl-6-[[(phenylmethoxy)carbonyl]amino]-1,4-thiazepine-4(5H)-acetic acid, methyl ester A solution of the product from part (a) (1.95 g., 6.05 mmol) in distilled tetrahydrofuran, under an atmosphere of argon, was cooled to 0° C. and treated with powdered potassium hydroxide (1.10 g., 18.15 mmol, 3 eq.) and tetrabutylammonium bromide (195 mg.). Ethyl bromoacetate (800 μL., 7.26 mmol, 1.2 eq) was added dropwise over a period of 30 minutes. The mixture was stirred cold for two hours and then diluted with dichloromethane (300 ml.) and water (50 ml.). Dilute hydrochloric acid solution (75 ml.) was then added and the layers were separated. The aqueous layer was reextracted with dichloromethane (100 ml.). The combined organic layers were dried (magnesium sulfate), filtered and freed of solvent in vacuo leaving a white foam. The foam was dissolved in a mixture of ethyl acetate and dichloromethane and treated with an excess of a solution of diazomethane in ether. The resulting methyl ester was purified by chromatography on silica gel, eluting with ethyl acetate:hexane (1:1) to give 2.193 g. of product; $R_f$=0.49 (ethyl acetate:hexanes, 1:1).

c) (2R-trans)-6-Aminotetrahydro-5-oxo-2-phenyl-1,4-thiazepine-4(5H)-acetic acid, methyl ester, hydrochloride salt The product from part (b) (2.19 g., 5.56 mmol) was cooled in an ice bath and treated with a 4N solution of hydrochloric acid in dioxane (15 ml.). The mixture was stirred cold for one hour, during this period a gel formed. The cooling bath was removed and the mixture was stirred at room temperature for one hour. The solvent was removed in vacuo and toluene was added once and removed in vacuo leaving 1.84 g. of product as a solid.

d) [2R-[2α,6β(S*))]]-Tetrahydro-6-[[2-[(acetyl-thio)methyl]-1-oxo-3-phenylpropyl]amino]-1-oxo-2-phenyl-1,4-thiazeoine-4(5H)-acetic acid, methyl ester A suspension of the ephredine salt of (S)-2-[(acetylthio)methyl]benzenepropanoic acid (1.13 g., 2.80 mmol) in ethyl acetate was washed twice with 0.1N hydrochloric acid (50 ml., 25 ml.), once with brine (25 ml.), dried (magnesium sulfate), filtered and freed of solvent in vacuo leaving the free acid as an oil. This was dissolved in dichloromethane (15 ml.) under an atmosphere of argon and cooled to 0° C. 1-Hydroxybenzotriazole hydrate (405 mg., 3.0 mmol) and 1-ethyl-3-(3-dimethylaminopropyl)carbodiimide (592 mg., 3.1 mmol) were added. The mixture was stirred cold one hour before the hydrochloride salt product of part (c) (920 mg., 2.79 mmol) was added followed by 4-methylmorpholine (306 μL., 2.79 mmol). The mixture was stirred cold one hour and one hour at room temperature, then diluted with dichloromethane (70 ml.). The solution was washed with water (15 ml.), 5% potassium bisulfate solution (15 ml.), sodium bicarbonate solution (15 ml.), and water (15 ml.). The dichloromethane solution was dried (magnesium sulfate), filtered and freed of solvent in vacuo. The remaining material was chromatographed on silica gel (Merck, 170 ml.), eluting with mixtures of ethyl acetate and hexane (1:3 followed by 1:2) to give 1.058 g. of product; $R_f$=0.51 (ethyl acetate: hexanes, 1:1).

e) [2R-[2α,6β(S*)]]-Tetrahydro-6-[[2-(mercapto-methyl)-1-oxo-3-phenylpropyl]amino]-5-oxo-2-phenyl-1,4-thiazepine-4(5H)-acetic acid A solution of the product from part (d) (840 mg., 1.63 mmol) in methanol (12 ml.) was purged with argon for 15 minutes, cooled in an ice-salt bath and, while stirring and continuing the argon purge, treated dropwise with 1N sodium hydroxide solution (6.5 ml.) which had been purged with argon for 30 minutes just before use. The mixture was stirred cold for one hour and then acidified to pH 1 with 5% potassium bisulfate solution. The product was extracted into ethyl acetate (2×40 ml.). The combined organic extracts were washed with brine, dried (magnesium sulfate), filtered and freed of solvent in vacuo leaving a white solid foam. Dichloromethane and ethyl acetate were added and then removed in vacuo. Ether was added to the remaining material and a white solid was harvested by filtration and washed with additional ether to give 685 mg. of product; m.p.197°–199° C.; $R_f$=0.41 (5% methanol in dichloromethane plus 2 drops acetic acid/5 ml.); $[\alpha]_D$=+27.1° (c=0.5, methanol).HPLC: $R_T$=10.3 min., 66.8% aqueous methanol containing 0.2% phosphoric acid, 1.5 ml/min., detected at 220 mm, YMC S-3 (ODS), 6.0×150 mm, 3 micron spherical end capped column. H.I. =>98%.

Anal. calc'd. for $C_{23}H_{26}N_2O_4S_2$: C,60.24; H,5.71; N,6.11; S,13.98 Found: C,60.01; H,5.77; N, 5.94; S,13.64.

EXAMPLE 21

[2R-[2α,6β(S*)]]-Tetrahydro-6-[{2-mercapto-1-oxo-3-phenylpropyl)amino]-5-oxo-2-phenyl-1,4-thiazepine-4(5H)-acetic acid a) [2R-[2α,6β(S*)]]-Tetrahydro-6-[[2-(acetylthio)-1-oxo-3-phenylpropyl]amino]-5-oxo-2-phenyl-1,4-thiazepine-4(5H)-acetic acid, methyl ester A suspension of the dicyclohexylamine salt of (S)-2-(acetylthio)benzenepropanoic acid (1.13 g., 2.8 mmol) in ethyl acetate (50 ml.) was washed twice with 0.1N hydrochloric acid (50 ml., 25 ml.), once with brine (25 ml.), dried (magnesium sulfate), filtered and freed of solvent in vacuo leaving the free acid as an oil. This was dissolved in dichloromethane (15 ml.) under an atmosphere of argon and cooled to 0° C. 1-Hydroxybenzotriazole hydrate (405 mg., 3.0 mmol) and 1-ethyl-3-(3-dimethylaminopropyl) carbodiimide (592 mg, 3.1 mmol) were added. The mixture was stirred cold one hour before the amine hydrochloride salt product from Example 20(c) (920 mg., 2.79 mmol, was added followed by 4-methylmorpholine (306 µl., 2.79 mmol). The mixture was stirred cold for one hour and one hour at room temperature, then diluted with dichloromethane (70 ml.). The solution was washed with water (15 ml.), 5% potassium bisulfate solution (15 ml.), sodium bicarbonate solution (15 ml.), and water (15 ml.). The dichloromethane solution was dried (magnesium sulfate), filtered and freed of solvent in vacuo. The remaining material was chromatographed on silica gel (Merck, 160 ml.), eluting with mixtures of ethyl acetate and hexane (1:3 followed by 1:2) to give 880 mg. of product; $R_f$=0.57 (ethyl acetate:hexanes 1:1).

b) [2R-[2α,6β(S*)]]-Tetrtahydro-6-[(2-mercapto-1-oxo-3-phenylpropyl)amino]-5-oxo-2-phenyl-1,4-thiazepine-4(5H)-acetic acid A solution of the product from part (a) (880 mg., 1.75 mmol) in methanol (12 ml.) was purged with argon for 15 minutes, cooled in an ice-salt bath and, while stirring and continuing the argon purge, treated dropwise with 1N sodium hydroxide solution (7.0 ml.) which had been purged with argon for 30 minutes just before use. The mixture was stirred cold for 70 minutes and then acidified to pH 1 with 5% potassium bisulfate solution. The product was extracted into ethyl acetate (2×40 ml.). The combined organic extracts were washed with brine, dried (magnesium sulfate), filtered and freed of solvent in vacuo leaving a white partially solid material. Ether was added and a white solid was harvested by filtration and washed with additional ether to give 494 mg. of product; m.p.181°–183° C., $R_f$=0.43 (5% methanol in dichloromethane+2 drops acetic acid/5 ml.); $[\alpha]_D$=+6°–7° (c=0.7, methanol). HPLC: $R_T$=9.6 min., 66.8% aqueous methanol containing 0.2% phosphoric acid, 1.5 ml./min., detected at 220 mm, YMC S-3 (ODS), 6.0×150 mm, 3 micron spherical end capped column. H.I. =98%. The NMR indicates approximately 0.1M of trapped ethyl acetate.

Anal. calc'd. for $C_{22}H_{24}N_2O_4S_2 \cdot 0.1\ C_4H_8O_2$: C,59.34; H,5.51; N,6.18; S,14.14 Found: C,59.22; H,5.41; N,6.12; S,13.72.

EXAMPLE 22

[R-(R*,S*)]-2,3,4,5-Tetrahydro-3-[(2-mercapto-1-oxo-3-phenylpropyl)amino]-2-oxo-1H-benzazepine-1-acetic acid a) (R)-2,3,4,5-Tetrahydro-3-amino-2-oxo-1H-benzazepine-1-acetic acid, ethyl ester 2,3,4,5-Tetrahydro-3-amino-2-oxo-1H-benzazepine-1-acetic acid, ethyl ester [prepared as described by Watthey et al., J. Med Chem., 28, p 1511–1516 (1985)] (14.8 g., 56.4 mmoles) was resolved via its L-tartaric acid salt by the method described in the aforementioned reference to give the S-amine (3.927 g., m.p. 105°–107°; $[\alpha]_D$=−277° (c=0.99, ethanol). The residue from the combined mother liquors (21.5 g., 52.1 mmoles) was suspended in ethyl acetate (340 ml.), washed twice with 10% $NH_4OH$ (41 ml. then 30 ml.) and brine (25 ml.), dried (anhydrous sodium sulfate), filtered, evaporated to dryness, and the resulting product dried in vacuo to give the amine mixture (7.01 g.) enriched with the E isomer. A solution of the isomer mixture (2.285 g., 8.71 mmoles) in absolute ethanol (18 ml.) was treated with D-tartaric acid (1.31 g., 8.73 mmoles) and heated on a steam bath until solution was effected. The clear solution was cooled down to room temperature, allowed to stand for two days then cooled down to 0° (ice-salt bath) and scratched until crystals formed. The crude salt (2.585 g.) was recrystallized once from absolute ethanol (14 ml.) to give the desired salt [2.158 g., $[\alpha]_D$=+154.1°,(c=0.6, methanol)]. The salt was then suspended in ethyl acetate (35 ml.), washed with 10% $NH_4OH$ (2×4 ml.) and brine (6 ml.), dried (anhydrous sodium sulfate), filtered, evaporated to dryness and dried in vacuo to give 1.31 g. of product; $R_f$=0.60 (methylene chloride:methanol 9:1); $[\alpha]_D$+273.1° (c=0.677, methanol).

b) [R-(R*,S*)]-2,3,4,5-Tetrahydro-3-[[2-(acetylthio)-1-oxo-3-phenylpropyl]amino]-2-oxo-1H-benzazepine-1-acetic acid, ethyl ester A suspension of the dicyclohexylamine salt of (S)-2-(acetylthio)benzenepropanoic acid (1.18 g., 2.91 mmoles, 1.1 eq.) in ethyl acetate (84 ml.) was washed with 5% potassium bisulfate (5×13 ml.) and brine (18 ml.), dried (anhydrous magnesium sulfate), filtered, evaporated to dryness and dried in vacuo to give the free acid as a clear syrup (720 mg.) in quantitative yield.

The free acid was dissolved in dry methylene chloride (17 ml.), cooled down to 0° (ice-salt bath) and treated with 1-hydroxybenzotriazole hydrate (412 mg., 3.05 mmoles) and 1-ethyl-3-(3-dimethylamino-propyl)carbodiimide (603.8 mg., 3.15 mmoles). The reaction mixture was stirred at 0° for 1.0 hour under argon, treated with the product from part (a) (800 mg., 3.05 mmoles) and stirring was continued at 0° for 1.0 hour and at room temperature for 1.0 hour. The solution was diluted with ethyl acetate (70 ml.), washed successively with water (11 ml.), 5% potassium bisulfate (2×11 ml.), water (11 ml.), saturated sodium bicarbonate (11 ml.) and brine (11 ml.), dried (anhydrous magnesium sulfate), filtered, evaporated to dryness and dried in vacuo. The crude product was chromatographed on a silica gel column (Merck) eluting with ethyl acetate-hexanes (1:4) to give 1.212 g. of the product as a syrup; $R_f$=0.57 (ethyl acetate:hexanes, 1:1).

c) [R-(R*,S*)]-2,3,4,5-Tetrahydro-3-[(2-mercapto-1-oxo-3-phenylpropyl)amino]-2-oxo-1H-benzazepine-1-acetic acid A solution of the product from part (b) (1.212 g., 2.59 mmoles) in methanol (14 ml.) was purged with argon for 30 minutes, cooled down to 0° (ice-salt bath) then treated dropwise with a previously purged (argon, 30 minutes) solution of 1.0N sodium hydroxide (13.4 ml., 4.0 eq.) maintaining the bubbling of argon throughout the addition and length of the reaction. The reaction mixture was stirred at 0° for 1.0 hour, acidified at 0° with 5% potassium bisulfate (46 ml.) to pH 1.5, warmed up to room temperature then extracted with ethyl acetate (2×90 ml.). The organic extracts were washed with brine (22 ml.), dried (anhydrous sodium sulfate), filtered, evaporated to dryness and dried in vacuo. The crude product was dissolved in methylene chloride (10 ml.) and treated portionwise with hexane (100 ml.), scratching the mixture to form a solid. The supernatant was decanted and the solids triturated with more hexane (50 ml.) and pentane (2×100 ml.), stirring with the first 100 ml. of pentane for 4 hours and the next 100 ml. overnight under argon. The product obtained was then dried in vacuo (pump) for 7 hours to give 1.068 g. of product as an amorphous solid; $R_f$=0.67 (methylene chloride:methanol:acetic acid, 20:1:1); $\{\alpha\}_D$ =230.9° (c=0.57, methanol).

Anal.calc'd. for $C_{21}H_{22}N_2O_4S$: C,63.30; H,5.56; N,7.03; S,8.05; SH,8.30 Found: C,63.23; H,5.80; N,6.76; S,7.99; SH,7.67.

$^1$H-NMR (400 MHz, CDCl$_3$) : δ1.65 (m, 1 H), 2.06 (d, 1 H), 2.51 (m, 2 H), 2.94 (dd, 1 H, J=7, 13 Hz), 3.17 (m, 2 H), 3.40 (m, 1 H), 4.39 (d, 1 H, J=17 Hz), 4.45 (m, 1 H), 4.67 (d, 1 H, J=17 Hz), 7.05–7.31 (m, 9 H).

EXAMPLE 23

[R-(R*,S*)]-2,3,4,5-Tetrahydro-3-[[2-(mercaptomethyl)-1-oxo-3-phenylpropyl]amino]-2-oxo-1H-benzazepine-1-acetic acid a) [R-(R*,S*)-2,3,4,5-Tetrahydro-3-[[2-[(acetylthio)-methyl]-1-oxo-3-phenylpropyl]amino]-2-oxo-1H-benzazepine-1-acetic acid, ethyl ester The ephedrine salt of (S)-2-[(acetylthio)-methyl] benzenepropanoic acid (774 mg., 1.92 mmoles, 1.03 eq.) was suspended in ethyl acetate (35 ml.), washed with dilute hydrochloric acid (35 ml. water +2.7 ml. 1.0N hydrochloric acid then 20 ml. water+0.9 ml. 1.0N. hydrochloric acid), and brine (7 ml.), dried (anhydrous magnesium sulfate), filtered and evaporated to dryness. The colorless syrup was dried in vacuo (pump) for 1.0 hour to afford a quantitative yield of the free acid (471 mg.).

The free acid was dissolved in dry methylene chloride (15 ml.), cooled down to 0° (ice-salt bath), treated with 1-hydroxybenzotriazole hydrate (270 mg., 2.0 mmoles) and 1-ethyl-3-(3-dimethylamino-propyl)carbodiimide (396 mg., 2.07 mmoles) and stirred at 0° under argon for 1.0 hour. The clear solution was treated with the product of Example 22(a) (489 mg., 1.86 mmoles) and stirring was continued at 0° for 1.0 hour and at room temperature for 1.0 hour. The reaction mixture was diluted with ethyl acetate (50 ml.), washed successively with water (10 ml.), 5% potassium bisulfate (2×10 ml.), water (10 ml.), saturated sodium bicarbonate (10 ml.) and brine (10 ml.), dried (anhydrous magnesium sulfate), filtered, and evaporated to dryness. The crude product was chromatographed on a silica gel column (Merck) eluting the column with ethyl acetate:hexane mixtures (1:4; 1:1) to give 803 mg. of product as a colorless syrup; $R_f$=0.55 (ethyl acetate:hexanes, 1:1).

b) [R-(R*,S*)]-2,3,4,5-Tetrahydro-3-[[2-(mercaptomethyl)-1-oxo-3-phenylpropyl]amino]-2-oxo-1H-benzazepine-1-acetic acid A solution of the product from part (a) (667 mg., 1.38 mmoles) in methanol (7 ml.) was purged with argon for 30 minutes, cooled down to 0° (ice-salt bath) then treated dropwise with a previously purged (argon, 30 minutes) solution of 1.0 [sodium hydroxide (5.5 ml., 4.0 eq.), maintaining the bubbling of argon throughout the addition and length of the reaction. The reaction mixture was stirred at 0° for 1.0 hour, acidified at 0° with 5% potassium bisulfate (23 ml.) to pH 2.0, warmed up to room temperature and extracted with ethyl acetate (2×50 ml.). The organic extracts were washed with brine (15 ml.), dried (anhydrous sodium sulfate), filtered, and evaporated to dryness. The crude product was dissolved in methylene chloride (5 ml.) and treated portionwise with hexane (50 ml.), scratching the mixture to form a solid. The supernatant was decanted and the solids were triturated with additional hexane (50 ml.) and pentane (2×100 ml.), stirring with the first 100 ml. of pentane for 4.0 hours and the next 100 ml. overnight under argon. The product obtained was then dried in vacuo (pump) for 9.0 hours to give 486 mg. of product as an amorphous solid;

$R_f$=0.53 (methylene chloride:methanol:acetic acid, 20:1:1); $[\alpha]_D$=+253.9° (c=0.38, methanol).

Anal. calc'd. for $C_{22}H_{24}N_2O_4S$: C,64.06; H,5.86; N,6.79; S,7.77 Found: C,63.83; H,6.08; N,6.40; S,7.75.

$^1$H-NMR (400 MHz, CDCl$_3$): δ1.51 (m, 2 H), 2.32–2.52 (m, 4 H), 2.77 (m, 3 H), 3.17 (m, 1 H), 4.36 (d, 1 H, J=17 Hz), 4.48 (m, 1 H), 4.70 (d, 1 H, J=17 Hz), 6.53 (d, 1 H), 7.11–7.30 (m, 9 H).

EXAMPLE 24

[S-(R*,S*)]-2,3,4,5-Tetrahydro-3-[(2-mercapto-1-oxo-3-phenylpropyl)amino]-2-oxo-1H-1-benzazepine-1-acetic acid a) (S)-α-Bromobenzenepropanoic acid A solution of L-phenylalanine (30.0 g., 0.175 mole) and potassium bromide (73.5 g., 0.618 mole) in 2.5N sulfuric acid (365 ml.) was cooled down to 0° (ice-salt bath) and treated portionwise with sodium nitrite (19.3 g., 0.28 mole) over a period of 1.0 hour. Stirring was continued for 1.0 hour at 0° and at room temperature for 1.0 hour after which the reaction mixture was extracted with ether (3×250 ml.). The combined organic extracts were washed with water (100 ml.) and brine (50 ml.), dried (anhydrous magnesium sulfate), filtered, evaporated to dryness and dried in vacuo to give 34.46 g., of product; $R_f$=0.45 (toluene:acetic acid, 95:5).

b) (R)-α-(Acetylthio)benzenepropanoic acid, dicyclohexylamine salt

A suspension of potassium thioacetate (19.25 g., 0.168 mole) in dry acetonitrile (300 ml.) was cooled down to 0° (ice-salt bath) and treated dropwise with a solution of the product from part (a) (34.462 g., 0.15 mole) in dry acetonitrile (35 ml.) over a period of 15 minutes. The reaction mixture was warmed up to room temperature, stirred for 5.0 hours under argon then filtered, washing the solids thoroughly with acetonitrile (125 ml.). The clear filtrate was evaporated to dryness and dried in vacuo. The free acid (39.717 g., orange syrup) was dissolved in ether (400 ml.), treated with dicyclohexylamine (30.2 ml.,1.0 eq.) and stirred for 30 minutes at room temperature under argon. The white precipitates were filtered off, washed thoroughly with ethyl ether (2×100 ml.) and dried in vacuo overnight at room temperature to give 41.0 g. of product; $[\alpha]_D$=+31.8° (c=1.4, methanol).

c) [S-(R*,S*)]-2,3,4,5-Tetrahydro-3-[[2-(acetyl-thio)-1-oxo-3-phenylpropyl]amino]-2-oxo-1H-1-benzazepine-1-acetic acid, ethyl ester A suspension of the dicyclohexylamine salt of (R)-α-(acetylthio)benzenepropanoic acid (850 mg., 2.1 mmoles) in ethyl acetate (60 ml.) was washed with 5% potassium bisulfate (5×10 ml.) and brine (10 ml.), dried (anhydrous magnesium sulfate), filtered, evaporated to dryness and dried in vacuo to give the free acid as a clear syrup (497 mg.) in quantitative yield.

The free acid was dissolved in dry methylene chloride (12 ml.), cooled down to 0° (ice-salt bath) and treated with 1-hydroxybenzotriazole hydrate (297 mg., 2.20 mmoles) and 1-ethyl-3-(3-dimethyl-aminopropyl)carbodiimide (435 mg., 2.27 mmoles). The reaction mixture was stirred at 0° under argon for 1.0 hour, treated with (S)-2,3,4,5-tetrahydro-3-amino-2-oxo-1H-benzazepine-1-acetic acid, ethyl ester [prepared as described by Watthey et al., J. Med. Chem., 28, p 1511–1516 (1985)](500 mg., 1.91 mmoles) and stirring was continued at 0° for 1.0 hour and at room temperature for 1.0 hour. The solution was diluted with ethyl acetate (50 ml.), washed successively with water (8.0 ml.), 5% potassium bisulfate (2×8 ml.), water (8.0 ml.), saturated sodium bicarbonate (8.0 ml.) and brine (8.0 ml.), dried (anhydrous sodium sulfate), filtered, evaporated to dryness and dried in vacuo. The crude product was chromatographed on a silica gel column (Merck), eluting the column with ethyl acetate: hexanes (1:4) to give 714 mg. of product as a clear syrup; $R_f$=0.62 (ethyl acetate:hexanes, 1:1).

d) [S-(R*,S*)]-2-3,4,5-Tetrahydro-3-[(2-mercapto-1-oxo-3-phenylpropyl)amino]-2-oxo-1H-1-benzazepine-1-acetic acid A solution of the product from part (c) (714 mg., 1.52 mmoles) in methanol (9.0 ml.) was purged with argon for 30 mintues, cooled down to 0° (ice-salt bath) then treated dropwise with a previously purged solution of 1.0N sodium hydroxide (6.0 ml., 4 eq.), maintaining the bubbling of argon throughout the addition and length of the reaction. The reaction mixture was stirred at 0° for 1.0 hour, acidified to pH 2.0 with 5% potassium bisulfate (26 ml.) and then extracted with ethyl acetate (2×50 ml.). The combined organic extracts were washed with brine (14 ml.), dried (anhydrous sodium sulfate), filtered, evaporated to dryness and dried in vacuo. The crude product was dissolved in methylene chloride (5.0 ml.) and treated protionwise with hexane (50 ml.), scratching to form a solid. The supernatant was decanted and the solids triturated with additional hexane (50 ml.) and pentane (2×100 ml.), stirring with the first 100 ml. of pentane for 4.0 hours and the next 100 ml. overnight under argon. The product obtained was then dried in vacuo to give the product as an amorphous solid; $R_f$=0.47 (methylene chloride: methanol:acetic acid, 20:1:1); $[\alpha]_D$=−228° (c=0.51, methanol).

Anal.calc'd. for $C_{21}H_{22}N_2O_4S \cdot 0.26\ C_5H_{12} \cdot 0.176\ CH_2Cl_2$: C,62.46; H,5.94; N, 6.48; S,7.42 Found: C,62.81; H,5.87; N, 6.53; S,7.29.

$^1$H-NMR (400 MHz, CDCl$_3$): δ1.65 (m, 1 H), 2.06 (d, 1 H), 2.51 (m, 2 H), 2.95 (dd, 1 H, J=7, 14 Hz), 3.17 (m, 2 H), 4.39 (d, 1 H, J=17 Hz), 4.46 (m, 1 H), 4.67 (d, 1 H, J=17 Hz), 7.02–7.31 (m, 9 H).

EXAMPLE 25

[S-(R*,R*)]-Hexahydro-3-[(2-mercapto-1-Oxo-3-phenylpropyl)amino]-2-oxo-1(2H)-azocineacetic acid a) [S-(R*,R*)]-Hexahydro-3-[[(2-acetylthio)-1-oxo-3-phenylpropyl]amino]-2-oxo-1(2H)-azocineacetic acid, 1,1-dimethylethyl ester A suspension of the dicyclohexylamine salt of (S)-2-(acetylthio)benzenepropanoic acid (2.63 g, 6.6 mmol) in ethyl acetate (50 ml.) was washed twice with 0.1N hydrochloric acid (50 ml., 25 ml.) and once with brine (25 ml.), dried (magnesium sulfate), filtered and freed of solvent in vacuo leaving the free acid as an oil. This free acid and (S)-3-aminohexahydro-2-oxo-1(2H)-azocineacetic acid, 1,1-dimethylethyl ester [prepared according to the procedure of Thorsett et al., J. Med. Chem.,29, 251–60 (1986)] (1.66 g, 6.5 mmol) were dissolved in dichloromethane (30 ml.) under an atmosphere of argon and cooled to 0° C. 1-Hydroxybenzotriazole hydrate (891 mg, 6.6 mmol) and 1-ethyl-3-(3-dimethylamino-propyl)-carbodiimide (1.26 g., 6.6 mmol) were added. The mixture was stirred cold for four hours. The mixture was diluted with dichloromethane (100 ml.). The solution was washed with water (50 ml.), 5% potassium bisulfate solution (50 ml.), sodium bicarbonate solution (50 ml.), and brine (50 ml.). The dichloromethane solution was dried (magnesium sulfate), filtered and freed of solvent in vacuo. The remaining foam was chromatographed on silica gel (Merck, 500 ml.), eluting with 25–50% ethyl acetate in hexane to give 2.252 g. of product; $R_f$=0.35, (ethyl acetate:hexane, 1:1).

b) [S-(R*,R*)]-Hexahydro-3-[[(2-acetylthio)-1-oxo-3-phenylpropyl]amino]-2-oxo-1(2H)-azocineacetic acid The product from part (a) was dissolved in trifluoroacetic acid (20 ml. and stirred at room temperature for 1.75 hours, under an argon atmosphere. The trifluoroacetic acid was removed in vacuo and toluene was added twice and removed in vacuo to leave the acid product as a white foam.

c) [S-(R*,R*)]-Hexahydro-3-[(2-mercapto-1-oxo-3-phenylpropyl)amino]-2-oxo-1(2H)-azocineacetic acid A solution of the product from part (b) (5.45 mmol) in methanol (30 ml.) was purged with argon for 15 minutes, cooled in an ice-salt bath and, while stirring and continuing the argon purge, treated dropwise with concentrated ammonium hydroxide solution (2.0 ml.). After stirring cold for 6.5 hours, additional ammonium hydroxide solution (1.0 ml.) was added and the mixture was capped and left in the refrigerator for 18 hours. The mixture was acidified to pH 2 with 5% potassium bisulfate solution. The product was extracted into dichloromethane (3×50 ml.). The combined organic extracts were dried (magnesium sulfate), filtered and freed of solvent in vacuo leaving a white foam. Ether and hexane were added and the suspension was stirred under an argon atmosphere for 1 hour. A white solid was harvested by filtration, washed with more ether and hexane, and dried in vacuo to give 1.531 g. of product as a white foam; m.p. 71°–90° C.; $R_f$=0.41 (10 % methanol in methylene chloride +2 drops acetic acid/5 ml.); $[\alpha]_D$=+3.5° (c=0.75, methanol).

Anal. calc'd. for $C_{18}H_{24}N_2O_4S$: C,59.32; H, 6.64; N,7.69; S,8.80 Found: C,59.02; H,6.77; N,7.67; S,8.70.

HPLC: $R_T$=6.1 min., 62% aqueous methanol containing 0.2% phosphoric acid, 1.5 ml. min., detected at 220 mm, YMC S-3 (ODS), 6.0×150 mm, 3 micron spherical end capped column. H.I. >95%.

EXAMPLE 26

(3S)-2,3,4,5-Tetrahydro-3-[[(2-mercapto-3-(1-naphthalenyl)-1-oxopropyl]amino]-2-Oxo-1H-benzazepine-1-acetic acid a) (Acetylamino)(1-naphthalenylmethyl)propanedioic, diethyl ester To a solution of sodium ethoxide (21% in ethanol, 4.613 gm, 67.8 mmol) in ethanol (100 ml) was added diethyl acetamidomalonate (14.74 gm, 67.8 mmol), then 1-(bromomethyl)napthalene (10.0 gm, 45.2 mmol). The solution was stirred at room temperature for one hour. The reaction mixture was then concentrated to an orange oil. The oil was dissolved in ethyl acetate and washed with 50% saturated ammonium chloride water and brine, then dried over sodium sulfate, filtered and concentrated to afford an orange solid. The solid was recrystallized from ethyl acetate and hexane to afford beige crystals contaminated with malonate. The solid was dissolved in 50% ethyl acetate in hexane and purified by flash chromatography on Merck silica gel in 50% ethyl acetate in hexane. Those fractions containing pure product were combined and concentrated to afford 10.225 g. of product as a white solid; m.p. 105°–108° C.; $R_f$=0.57 (50% ethyl acetate in hexane).

b) α-Amino-1-naphthalenepropanoic acid

A solution of the product from part (a) (16.182 gm., 47.5 mmol) was suspended in 48% hydrogen bromide (100 ml) and refluxed under argon for 14 hours. The hydrogen bromide salt of the product was filtered out of solution as a white solid, then taken up in hot (50° C.) water (500 ml) and the solution neutralized with concentrated ammonium hydroxide. The product precipitated out of solution as a fine white solid. Upon filtration and drying under high vacuum overnight (18 hours), 8.335 g. of product was obtained as a fluffy white solid; m.p. 264° C.

c) α-Bromo-1-naphthalenepropanoic acid

To a solution of the product from part (b) (4.000 g., 18.6 mmol) and potassium bromide (7.63 g., 63.2 mmol) in 2.5N sulfuric acid (35 ml) kept at 0° C. was added sodium nitrite (1.92 g., 27.8 mmol) over one hour. The mixture was stirred for an additional hour at 0° C., then was warmed to room temperature and stirred for 2.5 hours. The reaction mixture was then extracted with ether (3x). The ether layers were combined and washed with water and brine, then dried over sodium sulfate, filtered and concentrated to give an orange oil. The oil was purified by flash chromatography on Merck silica gel in 70% ethyl acetate in hexane with 1% acetic acid added to reduce tailing. Those fractions containing the bromide were combined and concentrated to afford slightly contaminated product as an orange oil which solidified upon sitting overnight. $R_f$=0.40 (40% ethyl acetate in hexane with 1% acetic acid).

d) α-(Acetylthio)-1-naphthalenepropanoic acid

To a slurry of potassium thioacetate (0.912 g., 8.00 mmol) in acetonitrile (300 ml) at 0° C. was added the product from part (c) (2.030 g., 7.27 mmol) as a solution in acetonitrile (3 ml). The solution was stirred for one hour at 0° C., then was warmed to room temperature and stirred for 15 hours. Potassium bromide was then filtered out of the reaction mixture and the filtrate concentrated to afford an orange oil. The oil was dissolved in ethyl acetate and washed with 10% potassium bisulfate and brine, then dried over sodium sulfate, filtered and concentrated to afford an orange oil. The oil was purified by flash chromatography on Merck silica gel in 50% ethyl acetate in hexane with 1% acetic acid added to reduce tailing. Those fractions containing product were all contaminated with a compound with an $R_f$=0.43. Those fractions were pooled and concentrated to give an orange oil. The crude product was purified via the dicyclohexylamine salt by dissolving the orange oil in ether and adding an equivalent of dicyclohexylamine (18.13 g., 100 mmol) to the solution. The dicyclohexylamine salt was obtained in 2 crops of brown crystals (1.450 gm) still slightly contaminated with impurity. The crystals were suspended in ethyl acetate and shaken with 10% potassium bisulfate (3x). The organic layer was then washed with water and brine, then dried over sodium sulfate filtered and concentrated to afford 875 mg. of product as a yellow oil; $R_f$=0.40 (40% ethyl acetate in hexane with 1% acetic acid).

e) (3S)-2,3,4,5-Tetrahydro-3-[[2-(acetylthio)-3-(1-naphthalenyl)-1-oxopropyl]amino]-2-oxo-1H-1-benzazepine-1-acetic acid The racemic acid product from part (d) (338 mg., 1.23 mmol) and (S)-2,3,4,5-tetrahydro-3-amino-2-oxo-1H-1-benzazepine-1-acetic acid, ethyl ester [prepared as described by Watthey et al., J. Med. Chem., 28, p 1511–1516 (1985)] (321 mg., 1.23 mmol) were dissolved in methylene chloride (11 ml) at room temperature under argon. The mixture was cooled to 0° C. and treated with hydroxybenzotriazole hydrate (166 mg, 1.23 mmol) and 1-ethyl-3-(3-dimethylaminopropyl)carbodiimide (259 mg, 1.35 mmol). After stirring for 1 hour, the mixture was warmed to room temperature and stirred an additional 4 hours. The volatiles were evaporated and the residue was dissolved in ethyl acetate and washed successively with 1N hydrochloric acid, water, saturated sodium bicarbonate, and brine. The organic layer was dried (sodium sulfate), filtered, and concentrated and the residue was flash chromatographed (Merck silica gel) eluting with 50% ethyl acetate in hexanes to give 510 mg. of product as an oil (1:1 mixture of diastereomers). $R_f$=0.40 (5% acetic acid in ethyl acetate).

f) (3S)-2,3,4,5-Tetrahydro-3-[[2-mercapto-3-(1-naphthalenyl)-1-oxopropyl]amino]-1-oxo-1H-1-benzazepine-1-acetic acid A solution of the product form part (e) (508 mg., 0.98 mmol) in methanol (6 ml., deoxygenated via argon bubbling) was cooled to 0° C. and treated with 1N sodium hydroxide (6 ml., deoxygenated via argon bubbling). The resulting mixture was stirred under argon for 1 hour. The solution was acidified with 10% potassium bisulfate and extracted with ethyl acetate. The organic layer was washed with brine, dried (sodium sulfate), filtered and concentrated to give a clear oil. This residue was flash chromatographed (Merck silica gel) eluting with 1% acetic acid in 1:1 hexanes/ethyl acetate. The fractions containing pure product were combined, concentrated, azeotroped with ethyl acetate, and washed with water to remove the acetic acid. The organic layer was dried (sodium sulfate), filtered and concentrated. The residue was taken up in ethyl acetate and triturated with ethyl ether and hexane. The solvent was removed and the residue was slurried in hexane, stripped, and dried in vacuo to give 327 mg of product as a white powdery foam; $R_f$=0.64 (5% acetic acid in ethyl acetate); $[\alpha]_D$=−187.3° (C=0.43, chloroform).

Anal. calc'd for $C_{25}H_{23}N_2O_4S \cdot 0.42\ H_2O$: C,65.98; H,5.28; N, 6.16; S,7.05 Found: C,66.29; H,5.29; N,5.85; S,6.65.

HPLC: $t_R$=12.3 min (48.1%) and 14.4 min (51.8 %) ($\lambda$=220 nm), YMC S-30DS (C-18) 6.0×150 mm; 68% (10% water-90% methanol-0.2 % phosphoric acid)/32% (90% water-10% methanol.2% phosphoric acid), flow rate=1.5 ml/min, isocratic.

EXAMPLE 27

[S-(R*,R*)]-3-[[2-(Acetylthio)-1-oxo-3-phenylpropyl]amino]-2,3,4,5-tetrahydro-1-oxo-1H-benzazepine-1-acetic acid The product from Example 6 (799 mg., 2.0 mmol.) was added to a de-oxygenated (argon bubbling) solution of potassium bicarbonate (378 mg., 3.8 mmol.) in water (25 ml.). Upon dissolution of the starting material, acetic anhydride (1.5 ml., 1.62 g., 15.9 mmol.) was added. A milky white solution was obtained which eventually produced a gum. After stirring at room temperature for minutes, the mixture was acidified with 10% hydrochloric acid and extracted with ethyl acetate. The ethyl acetate extract was washed with water (3 times) and brine, then dried (sodium sulfate), filtered, and stripped. The residue was flash chromatographed (Merck silica gel, 1% acetic acid in ethyl acetate) and the desired fractions were stripped, azeotroped with ethyl acetate (3 times), taken up in a small volume of ethyl acetate and triturated with hexane. The solvent was stripped and the residue was slurried and stripped twice from hexane to give the title compound as a hard white foam. TLC (1% acetic acid in ethyl acetate) $R_f$=0.41; $[\alpha]_D$=−190.8° (c=0.68, chloroform).

Anal.calc'd. for $C_{23}H_{24}N_2O_5S \cdot 0.13\ C_4H_8O_2 \cdot 0.5\ H_2O$: C, 61.28; H, 5.69; N, 6.08; S, 6.96 Found: C, 61.18; H, 5.64; N, 5.90; S, 6.70.

EXAMPLES 28–30

Following the procedure of Example 27 but employing benzoyl chloride as the acylating agent, [S-(R*,R*)]-[3-[[2-(benzoylthio)-1-oxo-3-phenylpropyl]amino]-2,3,4,5-tetrahydro-2-oxo-1H-benzazepine-1-acetic acid was obtained; m.p. 170°–171° C.; $[\alpha]_D$=−244° (c=0.30, chloroform). TLC (hexane:ethyl acetate:acetic acid, 40:60:1) $R_f$=0.31.

Anal. calc'd. for $C_{28}H_{26}N_2O_5S \cdot 0.1\ C_4H_8O_2 \cdot 0.2H_2O$: C, 66.24; H, 5.32; N, 5.44; S, 6.23 Found: C, 66.28; H, 5.23; N, 5.40; S, 6.18.

Following the procedure of Example 27 but employing propionic anhydride as the acylating agent, [S-(R*,R*)]-2,3,4,5-tetrahydro-3-[[1-oxo-2-[(1-oxpropyl)thio]-3-phenylpropyl]amino]-2-oxo-1H-benzazepine-1-acetic acid was obtained; m.p. 156°–157° C.; $[\alpha]_D$=−210° (c=0.31, chloroform). TLC (hexane:ethyl acetate:acetic acid, 40:60:1) $R_f$=0.34.

Anal. calc'd. for $C_{24}H_{26}N_2O_5S \cdot 0.07\ C_4H_8O_2$: C, 63.30; H, 5.81; N, 6.08; S, 9.96 Found: C, 63.32; H, 5.77; N, 5.90; S, 6.96.

Following the procedure of Example 27 but employing trimethylacetic anhydride as the acylating agent, [S-(R*,R*)]-3-[[2-[(2,2-dimethyl-1-oxopropyl)thio]-1-oxo-3-phenylpropyl]amino]-2,3,4,5-tetrahydro-2-oxo-1H-benzazepine-1-acetic acid was obtained; m.p. 86°–90° C.; $[\alpha]_D$=−190° (c =3.06, chloroform). TLC (hexane:ethyl acetate:acetic acid, 30:70:1) $R_f$=0.42.

Anal. calc'd. for $C_{26}H_{30}N_2O_5S \cdot 0.2\ C_6H_{14} \cdot 0.25\ H_2O$: C, 64.78; H, 6.65; N, 5.50; S, 6.36 Found: C, 64.79; H, 6.56; N, 5.53; S, 6.30.

EXAMPLE 31

[S-(R*,R*)]-3,4-Dihydro-3-[(2-mercapto-1-oxo-3-phenylpropyl)amino]-4-oxo-1,5-benzoxazemine-5 (2H)-propionic acid a) (S)-3-[[(Dimethylethoxy)carbonyl]amino]-3,4-dihydro-4-oxo-1,5-benzoxazepine-5(2H)-propanoic acid, ethyl ester A solution of (S)-3-[[(dimethylethoxy)-carbonyl]amino]-2,3-dihydro-1,5-benzoxazepin-4(5H)-one [prepared as described in Example 13(c), 1.49 g., 5.35 mmol.) in tetrahydrofuran:t-butanol (2:1, 21 ml.) was cooled to 0° C. and treated with ethyl acrylate (0.81 ml. 7.50 mmol., 1.4 eq.) and then 1.0N t-butanol, potassium salt (535 µL, 0.1 eq.). The reaction mixture was stirred at 0° C. for 15 minutes then at room temperature for 2.5 hours under argon. An additional amount of 1.0N t-butanol, potassium salt/tetrahydrofuran (270 µL, 0.05 eq.) was added to the reaction. The reaction was stirred at room temperature for 45 minutes and then heated to 60° C. for 2 hours. The reaction was quenched with 25% ammonium chloride (50 ml.) and extracted with ethyl acetate (2×100 ml.). The combined organics were washed with 25% ammonium chloride (50 ml.), water (50 ml.), and brine (50 ml.), dried over magnesium sulfate, filtered and concentrated to yield a clear syrup. The residue showed two spots by TLC.

The reaction was restarted by treating a solution of the mixture (1.42 g., 5.10 mmol.) in tetrahydrofuran:t-butanol (2:1, 15 ml.) cooled to 0° C., with ethyl acrylate (0.77 ml., 7.14 mmol., 1.4 eq.) and then 1.0N t-butanol, potassium salt/tetrahydrofuran (510 µL, 0.1 eq.). The reaction mixture was stirred at 0° C. for 15 minutes then at room temperature for 3 hours. The reaction was quenched with 25% ammonium chloride (50 ml.) and extracted with ethyl acetate (2×100 ml.). The combined organics was washed with 25% ammonium chloride (50 ml.), water (50 ml.), and brine (50 ml.), dried over magnesium sulfate, filtered and concentrated to yield a yellow syrup. The residue was purified by chromatography on a 5×15 cm. silica gel column eluting with 30% ethyl acetate/hexane mixture (2 l.). The desired fractions were combined and concentrated to afford 1.40 g. of the title compound as a clear syrup. TLC (5% methanol/chloroform) $R_f$=0.63.

b) (S)-3-Amino-3,4-dihydro-4-oxo-1,5-benzoxazepine-5 (2H)-propanoic acid, ethyl ester, hydrochloride salt The product from part (a) (1.4 g., 3.7 mmol.) was treated with 4.0M hydrochloric acid/dioxane (20 ml., 80 mmol.) and cooled to 0° C. The resultant solution was stirred at 0° C. for 30 minutes, then at room temperature for 2 hours. The reaction mixture was concentrated, stripped with ethyl ether (twice), azeotroped with toluene (three times) and dried in vacuo for 4 hours affording 1.05 g. of title compound.

c) [(S-(R*,R*)]-3-[[2-(Acetylthio)-1-oxo-3-phenylpropyl]amino]-3,4-dihydro-4-oxo-1,5-benzoxazepine-5(2H)-propanoic acid, ethyl ester (S)-2-(Acetylthio)benzenepropanoic acid, dicyclohexylamine salt (1.8 g., 4.40 mmol.) was suspended in ethyl acetate (100 ml.) and washed with 5% potassium bisulfate (5×25 ml.) and brine (30 ml.), dried (anhydrous magnesium sulfate), filtered, evaporated to dryness and dried in vacuo to give the free acid.

This free acid was dissolved in dry methylene chloride (10 ml.), cooled to 0° C. (ice - salt bath) and treated with a solution of the product from part (b) (1.05 g., 3.33 mmol.) in dry methylene chloride (25 ml.), followed by triethylamine (0.62 ml., 4.44 mmol., 1.3 eq.) and benzotriazol-1-yloxytris-(dimethylamino)phosphonium hexafluorophosphate (1.96 g., 4.44 mmol., 1.3 eq.). The reaction mixture was stirred at 0° C. for 1 hour then at room temperature overnight. The reaction mixture was concentrated to dryness, diluted with ethyl acetate (150 ml.) and washed with 5% potassium bisulfate (2×50 ml.), water (2×50 ml.), and brine (50 ml.), dried (anhydrous magnesium sulfate), filtered, and evaporated to dryness. The crude product was chromatographed on a silica gel column (5×15 cm), eluting with 30% ethyl acetate/hexane. The desired fractions were combined and concentrated, affording 740 mg. pure product. TLC (10% methanol in chloroformm) $R_f$=0.74.

d) [S-(R*,R*)]-3,4-Dihydro-3-[(2-mercapto-1-oxo-3-phenylpropyl)amino]-4-oxo-1,5-benzoxazepine-5(2H)-propanoic acid A solution of the product from part (c) (740 mg., 1.53 mmol.) in methanol (15 ml.) was cooled to 0° C. (ice-salt bath), purged with argon for 30 minutes and then treated dropwise with a previously purged (argon, 30 minutes) solution of 1.0N sodium hydroxide (6.1 ml., 4 eq.) maintaining the bubbling of argon throughout the addition and length of the reaction. The reaction mixture was stirred at 0° C. for 1 hour, acidified at 0° C. with 5% potassium bisulfate (150 ml.) to pH 1.5 and then extracted with ethyl acetate (3×100 ml.). The combined organic extracts were washed with brine (100 ml.), dried (anhydrous sodium sulfate), filtered, evaporated to dryness and dried in vacuo to a white foam (612 mg.). The residue was purified by column chromatography on a 5×15 cm. silica gel column eluting with 0.5% acetic acid in ethyl acetate. The residue was dissolved in methylene chloride (5 ml.) and stripped with hexane (5 times) on the rotovap, scratching the mixture to form a white foam/solid. The solid was dried in vacuo overnight to give 590 mg. of product. TLC (1% acetic acid in ethyl acetate) $R_f$=0.42. $[\alpha]_D$=−127.6° (c=1.12, methanol).

Anal. calc'd. for $C_{21}H_{22}N_2O_5S \cdot 0.03\ H_2O$: C, 60.86; H, 5.36; N, 6.75; S, 7.73 Found: C, 61.08; H, 5.68; N, 6.45; S, 7.51.

EXAMPLE 32

[2R-[2α,3α(S*)]]-3,4-Dihydro-3-F(2-mercapto-1-oxo-3-phenylpropyl)amino]-2-methyl-4-oxo-1,5-benzoxazepine-5(2H)-acetic acid a) N-[(1,1-Dimethylethoxy)carbonyl]-O-(2-nitrophenyl)-L-threonine A solution of N-[(1,1-dimethylethoxy)-carbonyl]-L-threonine (5.02 g., 22.9 mmol.) in dry dimethylformamide (10 ml.) was added dropwise over a period of 30 minutes to a cooled (0° C.) suspension of 60% sodium hydride (1.93 g., 48.25 mmol., 2.11 eq.) in dry dimethylformamide (40 ml.). The reaction was stirred at 0° C. until the frothing subsided (about 3.5 hours). The reaction mixture was treated dropwise with 1-fluoro-2-nitrobenzene (2.67 ml., 25.2 mmol., 1.1 eq.) over a period of 20 minutes and stirred at 0° C. under argon for 2 hours. The reaction mixture was then placed in the cold room (5° C.) and stirred overnight. The reaction mixture was poured into ice-water (500 ml.) and extracted with ethyl ether (2×200 ml.). The aqueous phase was brought to pH 1.0 with 6N hydrochloric acid (200 ml.) and extracted with ethyl acetate (3×300 ml.). The combined ethyl acetate extracts were washed with water (2×300 ml.), and brine (300 ml.), dried (anhydrous sodium sulfate), filtered, evaporated to dryness and dried in vacuo. The crude residue was loaded onto celite and purified by chromatography on a 10×20 cm. silica gel column. Elution with methylene chloride (3 l.), 99:1 methylene chloride:methanol (2 l.), 95:5 methylene chloride:methanol, and 100:5:0.5 methylene chloride:methanol:acetic acid (5 l.) gave 6.07 g. of title compound. TLC (methylene chloride:methanol:acetic acid, 100:5;0.5) $R_f$=0.16.

b) N-[(1,1-Dimethylethoxy)carbonyl]-O-(2-aminophenyl)-L-threonine

A solution of the product from part (a) (1.0 g., 2.94 mmole) in dry methanol (20 ml.) was treated with 10% palladium on carbon catalyst (35 mg.) and hydrogenated at 40 psi for 5.5 hours. The reaction was not complete so an additional 50 mg. of 10% palladium on carbon catalyst was added and the reaction mixture was hydrogenated for an additional 1.5 hours. The reaction mixture was filtered through a celite pad in a millipore unit, washing the pad with methanol. The dark filtrate was evaporated to dryness and dried in vacuo to give 0.856 g. of title product as a dark solid. TLC (methylene chloride: methanol:acetic acid, 20:1:1) $R_f$=0.16.

c) (2R-cis)-3-[[(Dimethylethoxy)carbonyl]amino]-2,3-dihydro-2-methyl-1,5-benzoxazepin-4(5H)-one A solution of the product from part (b) (0.8 g., 2.58 mmol.) in dry dimethylformamide (6 ml.) was treated with 1-ethyl-3-(3-dimethylamino-propyl)carbodiimide (495 mg., 2.58 mmol.) and stirred at room temperature for 3 hours. The reaction mixture was partitioned between ethyl acetate (50 ml.) and 50% sodium bicarbonate solution (50 ml.). The aqueous layer was separated and extracted with ethyl acetate (2×50 ml.). The combined organic extracts were washed with water (3×50 ml.) and brine (50 ml.), dried (anhydrous magnesium sulfate), filtered, evaporated and dried in vacuo to yield a crude yellow solid. The crude product was chromatographed on a silica gel column(5×15 cm.), eluting with 25% ethyl acetate/hexane to give 568 mg. of title compound as an off white solid. TLC (ethyl acetate:hexane, 1:1) $R_f$=0.47.

d) (2R-cis)-3-[[(Dimethylethoxy)carbonyl]amino]-3,4-dihydro-2-methyl-4-oxo-1,5-benzoxazepine-5(2H)-acetic acid, ethyl ester A solution of the product from part (c) (319 mg., 1.09 mmol.) and ethyl bromoacetate (151.3 µl. 1.36 mmol., 1.25 eq.) in dry tetrahydrofuran (3 ml.) was added to a cooled 0° C. suspension of 60% sodium hydride (53 mg., 1.32 mmol., 1.21 eq., washed with hexane, 3 times) in dry tetrahydrofuran (2 ml.) over a period of 5 minutes. The reaction mixture was stirred at 0° C. for 1 hour and then at room temperature for 30 minutes. The reaction mixture was quenched with 25% ammonium chloride solution (5 ml.) and extracted with methylene chloride (2×20 ml.). The combined organics were washed with 25% ammonium chloride solution (10 ml.) and brine (10 ml.), dried (anhydrous magnesium sulfate), filtered. concentrated and dried in vacuo to yield 400 mg. of title product. TLC (ethyl acetate:hexane, 1:1) $R_f$=0.55.

e) (S)-3-Amino-3,4-dihydro-2-methyl-4-oxo-1,5-benzoxazepine-5(2H)-acetic acid, ethyl ester, hydrochloride salt 4.0M Hydrochloric acid in dioxane (5.5 ml., 22 mmole, 20.8 eq.) was added to the product from part (d) (400 mg., 1.06 mmol.) cooled to 0° C. The resultant solution was stirred at 0° C. for thirty minutes, then at room temperature for 3 hours. The reaction mixture was removed by rotovap, concentrated with ethyl ether (3×10 ml.) and dried in vacuo over sodium hydroxide pellets overnight to yield 350 mg. of title product. TLC (methylene chloride:methanol, 9:1) $R_f$=0.49.

f) [2R-[2α,3α(S*)]]-3-[[2-(Acetylthio)-1-oxo-3-phenylpropyl]amino]-2-methyl-4-oxo-1.5-benzoxazepine-5 (2H)-acetic acid A suspension of (S)-2-(acetyl-thio)benzenepropanoic acid, dicyclohexylamine salt (495 mg., 1.22 mmol., 1.1 eq.) in ethyl acetate (30 ml.) was washed with 5% potassium bisulfate (5×5 ml.) and brine (10 ml.), dried (anhydrous magnesium sulfate), filtered, evaporated to dryness and dried in vacuo to give the free acid as a clear syrup (278 mg.) in quantitative yield.

This free acid was dissolved in dry methylene chloride (10 ml.), cooled to 0° C. (ice-salt bath) and treated with a solution of the product from part (e) (350 mg., 1.11 mmol.) in dry methylene chloride (2 ml.), followed by triethylamine (163 μl., 1.17 mmol., 1.05 eq. ) and benzotriazol-1-yloxytris-(dimethylamino)phosphonium hexafluorophosphate (515.5 mg., 1.17 mmol., 1.05 eq.). The reaction mixture was stirred at 0° C. for 1 hour then at room temperature for 3.5 hours. The reaction was not complete by TLC so an additional amount of triethylamine (54 μl., 0.389 mmol.) and benzotriazol-1-yloxytris(dimethyl-amino) phosphonium hexafluorophosphate (172 mg., 0.389 mmol.) was added and the reaction was stirred for 1 hour. The reaction mixture was concentrated to dryness, dissolved in ethyl acetate, washed with 0.5N hydrochloric acid (2×10 ml.), water (10 ml.), and brine (10 ml.), dried (anhydrous magnesium sulfate), filtered, and evaporated to dryness. The crude product was chromatographed on a silica gel column (3×16 cm.), eluting with 20% ethyl acetate/hexane. The desired fractions were combined and concentrated, affording 378 mg. of pure title product. TLC (ethyl acetate:hexane, 1:1) $R_f=0.48$.

g) [2R-[2α,3α(S*)]]-3,4-Dihydro-3-[(2-mercapto-1-oxo-3-phenylpropyl)amino]-2-methyl-4-oxo-1,5-benzoxazepine-5 (2H) -acetic acid A solution of the product from part (f) (297 mg., 0.61 mmol. ) in methanol (4 ml.) was purged with argon for 30 minutes, cooled to 0° C. (ice-salt bath) then treated dropwise with a previously purged (argon, 30 minutes) solution of 1.0N sodium hydroxide (2.45 ml., 4 eq.) maintaining the bubbling of argon throughout the addition and length of the reaction. The reaction mixture was stirred at 0° C. for 1 hour, acidified at 0° C. with 5% potassium bisulfate (20 ml.) to pH 1.5 and then extracted with ethyl acetate (2×50 ml.). The combined organic extracts were washed with brine (25 ml.), dried (anhydrous sodium sulfate), filtered, evaporated to dryness and dried in vacuo to yield a glassy oil (351 mg.). The crude residue was dissolved in methylene chloride (5 ml.) and treated portionwise with hexane (50 ml.), scratching the mixture to form a solid. The supernatant was decanted and the solids triturated with more hexane (50 ml.) and pentane (2×100 ml.), stirring with the first 100 ml. of pentane for 4 hours and the next 100 ml. overnight under argon. The pentane was decanted and the white amorphous solid was dried in vacuo overnight to give 240 mg., of title product. TLC (2% acetic acid in ethyl acetate) $R_f=0.48$; $[\alpha]_D=-101.1$ (c=1, methanol).

Anal.calc'd. for $C_{21}H_{22}N_2O_5S \cdot 0.40\ C_4H_8O_2 \cdot 0.08\ H_2O$: C, 60.36; H, 5.65; N, 6.23; S, 7.13 Found: C, 60.17; H, 5.57; N, 6.16; S, 7.45.

EXAMPLE 33

Following the procedure of Example 32 but starting with allo-L-threonine, [2S-[2α,3β(R*)]]-3,4-dihydro-3-[(2-mercapto-1-oxo-3-phenylpropyl)amino]-2-methyl-4-oxo-1,5-benzoxazepine-5(2H)-acetic acid was obtained; $[\alpha]_D=-174.3°$ (c=0.89, methanol) TLC (1% acetic acid in ethyl acetate) $R_f=0.43$.

EXAMPLE 34

(2S)-3-[(2-Mercapto-1-oxo-3-phenylpropyl)amino]-3,4,5,6-tetrahydro-2-oxo-1-benzazocine-1(2H)-acetic acid a) 1-Benzosuberone, oxime A solution of hydroxylamine hydrochloride (2.39 g., 34.33 mmole, 1.1 eq.) in water (16 ml.) was added to a solution of 1-benzosuberone (4.67 ml., 31.21 mmole) in pyridine (9.0 ml.) and ethanol (16 ml.). The reaction mixture was refluxed (bath temperature 105° C.) for 35 minutes. The reaction mixture was cooled, diluted with ethyl acetate (100 ml.) and water (40 ml.) and the layers were separated. The aqueous layer was extracted with ethyl acetate (2×50 ml.). The combined organic extracts were washed with 1N hydrochloric acid (3×100 ml.), dried (anhydrous magnesium sulfate), filtered, and concentrated to obtain a crude off-white solid (5.60 g.). The residue was purified by chromatography on 10×20 cm. silica gel column. Elution with hexane (21), followed by 10% ethyl acetate/hexane (5 l.) afforded 4.40 g. of title compound as an off-white solid. TLC (10% ethyl acetate/hexane) $R_f=0.35$.

b) 3,4,5,6-Tetrahydro-1-benzazocin-2(1H)-one

Concentrated sulphuric acid (8.8 ml.) was added in one portion to a suspension of the product from part (a) (4.33 g., 24.71 mmol.) in glacial acetic acid (4.4 ml.). The temperature rose to 83° C. and the reaction mixture was heated to 160° C. (oil bath) for 10 minutes. The reaction mixture was allowed to cool to room temperature and was then poured into ice-water (100 ml.). The reaction mixture was adjusted to pH 11 with 10N sodium hydroxide solution. The mixture was diluted with ethyl acetate (250 ml.) and water (100 ml.) and the layers were separated. The aqueous layer was extracted with ethyl acetate (3×100 ml.). The combined ethyl acetate extracts were washed with water (150 ml.) and brine (150 ml.), dried (anhydrous sodium sulfate), filtered and concentrated to yield 2.8 g. of title product. TLC (ethyl acetate) $R_f=0.33$.

c) 3,4,5,6-Tetrahydro-3-bromo-1-benzazocin-2(1H)-one

A solution of the product from part (b) (8.31 g., 47.42 mmole) in chloroform (115 ml.) was cooled to 0° C., treated with phosphorus pentachloride (11.36 g., 54.53 mmole, 1.15 eq.) and iodine (114 mg.) and stirred for 30 minutes at 0° C. under argon. The yellow reaction mixture was treated with bromine (2.92 ml., 56.90 mmole, 1.2 eq.), warmed to room temperature and refluxed under argon for 3.5 hours. The reaction mixture was allowed to cool to room temperature and added to ice-water (100 ml.). The layers were separated and the chloroform layer was washed with water (100 ml.), dried over magnesium sulfate, filtered and concentrated. The crude residue was recrystallized from hot ethyl acetate affording 8.69 g. of title product. TLC (ethyl acetate:hexane, 1:1) $R_f=0.36$.

d) 3,4,5,6-Tetrahydro-3-azido-1-benzazocin-2(1H)-one

A solution of the product from part (c) (6.87 g., 27.03 mmole) and sodium azide (2.28 g., 35.14 mmole, 1.3 eq.) in dimethylsulfoxide (130 ml.) was stirred at 60° C. (oil bath) under argon for 5 hours. The reaction mixture was cooled to room temperature and poured into cold water (400 ml.) and stirred for 15 minutes. The precipitate was filtered, washing the solids with water (1 l.) and dried overnight in vacuo over drierite to give the title product. TLC (ethyl acetate:hexane, 1:1) $R_f=0.63$.

e) 3-Azido-3,4,5,6-tetrahydro-2-oxo-1-benzazocine-1(2H)-acetic acid, ethyl ester A solution of the product from part (d) (5.454 g., 25.22 mmole) and ethyl bromoacetate (3.5 ml., 31.53 mmole, 1.25 eq.) in dry tetrahydrofuran (50 ml.) was added to a cooled (0° C.) suspension of 60% sodium hydride [1.23 g., 30.77 mmole, 1.22 eq.; washed with hexane (3×10 ml.)]in dry tetra-hydrofuran (15 ml.) over a period of 15 minutes. The mixture was stirred at 0° C. for 1 hour and then at room temperature for 30 minutes. The reaction mixture was quenched with 25% ammonium chloride solution (100 ml.) and extracted with ethyl acetate (2×250 ml.). The combined ethyl acetate extracts were washed with 25% ammonium chloride solution (100 ml.) and brine (100 ml.), dried (anhydrous magnesium sulfate), filtered, and concentrated to yield the title compound as a yellow oil. TLC (35% ethyl acetate/hexane) $R_f$=0.35.

f) 3-Amino-3,4,5,6-tetrahydro-2-oxo-1-benzazocine-1 (2H)-acetic acid, ethyl ester A solution of the product from part (e) (9.0 g., 29.83 mole) in absolute ethanol (50 ml.) was treated with 10% palladium on carbon catalyst (900 mg.) and hydrogenated at 45 psi for 5 hours, venting the Parr bottle twice in the first 1.5 hours. The mixture was filtered through a millipore unit, washing thoroughly with ethanol. The clear filtrate was evaporated to dryness and dried in vacuo to afford 7.59 g. of the title product as a thick yellow syrup. TLC (10% methanol/ methylene chloride) $R_f$=0.29.

g) (2S)-3-[[2-(Acetylthio)-1-oxo-3-phenylpropyl]-amino]-3,4,5,6-tetrahydro-2-oxo-1-benzazocine-1(2H) -acetic acid, ethyl ester A suspension of (S)-2-(acetylthio)benzene-propanoic acid dicyclohexylamine salt (2.1 g., 5.18 mole. 1.1 eq..) in ethyl acetate (100 ml.) was washed with 5% potassium bisulfate (5×25 ml.) and brine (30 ml.), dried (anhydrous magnesium sulfate), filtered, evaporated to dryness and dried in vacuo to give the free acid as a clear syrup (1.24 g.) in quantitative yield.

This free acid was dissolved in dry methylene chloride (45 ml.), cooled to 0° C. (ice-salt bath) and treated with a solution of the product from part (f) (1.3 g., 4.71 mole) in dry methylene chloride (10 ml.), followed by triethylamine (723 μL., 5.18 mmol., 1.1 eq.) and benzotriazol-1-yloxytris-(dimethylamino)phosphonium hexafluorophosphate (2.29 g., 5.18 mmol., 1.1 eq.). The reaction mixture was stirred at 0° C. for 1 hour then at room temperature overnight. The reaction mixture was concentrated to dryness, diluted with ethyl acetate (125 ml.), washed with 0.5N hydrochloric acid (2×25 ml.), water (25 ml.), and brine (25 ml.), dried (anhydrous magnesium sulfate), filtered, and evaporated to dryness. The crude product was chromatographed on a silica gel column (3×16 cm.), eluting with 30% ethyl acetate/ hexane. The desired fractions were combined and concentrated, affording 1.77 g. of pure title compound. (1:1 mixture of diastereoisomers). TLC (ethyl acetate:hexane, 1:1) $R_f$=0.39.

h) (2S)-3-[(2-Mercapto-1-oxo-3-phenylpropyl)amino]-3, 4,5,6-tetrahydro-2-oxo-1-benzazocine-1(2H)-acetic A solution of the product from part (g) (1.75 g., 3.62 mmole) in methanol (25 ml.) was purged with argon for 30 minutes, cooled to 0° C. (ice-salt bath) then treated dropwise with a previously purged (argon, 30 minutes) solution of 1.0N sodium hydroxide (14.5 ml., 4 eq.) maintaining the bubbling of argon throughout the addition and length of the reaction. The reaction mixture was stirred at 0° C. for 1 hour, acidified at 0° C. with 5% potassium bisulfate (200 ml.) to pH 1.5 and then extracted with ethyl acetate (2×200 ml.). The combined organic extracts were washed with brine (200 ml.), dried (anhydrous sodium sulfate), filtered, evaporated to dryness and dried in vacuo to yield a white foam (1.67 g.). The crude residue was dissolved in methylene chloride (10 ml.) and treated portionwise with hexane (50 ml.), scratching the mixture to form a solid. The supernatant was decanted and the solids triturated with more hexane (50 ml.) and pentane (2×100 ml.), stirring with the first 100 ml. of pentane for 4 hours and the next 100 ml. overnight under argon. The pentane was decanted and the white amorphous solid was dried in vacuo overnight to give 1.388 g. of title product (1:1 mixture of diastereoisomers); m.p. 107°–111° C.; $[\alpha]_D$=+28.3° (c=1.0, methanol). TLC (methylene chloride:methanol:acetic acid, 20:1:1) $R_f$=0.44.

EXAMPLE 35

[4S-[4α,7α(R*),10aβ]]-Decahydro-7-[(2-mercapto-1-oxo-3-phenylpropyl)amino]-6-oxopyrido[1,2-a]azepino-4-carboxylic acid a) (S)-2-Phthalimido-4-pentenoic acid, dicyclohexylamine salt A homogeneous solution of (S)-2-amino-4-pentenoic acid (2.988 g., 25.9 mmol) and sodium carbonate (2.600 g., 24.5 mmol.) in water (55 ml.) was treated with solid N-(carbethoxy)phthalamide (5.677 g., 25.9 mmol.). After stirring at room temperature for 2.5 hours, the mixture was acidified with 10% hydrochloric acid and extracted with ethyl acetate. The ethyl acetate extract was washed with brine, dried (sodium sulfate), filtered, and stripped. The residue was flash chromatographed twice (2% acetic acid in ethyl acetate) and the desired product fractions were combined, stripped, and azeotroped with toluene. The residue was dissolved in ethyl ether, treated with 5.3 ml. of dicyclohexylamine and seeded. The resulting white precipitate was collected by filtration, washed with ethyl ether, and dried in vacuo to give 7.620 g. of pure title product; m.p. 196°–197° C.; $[\alpha]_D$=–13.9° (c=0.8, methanol). TLC (5% acetic acid in ethyl acetate) $R_f$=0.57.

b) [S-(R*,R*)]-2-[(2-Phthalimido-1-oxo-4-pentenyl) amino]-6-hydroxyhexanoic acid, methyl ester A slurry of (S)-2-amino-6-hydroxyhexanoic acid (2.42 g., 16.4 mmole) in dry methanol (60 ml.) was treated with gaseous hydrogen chloride until the mixture began to reflux. The homogeneous solution was then stirred at room temperature for 2.5 hours. The solvent was stripped and the residue azeotroped three times with toluene to give crude (S)-2-amino-6-hydroxyhexanoic acid, methyl ester, hydrochloride salt as an oil. This oil was dissolved in dimethylformamide (20 ml.) and methylene chloride (50 ml.) and treated with 4-methyl morpholine (3.20 ml., 2.94 g., 29.1 mmole). This mixture was cooled to 0° C. and treated with (S)-2-phthalimido-4-pentenoic acid [obtained from 7.0 g., 16.4 mmole of the salt product from part (a) by partitioning between 10% potassium bisulfate and ethyl acetate] in methylene chloride (10 ml.), followed by solid hydroxybenzo-triazole (2.22 g., 16.4 mmole) and ethyl-3-(3-dimethylamino)propyl carbodiimide, hydrochloride salt (3.458 g., 18.0 mmole). After stirring at 0° C. for 0.5 hour and at room temperature for 2 hours, the reaction was partitioned between ethyl acetate and 0.5N hydrochloric acid. The ethyl acetate extract was washed successively with water, 50% saturated sodium bicarbonate, and brine, then dried (sodium sulfate), filtered and stripped. The residue was flash chromatographed (Merck silica gel, ethyl acetate) to give pure title compound as an oil which solidified upon standing. The solid was triturated with ethyl ether and hexane and collected by filtration to give 5.149 g. of analytically pure title product; m.p. 90°–92° C.; $[\alpha]_D$=+25.6 (c=1.1, chloroform). TLC (ethyl acetate) $R_f$=0.36.

c) [S-(R*,R*)]-2-[(2-Phthalimido-1-oxo-4-pentenyl) amino]-6-oxohexanoic acid, methyl ester A –78° C. solution of oxalyl chloride (1.38 ml., 0.95 g., 7.5 mmol.) in methylene chloride (70 ml.) was treated dropwise with a solution of dry dimethylsulfoxide (2.20 ml., 2.00 g., 25.6 mmol.) in methylene chloride (2 ml.). After 10 minutes, the mixture was treated with a solution of the product from part (b) (5.04 g., 13.0 mmol.) in methylene chloride (15 ml.). After an additional 10 minutes, triethylamine (9.0 ml.) was added and the mixture was stirred at −78° C. for 5 minutes, then allowed to warm gradually to 0° C. The mixture was partitioned between ethyl acetate/ethyl ether and 0.5N hydrochloric acid. The organic extract was washed with 50% saturated sodium bicarbonate and brine, then dried (sodium sulfate), filtered and stripped. The residue was crystallized from ethyl acetate/ethyl ether to afford compound 4.567 g. of title product as a white solid. The mother liquor was flash chromatographed (Merck silica gel, 6/4-ethyl acetate/hexanes) and crystallized to give an additional 184 mg. of product for a total of 4.751 g.; m.p. 74°–76° C.; $[\alpha]_D$=+25.2° (c=1.3, chloroform). TLC (ethyl acetate:hexanes, 6:4) $R_f$=0.22.

d) [S-(R*,R*)-1,2,3,4-Tetrahydro-(1-oxo-2-phthalimido-4-pentenyl)-2-pyridinecarboxylic acid, methyl ester A solution of the product from part (c) (3.657 g., 9.46 mmole) and trifluoroacetic acid (190 μl.) in methylene chloride (70 ml.) was refluxed under argon for 1.5 hours. The cooled mixture was washed with dilute aqueous sodium bicarbonate, dried (sodium sulfate), filtered and stripped. The residue was flash chromatographed (Merck silica gel), 1:1 ethyl acetate:hexanes) to afford 3.417 g. of the title product as an oil/foam. TLC (ethyl acetate:hexanes) $R_f$=0.50.

e) [4S-(4α,7α,10aβ)]-Decahydro-9-iodo-6-oxo-7-phthalimidopyrido[1,2-a]azepine,4-carboxylic acid, methyl ester A solution of the product from part (d) (1.427 g., 3.87 mmole) in methylene chloride (8.8 ml.) was added dropwise to a mixture of trifluoromethane-sulfonic acid (2.2 ml.) and trifluoromethanesulfonic anhydride (210 μl.) at room temperature. The bright yellow solution was stirred for 5.5 hours, then poured into ice water and extracted with ethyl acetate. The ethyl acetate extract was washed with brine, dried (sodium sulfate), filtered and stripped. The crude residue (predominantly a mixture of carboxylic acids) was dissolved in methanol (3 ml.) and methylene chloride (20 ml.) and treated with excess ethereal diazomethane for 25 minutes. The excess diazomethane was removed via argon bubbling and the solvent was stripped. The residue was dissolved in methyl ethyl ketone (40 ml.) and treated with sodium iodide (2.48 g.). After stirring at room temperature for 1 hour, the mixture was partitioned between ethyl acetate and water which contained a small amount of sodium bisulfite. The organic layer was washed with brine, dried (sodium sulfate), filtered and stripped. The residue was flash chromatographed (Merck silica gel, 1:1 ethyl acetate:hexanes followed by 6:4 ethyl acetate: hexanes) to give 1.125 g. of title product as a white foam; $[\alpha]_D$=−17.1° (c=0.7, chloroform). TLC (ethyl acetate:hexanes, 6:4) $R_f$=0.43.

In addition 206 mg. of [4S-(4α,7α,10aβ)]-1,2,3,4,6,7,8,10a-octahydro-6-oxo-7-phthalimido-pyrido[1,2-a]azepine, 4-carboxylic acid, methyl ester was obtained and was triturated with ethyl ether to a white solid; m.p. 162°–166° C.; $[\alpha]_D$=−106.0° (c=0.8, chloroform). TLC (ethyl acetate:hexanes, 6:4) $R_f$=0.36.

f) [4S- (4α,7α,10aβ)]-Decahydro-6-oxo-7-phthalimio-pyrido[1,2-a]azepine, 4-carboxylic acid, methyl ester A solution of the title product from part (e) (1.068 g., 2.15 mmole) and tris(trimethylsilyl)silane (1.0 ml., 806 mg., 3.2 mmol.) in dry benzene (10 ml.) was heated to 50° C. and treated every 30 minutes with a catalytic amount (2–3 mg) of 2,2'-azobisisobutyronitrile. After 3.5 hours, additional silane (400 μL) was added and the reaction was continued.

After 5 hours, the slightly cloudy solution was cooled to room temperature and concentrated. The residue was triturated with ethyl ether and the resulting solid was collected by filtration and washed thoroughly with ethyl ether affording 522 mg. of essentially pure title product. The mother liquor was flash chromatographed (Merck silica gel, ethyl acetate:hexanes, 1:1) to give an additional 261 mg. of pure product for a total of 783 mg.; m.p. 179°–181° C.; $[\alpha]_D$=−10.6° (c=0.9, chloroform). TLC (ethyl acetate:hexanes, 1:1) $R_f$=0.25.

g) [4S-[4α,7α(R*),10aβ]]-Decahydro-7-[[2-(acetylthio)-1-oxo-3-phenylpropyl]amino]-6-oxopyrido-[1,2-a]azepine-4-carboxylic acid, methyl ester The product from part (f) (786 mg., 2.12 mpole) in methanol (10 ml.) and methylene chloride (2 ml.) was treated with hydrazinc monohydrate (135 μl 2.8 mmol.) and the solution was stirred at room temperature for 66 hours. The mixture was filtered and the solid was washed with methanol. The filtrate was stripped, triturated with methylene chloride, and filtered again. The filtrate was washed with water and the aqueous layer was back-extracted with methylene chloride. The pooled methylene chloride extracts were dried (sodium sulfate), filtered and stripped to afford 479 mg. of crude [4S-(4α,7α,10aβ)]-decahydro-7-amino-6-oxopyrido[1,2-a]-azapine-4-carboxylic acid, methyl ester as a colorless oil. TLC (10% methanol in methylene chloride) $R_f$=0.18.

A cold (0° C.) solution of (S)-2-(acetylthio) benzenepropanoic acid [obtained from the dicyclohexylamine salt as described previously, 524 mg., 2.33 mmol.), triethylamine (295 μl., 214 mg., 2.11 mmol.) and the above crude amine in methylene chloride (15 ml.) was treated with benzotriazol-1-yloxytris(dimethylamino)phosphonium hexafluorophosphate (940 mg., 2.12 mmol.). The solution was stirred at 0° C. for 1 hour and then at room temperature for 2 hours. The solvent was stripped and the residue was partitioned between ethyl acetate and 1N hydrochloric acid. The organic layer was washed successively with water, 50% saturated sodium bicarbonate and brine, then dried (sodium sulfate), filtered and stripped. The residue was flash chromatographed (Merck silica gel, ethyl acetate:hexanes, 1:1) to give 770 mg. of pure title compound as a white foam. TLC (ethyl acetate:hexanes) $R_f$=0.27.

b) [4S-[4α,7α(R*),10aβ]]-Decahydro-7-[(2-mercapto-1-oxo-3-phenylpropyl)amino]-6-oxopyrido[1,2-a]azepine-4-carboxylic acid A room temperature solution of the product from part (g) (755 mg., 1.70 mmol.) in methanol (8 ml., deoxygenated via argon bubbling) was treated with 1N sodium hydroxide (10 ml., deoxygenated via argon bubbling). After stirring for 3 hours, the mixture was acidified with 10% hydrochloric acid, diluted with water and extracted with ethyl acetate. The ethyl acetate extract was washed with brine, then dried (sodium sulfate), filtered and stripped. The residue was flash chromatographed (Merck silica gel, 1% acetic acid in ethyl acetate). The desired product fractions were stripped, azeotroped three times with ethyl acetate, taken up in a small amount of ethyl acetate and triturated with hexanes. The solvents were removed by rotary evaporation and the residue was again triturated with hexanes, stripped and dried in vacuo to afford 654 mg. of title product as a white amorphous powder; $[\alpha]_D$=−31.0° (c=0.8, chloroform). TLC (2% acetic acid in ethyl acetate) $R_f$=0.51.

Anal. calc'd. for $C_{20}H_{26}N_2O_4S \cdot 0.16\ C_4H_8O_2 \cdot 0.3\ H_2O$: C, 60.46; H, 6.85; N, 6.83; S, 7.82 Found: C, 60.57; H, 7.07; N, 6.57; S, 7.63.

EXAMPLE 36

[3S-[3α(R*),7β]]-Hexahydro-3-[2-mercapto-2-oxo-3-phenylpropyl)amino]-2-oxo-7-(2-propenyl)-1H-azepine-1-acetic acid a) (S)-N-(2-Phthalimido-1-oxohexyl)glycine, ethyl ester A slurry of glycine, ethyl ester, hydrochloride salt (2.718 g., 19.5 mmol.) in dimethylformamide (36 ml.) was treated with 4-methyl morpholine (2.60 ml., 2.39 g., 23.6 mmol.) and stirred at room temperature for 5 minutes. The mixture was then treated with (S)-2-phthalimido-6-hydroxyhexanoic acid (4.50 g., 16.2 mmol.) and hydroxybenzotriazole (2.225 g., 16.5 mmol.), cooled to 0° C., and then treated with ethyl-3-(3-dimethylamino)propyl carbodiimide, hydrochloride salt (3.438 g., 17.9 mmol.). After stirring at 0° C. for 1 hour and at room temperature for 2 hours, the mixture was partitioned between ethyl acetate and 0.5N hydrochloric acid and subsequently extracted three times with ethyl acetate. The pooled ethyl acetate extracts were washed in succession with water, saturated sodium bicarbonate, and brine, then dried (sodium sulfate), filtered and stripped to give 5.77 g. of title product as a colorless oil. TLC (ethyl acetate) $R_f$=0.34.

b) (S)-N (2-Phthalimido-1,6-dioxohexyl)glycine, ethyl ester

A -78° C. solution of oxalyl chloride (1.67 ml., 2.43 g., 19.1 mmol.) in methylene chloride (50 ml.) was treated dropwise with a solution of dry dimethylsulfoxide (2.70 ml., 2.97 g., 38.0 mmol.) in methylene chloride (2 ml.). After 15 minutes, a solution of the product from part (a) (5.770 g., 15.9 mmol.) in methylene chloride (25 ml.) was added. After an additional 15 minutes, the mixture was treated with triethylamine (10.0 ml.), stirred at -78° C. for 5 minutes, then let warm to 0° C. The resulting mixture was washed with 1N hydrochloric acid and brine, then dried (sodium sulfate), filtered and stripped. The residue was flash chromatographed (Merck silica gel, ethyl acetate:hexanes, 80:20) to give 5.170 g. of title compound as a colorless oil.

c) (6S-trans)-Tetrahydro-6-phthalimido-oxazolo[3.2-b]azepine-2,5(3H,6H)-dione

A solution of the product from part (b) (5.16 g., 14.3 mmol.) in trifluoroacetic acid (40 ml.) and chloroform (160 ml.) was refluxed under argon for 42 hours. The mixture was cooled to room temperature and neutralized with saturated aqueous sodium bicarbonate. The layers were separated and the aqueous layer was extracted with methylene chloride. The pooled organic layers were washed with brine, dried (sodium sulfate), and filtered through a short plug of silica gel, washing with 1:1-ethyl acetate:methylene chloride. The filtrate was stripped to give a solid residue. The residue was slurried in methylene chloride and triturated with ethyl ether to give 3.437 g. of title product as a white solid. m.p. 234°-240° C. TLC (acetone:hexane, 1:1) $R_f$=0.51.

d) (3S-trans)-Hexahydro-3-phthalimido-2-oxo-7-(2-propenyl)-1H-azepine-1-acetic acid A solution of the product from part (c) (2.6 g., 8.27 mmol.) and allyltrimethylsilane (10.0 ml., 7.19 g., 62.9 mmol.) in methylene chloride (75 ml.) at room temperature was treated with stannic bromide (1.0M in methylene chloride, 16.5 ml., 16.5 mmol.). After stirring at room temperature for 9 hours and then at -20° C. for 14 hours, the mixture was quenched with water and extracted with ethyl acetate/ethyl ether. The extract was washed with brine, dried (sodium sulfate), filtered and stripped to give a cloudy white oil. The oil was flash chromatographed (Merck silica gel, 2% acetic acid in ethyl acetate) to give 2.810 g. of the diastereomerically pure title compound as a white foam. TLC (5% acetic acid in ethyl acetate) $R_f$=0.55.

e) (3S-trans)-Hexahydro-3-phthalimido-2-oxo-7-(2-propenyl)-1H-azepine-1-acetic acid, methyl ester A cold (0° C.) solution of the product from part (d) (2.50 g., 7.0 mmol.) in methanol (20 ml.) and ethyl ether (30 ml.) was treated with excess ethereal diazomethane for 10 minutes. The excess diazomethane was destroyed by the addition of acetic acid and the solvent was removed on the rotary evaporator to give a yellow oil. The oil was flash chromatographed (Merck silica gel, 1:1-ethyl acetate:hexanes) to obtain the product as a foam. The foam was dissolved in hot ethyl ether containing a little methylene chloride, cooled, and seeded to give 2.072 g. of crystalline title product. The mother liquor yielded an additional 262 mg. of product for a total of 2.334 g.; m.p. 107°-109° C. TLC (ethyl acetate:hexane, 1:1) $R_f$=0.29 f) [3S-[3α(R*),7β]]-Hexahydro-3-[[2-(acetylthio)-1-oxo-3-phenylpropyl]amino]-2-oxo-7-(2-propenyl)-1H-azepine-1-acetic acid, methyl ester A slurry of the crystalline product from part (e) (492 mg., 1.33 mmol.) in methanol (10 ml.) was treated with hydrazine monohydrate (142 μl., 147 mg., 2.93 mmol.) and the solution was briefly warmed to effect solubilization of the starting material. After stirring at room temperature for 18 hours, the mixture was diluted with methylene chloride and filtered. The filtrate was stripped, slurried in methylene chloride, filtered and stripped again to give the crude amine (270 mg.,) as a colorless oil. A cold (0° C.) solution of the amine and (S)-2-(acetylthio)benzenepropanoic acid (obtained from the dicyclohexylamine salt as described previously, 287 mg., 1.28 mmol.) in methylene chloride (12 ml.) was treated with triethylamine (172 μl., 125 mg., 1.23 mmol.) followed by benzotriazol-1-yloxy-tris (dimethylamino)phosphonium hexafluorophosphate (547 mg., 1.24 mmol.). The clear, nearly colorless solution was stirred at 0° C. for one hour and then at room temperature for 2 hours. The mixture was stripped, then partitioned between ethyl acetate and 1N hydrochloric acid. The ethyl acetate extract was washed successively with water, 50% saturated sodium bicarbonate and brine. The solution was dried (sodium sulfate), filtered and stripped. The residue was flash chromatographed (Merck silica gel, hexanes:acetone:ethyl ester, 6:3:1) to give 352 mg. of title product as an 84:16 mixture of diastereomers. This material was pooled with a similarly impure batch of product and the combined material was purified by preparative reverse-phase high performance liquid chromatography (YMC SH-365-10 S-10 120A ODS, 30×400 mm column, isocratic 66% methanol/34% water, 50 ml/min, detecting at 220 nm, title product $t_R$=22.6 min., impurity $t_R$=28.7 min.). The title product was obtained as a colorless oil in 98.2% purity. TLC(acetone:hexanes, 4:6) $R_f$=0.38.

g) [3S-[3α(R*),7β]]-Hexahydro-3-[(2-mercapto-1-oxo-3-phenylpropyl)amino]-2-oxo-7-(2-propenyl)-1H-azepine-1-acetic acid A room temperature solution of the product from part (f) (720 mg., 1.61 mmol.) in methanol (12 ml., deoxygenated via argon bubbling) was treated with 1N sodium hydroxide (10 ml., deoxygenated via argon bubbling). After stirring for 20 minutes, the solution was acidified with 10% hydrochloric acid (5 ml.) and extracted with ethyl acetate. The ethyl acetate extract was washed with water and brine, then dried (sodium sulfate), filtered and stripped to afford an oil. The material was flash chromatographed (Merck silica gel, 2-5% acetic acid in ethyl acetate). The product containing fractions were pooled and stripped, and the residue was azeotroped three times with ethyl acetate. The resulting oil/foam was dissolved in a small amount of ethyl acetate and then triturated with hexane to produce a white oil/foam. The mixture was stripped to dryness, slurried in hexane, stripped to dryness again, and dried in vacuo to give 616 mg. of title product as a hard white foam; $[\alpha]_D=-48.5°$ (c=0.63, chloroform). TLC (5% acetic acid in ethyl acetate) $R_f=0.56$.

Anal.cal'd. for $C_{20}H_{26}N_2O_4S\cdot 0.2\ H_2O$: C, 60.95; H, 6.75; N, 7.11; S, 8.14 Found: C, 60.98; H, 6.93; N, 6.93; S, 7.94

EXAMPLE 37

[3S-[3α,(R*),7β]]-Hexahydro-3-[(2-mercapto-2-oxo-3-phenylpropyl)amino]-2-oxo-7-propyl-1H-azepine-1-acetic acid a) (3S-trans]-Hexahydro-3-phthalimido-2-oxo-7-propyl-1H-azepine-1-acetic acid, methyl ester A solution of the product from Example 36(e) (767 mg., 2.07 mmol.) in methanol (10 ml.) and ethyl acetate (10 ml.) was hydrogenated (balloon) over palladium (10% on carbon, 62 mg.) at room temperature for one hour. The mixture was filtered through Celite, stripped, redissolved in ethyl acetate, filtered through a plug of silica gel and stripped again to afford 780 mg. of title product as a colorless oil. TLC (ethyl acetate:hexanes, 1:1) $R_f=0.29$.

b) [3S-[3α(R*),7β]]-Hexahydro-3-[[2-(acetylthio)-1-oxo-3-phenylpropyl]amino]-2-oxo-7-propyl-1H-azepine-1-acetic acid, methyl ester The product from part (a) (774 mg., 2.07 mmol.) in methanol (8 ml.) was treated with hydrazine monohydrate (222 μL, 229 mg., 4.58 mmol.) and the solution was stirred at room temperature for 23 hours. The mixture was diluted with 0.5N hydrochloric acid (20 ml.) and stirred at 0° C. for 2 hours. The solution was filtered and the filtrate was washed with ethyl acetate. The ethyl acetate extract was back-extracted once with water and the pooled aqueous layers were made basic with 1N sodium hydroxide. Extraction with methylene chloride (three times) followed by drying (sodium sulfate) and evaporation of the solvent afforded the crude amine (354 mg.,) as a colorless oil.

A cold (0° C.) solution of this crude amine and (S)-(acetylthio)benzenepropanoic acid (obtained from the dicyclohexylamine salt as described previously, 344 mg., 1.53 mmol.) in methylene chloride (12 ml.) was treated with triethylamine (214 μL, 154 mg., 1.53 mmol.) followed by benzotriazol-1-yloxytris(dimethylamino)phosphonium hexafluoro-phosphate (679 mg., 1.54 mmol.). The clear, nearly colorless solution was stirred at 0° C. for one hour and then at room temperature for one hour. The mixture was stripped, then partitioned between ethyl acetate and 0.5N hydrochloric acid. The ethyl acetate extract was washed successively with water, 50% saturated sodium bicarbonate and brine. The solution was dried (sodium sulfate), filtered and stripped. The residue was flash chromatographed (Merck silica gel, 6:4-hexanes:acetone) to give 510 mg. of pure title product as a colorless oil. TLC (acetone:hexanes, 4:6) $R_f=0.31$.

c) [3S-[3α(R*),7β]]-Hexahydro-3-[(2-mercapto-1-oxo-3-phenylpropyl)amino]-2-oxo-7-propyl-1H-azepine-1-acetic acid A room temperature solution of the product from part (b) (502 mg, 1.12 mmol) in methanol (8 ml., deoxygenated via argon bubbling) was treated with 1N NaOH (6 mL, deoxygenated via argon bubbling). After stirring for 25 minutes, the solution was acidified with 10% hydrochloric acid and extracted with ethyl acetate. The ethyl acetate extract was washed with water and brine, then dried (sodiuum sulfate), filtered and stripped to afford an oil. The material was flash chromatographed (Merck silica gel, 2% acetic acid in ethyl acetate). The product containing fractions were pooled and stripped, and the residue was azeotroped two times with ethyl acetate. The resulting oil/foam was dissolved in a small amount of methylene chloride and then triturated with hexane to produce a white oil/foam. The mixture was stripped to dryness, slurried in hexane, stripped to dryness again, and dried in vacuo to give 394 mg. of title product as a hard white foam; $[\alpha]_D=-51.2°$ (c=0.65, chloroform). TLC (2% acedic acid in ethyl acetate) $R_f=0.47$.

Anal. calc'd. for $C_{20}H_{28}N_2O_4S\cdot 0.2\ H_2O$: C, 60.95; H, 6.75; N, 7.11; S, 8.14 Found: C, 60.98; H, 6.93; N, 6.93; S, 7.94.

EXAMPLE 38

[3S-[3α(R*),7β]]-7-(Cyclopropylmethyl)hexahydro-3-](2-mercapto-1-oxo-3-phenylpropyl)amino]-2-oxo-1H-azepine-1-acetic acid a) (3S-trans-7-(Cyclopropylmethyl)hexahydro-3-phthalimido-2-oxo-1H-azepine-1-acetic acid, methyl ester To a solution of the product from Example 36(e) (700 mg. 1.89 mmol.) in 5 ml. of methylene chloride, cooled to 0° C., was added a 75 ml. portion of diazomethane/ethyl ether solution (prepared according to the procedure of Fieser & Fieser, Vol. I, p. 192), followed by 7 mg. (0.03 mmol.) of palladium(II) acetate. The reaction mixture bubbled violently and turned clear. After stirring for 10 minutes an additional 25 ml. of diazomethane/ethyl ether solution was added to the reaction. The reaction was stirred at 0° C. for 50 minutes, then filtered through celite and concentrated in vacuo to give a crude oil. The crude oil was flash chromatographed (Merck silica, 50×150 mm, 1:2 ethyl acetate/hexane) to give 717 mg. of title product as a white foam.

b) [3S-[3α(R*),7β]]-7-(Cyclopropylmethyl)hexahydro-3-[[2-(acetylthio)-1-oxo-3-phenylpropyl]amino]-2-oxo-1H-azepine-1-acetic acid, methyl ester To a solution of the product from part (a) (697 mg., 1.81 mmol.) in 8 ml. of methanol, stirred at room temperature, was added dropwise 92 μL (1.90 mmol.) of hydrazine monohydrate. The reaction was stirred at room temperature for 48 hours, then filtered to remove the solid byproducts. The filtrate was concentrated in vacuo, dissolved in methylene chloride, refiltered and reconcentrated to give a crude oil. The crude oil was dried under vacuum to give 441 mg. of crude amine as a white foam. This crude foam was used in the next reaction without further purification.

To a cold (0° C.) solution of 420 mg.(1.64 mmol.) of this crude amine and 384 mg. (1.81 mmol. of (S)-2-(acetylthio) benzenepropanoic acid (obtained from the dicyclohexylamine salt as described previously) in 10 ml. of chloroform was added 280 μl. (1.97 mmol.) of triethylamine. The reaction mixture was stirred 30 minutes, then 799 mg. (1.81 mmol.) of benzotriazol-1-yloxytris(dimethylamino) phosphonium hexafluorophosphate was added. The reaction was stirred at 0° C. for 48 hours, then an additional 399 mg. (0.904 mmol.) of benzotriazol-1-yloxytris(dimethylamino) phoisphonium hexafluorophosphate and 4 drops of triethylamine were added. The reaction was stirred at 0° C. for an additional 24 hours, then partitioned between 50 ml. ethyl acetate/50 ml. 5% potassium bisulfate solution. The water layer was separated and extracted with 2–25 ml. portions of ethyl acetate; the combined ethyl acetate layers were washed with 25 ml. of 5% potassium bisulfate solution, 40 ml. saturated sodium bicarbonate, 40 ml. brine, dried (magnesium sulfate) and concentrated in vacuo to give a crude oil. The oil was flash chromatographed (Merck silica gel, 50×200 mm, 1:3 ethyl acetate/hexane, then 1:2 ethyl acetate/hexane) to give 678 mg. of title product as a white foam.

c) [3S-[3α(R*),7β]]-7-(Cyclopropylmethyl)hexahydro-3-[(2-mercapto-1-oxo-3-phenylpropyl)amino]-2-oxo-1H-azepine-1-acetic acid, A solution of 658 mg. (1.43 mmol.) of the product from part (b) in 10 ml. of methanol was purged with argon for 30 minutes and cooled to 0° C. To this solution was added dropwise 6 ml. of 1M sodium hydroxide, also purged with argon for 30 minutes and cooled to 0° C. The reaction was stirred at 0° C. for 1 hour with continuous argon purging, then acidified to pH 1 with 5% potassium bisulfate solution. The mixture was extracted with 3–80 ml. portions of ethyl acetate; the combined ethyl acetate layers were dried (magnesium sulfate) and concentrated in vacuo to give a crude oil. The oil was flash chromatographed (Merck silica gel, 50×150 mm, 0.2% acetic acid/ethyl acetate) to give a white foam. The foam was triturated from methylene chloride/hexane to give 490 mg. of title product as a white hard solid; $[\alpha]_D=-78.9°$ (c=1.0, $CDCl_3$). TLC (5% methanol in methylene chloride plus 3 drops acetic acid) $R_f=0.41$.

Anal.calc'd. for $C_{21}H_{28}N_2SO_4 \cdot 0.50$ $H_2O$: C, 61.00; H, 7.07; N, 6.77; S, 7.93 Found: C, 61.40; H, 6.75; N, 6.37; S, 7.75.

EXAMPLE 39

[3S-[3α(R*),7β]]-7-(Cyclopentyl)hexahydro-3-[(2-mercapto-1-oxo-3-phenylpropyl)amino]-2-oxo-1H-azepine-1-acetic acid a) (3S-trans)-7-(2-Cyclopentenyl)hexahydro-3-phthalimido-2-oxo-1H-azepine-1-acetic acid, methyl ester Tin tetrachloride (5.1 ml., 5.1 mmol., 1M methylene chloride) was added dropwise to a solution of the product from Example 36 (e) (800 mg., 2.55 mmol.) and (2-cyclopentenyl)trimethylsilane (2.85 g., 20.4 mmole) in methylene chloride (60 ml.). The mixture was stirred at room temperature for 18 hours, then quenched by the addition of 100 ml. of water. The mixture was extracted with 3–100 ml. portions of ethyl acetate and 2–100 ml. portions of ethyl ether; the combined organic layers were washed with 100 ml. of brine, dried (sodium sulfate) and concentrated in vacuo to give a crude oil. The oil was flash chromatographed (Merck silica gel, 50×100 mm, 1:1 ethyl acetate/hexane then 2% acetic acid/ethyl acetate) to give 788 mg. of (3S-trans)-7-(2-cyclopentenyl)hexahydro-3-phthalimido-2-oxo-1H-azepine-1-acetic acid as a white foam.

A solution of this acid (768 mg., 2.01 mmol.) in methanol (7 ml.)/ethyl ether (10 ml.) stirred at room temperature, was treated dropwise with a solution of diazomethane/ethyl ether (prepared according to the procedure of Fieset & Fieser, Vol. I, p. 192). The diazomethane/ethyl ether solution was added until the reaction mixture remained yellow and the bubbling ceased. The mixture was stirred 10 minutes, then the excess diazomethane was quenched by the dropwise addition of 0.3 ml. of acetic acid. The colorless solution was concentrated in vacuo to give a crude oil. The oil was flash chromatographed (Merck silica gel, 50×100 mm, 1:2 ethyl acetate/hexane) to give 640 mg. of title product as a white foam.

b) (3S-trans)-7-(Cyclopentyl)hexahydro-3-phthalimido-2-oxo-1H-azepine-1-acetic acid, methyl ester A solution of the product from part (a) (700 mg., 1.89 mmol.) in 5 ml. of methanol was purged with argon for 15 minutes, then 150 mg. (25% by weight) of 10% palladium on carbon was added. The reaction vessel was evacuated and filled with hydrogen three times and stirred under hydrogen (1 atm, balloon) for 5 hours. The reaction mixture was filtered through Celite; the filtrate was concentrated in vacuo to give 594 mg. of title product as a white foam.

c) [3S-[3α(R*),7β]]-7-(Cyclopentyl)hexahydro-3-[[2-(acetylthio)-1-oxo-3-phenylpropyl]amino]-2-oxo-1H-azepine-1-acetic acid, methyl ester A solution of the product from part (b) in methanol was treated with hydrazine monohydrate according to the procedure described in Example 38 part (b) affording crude (3S-trans)-7-(cyclopentyl)hexahydro-3-amino-2-oxo-1H-azepine-1-acetic acid, methyl ester as a white foam.

This white foam was treated with (S)-(acetylthio) benzenepropanoic acid according to the procedure described in Example 38 part (b) affording the title product as a clear oil.

d) [3S-[3α(R*),7β]]-7-(Cyclopentyl)hexahydro-3-[(2-mercapto-1-oxo-3-phenylpropyl)amino]-2-oxo-1H-azepine-1-acetic acid A solution of the product from part (c) in methanol was treated with 1M sodium hydroxide according to the procedure of Example 38 part (c) affording the title product as a white hard solid; $[\alpha]_D=-78.1°$ (c=1, $CDCl_3$). TLC (5% methanol in methylene chloride plus 3 drops acetic acid) $R_f=0.39$.

Anal. Calc'd. for $C_{22}H_{30}N_2SO_4 \cdot 0.03$ $H_2O$: C, 63.06; H, 7.23; N, 6.69; S, 7.65 Found: C, 63.25; H, 7.25; N, 6.50; S, 7.55.

EXAMPLE 40

[S-(R*,R*)]-Hexahydro-3-[(2-mercapto-1-oxo-3-phenylpropyl)amino]-2-oxo-1H-azepine-1-propanoic acid a) (S)-3-[[(1,1-Dimethylethoxy)carbonyl]amino]-hexahydro-2-oxo-1H-azepine-1-propanoic acid, ethyl ester A solution of the product from Example 9(b) (1.75 g., 7.67 mmol.) in tetrahydrofuran:t-butanol (2:1, 30 ml.) was cooled to 0° C. and treated with ethyl acrylate (1.16 ml., 10.74 mmol., 1.4 eq.) and then 1.0N t-butanol, potassium salt (767 μl., 0.1 eq.). The reaction mixture was stirred at 0° C. for 15 minutes then at room temperature for 1 hour. The reaction was quenched with 25% ammonium chloride (50 ml.) and extracted with ethyl acetate (2×125 ml.). The combined organics was washed with 25% ammonium chloride (50 ml.), water (100 ml.), and brine (100 ml.), dried over magnesium sulfate, filtered and concentrated to yield a clear syrup. The residue was purified by chromatography on a 5×15 cm silica gel column eluting with 30% ethyl acetate/hexane mixture. The desired fractions were combined and concentrated to afford 2.18 g. title product as a clear syrup. TLC (ethyl acetate:hexane, 1:1) $R_f=0.38$.

b) [S-(R*,R*)]Hexahydro-3-[[2-(acetylthio)-1-oxo-3-phenylpropyl]amino]-2-oxo-1-azepine-1-propanoic acid, ethyl ester The product from part (a) (2.15 g., 6.55 mmole) was treated with 4N hydrochloric acid/dioxane (30 ml., 120 mmole) at 0° C. for 30 minutes, then at room temperature for 2 hours. The reaction mixture was concentrated, stripped with ethyl ether (twice), azeotroped with toluene (3 times) and dried in vacuo for 5 hours affording (S)-3-aminohexahydro-2-oxo-1H-azepine-1-propanoic acid, ethyl ester, hydrochloride salt.

This amine was them coupled with (S)-(acetylthio) benzenepropanoic acid in the presence of triethylamine and benzotriazol-1-yloxytris(dimethylamino)phosphonium hexafluorophosphate as described in Example 31 part (c) affording the title product. TLC (ethyl acetate:hexane, 1:1) $R_f$=0.19.

c) [S-(R*,R*)-Hexahydro-3-[(2-mercapto-1-oxo-3-phenylpropyl)amino]-2-oxo-1H-azepine-1-propanoic acid The product from part (b) in methanol was treated with 1N sodium hydroxide as described in Example 31 part (d) affording the title product as a white foam; $[\alpha]_D$=+4.44° (c=1.24, methanol). TLC (1% acetic acid in ethyl acetate) $R_f$=0.27.

Anal. calc'd. for $C_{18}H_{24}N_2O_4S \cdot 0.17$ $H_2O$: C, 58.83; H, 6.67; N, 7.62; S, 8.72 Found: C, 58.83; H, 6.87; N, 7.33; S, 8.49.

EXAMPLE 41

[S-(R*,R*)]-Hexahydro-3-[(2-mercapto-1-oxo-3-phenylpropyl)amino]-2-oxo-α-(phenylmethyl)-1H-azepipo-1-acetic acid a) (R*)-N-(2-Phthalimido-6-hydroxy-1-oxohexyl)-L-phennylalanine, ethyl ester To a solution of L-phenylalanine, ethyl ester, hydrochloride salt (998 mg., 4.3 mmol.) in dimethylformamide (10 ml.) was added 4-methylmorpholine (575 µL, 529 mg, 5.2 mmol). After stirring at room temperature for 5 minutes, the solution was cooled to 0° C. and treated successively with (S)-2-phthalamido-6-hydroxyhexanoic acid (1.002 g., 3.6 mmol.), hydroxybenzotriazole (582 mg., 4.3 mmol.), and ethyl-3-(3-dimethylamino)propyl carbodiimide, hydrochloride salt (770 mg., 4.0 mmol.). The resulting mixture was stirred at 0° C. for 0.5 hour and at room temperature for 1.5 hours. The solution was partitioned between ethyl acetate and water and the organic extract was washed successively with 0.5N hydrochloric acid, water, 50% saturated sodium bicarbonate, and brine, then dried (sodium sulfate), filtered and stripped to give 1.63 g. of essentially pure title product as an oil/foam. TLC (acetone:hexanes, 1:1) $R_f$=0.30.

b) (R*)-N-(2-Phthalimido-1,6-dioxohexyl)-L-phenylalanine, ethyl ester

A −78° C. solution of oxalyl chloride (370 µL, 538 mg., 4.2 mmol.) in methylene chloride (10 ml.) was treated dropwise with a solution of dry dimethylsulfoxide (610 µL, 672 mg., 8.6 mmol.) in methylene chloride (1.5 ml.). After 10 minutes, a solution of the product from part (a) (1.616 g., 3.6 mmol.) in methylene chloride (10 ml.) was added. After an additional 15 minutes, the mixture was treated with triethylamine (4.0 ml.), stirred at −78° C. for 5 minutes, then let warm to 0° C. The resulting white slurry was partitioned between 0.5N hydrochloric acid and ethyl acetate. The organic extract was washed with brine, then dried (sodium sulfate), filtered and stripped. The residue was flash chromatographed (Merck silica gel, 40:60-acetone:hexanes) to afford 1.474 g.of title product as an oil/foam.

TLC (acetone:hexanes, 1:1) $R_f$=0.45.

c) [3S-(3α,6β,9aα)]-Tetrahydro-3-(phenylmethyl)-6-phthalimido-oxazole [3.2-a]azepine-2,5 (3H, 6H)-dione A mixture of the product from part (b) (6.11 g., 13.6 mmol.) and trifluoroacetic acid (34 ml.) in chloroform (205 ml.) was refluxed for 6 days. The solution was cooled to room temperature and neutralized with saturated sodium bicarbonate. The layers were separated and the aqueous layer was extracted with methylene chloride. The pooled organic layers were washed with water, dried (sodium sulfate), filtered and stripped to give a dark yellow-orange oil. The residue was flash chromatographed (Merck silica gel, 40 to 60% ethyl acetate in hexanes) to afford 3.075 g. of title product as a white foam.

d)[S-(R*,R*)]-Hexahydro-2-oxo-3-phthalimido-α-(phenylmethyl)-1H-azepine-1-acetic acid, methyl ester A solution of the product from part (c) (1.40 g., 3.46 mmol.) and triethylsilane (4.4 ml., 3.20 g., 27.5 mmol.) in methylene chloride (42 ml.) at room temperature was treated dropwise with titanium tetrachloride (1.0M in methylene chloride, 7.0 ml., 7.0 mmol.). The clear colorless solution became bright yellow upon the addition of titanium tetrachloride; no precipitate resulted. After stirring for 66 hours, the mixture was quenched with water and extracted with ethyl acetate. The ethyl acetate extract was washed with water and brine, dried (sodium sulfate), filtered and stripped to give an oil. Flash chromatography (Merck silica gel, ethyl acetate followed by 2% acetic acid in ethyl acetate) provided 870 mg. of [S-(R*,R*)]-hexahydro-2-oxo-3-phthalimido-α-(phenylmethyl)-1H-azepine-1-acetic acid as a white foam.

A cold (0° C.) solution of this acid (898 mg., 2.21 mmol.) in methanol (8 ml.) and methylene chloride (12 ml.) was treated with excess ethereal diazomethane for 5 minutes. The excess diazomethane was destroyed by the addition of acetic acid and the solvent was removed on the rotary evaporator to give a yellow oil. The residue was flash chromatographed (Merck silica gel, 50 to 60% ethyl acetate in hexanes) affording 858 mg. of title product as a white foam. TLC (ethyl acetate:hexanes, 1:1) $R_f$=0.30.

e) [S-(R*,R*)]-Hexahydro-3-[[2-(acetylthio)-1-oxo-3-phenylpropyl]amino]-2-oxo-α-(phenylmethyl)-1H-azepine-1-acetic acid, methyl ester A solution of the product from part (d) in methanol was treated with hydrazine monohydrate according to the procedure of Example 36 part (f) affording [S-(R*,R*)]-hexahydro-3-amino-2-oxo-α-(phenylmethyl)-1H-azepine-1-acetic acid, methyl ester as a pale yellow oil. TLC (methylene chloride:acetic acid:methanol, 8:1:1) $R_f$=0.60.

A cold (0° C.) solution of this amine was reacted with (S)-2-(acetylthio)benzenepropanoic acid in the presence of triethylamine and benzotriazol-1-yloxytris(dimethylamino) phosphonium hexafluoro-phosphate according to the procedure of Example 36 (f) affording the title product as a colorless oil/foam. TLC (acetone:hexanes, 1:1) $R_f$=0.54.

f) [S-(R*,R*)]-Hexahydro-3-[(2-mercapto-1-oxo-3-phenylpropyl)amino]-2-oxo-α-(phenylmethyl)-1H-azepine-1-acetic acid A solution of the product from part (e) in methanol was treated with 1N sodium hydroxide according to the procedure of Example 36 part (g) affording the title product as a relatively hard white foam; $[\alpha]_D$=−64.2° (c=0.54, chloroform). TLC (5% acetic acid in ethyl acetate) $R_f$=0.60.

Anal.calc'd. for $C_{24}H_{28}N_2O_4S \cdot 0.31$ $H_2O$: C, 64.61; H, 6.47; N, 6.28; S, 7.19 Found: C, 64.61; H, 6.78; N, 5.89; S, 7.46

EXAMPLE 42

[6(S)]-Hexahydro-6-[(2-mercapto-1-oxo-3-phenylpropyl)amino]-2,2-dimethyl-7-oxo-1H-azepine-1-acetic a) 2,2-Dimethylcyclohexanone, oxime A solution of 2,2-dimethylcyclohexanone (8.960 g., 65 mmol.), pyridine (12.0 ml., 12.27 g., 155 mmol.), and hydroxylamine hydrochloride (10.30 g., 148 mmol.) in absolute ethanol (50 ml.) was heated at 85° C. for 2 hours. The cooled mixture was partitioned between ethyl ether and water and the ethereal layer was washed successively with 1N hydrochloric acid and brine, then dried (sodium sulfate), filtered and stripped. The solid residue was dissolved in a small amount of hot hexane and cooled to 0° C. to afford 6.801 g. of title product as white flakes; m.p. 91°–93° C. TLC (ethyl acetate:hexane, 4:6) $R_f$=0.60.

b) Hexahydro-3,3-dichloro-7,7-dimethyl-2-oxo-2H-azepine

A cold (0°–10° C.) slurry of phosphorus pentachloride (32.50 g., 156.1 mmol.) in methylene chloride (250 ml.) was treated with a solution of the product from part (a) (7.353 g., 52.1 mmol.) in methylene chloride (50 ml.) over a 10 minute period. The mixture was warmed to room temperature and chlorine gas was bubbled through the solution at 0.5 and 1.5 hours after addition of the oxime. After a total of 3 hours, the mixture was quenched with crushed ice (70 ml.) followed by saturated sodium bicarbonate (150 ml.). Periodic cooling was necessary. The biphasic mixture was stirred vigorously at room temperature for 18 hours, then the layers were separated and the methylene chloride extract was washed with saturated sodium bicarbonate/brine. The organic layer was dried (sodium sulfate), filtered, stripped, and flash chromatographed (Merck silica gel, 2/8-ethyl acetate/methylene chloride). Fractions containing the desired product were stripped and the residue was dissolved in hot methylene chloride/ethyl acetate and cooled to afford 5.152 g. of pure title product. The mother liquor was re-chromatographed (Merck silica gel, 1/9-ethyl acetate/methylene chloride) to give an additional 2.054 g. of pure product for a total yield of 7.206 g.; m.p. 148°–155° C. (broad). TLC (ethyl acetate:methylene chloride, 1:9) $R_f$=0.36.

c) Hexahydro-3-chloro-7,7-dimethyl-2H-azepine

A solution of the product from part (b) (7.180 g., 34.2 mmol.) in glacial acetic acid (150 ml.) was hydrogenated (balloon) over 10% palladium on carbon catalyst (2.5 g.) for 1.75 hours. The mixture was filtered through Celite and the solvent was removed by rotary evaporation. The residue was flash chromatographed (Merck silica gel, 3/7-ethyl acetate/methylene chloride) to afford impure desired product as an oily solid. The residue was treated with ethyl ether and triturated with hexane to afford 2.845 g. of pure title product as a white solid. The mother liquor was re-chromatographed (Merck silica gel, 3/7-ethyl acetate/methylene chloride) to give 1.93 g. of additional pure solid product. The solids were pooled to give 4.775 g.of pure title product; m.p. 115°–117° C. TLC (ethyl acetate:methylene chloride, 3:7) $R_f$=0.41.

d) Hexahydro-3-azido-7,7-dimethyl-2-oxo-2H-azepine

A slurry of the product from part (c) (4.670 g., 26.6 mmol.) and sodium azide (4.360 g., 67.0 mmol.) in dry dimethylsulfoxide (100 ml.) was heated at 80° C. for 6 hours. The solution was cooled to 0° C. and treated with 175 ml. of ice cold water. The resulting snow white precipitate was collected by filtration, washed with water and dried to give 2.37 g. of pure title product. The filtrate was extracted with ethyl acetate and the organic extract was washed twice with water and once with brine, then dried (sodium sulfate), filtered and stripped. Trituration of the residue with ethyl ether and hexane afforded 1.637 g. of additional product. The isolated solids were pooled to give 4.007 g. of pure title product; m.p. 98°–100° C. TLC (ethyl acetate:hexane, 75:25) $R_f$=0.51.

e) Hexahydro-3-[[(1,1-dimethylethoxy)carbonyl]-amino]-7,7-dimethyl-2-oxo-2H-azepine A solution of the product from part (d) (3.469 g., 19.0 mmol.) in methanol (80 ml.) was hydrogenated (balloon) over 10% palladium on carbon catalyst (850 mg.) for 1.5 hours. The mixture was filtered through Celite and the solvent was removed by rotary evaporation. The residue was evaporated once from methylene chloride to afford the crude amine as a white solid. The solid was redissolved in chloroform and treated successively with triethylamine (2.65 ml., 1.92 g., 19.0 mmol.) and di-tert-butyl-dicarbonate (5.000 g., 22.9 mmol.). After stirring at room temperature for 1 hour, the solution was stripped and the residue was triturated with ethyl acetate/ethyl ether to afford 2.668 g. of title product as a white solid. The filtrate was flash chromatographed (Merck silica gel, 2/8-ethyl acetate/methylene chloride) to give additional pure product which was pooled with the above solid to give a total of 4.082 g. of pure title product; m.p. 156°–158.5° C. TLC (ethyl acetate:methylene chloride, 2:8) $R_f$=0.26.

f) Hexahydro-3-[[(1,1-dimethylethoxy)carbonyl]-amino]-7,7-dimethyl-2-oxo-1H-azepine-1-acetic acid, A room temperature solution of the product from part (e) (3.512 g., 13.7 mmol.) in dry tetrahydrofuran (110 ml.) was treated with lithium hexamethyldisilazane (1.0M in tetrahydrofuran, 21 ml., 21 mmol.) followed by ethyl bromoacetate (3.0 ml., 4.52 g., 27.0 mmol.). After 20 minutes, additional lithium hexamethyldisilazane (21 ml.) was added followed by an additional 1.5 ml. of ethyl bromoacetate. The dark orange solution was stirred at room temperature for an additional 30 minutes, then quenched by the addition of saturated ammonium chloride and water. The mixture was extracted with ethyl acetate and the organic extract was washed with brine, dried (sodium sulfate), filtered, and stripped to give a dark oil. The residue was flash chromatographed (Merck silica gel, 35 to 50% ethyl acetate in hexane) to give 1.363 g. of pure title product as a pale yellow oil. TLC (ethyl acetate:hexane, 1:1) $R_f$=0.48.

g) [6(S)]-Hexahydro-6-[[2-(Acetylthio)-1-oxo-3-phenylpropyl]amino]-2,2-dimethyl-7-oxo-1H-azepine-1-acetic acid, ethyl ester A solution of the product from part (f) (1.349 g., 3.94 mmol.) in p-dioxane (3 ml.) was treated with hydrochloric acid (4.0M in p-dioxane, 12 ml.). The mixture was stirred at room temperature for 1.5 hours. The solvent was stripped and the residue was partioned between methylene chloride and 0.2N sodium hydroxide (26 ml.). The layers were separated and the aqueous layer was extracted with ethyl ether/ethyl acetate. The pooled organic extracts were dried (sodium sulfate), filtered and stripped to give 982 mg. of the crude free amine as a yellow oil. TLC (methanol:methylene chloride, 1:9) $R_f$=0.16.

A solution of (S)-2-(acetylthio) benzene-propanoic acid [obtained from the dicyclohexylamine salt as previously described (973 mg., 4.3 mmol.)] and the above crude amine in methylene chloride (30 ml.) was treated with triethylamine (1.15 ml., 835 mg., 8.2 mmol.) and the mixture was cooled to 0° C. Benzotriazol-1-yloxy-tris(dimethylamino) phosphonium hexafluorophosphate (1.915 g., 4.3 mmol.) was then added as a solid. The solution was stirred at 0° C. for 1 hour and then at room temperature for 1.5 hours. The solvent was stripped and the residue was partitioned between ethyl acetate and 0.5N hydrochloric acid. The organic layer was washed successively with water, 50% saturated sodium bicarbonate and brine, then dried (sodium sulfate), filtered and stripped. The residue was flash chromatographed (Merck silica gel, 3:7 acetone:hexanes) to give 1.564 g. of title product as an oil. (1:1 mixture of diastereomers). TLC (acetone:hexanes, 3:7 ) $R_f$=0.30.

h) [6(S)]-Hexahydro-6-[(2-mercapto-1-oxo-3-phenylpropyl)amino]-2,2-dimethyl-7-oxo-1H-azepine-1-acetic acid A room temperature solution of the product from part (g) (1.548 g., 3.45 mmol.) in methanol (20 ml., deoxygenated via argon bubbling) was treated with 1N sodium hydroxide (15 ml., deoxygenated via argon bubbling). After stirring for 30 minutes, additional 1N sodium hydroxide (15 ml.) was added and stirring under argon continued. After a total of 3 hours, the solution was acidified with 6N hydrochloric acid and extracted with ethyl acetate. The ethyl acetate extract was washed with water and brine, then dried (sodium sulfate), filtered and stripped to afford an oil. The material was flash chromatographed (Merck silica gel, ethyl acetate followed by 1.5% acetic acid in ethyl acetate). The fractions containing essentially pure title product were pooled, stripped, and azeotroped twice with ethyl acetate. The mixture was dissolved in a small amount of ethyl acetate and triturated with hexane to give a foam. The volatiles were stripped, the residue was slurried in hexane, stripped to dryness again, and dried in vacuo to give 863 mg. of title product as a relatively hard white foam as a 45:55 mixture of diastereomers.

TLC (2% acetic acid in ethyl acetate) $R_f$=0.40.

Anal. calc'd. for $C_{19}H_{26}N_2O_4S \cdot 0.2\ H_2O$: C, 59.73; H, 6.96; N, 7.33; S, 8.39 Found: C, 59.79; H, 7.13; N, 7.13; S, 7.99.

EXAMPLE 43

[S-(R*,S*)]-3,4-Dihydro-3-[(2-mercapto-1-oxo-3-phenylpropyl)amino]-4-oxo-1,5-benzothiazepine-5 (2H)-propanoic acid a) 2.3-Dihydro-3-amino-4-oxo-1,5-benzothiazepine-5 (4H)-propionic acid, ethyl ester 2,3-Dihydro-3-[[(phenylmethoxy)carbonyl]-amino]-1,5-benzothiazepine-4(5H)-one [prepared according to the procedure of Slade et al., J. Med. Chem., 28, p 1517–1521 (1985)] (2.04 g., 6.21 mmol.) was azeotroped with a mixture of methylene chloride/toluene (3x) and dried in vacuo for one hour. A suspension of this compound in tetrahydrofuran:tert-butanol (2:1, 21 ml.), cooled to 0° C., was treated with ethyl acrylate (1.08 ml., 9.94 mmol., 1.6 eq.) and then 1.0N t-butanol, potassiun salt/tetrahydrofuran (621 µl., 0.1 eq.). The reaction mixture was stirred at 0° C. for 15 minutes then at room temperature for 20 hours under argon. The reaction was quenched with 50% ammonium chloride (50 ml.) and extracted with ethyl acetate (2×150 ml.). The combined organics were washed with saturated ammonium chloride (75 ml.), water (75 ml.), and brine (100 ml.), dried over magnesium sulfate, filtered and concentrated to yield a clear yellow syrup. The residue was purified by chromatography on a 5×20 cm silica gel column eluting with 20% ethyl acetate/hexane mixture (2 l.). The desired fractions were combined and concentrated to afford 2.33 g of a mixture of 2,3-dihydro-3-[(3-ethoxy-3-oxopropyl)-[(phenylmethoxy)carbonyl]amino]-4-oxo-1,5-benzothiazepine-5(4H)-propanoic acid, ethyl ester (25%) and 2,3-dihydro-3-[[(phenylmethoxy)carbonyl]-amino]-4-oxo-1,5-benzothiazepine-5(4H)-propanoic acid, ethyl ester (75%) as a clear syrup.

The above mixture (698 mg., 1.32 mmol. of the first named compound and 1.698 g., 3.96 mmol. of the second named compound) and 30% hydrogen bromide/acetic acid solution (8.71 ml., 41.98 mmol.) was stirred under argon at room temperature for 1.5 hours. The reaction mixture was diluted with ethyl ether (200 ml.), stirred until off-white precipitates formed and filtered, washing the orange solids with ethyl ether (4×50 ml.). The crude residue was then dissolved in 1N hydrochloric acid (100 ml.) and extracted with ethyl acetate (2×100 ml.). The aqueous phase was then brought to pH 9 with 1N sodium hydroxide and extracted with ethyl acetate (3×100 ml.). The combined organics were washed with brine (75 ml.), dried over magnesium sulfate, filtered and concentrated to yield 1.50 g. crude yellow oil. The residue was purified by chromatography on a 5×20 cm silica gel column eluting with 1% (2 l.), 2% (1 l.), and finally 5% (1 l.) of methanol in methylene chloride. The desired fractions were concentrated and dried in vacuo to yield 1.163 g. of title product. TLC (methylene chloride:methanol, 9:1) $R_f$=0.40.

b) [S-(R*,S*)]-3.4-Pihydro-3-[[2-(acetylthio)-1-oxo-3-phenylpropyl]amino]-4-oxo-1,5-benzothiazepine-5(2H)-propanoic acid, ethyl ester (S)-2-(Acetylthio)benzenepropanoic acid (obtained from the dicyclohexylamine salt as previously described) was dissolved in dry methylene chloride, cooled to 0° C., and treated with a solution of the product from part (a) in dry methylene chloride followed by triethylamine and benzotriazol-1-yloxy(dimethylamino)phosophonium hexafluorophosphate as described in Example 36 part (f) affording the title product. TLC (ethyl acetate:hexane, 1:1) $R_f$=0.39.

c) [S-(R*,R*)]-3,4-Dihydro-3-[[2-mercapto-1-oxo-3-phenylpropyl)amino]-1,5-benzothiazepine-5(2H)-propionic acid A solution of the product from part (b) in methanol was treated with 1N sodium hydroxide according to the procedure of Example 36 part (g) affording the title product as a white foam; $[\alpha]_D$=−161.6° (c=1.16, methanol). TLC (1% acetic acid in ethyl acetate) $R_f$=0.45.

Anal. calc'd. for $C_{21}H_{22}N_2O_4S_2 \cdot 0.4\ H_2O$: C, 57.63; H, 5.25; N, 6.40; S, 14.65 Found: C, 57.65; H, 5.04; N, 6.38; S, 14.44.

EXAMPLE 44

[3(S)]-2,3,4,5-Tetrahydro-3-[(2-mercapto-1-oxo-3-phenylpropyl)amino]-2-oxo-1H-1-benzazepine-1-propanoic acid a) 3-Amino-2,3,4,5-Tetrahydro-2-oxo-1H-1-benzazepine-1-propionic acid, ethyl ester A solution of 3-azido-1,3,4,5-tetrahydro-2H-1-pbenzazepin-2-one [prepared as described by Watthey et al., J. Med. Chem., 28, p. 1511–15156 (1985)]in tetrahydrofuran/tert-butanol was cooled to 0° C. and treated with ethyl acrylate and 1N tert-butanol, potassium salt/tetrahydrofuran according to the procedure of Example 40 part (a) affording 3-azido-2,3,4,5-tetrahydro-2-oxo-1H-1-benzazepine-1-propanoic acid, ethyl ester as a syrup. TLC (ethyl ether:hexane, 1:1) $R_f$=0.45.

A solution of this compound (2.258 g., 6.94 mmol.) in absolute ethanol was treated with 10% palladium on carbon catalyst and hydrogenated at 40 psi for 4 hours, venting the Parr bottle after the first hour. The mixture was diluted with ethanol (50 ml.) and filtered through a Celite pad, washing the pad thoroughly with ethanol (2×50 ml.). The clear filtrate was evaporated to dryness and dried in vacuo to give 2.098 g. of the title product as a clear light yellow syrup. TLC (methylene chloride: methanol, 9:1) $R_f$=0.32.

b) [3(S)]-2,3,4,5-Tetrahydro-3-[[2-(acetylthio)-1-oxo-3-phenylpropyl]amino]-2-oxo-1H-1-benzazepine-1-propionic acid (S)-2-(Acetylthio)benzenepropanoic acid [obtained from the dicyclohexylamine salt as previously described] was dissolved in methylene chloride, cooled down to 0° C., and treated sequentially with a solution of the product from part (a) in dry methylene chloride, triethylamine, and benzotriazol-1-yloxytris (dimethylamino)phosphonium hexafluorophosphate according to the procedure of Example 36 part (f) affording the title product as a syrup. TLC (ethyl acetate:hexane, 1:1) $R_f$=0.56 and 0.52.

c) [3(S)]-2,3,4,5-Tetrahydro-3-[(2-mercapto-1-oxo-3-phenylpropyl)amino]-2-oxo-1H-1-benzazepine-1-propanoic acid A solution of the product from part (b) in methanol was cooled down to 0° C. and treated with 1N sodium hydroxide according to the procedure of Example 36 part (g) affording the title product as a solid foam; $[\alpha]_D$=+41.8° (c=0.608, methanol). TLC (methylene chloride:methanol:acetic acid, 20:1:1) $R_f$=0.47.

Anal. calc'd.for $C_{22}H_{24}N_2O_4S \cdot 0.25 \, C_5H_{12} \cdot 0.413 \, H_2O$: C, 63.76; H, 6.21; N, 6.40; S, 7.32 Found: C, 63.76; H, 6.18; N, 6.38; S, 7.45.

EXAMPLE 45

(3(S)]-2,3,4,5-Tetrahydro-3-[[2-(mercaptomethyl)-1-oxo-3-phenylpropyl]amino]-2-oxo-1H-1-benzazepine-1-propanoic acid a) [3(S)]-2,3,4,5-Tetrahydro-3-[[2-F(acetylthio)-methyl]-1-oxo-3-phenylpropyl]amino]-2-oxo-1H-1-benzazepine-1-propanoic acid (S)-2-[(Acetylthio)methyl]benzenepropanoic acid [obtained from the ephedrine salt as described previously] was dissolved in dry methylene chloride, cooled down to 0° C., and treated with 1-hydroxybenzotriazole hydrate and 1-ethyl-3-(3-dimethylaminopropyl)carbodiimide and a solution of the product from Example 44(a) in dry methylene chloride according to the procedure of Example 8 part (a) to afford the title product as a syrup. TLC (ethyl acetate:hexane, 1:1) $R_f$=0.58.

b) [3(S)]-2,3,4,5-Tetrahydro-3-[[2-(mercaotomethyl)-1-oxo-3-phenylpropyl]amino]-2-oxo-1H-1-benzazepine-1-propanoic acid A solution of the product from part (a) in methanol was cooled down to 0° C. and treated with 1N sodium hydroxide according to the procedure of Example 8 part (b) to afford the title product as an amorphous solid; $[\alpha]_D$=+46.9° (c=0.608, methanol).

TLC (chloroform:methanol:acetic acid, 20:1:1) $R_f$=0.42.

Anal.calc'd.for $C_{23}H_{26}N_2O_4S \cdot 0.233 \, C_5H_{12} \cdot 0.61 \, H_2O$: C, 63.89; H, 6.65; N, 6.17; S, 7.06 Found: C, 63.89; H, 6.40; N, 6.18; S, 6.82.

EXAMPLE 46

[1S-[1α,9α(R*)]]-Octahydro-9-[(2-mercapto-1-oxo-3-phenylpropyl)amino]-6.10-dioxo-6H-pyridazino[1,2-a][1.2]diazepine-1-carboxylic acid a) (1S-cis)-Octahydro-9-phthalimido-6,10-dioxo-6H-pyridazino[1.2-a][1,2]diazepine-1-carboxylic acid. 1.1-dimethylethyl ester 5,6-Dihydro-1,3(2H,4H)-pyridazinedicarboxylic acid, 3-(1,1-dimethylethyl)-1-(phenylmethyl)ester [prepared as described by Adams et al., Synthetic Communications, 18(18), 2225–2231 (1988)] was reacted with (S)-2-phthalimidopentanedioic acid, 5-(phenylmethyl) ester according to the procedure described by Attwood et al.(J. Chem. Soc. Perkins Trans I, 1986, p. 1011–1019) affording (S)-2-[2-phthalimido-1,5-dioxo-5-(phenylmethoxy)pentyl]-5,6-dihydro-1,3(2H,4H)-pyridazinedicarboxylic acid, 3-(1,1-dimethylethyl)-1-(phenylmethyl) ester.

A solution of this material (12.11g., 18.5 mmol.) in dry dimethylformamide (190 ml.) was treated with 10% palladium on carbon catalyst (372 mg.) and hydrogenated at room temperature for 24 hours. The mixture was filtered through a Celite pad, the clear dark filtrate obtained was evaporated to dryness and the syrup was obtained redissolved in methanol (200 ml.). The solution was filtered through another Celite pad to remove remaining traces of the catalyst, and the clear filtrate was evaporated to dryness and dried in vacuo. The product obtained was dissolved in dry methylene chloride (185 ml.), cooled down to 0° C. (ice-salt bath) and treated with thionyl chloride (1.56 ml., 21.36 mmoles, 1.15 eq.). The reaction mixture was stirred at room temperature for 5.0 hours under argon, treated with a solution of potassium bicarbonate (3.95 g.) in water (34 ml.) and stirred for 10 minutes. The phases were separated, re-extracting the aqueous phase with more methylene chloride (270 ml.) and the combined organic extracts were dried (anhydrous sodium sulfate), filtered, evaporated to dryness and dried in vacuo.

The crude product mixture was chromatographed on a silica gel column (Merck), eluting the column with ethyl acetate:hexane mixtures (1:3; 1:1) to give 3.053 g. of the title compound as a solid. TLC (ethyl acetate:hexane, 1:1) $R_f$=0.40.

b) (1S-cis)-Octahydro-9-amino-6,10-dioxo-6H-pyridazino[1,2-a][1,2]diazepine-1-carboxylic acid, 1,1-dimethylethyl ester A suspension of the product from part (a) (1.0 g., 2.41 mmol.) in absolute ethanol was treated with hydrazine hydrate (0.26 ml., 2.2 eq.) and stirred at room temperature for one hour under argon. The mixture was stripped to dryness, evaporated once from toluene (25 ml.) and the residue obtained was stirred with 2.0M acetic acid (10 ml.) for 24 hours under argon. The solids were filtered off, washed with 2.0 M acetic acid (5.0 ml.) and water (2×2.0 ml.), and the clear filtrate was adjusted to pH 10.0 with solid sodium bicarbonate (1.8 g.). The mixture was extracted with methylene chloride (2×25 ml) and the combined organic extracts were washed with brine (6.0 ml.), dried (anhydrous sodium sulfate) and filtered. The clear soluton was evaporated to dryness and dried in vacuo to give 755 mg. of title product as a syrup. TLC (methylene chloride:methanol, 9:1) $R_f$=0.20.

c) [1S-[1α,9α(R*)]]-Octahydro-9-[[2-(acetylthio)-1-oxo-3-phenylpropyl]amino]-6.10-dioxo-6H-pyridazino[1,2-a][1,2]diazepine-1-carboxylic acid, 1,1-dimethylethyl ester (S)-2-(Acetylthio)benzenepropanoic acid, dicyclohexylamine salt (1.07 g., 2.64 mmol.) was suspended in ethyl acetate (80 ml.), washed with 5% potassium bisulfate (5×12 ml.) and brine (14 ml.), dried (anhydrous magnesium sulfate), filtered, evaporated to dryness and dried in vacuo.

The free acid was dissolved in dry methylene chloride (20 ml.), cooled down to 0° C. (ice-salt bath), treated sequentially with a solution of the product from part (b) (755 mg., 2.41 mmol.) in dry methylene chloride (5.0 ml.), triethylamine (0.33 ml., 2.37 mmol.) and benzotriazol-1-yloxytris-(dimethylamino)phosphonium hexafluorophosphate (1.08 g., 2.44 mmol.). The reaction mixture was stirred at 0° C. for 1.0 hour and at room temperature for 2.0 hours under argon. The reaction mixture was stripped to dryness and the syrup obtained was redissolved in ethyl acetate (80 ml.), washed with 0.5N hydrochloric acid (2×14 ml.), water (14 ml.) and brine (14 ml.), dried (anhydrous magnesium sulfate), filtered and evaporated to dryness. The crude product was chromatographed on a silica gel column (Merck), eluting the column with ethyl acetate:hexane mixtures (1:3; 1:1), to give 747 mg. of title product as a clear syrup. TLC (ethyl acetate:hexane, 1:1) $R_f$=0.23.

d) [1S-[1α,9α(R*)]]-Octahydro-9-[[2-(acetylthio)-1-oxo-3-phenylpropyl]amino]-6,10-dioxo-6H-pyridazino[1,2-a][1,2]diazepine-1-carboxylic acid A solution of the product from part (c) (747 mg., 1.48 mmol.) in dry methylene chloride (10 ml.) was treated with anisole (0.69 ml., 6.35 mmol.) followed by trifluoroacetic acid (1.04 ml., 13.5 mmol.) and the reaction mixture was stirred at room temperature under argon for 5.5 days. The clear solution was stripped to dryness, evaporated from ethyl acetate (2×100 ml.) and the crude product was chromatographed on a silica gel column (Merck), eluting the column with ethyl acetate:hexane (4:1) followed by ethyl acetate:hexane:acetic acid (85:10:5). The desired fractions were combined, stripped to dryness and evaporated from toluene (2×100 ml.). The syrup obtained was redissolved in ethyl acetate (59 ml.), washed with water (3×10 ml.) and brine (5.0 ml.), dried (anhydrous sodium sulfate), filtered, evaporated to dryness and dried in vacuo to give 556 mg. of title product as a syrup. TLC (ethyl acetate:acetic acid, 95:5) $R_f$=0.30.

e) [1S-[1α,9α(R*)]]-Octahydro-9-[(2-mercapto-1-oxo-3-phenylpropyl)amino]-6,10-dioxo-6H-pyridazino[1,2-a][1,2]diazeoine-1-carboxylic acid A solution of the product from part (d) (556 mg., 1.24 mmol.) in methanol (7.0 ml.) was cooled down to 0° C. (ice-salt bath), purged with argon for 30 minutes then treated with a previously purged (argon, 30 minutes) solution of 1.0N sodium hydroxide (2.5 ml., 2.5 mmol.) maintaining the bubbling of argon throughout the addition and length of the reaction. The reaction mixture was stirred at 0° C. for 30 minutes, brought to pH 2.0 with 5% potassium bisulfate (11.0 ml) at 0° C., warmed up to room temperature and extracted with ethyl acetate (2×40 ml.). The combined organic extracts were washed with brine (11.0 ml.), dried (anhydrous sodium sulfate), filtered, evaporated to dryness and dried in vacuo. The crude product was dissolved in methylene chloride (5.0 ml.) and treated portionwise with hexane (50 ml.) while scratching until solids were obtained. The solids were triturated with more hexane (50 ml.) and pentane (2×50 ml.), stirring the solids with the first 50 ml. for 2.0 hours and with the next 50 ml. overnight at room temperature under argon. The product was dried in vacuo to give 468.5 mg. of title product as a solid foam; $[α]_D$=-83.5° (c=0.492, methanol). TLC (ethyl acetate:acetic acid, 95:5) $R_f$=0.33.

Anal. calc'd. for $C_{19}H_{23}N_3O_5S·0.34\ H_2O$: C, 55.45; H, 5.80; N, 10.21; S, 7.79 Found: C, 55.45; H, 5.95; N, 9.84; S, 7.49.

EXAMPLE 47

[1S-[1α,9α(R*)]]-Octahydro-9-[(2-mercapto-1-oxo-3-phenylpropyl)amino]-10-oxo-6H-pyridazino[1,2-a][1,2]diazepine-1-carboxylic acid a) (1S-cis)-Octahydro-9-phthalimido-10-oxo-6H-pyridazino[1,2-a][1,2]diazepine-1-carboxylic acid, 1,1-dimethylethyl ester A solution of the product from Example 46(a) (1.0 g., 2.35 mmole) in dry tetrahydrofuran (8.0 ml.) was cooled down to about 5° C. (ice-water bath), treated with 1.0M diborane/tetrahydrofuran (2.88 ml., 2.88 mmol.) over a period of 30 minutes, warmed up to room temperature and stirred overnight under argon. The reaction mixture was diluted with methylene chloride (14.0 ml.), treated with 2.0N hydrochloric acid (6.8 ml.) and stirred for 15 minutes. The mixture was then brought to pH 10.0 with anhydrous sodium bicarbonate (1.92 g.) and the phases separated, re-extracting the aqueous phase with more methylene chloride (30 ml.). The combined organic extracts were washed with brine (5.0 ml.), dried (anhydrous magnesium sulfate), filtered, evaporated to dryness and dried in vacuo. The crude product was chromatographed on a silica gel column (Merck), eluting the column with ethyl acetate:hexane mixtures (1:3; 1:1) to give 877 mg. of title product as a syrup. TLC (ethyl acetate:hexane, 1:1) $R_f$=0.63.

b) (1S-cis)-Octahydro-9-amino-10-oxo-6H-pyridazino[1,2-a][1,2]diazeoine-1-carboxylic acid, 1,1-dimethylethyl ester A solution of the product from part (a) (1.257 g., 3.0 mmol.) in absolute ethanol (13.0 ml.) was treated with hydrazine hydrate (0.33 ml., 2.2 eq.) according to the procedure of Example 46 part (b) affording 704 mg. of title product as a syrup. TLC (methylene chloride:methanol, 9:1) $R_f$=0.35.

c) [1S-[(1α,9α(R*)]]-Octahydro-9-[[2-(acetylthio)-1-oxo-3-phenylpropyl]amino]-10-oxo-6H-pyridazino[1,2-a][1,2]diazepine-1-carboxylic acid, 1,1-dimethylethyl ester (S)-2-(Acetylthio)benzenepropanoic acid, dicyclohexylamine salt (1.10 g., 2.71 mmol.) was suspended in ethyl acetate (85 ml.), washed with 5% potassium bisulfate (5×12.4 ml.) and brine (14.4 ml.), dried (anhydrous magnesium sulfate), filtered, evaporated to dryness and dried in vacuo.

The free acid was dissolved in dry methylene chloride (21 ml.). cooled down to 0° C. (ice-salt bath), treated sequentially with a solution of the product from part (b) (704 mg., 2.48 mmol.) in dry methylene chloride (5.0 ml.), triethylamine (0.34 ml., 2.44 mmol.) and benzotriazol-1-yloxytris-(dimethylamino)phosphonium hexafluorophosphate (1.113 g., 2.55 mmol.). The reaction mixture was stirred at 0° C. for 1.0 hour and at room temperature for 2.5 hours under argon. The reaction mixture was stripped to dryness and the syrup obtained was re-dissolved in ethyl acetate (80 ml.), washed with 0.5N hydrochloric acid (2×14.0 ml.), water (14.0 ml.) and brine (14.0 ml.), dried (anhydrous magnesium sulfate), filtered, evaporated to dryness and dried in vacuo. The crude product was chromatographed on a silica gel column (Merck), eluting the column with ethyl acetate:hexane (1:3) to give 1.085 g. of title product as a syrup. TLC (ethyl acetate:hexane, 1:1) $R_f$=0.53.

d) [1S-[[1α,9α(R*)]]-Octahydro-9-[(2-mercapto-1-oxo-3-phenylpropyl)amino]-10-oxo-6H-pyridazino[1,2-a][1,2]diazepine-1-carboxylic acid A solution of the product from part (c) (1.085 g., 2.216 mmol.) in dry methylene chloride (15 ml.) was treated with anisole (1.03 ml., 9.5 mmol.) followed by trifluoroacetic acid (1.56 ml., 20.2 mmol.) and the reaction mixture was stirred at room temperature under argon for 4.0 days. The clear solution was stripped to dryness, evaporated from ethyl acetate (2×150-ml) and the crude product suspended in a mixture of ethyl acetate (10 ml.) and hexane (50 ml.). The solids were filtered off, washed well with hexane (50 ml.) then evaporated from toluene (2×100 ml) and dried in vacuo to give 865 mg. of [1S-[1α,9α(R*)]]-octahydro-9-[[2-(acetylthio)-1-oxo-3-phenylpropyl]amino]-10-oxo-6H-pyridazino[1,2-a][1,2]diazepine-1-carboxylic acid as a solid.

The above material was suspended in methanol (15 ml.), cooled down to 0° C. (ice-salt bath), purged with argon for 30 minutes then treated dropwise with a previously purged solution of 1.0N sodium hydroxide (6.03 ml., 3 eq.), maintaining the bubbling of argon throughout the addition and length of the reaction. The reaction mixture was stirred at 0° C. for 30 minutes (the solids went into solution within the first 5 minutes) brought to pH 2.0 with 5% potassium bisulfate (26.6 ml.), warmed up to room temperature and extracted with ethyl acetate (2×65 ml.). The combined organic extracts were washed with brine (18 ml.), dried (anhydrous sodium sulfate), filtered, evaporated to dryness and dried in vacuo. The product was dissolved in methylene chloride (7.0 ml.) and treated portionwise with hexane (70 ml.) while scratching until a solid was obtained. The solids were triturated with more hexane (100 ml.) and pentane (2×100 ml.), stirring the solids with the first 100 ml. for 2.0 hours and the next 100 ml. overnight at room temperature under argon. The product was dried in vacuo to give 790.6 mg. of title product as a solid foam; $[\alpha]_D=-44.4°$ (c=0.63, methanol). TLC (ethyl acetate:acetic acid, 95:5) $R_f=0.67$.

Anal.calc'd. for $C_{19}H_{25}N_3O_4S \cdot 0.20\ C_5H_{12} \cdot 0.80\ H_2O$: C, 57.11; H, 6.95; N, 9.99; S, 7.62 Found: C, 57.11; H, 6.72; N, 9.83; S, 7.44.

EXAMPLE 48

[S-(R*,R*)]-Hexahydro-6-[(2-mercapto-1-oxo-3-phenylpropyl)amino]-2-methyl-3,7-dioxo-1H-1,2-diazepine-1-acetic acid a) [2-[(1,1-Dimethylethoxy)carbonyl]hydrazino]acetic acid, ethyl ester Triethylamine (13.94 ml., 0.1 mol.) was added to a solution of hydrazine carboxylic acid, 1,1-dimethylethyl ester (13.216 g., 0.1 mole) in benzene (100 ml.), followed by the addition of ethyl bromoacetate (11.09 ml., 0.1 mol.). The reaction mixture was refluxed (oil bath, 95°–100° C.) for 14 hours, after which triethylamine (1.4 ml., 0.01 mol.) was added followed by ethyl bromoacetate (1.1 ml., 0.01 mole). After refluxing for an additional 8 hours, triethylamine (2 ml., 0.015 mol.) and ethyl bromoacetate (1.4 ml., 0.013 mole) were added. The mixture was allowed to reflux for another 14 hours (total 36 hours). After cooling to room temperature, the reaction mixture was filtered and the solid triethylamine, hydrochloride salt was washed with ethyl acetate/hexane (1:1). The combined filtrate was diluted with ethyl acetate, washed with saturated sodium bicarbonate, water, brine, dried (sodium sulfate) and filtered. The filtrate was concentrated in vacuo to afford 19.38 g. of crude product as a yellow syrup which was used for the next reaction without purification.

b) [2-[(1,1-Dimethylethoxy)carbonyl]-1-[(phenylmethoxy)carbonyl]hydrazino]acetic acid, ethyl ester Triethylamine (12.4 ml., 89 mmol.) was added to a solution of the crude product from part (a) (19.38 g.) in benzene (120 ml.) followed by the dropwise addition of [(phenylmethoxy)carbonyl]-chloride (13.4 ml., 89 mmol.) in benzene (30 ml.) over 30 minutes. The resulting suspension was stirred at room temperature under argon for 20 hours, then partitioned between ethyl acetate (500 ml.) and 1M potassium bisulfate solution. The organic phase was separated, washed with saturated sodium bicarbonate, water, brine, dried (sodium sulfate) and filtered. The filtrate was concentrated in vacuo and the residue was crystallized from ethyl acetate/hexane to afford, after drying in vacuo over phosphorus pentoxide, 15.736 g. of the title product as a white crystalline compound, m.p. 117°–119° C.

c) [2-[[(1,1-Dimethylethoxy)carbonyl]-1-[(phenylmethoxy)carbonyl]-2-methyl]pydrazino]acetic acid, ethyl ester Potassium carbonate (powdered and dried, 11.8 g., 85.15 mmol.) was added to a solution of the product from part (b) (6.0 g., 17.03 mmol.) in anhydrous dimethylformamide (30 ml.) followed by the addition of methyl iodide (5.3 ml, 85.15 mmol.). After stirring at 40° C. for 17 hours, additional methyl iodide (64 mmol.) was added and the reaction mixture stirred at 40° C. for an additional 28 hours. The suspension was filtered and to the filtrate was added 6.0 g. of fresh potassium carbonate (powdered and dried), followed by 5.0 ml. of methyl iodide. The suspension was stirred at 40° C. for 21 hours, then 1.2 ml. of methyl iodide was added and the reaction mixture stirred for additional 17 hours until starting material disappeared on TLC. The reaction mixture was filtered and the collected solid was washed with ethyl acetate. The filtrate was concentrated in vacuo to remove most of dimethylformamide, then diluted with 500 ml. of ethyl acetate, washed with water, 1M potassium bisulfate, water, brine and dried (magnesium sulfate). The filtrate was concentrated and the residue dried in vacuo to give 6.285 g. of crude product as a colorless oil.

d) [2-[[(1,1-Dimethylethoxy)carbonyl]-2-methyl]-hydrazino]acetic acid, ethyl ester A suspension of the product from part (c) (6.285 g., 17.03 mmol.) and palladium hydroxide (800 mg.) in ethanol (75 ml.) was vigorously stirred under hydrogen (balloon) for 4 hours. The suspension was filtered using a Millipore filter unit. The filtrate was concentrated and the residue dried in vacuo to afford 4.3 g. of title product as a light yellow oil.

e) (S)-2-Phthalimido-1.5-pentanedioic acid, 5-(phenylmethyl)ester

N-(Carbethoxy)phthalimide (9.7 g., 44.24 mmol., 1.05 eq.) was added to a suspension of L-glutamic acid, 5-(phenylmethyl)ester (10.0 g., 42.14 mmol.) and sodium bicarbonate (4.47 g., 42.14 mmole) in water (80 ml.) and dioxane (40 ml.). After stirring two hours, additional N-(carbethoxy)-phthalimide (4.4 g., 0.1 eq.) was added. The mixture was stirred for additional 2 hours. The reaction mixture was adjusted to pH 1–2 with solid potassium bisulfate, and extracted with ethyl acetate (3×150 ml.). The combined ethyl acetate extracts were washed with 1M potassium bisulfate, brine, dried (sodium sulfate) and filtered. The filtrate was concentrated in vacuo. The oily residue was taken into ethyl acetate and treated witch dicyclohexylamine (8.40 ml., 42.14 mmol.). Crystallization of the crude salt from ethyl acetate/hexane gave, after drying in vacuo, 13 g. of the title product as the dicyclohexylamine salt. The mother liquor was washed with 1M potassium bisulfate (2 x), water, brine, and dried (sodium sulfate). The filtrate was concentrated in vacuo. The oily residue was chromatographed using 0.5% acetic acid in heptane/ethyl acetate (3:7) as a mobile phase. The desired fractions were collected and concentrated. The oily residue was dried in vacuo to give 9.644 g. of the title product.

f) (S)-4-Phthalimido-5-oxo-5-[2-[(1,1-dimethyl-ethoxy)carbonyl]-1-(2-ethoxy-2-oxoethyl)-2-methylhydrazino] pentanoic acid, phenylmethyl ester Phosphorus pentachloride (5.10 g., 24.5 mmol.) was added to a cold (0° C.) solution of the product from part (e)

(about 17.10 mmol.) in ether (80 ml.). After stirring at 0° C. for 30 minutes and at room temperature for 30 minutes, the reaction mixture was concentrated in vacuo. The residue was stripped with toluene (3x) and dried in vacuo for 2 hours to give an oily compound that was used immediately in the following reaction.

Sodium bicarbonate solution (4 g. in 46 ml. of water) was added to a cold (0° C.) solution of the product from part (d) in toluene (40 ml.). With thorough stirring, the compound prepared above in toluene (30 ml.) was added dropwise via cannula. After addition, the reaction mixture was stirred at room temperature under argon for 19 hours. The reaction mixture was diluted with ethyl acetate (300 ml.), washed with water, 5% potassium bisulfate, water, brine and dried (sodium sulfate). The filtrate was concentrated and the residue dried in vacuo to give the title compound as an oil.

g) (S)-4-Phthalimido-5-oxo-5-[1-(2-ethoxy-3-oxoethyl)-2-methylhydrazino]pentanoic acid, phenylmethyl ester Anisole (7.4 ml.) followed by trifluoroacetic acid (13.10 ml., 170 mmol.) were added dropwise to a cooled (−10° C.) solution of the crude product from part (f) in methylene chloride (55 ml.). After the addition was completed, the reaction mixture was stirred at −10° C. for one hour. The reaction mixture was then allowed to warm to room temperature and stirring continued for 14 hours. After removal of the volatiles in vacuo, the residue was taken into 200 ml. of ethyl acetate, washed with saturated sodium bicarbonate with caution, then water, brine, and dried (sodium sulfate). The filtrate was concentrated in vacuo and the residue chromatographed using 20–40% ethyl acetate/hexane as a mobile phase. The desired fractions were collected and concentrated and the residue dried in vacuo to yield 7.254 g. of title product as a pale yellow oil.

h (S)-4-Phthalimido-S-oxo-5-[1-(2-ethoxy-3-oxoethyl)-2-methylhydrazino]pentanoic acid Palladium hydroxide (1.0 g.) was added to a solution of the product from part (g) (6.436 g., 13.38 mmol.) in warm ethanol (100 ml.). The suspension was vigorously stirred under hydrogen (balloon) for 4 hours. The suspension was filtered and the catalyst washed with ethanol. The combined filtrate was concentrated. The residue was stripped with toluene (2 x) and dried in vacuo overnight to yield 5.86 g. of product as a colorless oil which was used for the next reaction without purification.

i) (S)-Hexahydro-2-methyl-3,7-dioxo-6-phthalimido-1H-1,2-diazepine-1-acetic acid, ethyl ester Thionyl chloride (1.1 ml.) was added dropwise to a cooled (0° C.) solution of the product from part (h) (5.86 g., 13.38 mmol.) in methylene chloride (120 ml.). The reaction mixture was stirred at 0° C. for 15 minutes and then at room temperature for 3 hours. Additional thionyl chloride (0.3 ml., for a total of 1.4 ml.) was added and the reaction mixture was stirred for another 3 hours, then quenched with potassium bicarbonate solution (2.7 g. of potassium bicarbonate in 27 ml. of water). The separated organic phase was washed with saturated sodium bicarbonate. The aqueous phase was extracted with methylene chloride (2x). The combined methylene chloride phase was washed with water, brine and dried (magnesium sulfate). The filtrate was concentrated and the residue dried in vacuo to give 4.70 g. of desired product.

i) (S)-Hexahydro-2-methyl-3,7-dioxo-6-amino-1H-1,2-diazeoine-1-acetic acid, ethyl ester Hydrazine monohydrate (255 μl., 5.25 mmol.) was added to a suspension of the product from part (i) (1.867 g., 5.0 mmol.) in ethanol (30 ml.) and methylene chloride (10 ml.). After stirring for 2 hours, the volatiles were removed in vacuo and the residue stripped with toluene (2x), then dried in vacuo. The residue was taken into 2M aqueous acetic acid (20 ml.) and the resulting solution was stirred at room temperature for 14 hours. The suspension was filtered. The collected filtrate was basified with solid sodium bicarbonate to pH 10 and extracted with methylene chloride (3x). The combined methylene chloride phase was washed with 50% brine, brine, dried (sodium sulfate), filtered and evaporated. The residue was chromatographed using 2.5% methanol/methylene chloride as a mobile phase to afford 568 mg. of title product as a pale yellow oil.

k) [S-(R*,R*)-Hexahydro-6-[[2-(acetylthio)-1-oxo-3-phenylpropyl]amino]-2-methyl-3,7-dioxo-1H-1,2-diazepine-1-acetic acid, ethyl ester Triethylamine (302 μl, 2.171 mmol.) was added to a cooled (0° C.) solution of (S)-2-(acetylthio) benzenepropanoic acid (obtained from the dicyclohexylamine salt as described previously, 486 mg., 2.17 mmol) followed by the product from part (j) (480 mg., 1.973 mmol.) in methylene chloride (3 ml.), and benzotriazol-1-yloxytris(dimethylamino)-phosphonium hexafluorophosphate (960 mg., 2.171 mmol.) The mixture was stirred at 0° C. for 1 hour, then at room temperature for 2 hours. The volatiles were removed in vacuo. The residue was taken into ethyl acetate (100 ml.), washed with 5% potassium bisulfate, 50% saturated sodium bicarbonate, brine, dried (magnesium sulfate), filtered and evaporated to dryness. The crude product was flash chromatographed using 50–70% ethyl acetate/hexane as a mobile phase to give 824 mg. of title product as a white foaming compound.

l) [S-(R*,R*)]-Hexahydro-6-[(2-mercapto-1-oxo-3-phenylpropyl)amino]-2-methyl-3,7-dioxo-1H-1,2-diazeoine-1-acetic acid A solution of the product from part (k) (800 mg.,1.78 mmol) in methanol (9 ml.) cooled at 0° C. was purged with argon for 30 minutes, then treated dropwise with a previously purged 1M sodium hydroxide solution (7.12 m., 4.0 equiv.). The reaction was stirred at 0° C., while maintaining the bubbling of argon, for 1.5 hour, then acidified with 1M potassium bisulfate to pH 1–2 and extracted with ethyl acetate (3x). The combined ethyl acetate extract was washed with brine (2x), dried (magnesium sulfate), filtered and evaporated to dryness. The residue was flash chromatographed using 2% acetic acid/ethyl acetate as a mobile phase to give 668 mg. of desired product as a white foaming compound. Chloroform was used in the pooling of product-containing column fractions. $[\alpha]_D = -54.8°$ (c=0.8, methanol). TLC (3% acetic acid/ethyl acetate) $R_f=0.12$.

Anal. calc'd. for $C_{17}H_{21}N_3O_5S \cdot 0.57$ $CHCl_3$: C, 47.16; H, 4.86; N, 9.39; S, 7.16 Found: C, 47.48; H, 4.56; N, 9.01; S, 7.17.

EXAMPLE 49

[S-(R*,R*)]-Hexahydro-6-[(2-mercapto-1-oxo-3-Phenylpropyl)amino]-2-methyl-7-oxo-1H-1,2-diazepine-1-acetic acid a) (S)-Hexahydro-2-methyl-7-oxo-6-phthalimido-1H-1,2-diazepine-1-acetic acid, ethyl ester A solution of the product from Example 48 (i) (375 mg., 1.0 mmole) in dry tetrahydrofuran (2.4 ml.) was cooled to 0° C. and treated dropwise with a 1M solution of diborane in tetrahydrofuran. After the addition was completed, the reaction solution was stirred at 0° C. for 30 minutes (at that time it became a gel). The cooling bath was removed, and the semi-solid mixture was stirred at room temperature for an additional one hour before it was diluted with 2 ml. of methylene chloride and 2 ml. of 2M aqueous hydrochloric acid. After stirring for 15 minutes, the mixture was diluted with 20 ml. of methylene chloride, and washed with saturated sodium bicarbonate with caution. The separated aqueous phase was extracted with methylene chloride (3x). The combined methylene chloride extract was washed with 50% brine, brine, and dried (sodium sulfate). The filtrate was evaporated in vacuo to dryness to afford 344 mg. of crude product as an oil, which was used for the next reaction without purification.

b) (S)-Hexahydro-2-methyl-7-oxo-6-amino-1H-1,2-diazeoine-1-acetic acid, ethyl ester A solution of the product from part (a) (344 mg., 0.958 mmol.) in ethanol (3 ml.) was treated with hydrazine monohydrate (54.8 μL., 1.13 mmol.) according to the procedure of Example 48 part (j) affording 169 mg. of title product as a pale yellow oil.

c) [S-(R*,R*)]-Hexahydro-6-[[2-(acetylthio)-1-oxo-3-phenylpropyl]amino]-2-methyl-7-oxo-1H-1,2-diazeoine-1-acetic acid, ethyl ester A cold (0° C.) solution of (S)-2-(acetylthio) benzenepropanoic acid (obtained from the dicyclohexylamine salt as previously described, 198 mg., 0.885 mmol.) in methylene chloride (1 ml.) was treated with triethylamine (123 μL., 0.88 mmol.), the product from part (b) (169 mg., 0.738 mmol.) in methylene chloride (2 ml.) and benzotriazol-1-yloxytris(dimethylamino)phosphonium hexafluorophosphate (392 mg., 0.885 mmol.) The mixture was stirred at 0° C. for 1 hour, then at room temperature for 2 hours. The volatiles were removed in vacuo. The residue was taken into ethyl acetate (50 ml.), washed with 5% potassium bisulfate, saturated sodium bicarbonate, 50% brine, brine, and dried (magnesium sulfate). The filtrate was evaporated to dryness and the residue flash chromatographed using 40–50% ethyl acetate/hexane as a mobile phase to give 260.5 mg. of title product as a colorless oil.

d) [S-(R*,R*)]-Hexahydro-6-[(2-mercapto-1-oxo-3-phenylpropyl)amino]-2-methyl-7-oxo-1H-1,2-diazepine-1-acetic acid A solution of the product from part (c) (235 mg., 0.54 mmol.) in methanol (3 ml.) cooled at 0° C. was purged with argon for 30 minutes, then treated dropwise with a previously purged 1M sodium hydroxide solution (2.20 ml., 4.0 equiv.). The reaction was stirred at 0° C., while maintaining the bubbling of argon for 2 hours, then acidified with 1M potassium bisulfate to pH 1–2 and extracted with ethyl acetate (3x). The combined ethyl acetate extracts were washed with brine (2x), dried (sodium sulfate), filtered and evaporated to dryness. The residue was flash chromatographed using 2% acetic acid/ethyl acetate as a mobile phase to give 182.2 mg. of desired product as a white foaming compound; $[\alpha]_D = -9.6°$ (c=0.3, methanol). TLC (3% acetic acid in ethyl acetate) $R_f = 0.26$.

Anal. calc'd. for $C_{17}H_{23}N_3O_4S \cdot 0.2\ H_2O$: C, 55.32; H, 6.39; N, 11.39; S, 8.69 Found: C, 55.73; H, 6.44; N, 10.98; S, 8.56.

EXAMPLE 50

[S-(R*,R*)]-2,3,4,5-Tetrahydro-3-[(2-mercapto-1-oxohexyl)amino]-2-oxo-1H-benzazepine-1-acetic acid a) (S)-2-Bromohexanoic acid Potassium bromide (15.9 g., 133 mmol.) was added to a stirred solution of D-norleucine (5.0 g., 38 mmol.) in 2.5N sulfuric acid (77 ml.) at room temperature. The reaction mixture was cooled to −10° C. and solid sodium nitrite (3.94 g., 57 mmol.) was added portionwise, maintaining the temperature between −10° and −5° C. After addition was complete, the foamy reaction was stirred for 1 hour and then warmed to room temperature and stirred for another hour. The reaction mixture was then extracted twice with ether, the ether extracts were washed once with water, dried (magnesium sulfate), filtered and evaporated to give 3.3 g. of crude title product.

b) (S)-2-(Acetylthio)hexanoic acid, dicyclohexylamine salt

To a stirred slurry of potassium thioacetate (2.11 g., 18.5 mmol.) in 50 ml. of dry acetonitrile at room temperature under argon was added a solution of the product from part (a) (3.27 g., 16.8 mmol.) in 26 ml. of acetonitrile. The reaction was stirred 5 hours. The resulting slurry was filtered and evaporated. The residue was redissolved in ethyl ether, washed once with 5% potassium hydrogen sulfate solution and once with brine, dried (magnesium sulfate) and evaporated. The residue was dissolved in ether (64 ml.) and treated with dicyclohexylamine (3.4 ml., 16.8 mmol.). The ethereal solution was concentrated in vacuo, and triturated from hexanes to give a white solid which was recrystallized from ethyl ether/hexanes to give the title product. The mother liquor was concentrated and recrystallized twice to provide a total yield of 2.2 g. of title product; m.p. 145°–147° C.; $[\alpha]_D = -33.8°$ (c=1.08, chloroform).

c) [S-(R*,R*)]-2,3,4,5-Tetrahydro-3-[(2-mercapto-1-oxohexyl)amino]-2-oxo-1H-benzazepine-1-acetic acid, ethyl ester A stirred suspension of the product from part (b) (295 mg., 0.795 mmol.) in 5 ml. of ethyl acetate was washed twice with 5 ml. portions of 5% potassium hydrogen sulfate solution. The organic extract was dried (sodium sulfate), filtered, concentrated and dried in vacuo for 20 minutes. The resulting oil was dissolved in 3 ml. of methylene chloride and stirred under argon at 0° C. To this solution was added a solution of (S)-2,3,4,5-tetrahydro-3-amino-2-oxo-1H-benzazepine-1-acetic acid, ethyl ester [prepared as described by Watthey et al., J. Med. Chem., 28, p. 1511–1516 (1985) ](149 mg., 0.57 mmol.) in methylene chloride (3 ml.) then triethylamine (83 μL., 0.60 mmol.) and finally benzotriazol-1-yloxytris(dimethylamino)phosphonium hexafluorophosphate (264 mg., 0.60 mmol.). After 1 hour, the reaction was warmed to room temperature and stirred 90 minutes. The resulting solution was evaporated at less than 30° C. and the residue redissolved in ethyl acetate. The solution was washed once with 1M hydrochloric acid, once with water, once with a saturated solution of sodium bicarbonate and once with brine. The organic layer was dried (magnesium sulfate), filtered and evaporated. Purification by flash chromatography (eluting with 1:3 ethyl acetate/hexanes) provided. 193 mg. of the title product; $[\alpha]_D = -284.3°$ (c=0.21, chloroform).

d) [S-(R*,R*)]-2,3,4,5-Tetrahydro-3-[(2-mercapto-1-oxohexyl)amino]-2-oxo-1H-benzazepine-1-acetic acid A solution of the product from part (c) (183 mg., 0.42 mmol.) in 3.8 ml. of methanol was purged with nitrogen for 5 minutes and cooled to 0° C. To this solution was added dropwise 3.8 ml. of nitrogen-purged 1M sodium hydroxide. Nitrogen was slowly bubbled through the solution during the reaction. After one hour, the reaction was warmed to room temperature and stirred one hour. The reaction was acidified with a 5% potassium bisulfate solution and extracted with ethyl acetate, the extracts were washed with water and a saturated solution of sodium chloride, dried (magnesium sulfate) and evaporated. Reevaporation from hexanes yielded a white solid. The solid was gently heated in ethyl ether and crystallized with hexanes to give 117 mg. of title product as a white solid; m.p. 151°–153° C.; $[\alpha]_D=-214.1°$ (c=0.46, chloroform). TLC (ethyl acetate/hexane/acetic acid, 4:4:0.1) $R_f$=0.23.

Anal. calc'd.for $C_{18}H_{24}N_2O_4S$: C, 59.32; H, 6.64; N, 7.69; S, 8.80 Found: C, 59.10; H, 6.62; N, 7.72; S, 8.63.

EXAMPLE 51

[3S-[3α(R*),7β]]-Hexahydro-7-(2-hydroxyethyl)-3-[(2-mercapto-1-oxo-3-phenylpropyl)amino]-2-oxo-1H-azepine-1-acetic acid a) (3S-trans)-Hexahydro-3-[[(1,1-dimethylethoxy)carbonyl]amino]-2-oxo-7-(2-propenyl)-]H-azepine-1-acetic acid, methyl ester Hydrazine monohydrate (133 μL, 2.70 mmol.) was added dropwise to a solution of (3S-trans)-hexahydro-3-phthalimido-2-oxo-7-(2-propenyl)-1H-acetic acid, methyl ester [prepared as set forth in Example 36 part (e), 609 mg., 2.45 mmol.]. The reaction was stirred at room temperature for 64 hours, then filtered to remove the solid byproducts. The filtrate was concentrated in vacuo, dissolved in methylene chloride, refiltered and reconcentrated to give a crude oil. The crude oil was dried under vacuum to give 656 mg. of crude (3S-trans)-hexahydro-3-amino-2-oxo-7-(2-propenyl)-1H-azepine-1-acetic acid, methyl ester as a yellow oil.

To a solution of this crude amine (589 mg., 2.45 mmol.) in methylene chloride (10 ml.), purged with argon, was added 510 μl. (3.68 mmol.) of triethylamine. The reaction mixture was stirred 10 minutes, then 642 mg. (2.94 mmol.) of di-t-butyl dicarbonate was added. The reaction was stirred at room temperature for 16 hours, followed by the addition of a second portion of 170 μl (1.23 mmol.) of triethylamine and 160 mg. (0.74 pmol.) of di-t-butyl dicarbonate. The reaction was sitrred an additional 16 hours at room temperature, then diluted with 20 ml. of methylene chloride. The organic layer was washed with 2–10 ml. portions of water, dried (magnesium sulfate) and concentrated in vacuo to give a crude oil. The oil was flash chromatographed (Merck silica, 25×120 mm., 1:6 ethyl acetate/hexane, then 1:4 ethyl acetate/hexane) to give 651 mg. of title product as a clear oil.

b) (3S-trans)-Hexahydro-3-[[(1,1-dimethylethoxy)carbonyl]amino]-2-oxo-7-(hydroxyethyl)-1H-azepine-1-acetic acid, methyl ester To a solution of the product from part (a) (554 mg., 1.63 mmol.) in 3 ml. water/3 ml. dioxane was added 731 mg. (3.42 mmol.) of sodium periodate, followed after 10 minutes by the dropwise addition of 400 μl. (0.98 mmol.) of osmium tetroxide. The reaction was stirred at room temperature for 16 hours, filtered and rinsed with ethyl acetate. The resulting filtrate was concentrated in vacuo without heat and flash chromatographed (Merck silica, 25×120 mm., 1:4 ethyl acetate/hexane-no pressure) to give 309 mg. of (3S-trans)-hexahydro-3-[[(1,1-dimethylethoxy)carbonyl]amino]-2-oxo-7-acetaldehyde-1H-azepine-1-acetic acid, methyl ester as a clear oil.

To a solution of this aldehyde (309 mg., 0.90 mmol.) in methanol (5 ml.), cooled to 0° C., was added portionwise 68 mg. (1.80 mmol.) of sodium borohydride. The reaction was stirred at 0° C. for 1.5 hours, then quenched by the dropwise addition of 0.5 ml. water and warmed to room temperature.

The mixture was partitioned between 25 ml. ethyl acetate/25 ml. 1M hydrochloric acid; the aqueous layer was extracted with 2–20 ml. portions of ethyl acetate. The combined ethyl acetate layers were washed with 10 ml. of saturated sodium bicarbonate and 10 ml. brine, dried (magnesium sulfate) and concentrated in vacuo to give a crude oil. The oil was flash chromatographed (Merck silica, 25×90 mm., 2:1 ethyl acetate/hexane, then ethyl acetate) to give 292 mg. of title product as a clear oil.

c) [3S-[3α(R*),7β]]-Hexahydro-3-[[2-(acetylthio)-1-oxo-3-phenylpropyl]amino]-7-(2-hydroxyethyl)-2-oxo-1H-azepine-1-acetic acid, methyl ester To a solution of the product from part (b) (292 mg., 0.85 mmol.) in dioxane (1 ml.), cooled to 0° C., was added portionwise 2.5 ml. (9.34 mmol., 4M) of hydrochloric acid/dioxane. The reaction was warmed to room temperature and stirred for 16 hours, then concentrated in vacuo and azeotroped with toluene to give 248 mg. of (3S-trans)-hexahydro-3-amino-2-oxo-7-(2-hydroxyethyl)-1H-azepine-1-acetic acid, methyl ester, hydrochloride salt as a crude oil.

To a solution of this amine, hydrochloride salt (189 mg., 0.67 mmol.) and (S)-2-(acetylthio)-benzenepropanoic acid (prepared from the dicyclohexylamine salt as described previously, 157 mg., (0.74 mmol.) in methylene chloride (10 ml.), cooled to 0° C., was added triethylamine (230 μl., 1.68 mmol.). The mixture was stirred for 20 minutes, then benzotriazol-1-yloxytris(dimethylamino)phosphonium hexafluorophosphate (327 mg., 0.74 mmol.) was added. The reaction was stirred at 0° C. for one hour, then at room temperature for 3 hours. The reaction mixture was partitioned between 20 ml. ethyl acetate/20 ml. 5% potassium bisulfate solution. The water layer was separated and extracted with 2–20 ml. portions of ethyl acetate; the combined ethyl acetate layers were washed with 20 ml. of 5% potassium bisulfate solution, 20 ml. of saturated sodium bicarbonate, 2–20 ml. portions of brine, dried (magnesium sulfate) and concentrated in vacuo to give a crude oil. The oil was flash chromatographed (Merck silica, 25×80 mm., 1:4 ethyl acetate/hexane) to give 84 mg. of title product as a white foam.

d) [3S-[3α(R*),7β]]-Hexahydro-7-(2-hydroxyethyl)-3-[(2-mercapto-1-oxo-3-phenylpropyl)amino]-2-oxo-1H-azepine-1-acetic acid A solution of the product from part (c) (84 mg., 0.19 mmol.) in methanol (2 ml.) was purged with argon for 30 minutes and cooled to 0° C. To this solution was added drop.wise 2 ml. of 1M sodium hydroxide, also purged with argon for 30 minutes and cooled to 0° C. The reaction was stirred at 0° C. for 1 hour, with continuous argon purging, then acidified to pH 2 with 5% potassium bisulfate solution. The mixture was extracted with 3–20 ml. portions of ethyl acetate; the combined ethyl acetate layers were dried (magnesium sulfate) and concentrated in vacuo to give a crude foam. The foam was flash chromatographed (Merck silica, 15×60 mm., 0.5:5:95 acetic acid/methanol/methylene chloride) to give a white foam, which was azeotroped with toluene and dried in vacuo to give 48 mg. of title product as a white foam; $[\alpha]_D$=–42.9° (c=1.0, $CDCl_3$). TLC (acetic acid:methanol:methylene chloride, 1:10:90) $R_f$=0.25.

Anal. Calc'd. for $C_{19}H_{26}N_2SO_5$·0.5 $H_2O$: C, 56.55; H, 6.75; N, 6.94; S, 7.94 Found: C, 56.55; H, 6.64; N, 6.77; S, 7.51.

EXAMPLE 52

[1S-[1α,9β(R*)]]-Octahydro-9-[[2-mercapto-1-oxo-3-(2-thienyl)propyl]amino]-10-oxo-6H-pyridazino[1,2-a][1,2]diazepine-1-carboxylic acid a) (S)-α-(Acetylthio)-2-thiophenepropanoic acid Potassium chloride (3.0 g., 40.1 mmol.) was added to a solution of β-(2-thienyl)-D-alanine (1.37 g., 8.03 mmol.) in 2.5N hydrochloric acid (25 ml.) at room temperature under argon. After stirring for 10 minutes, the resulting mixture was cooled to 0° C. and treated with sodium nitrite (720 mg., 10.44 mmol.). After 2.5 hours, the reation mixture was warmed to room temperature and was stirred 1 hour. The mixture was partitioned between water and ethyl acetate and the organic layer was dried (sodium sulfate), filtered, and concentrated. The residue was flash chromatographed (Merck silica gel) eluting with 1% acetic acid in 3:1 hexane/ ethyl acetate to give 760 mg. of (R)-α-chloro-2-thiophenecarboxylic acid as a yellow oil.

Cesium thioacetate (2.95 g., 14.19 mmol.) was added to a solution containing the above chloride (750 mg., 4.73 mmol.) in dimethylformamide (15 ml.) at room temperature under argon. After stirring for 2 hours, the reaction mixture was partitioned between 10% potassium bisulfate and ethyl acetate. The organic layer was washed with brine, dried (sodium sulfate), filtered, and concentrated and the residue was flash chromatographed (Merck silica gel) eluting with 1% acetic acid in 4:1 hexane/ethyl acetate to give 500 mg. of the title product as an oil. TLC (2% acetic acid in 3:1 ethyl acetate/hexane) Rf 0.73.

b) [1S-{1α,9α(R*)]]-Octahydro-9-[[2-(acetylthio)-1-oxo-3-(2-thienyl)propyl]amino]-10-oxo-6H-pyridazino[1,2-a][1,2]diazepine-1-carboxylic acid The product from part (a) (246 mg., 1.07 mmol.) and (1S-cis)-octahydro-9-amino-10-oxo-6H-pyridazino[1,2-a][1,2]diazepine-1-carboxylic acid, 1,1-dimethyethyl ester from Example 47(b) (370 mg., 1.17 mmol.) were dissolved in methylene chloride (10 ml.) at room temperature under argon. The resulting mixture was cooled to 0° C. and triethylamine (0.15 ml., 1.07 mmol.) was added. The resulting mixture was stirred for 5 minutes then benzotriazol-1-yloxytris(dimethylamino)phosphonium hexafluorophosphate (517 mg., 1.17 mmol. was added. After being stirred at 0° C. for 1 hour, the reaction mixture was warmed to room temperature and was stirred for 16 hours. The volatiles were evaporated and the residue was dissolved in ethyl acetate and washed successively with 1N hydrochloric acid, water, 50% saturated sodium bicarbonate, and brine. The organic layer was dried (sodium sulfate), filtered, and concentrated and the residue was flash chromatographed (Merck silica gel ) eluting with 3:2 hexane/ethyl acetate. The product was resubjected to flash chromatography eluting with 3:1 hexane/ethyl acetate to give 395 mg. of [1S-[1α,9α(R*)]]-octahydro-9-[[2-(acetylthio)-1-oxo-3-(2-thienyl)propyl]amino]-10-oxo-6H-pyridazino[1,2-a][1,2]diazepine-1-carboxylic acid, 1,1-dimethylethyl ester as a white foam. TLC (ethyl acetate:hexane, 1:1) Rf=0.43.

Anisole (0.38 ml., 3.52 mmol.) was added to a solution of the above product(390 mg., 0.82 mmole) in methylene chloride (6 ml.) at room temperature under argon. The resulting mixture was treated with trifluoroacetic acid (0.58 ml., 7.5 mmol.) and was stirred for 36 hours. The volatiles were removed and the residue was chased with toluene and evacuated to give 380 mg. of a yellow oil. The oil was purified by column chromatography (Merck silica gel) eluting with 1% acetic acid in 1:1 ethyl acetate/hexane followed by 1% acetic acid in 2:1 ethyl acetate hexane to give 360 mg. of the title product. TLC (1% acetic acid in 1:1 ethyl acetate/hexane) Rf=0.28.

c) [1S-[1α,9α(R*)]]-Octahydro-9-[[2-mercapto-1-oxo-3-(2-thienyl)propyl]amino]-10-oxo-6H-pyridazino[1,2-a][1,2] diazeoine-1-carboxylic acid A solution of the product from part (b) (328 mg., 0.75 mmol.) in methanol (5 ml., deoxygenated via argon bubbling) was cooled to 0° C. and treated with 1N sodium hydroxide (4 ml., deoxygenated via argon bubbling). The resulting mixture was stirred under argon for 1 hour. The mixture was acidified with 10% potassium bisulfate and extracted with ethyl acetate. The organic layer was washed successively with water and brine, dried (sodium sulfate), filtered and concentrated to give a clear oil. This residue was flash chromatographed (Merck silica gel) eluting with 1% acetic acid in 1:2 hexane/ethyl acetate. The fractions containing clean desired product were combined, stripped, azeotroped with ethyl acetate, and washed with water to remove any acetic acid. The organic layer was dried (sodium sulfate), filtered and concentrated. The residue was taken up in ethyl acetate and triturated with hexane. The solvent was removed and the residue was slurried in hexane, stripped, and dried in vacuo to give 165 mg. of title product as a white powdery foam. $[α]_D$=131.6° (c=0.43, methylene chloride) TLC (1% acetic acid in 2:1 ethyl acetate/hexane) $R_f$=0.36.

Anal. calc'd for $C_{17}H_{23}N_3O_4S_2$.0.21 $H_2O$.0.09 $C_6H_{14}$.0.13 $C_4H_8O_2$: C, 51.58; H, 6.17; N, 9.99; S, 15.25 Found: C, 51.24; H, 6.08; N, 9.69; S, 15.22.

EXAMPLE 53

[1S-[1α,8α(R*)]]-Hexahydro-8-[(2-mercapto-1-oxo-3-phenylpropyl)amino]-9-oxo-1H,5H-pyrazolo[1,2-a][1,2]diazepine-1-carboxylic acid a) 1-[(Phenylmethoxy)carbonyl]-3-pyrazolidinecarboxylic acid, 1,1-dimethylethyl ester A solution of 3-pyrazolidinecarboxylic acid, 1,1-dimethylethyl ester (10.935 g., 63.5 mmol.) in dry acetonitrile (90 ml.) was cooled to 0° C. (ice-salt bath) and treated with dry pyridine (11.0 ml.) followed by a solution of benzylchloroformate (12.54 g., 10.5 ml., 69.9 mmol.) in dry acetonitrile (25 ml.). The reaction was stirred at 0° C. for 3 hours, evaporated to dryness and the syrup obtained was re-dissolved in ethyl acetate (250 ml.). The solution was washed with 5% sodium bicarbonate (2×25 ml.) and brine (25 ml.), dried (anhydrous sodium sulfate), filtered, evaporated to dryness and dried in vacuo. The crude product mixture was chromatographed on a silica gel column (Merck), eluting the column with ethyl acetate:hexane mixtures (1:4; 1:2) to give 11.144 g. of title product as a syrup. TLC (ethyl acetate:hexane, 1:1) $R_f$=0.25.

b) (S)-2-[2-Phthalimido-1,5-dioxo-5-(phenylmethoxy) pentyl]-1,3-pyrazolidinedicarboxylic acid, 3-(1,1-dimethylethyl)-1-phenylmethyl ester The dicylcohexylamine salt of (S)-2-phthalimidopentanedioic acid, 5-(phenylmethyl)ester (11.548 g., 21 mmol.) was suspended in ethyl acetate (700 ml.), washed with 5% potassium bisulfate (5×100 ml.) and brine (100 ml.), dried (anhydrous sodium sulfate), filtered, evaporated to dryness and dried in vacuo.

The free acid obtained was dissolved in dry ether (100 ml.), cooled to 0° C. (ice-salt bath), treated with phosphorous pentachloride (4.45 g., 21 mmol.) and stirred at 0° C. for 30 minutes then at room temperature for 15 minutes. The reaction mixture was evaporated to dryness, evaporated from toluene (2×230 ml.) and dried in vacuo. The crude acid chloride was dissolved in toluene (46 ml.), added to a cooled solution (10° C., ice-water bath) of the product from part (a) (5.52 g., 18 mmol.) in toluene (35 ml.)-sodium bicarbonate (4.77 g. in 46 ml. water), warmed up to room temperature and stirred under argon for 20 hours. The reaction mixture was diluted with ethyl acetate (650 ml.), washed with 5% potassium bisulfate (2×140 ml.) and brine (140 ml.), dried (anhydrous sodium sulfate), filtered, evaporated to dryness and dried in vacuo to give 11.587 g. of title product.

c) (1S-cis)-Hexahydro-8-phthalimido-5,9-dioxo-1H,5H-pyrazolo[1,2-a][1,2]diazepine-1-carboxylic acid, 1,1-dimethylethyl ester A solution of the product from part (b) (12.653 g., 18 mmol.) in dry dimethylformamide (196 ml.) was treated with 10% palladium on carbon catalyst (2.19 g.) and hydrogenated (balloon) at room temperature for 24 hours. The reaction mixture was diluted with methanol (200 ml.) and filtered through a Celite pad, washing the pad well with methanol (2×200 ml.). The clear filtrate was evaporated to dryness and dried in vacuo to give a light gold-colored syrup. The crude product was dissolved in dry methylene chloride (185 ml.), cooled to 0° C. (ice-salt bath), treated with thionyl chloride (1.62 ml., 22.2 mmol.), stirred at 0° C. for 15 minutes then at room temperature for 6.0 hours. The reaction mixture was quenched with a solution of potassium bicarbonate (3.93 g.) in water (34 ml.), stirred for 10–15 minutes then extracted with methylene chloride (2×290 ml.). The combined organic extracts were dried (anhydrous sodium sulfate), filtered, evaporated to dryness and dried in vacuo The crude product mixture was chromatographed on a silica gel column (Merck), eluting the column with ethyl acetate:hexane mixtures (1:3; 1:2) to give 2.427 g. of title TLC (ethyl acetate:hexane, 1:1) $R_f$=0.37.

d) (1S-cis)-Hexahydro-8-phthalimido-9-oxo-1H,5H-pyrazolo[1,2-a][1,2]diazepine-1-carboxylic acid, 1,1-dimethylethyl ester A solution of the product from part (c) (607 mg., 1.43 mmol.) in dry tetrahydrofuran (12 ml.) was cooled to 0° C. (ice-salt bath) and treated with 1.0M diborane/tetrahydrofuran according to the procedure of Example 47 part (a) to give 538 g. of title product as a syrup. TLC (ethyl acetate:hexane, 1:1) $R_f$=0.38.

e) (1S-cis)-Hexahydro-8-amino-9-oxo-1H,5H-pyrazolo[1,2-a][1,2]diazepine-1-carboxylic acid, 1,1-dimethylethyl ester A solution of the product from part (d) (505 mg., 1.25 mmol.) in absolute ethanol (5.5 ml.) was treated with hydrazine hydrate (0.14 ml., 2.2 eq.) according to the procedure of Example 46 part (b) affording 312 mg. of title compound as a syrup. TLC (methylene chloride:methanol, 9:1) $R_f$=0.63.

f) [1S-[1α,8α(R*)]]-Hexahydro-8-[[2-(acetylthio)-1-oxo-3-phenylpropyl]amino]-9-oxo-1H,5H-pyrazolo[1,2-a][1,2]diazepine-1-carboxylic acid (S)-2-(Acetylthio)benzenepropanoic acid (obtained from 554 mg. of the dicyclohexylamine salt as previously described) was dissolved in methylene chloride (11 ml.), cooled to 0° C. (ice-salt bath), and treated sequentially with a solution of the product from part (e) (350 mg., 1.25 mmol.) in dry methylene chloride (2.5 ml.), triethylamine (0.17 ml., 1.22 mmol.), and benzotriazol-1-yloxytris (dimethylamino) phosphonium hexafluorophosphate (561 mg., 1.29 mmol.) according to the procedure of Example 47 part (c) to give 400 mg. of [1S-[1α,8α(R*)]]-hexahydro-8-[[2-(acetylthio)-1-oxo-3-phenylpropyl]amino]-9-oxo-1H,5H-pyrazolo[1,2-a][1,2]diazepine-1-carboxylic acid, 1,1-dimethylethyl ester as a syrup. TLC (ethyl acetate:hexane, 1:1) $R_f$=0.28.

A solution of this material in dry methylene chloride was treated with anisole and trifluoroacetic acid according to the procedure of Example 47 part (d) affording the title product as a solid; $[\alpha]_D$=−111.5° (c=0.48, methanol). TLC (ethyl acetate: acetic acid, 95:5) $R_f$=0.38.

g) [1S-[1α,8α(R*)]]-Hexahydro-8-[(2-mercapto-1-oxo-3-phenylpropyl)amino]-9-oxo-1H,5H-pyrazolo[1,2-a][1,2]diazepine-1-carboxylic acid A solution of the product from part (f) in dry methanol was treated with 1.0N sodium hydroxide according to the procedure of Example 47 part (d) to give the title product as a white solid amorphous foam; $[\alpha]_D$=−71° (c=0.50, methanol). TLC (ethyl acetate:acetic acid, 95:5) $R_f$=0.25.

Anal calc'd. for $C_{18}H_{23}N_3O_4S.0.13\ C_5H_{12}.0.20\ H_2O$: C, 57.36; H, 6.44; N, 10.76; S, 8.21 Found: C, 57.36; H, 6.50; N, 10.47; S, 8.10.

EXAMPLE 54

[1S-[1α,8α(R*)]]-Hexahydro-8-[(2-mercapto-1-oxo-3-phenylpropyl)amino]-5,9-dioxo-1H,5H-pyrazolo [1,2-a][1,2]diazepine-1-carboxylic acid a) (1S-cis)-Hexahydro-8-amino-5,9-dioxo-1H,5H-pyrazolo[1,2-a][1,2]diazepine-1-carboxylic acid, 1,1-dimethylethyl ester A solution of the product from Example 53 part (c) (700 mg., 1.67 mmol.) in absolute ethanol (7.4 ml.) was treated with hydrazine hydrate (0.19 ml., 2.2 eq.) according to the procedure of Example 53 part (e) to give 436 mg. of title product as a white foam. TLC (methylene chloride:methanol, 9:1) $R_f$=0.30.

b) [1S-[1α,8α(R*)]]-Hexahydro-8-[(2-mercapto-1-oxo-3-phenylpropyl)amino]-5,9-dioxo-1H,5H-pyrazolo[1,2-a][1,2]diazepine-1-carboxylic acid The product from part (a) was reacted with (S)-2-(acetythio)benzenepropanoic acid in the presence of triethylamine and benzotriazol-1-yloxytris(dimethylamino) phosphonium hexafluorophosphate according to the procedure of Example 53 part (f) affording [1S-[1α,8α(R*)]]-hexahydro-8-[[2-(acetylthio)-1-oxo-3-phenylpropyl]amino]-5,9-dioxo-1H,5H-pyrazolo[1,2-a][1,2]diazepine-1-carboxylic acid, 1,1-dimethylethyl ester as a syrup. TLC (ethyl acetate:hexane, 1:1) $R_f$=0.22.

This material was treated with anisole followed by trifluoroacetic acid according to the procedure of Example 53 part (f). The resulting acid product was dissolved in methanol and treated with 1.0N sodium hydroxide according to the procedure of Example 53 part (g) affording the title product as a white solid amorphous foam; $[\alpha]_D$=−95.8° (c=0.72, methanol). TLC (methylene chloride:methanol:acetic acid, 20:1:1) $R_f$=0.13.

Anal. calc'd for $C_{18}H_{21}N_3O_5S.0.07\ C_6H_{14}.1.14\ H_2O$: C, 52.89; H, 5.83; N, 10.06; S, 7.67 Found: C, 52.89; H, 5.80; N, 9.18; S, 7.01.

EXAMPLE 55

[3S-[1(R*),3α(R*),7β]]-Hexahydro-α-methyl-3-[(2-mercapto-1-oxo-3-phenylpropyl]amino]-2-oxo-7-propyl-1H-azepine-1-acetic acid a) [3S-[1(R*),3α,7β]]-Hexahydro-α-methyl-3-phthalimido-2-oxo-7-(2-propenyl)-1H-azepine-1-acetic acid, methyl ester Allyltrimethylsilane (1.53 ml., 9.6 mmol.) was added to a solution of [S-(R*,R*)]-hexahydro-α-methyl-3-phthalimido-2-oxo-1H-azepine-1-acetic acid, methyl ester (485 mg., 1.48 mmol.) in methylene chloride (20 ml.) at room temperature under argon. Following the addition of of stannic bromide (1.0M in methylene chloride, 2.52 ml., 2.52 mmol.), the resulting mixture was stirred for 4 hours. Another portion of stannic bromide (1.48 ml.) was added and stirring was continued for 48 hours. The reaction mixture was quenched with aqueous ammonium chloride and extracted with ethyl acetate. The organic layer was washed with brine, dried (sodium sulfate), filtered, and concentrated to give 1.2 g. of a yellow residue. The crude acid was dissolved in methanol, cooled to 0° C., and treated with diazomethane to generate the methyl ester. The volatiles were removed and the residue was flash chromatographed (Merck silica gel) eluting with 1:3 ethyl acetate/hexane followed by 1:1 ethyl acetate/hexane to give 283 mg. of title product as a white foam; $[\alpha]_D=-13.7°$ (c=0.54, methylene chloride)). TLC (ethyl acetate:hexane, 1:1) $R_f=0.50$.

b) [3S-[1(R*),3α,7β]]-Hexahydro-α-methyl-3-phthalimido-2-oxo-7-propyl-1H-azepine-1-acetic acid, methyl ester A solution of the product from part (a) (463 mg., 1.24 mmol.) in 1:1 methanol/ethyl acetate (14 ml.) was hydrogenated over 10% palladium on carbon catalyst (41 mg.) for 3 hours. The mixture was filtered through Celite and the volatiles were removed to give 483 mg. of title product as a yellow oil.

c) [3S-[1(R*),3α(R*),7β]]-Hexahydro-α-methyl-3-[[2-(acetylthio)-1-oxo-3-phenylpropyl]amino]-2-oxo-7-propyl-1H-azepine-1-acetic acid, methyl ester The product from part (b) (483 mg.) was suspended in methanol (7 ml.) at room temperature under argon. The mixture was treated with hydrazine monohydrate (0.07 ml., 1.45 mmol.), became homogeneous, and was stirred for 18 hours. The mixture was filtered to remove the white precipitate and the filtrate was stripped, treated with methylene chloride, filtered and stripped again to give 282 mg. of [3S-[1(R*),3α,7β]]-hexahydro-α-methyl-3-amino-2-oxo-7-propyl-1H-azepine-1-acetic acid, methyl ester as a yellow oil.

(S)-2-(Acetylthio)benzenepropanoic acid (obtained from 491 mg. of the dicyclohexylamine salt as described previously) was dissolved in methylene chloride (15 ml.) at room temperature under argon. Following the addition of the above amine (282 mg., 1.10 mmol.), the mixture was cooled to 0° C. and treated with triethylamine (0.17 ml., 1.21 mmol.) and benzotriazol-1-yloxytris (dimethylamino) phosphonium hexafluorophosphate (511 mg., 1.16 mmol.) according to the procedure of Example 36 part (f) to give 385 mg. of the title product as a white foam. TLC (ethyl acetate:hexane, 1:1) $R_f=0.43$.

d) [3S-[1(R*),3α(R*),7β]]-Hexahydro-α-methyl-3-[(2-mercapto-1-oxo-3-phenylpropyl)amino]-2-oxo-7-propyl-1H-azepine-1-acetic acid A solution of the product from part (c) (385 mg., 0.83 mmol.) in methanol (10 ml.) was treated with 1N sodium hydroxide (8 ml.) according to the procedure of Example 36 part (g) to give 142 mg. of title product as a white powdery foam; $[\alpha]_D=-51.6°$ (c=0.48, methylene chloride) TLC (1% acetic acid in 2:1 ethyl acetate/hexane) $R_f=0.60$.

Anal. calc'd. for $C_{21}H_{30}N_2O_4S.0.14\ H_2O$: C, 61.67; H, 7.46; N, 6.85; S, 7.84 Found: C, 61.97; H, 7.50; N, 6.55; S, 7.62.

EXAMPLE 56

[S-(R*,R*)]-2,3,4,5-Tetrahydro-3-[(2-mercapto-1-oxo-3-phenylpropyl)amino]-2-oxo-1H-pyrrolo[1,2-b][1,2]diazepine-1-acetic acid a) [S-(R*,R*)]-2,3,4,5-Tetrahydro-3-[[2-(acetylthio)-1-oxo-3-phenylpropyl]amino]-2-oxo-1H-pyrrolo[1,2-b][1,2]diazepine-1-acetic acid, ethyl ester (S)-3-Amino-2-oxo-1H-pyrrolo[1,2-b][1,2]diazepine-1-acetic acid, ethyl ester [prepared as described by Bolos et al., J. Org. Chem., 57, p 3535–33539 (1992)] was reacted with (S)-2-(acetylthio)benzenepropanoic acid in the presence of triethylamine and benzotriazol-1-yloxytris-(dimethlamino) phosphonium hexafluorophosphate according to the procedure described above, as note Example 36 part (f), affording the title product as a colorless oil.

b) [S-(R*,R*)]-2,3,4,5-Tetrahydro-3-[(2-mercapto-1-oxo-3-phenylpropyl)amino]-2-oxo-1H-pyrrolo[1,2-b][1,2]diazepine-1-acetic acid A solution of the product from part (a) (135 mg., 0.30 mmol.) in methanol (2 ml.), tetrahydrofuran (1 ml.), and water (1 ml.) was sparged with argon for 30 minutes. Lithium hydroxide monohydride (50 mg., 1.2 mmol.) was added to the solution at room temperature. The reaction mixture was stirred for 2 hours with continuous argon sparge, then acidified by the addition of 1M aqueous hydrochloric acid solution (1.4 ml.), then added to water (20 ml.) and then extracted with ethyl acetate (2×15 ml.). The organic extracts were combined, dried (sodium sulfate), and concentrated in vacuo to give an oil. The crude material was purified by flash chromatography (Merck silica, 12×1.5 cm., 1:99 acetic acid/ethyl acetate) to afford 115 mg. of title product as a white solid foam; $[\alpha]_D=-67°$ (c=0.26, methanol). TLC (acetic acid:methanol:methylene chloride, 1:10:90) $R_f=0.43$.

Anal. calc'd. for $C_{19}H_{21}N_3O_4S$: C, 58.90; H, 5.46; N, 10.85; S, 8.27 Found: C, 58.55; H, 5.50; N, 10.74; S, 8.17.

EXAMPLE 57

[1S-[1α,9α(R*)]]-Octahydro-9-[[2-(methyldithio)-1-oxo-3-phenylpropyl]amino]-10-oxo-6H-pyridazino-[1,2-a][1,2]diazepine-1-carboxylic acid A solution of the product of Example 47 (100 mg., 0.247 mmol.) dissolved in ethanol (1.5 ml.) and water (0.15 ml.) was cooled to 0° C. and treated with methyl methanethiosulfonate (30.5 µl., 37.4 mg., 0.296 mmol.). After 2 hours at 0° C. and 6 hours at room temperature, the reaction mixture was diluted with water and extracted with a mixture of ethyl acetate and ethyl ether. The organic extract was rinsed with water and brine, dried (magnesium sulfate), and concentrated in vacuo to 157 mg. of crude product. Flash chromatography on 12 g. of Merck silica gel eluted with hexanes, then 1:1, hexanes:ethyl acetate, and finally 4:4:0.05 followed by 4:4:0.1, hexanes:ethyl acetate:acetic acid yielded purified product. Trituration with ethyl acetate-hexanes afforded 85.4 mg. of title product as a white solid foam; $[\alpha]_D=-104.2°$ (c=0.18, chloroform). TLC (hexanes:ethyl acetate:acetic acid, 4:4:0:1) $R_f=0.16$.

Anal. calc'd. for $C_{20}H_{27}N_3O_4S.0.05\ C_4H_{82}.0.01\ C_6H_{14}$: C, 54.95; H, 6.27; N, 9.49; S, 14.48 Found: C, 55.03; H, 6.22; N, 9.49; S, 14.40.

EXAMPLE 58

[S-((R*,R*)]-2,3,4,5-Tetrahydro-3-[[2-(methyldithio)-1-oxo-3-phenylpropyl]amino]-2-oxo-1H-benzazepine-1-acetic acid A solution of the product of Example 6 (100 mg., 0.235 mmol.) dissolved in ethanol (1.2 ml.) and water (0.112 ml.) was cooled to 0° C. and treated with methyl methanesulfonate (29 µl., 35.6 mg., 0.282 mmol.). After one hour at 0° C., the reaction was kept at room temperature for 8 hours, then refrigerated overnight. The reaction mixture was diluted with water and extracted with a mixture of ethyl acetate and ethyl ether. The organic extract was rinsed with water and brine, dried (magnesium sulfate), and concentrated in vacuo to 123 mg. of crude product. Flash chromatography on 9 g. of Merck silica gel eluted with hexanes, then 1:1, hexanes:ethyl acetate, and finally 4:4:0.1, hexanes:ethyl acetate:acetic acid yielded 108 mg. of product. Trituration with ethyl acetate-hexanes gave 97 mg. of title product as a white solid; m.p. 83°–95° C.; $[\alpha]_D=-185.17°$ (c=0.3, chloroform). TLC (hexanes:ethyl acetate:acetic acid, 4:4:0.1) $R_f=0.16$.

Anal. calc'd. for $C_{22}H_{24}N_2O_4S_2 \cdot 0.84\ H_2O \cdot 0.07\ C_4H_8O_2 \cdot 0.07\ C_6H_{14}$: C, 57.78; H, 5.81; N, 5.94; S, 13.59 Found: C, 57.70; H, 6.13; N, 6.27; S, 13.20.

EXAMPLE 59

[S-(R*,R*)]-2,3,4,5-Tetrahydro-3-[(2-mercapto-1-oxo-4-methylpentyl)amino]-2-oxo-1H-benzazepine-1-acetic acid a) (S)-2-Bromo-4-methylpentanoic acid Potassium bromide (9.5 g., 80 mmol.) was added to a stirred solution of D-leucine (3.0 g., 23 mmol.) in 2.5N sulfuric acid (47 ml.) at room temperature. The reaction mixture was cooled to -10° C. and solid sodium nitrite (2.4 g., 34 mmol.) was added portionwise, maintaining the temperature between −10° and −5° C. After addition was complete, the reaction was stirred for 1 hour and then warmed to room temperature and stirred for another hour. The reaction mixture was then extracted twice with ether, the ether extracts were washed once with water, dried (magnesium sulfate), filtered and evaporated to give 2.7 g. of crude title product.

b) (S)-2-(Acetylthio)-4-methylpentanoic acid, dicyclohexylamine salt

To a stirred slurry of potassium thioacetate (1.7 g., 15.0 mmol.) in 50 ml. of dry acetonitrile at room temperature under argon was added a solution of the product from part (a) (2.6 g., 13 mmol.) in 17 ml. of acetonitrile. The reaction was stirred 4 hours. The resulting slurry was filtered and evaporated. The residue was redissolved in ethyl ether, washed once with 5% potassium hydrogen sulfate solution and once with brine, dried (magnesium sulfate) and evaporated. The residue was dissolved in ether (64 ml.) and treated with dicyclohexylamine (2.7 ml., 14 mmol.). A white solid immediately began precipitating from the solution. The solution was filtered and the white solid collected to give 2.0 g. of title product; m.p. 153°–158° C.; $[\alpha]_D=-54.5°$ C. (c=0.61, chloroform).

c) [S-(R*,R*)]-2,3,4,5-Tetrahydro-3-[[2-(acetylthio)-1-oxo-4-methylpentyl]amino]-2-oxo-1H-benzazepine-1-acetic acid, ethyl ester A stirred suspension of the product from part (b) (312 mg., 0.840 mmol.) in 5 ml. of ethyl acetate was washed twice with 5 ml. portions of 5% potassium hydrogen sulfate solution. The organic extract was dried (sodium sulfate), filtered, concentrated and dried in vacuo for 20 minutes. The resulting oil was dissolved in 2.5 ml. of methylene chloride and stirred under argon at 0° C. To this solution was added a solution of (S)-2,3,4,5-tetrahydro-3-amino-2-oxo-1H-benzazepine-1-acetic acid, ethyl ester [prepared as described by Watthey et al., J. Med. Chem., 28, p. 1511–1516 (1985)] (142 mg., 0.54 mmol.) in methylene chloride (3 ml.), then triethylamine (80 μl., 0.57 mmol.) and finally benzotriazol-1-yloxytris(dimethylamino)phosphonium hexafluorophosphate (251 mg., 0.57 mmol.). After 1 hour, the reaction was warmed to room temperature and stirred 90 minutes. The resulting colorless solution was evaporated at less than 30° C. and the oily residue redissolved in ethyl acetate. The solution was washed once with 1M hydrochloric acid, once with water, once with a saturated solution of sodium bicarbonate and once with brine. The organic layer was dried (magnesium sulfate), filtered and evaporated. Purification by flash chromatography (eluting with 2:5 ethyl acetate/hexanes) provided 223 mg. of the title product; $[\alpha]_D=-243.9°$ (c=0.62, chloroform).

d) [S-(R*,R*)]-2,3,4,5-Tetrahydro-3-[(2-mercapto-1-oxo-4-methylpentyl)amino]-2-oxo-1H-benzazepine-1-acetic acid A solution of the product from part (c) (190 mg., 0.44 mmol.) in 4 ml. of methanol was purged with nitrogen for 5 minutes and cooled to 0° C. To this solution was added dropwise 4 ml. of nitrogen-purged 1M sodium hydroxide. Nitrogen was slowly bubbled through the solution during the reaction. After one hour, the reaction was warmed to room temperature and stirred one hour. The reaction was acidified with a 5% potassium bisulfate solution and extracted with ethyl acetate, the extracts were washed with water and a saturated solution of sodium chloride, dried (sodium sulfate) and evaporated. Reevaporation from hexanes yielded a white solid. The solid was gently heated in ethyl ether, filtered to remove an insoluble oil, and crystallized with hexanes to give 117 mg. of title product as a white solid; m.p. 143°–144° C.; $[\alpha]_D=-224.3°$ (c=0.46, chloroform). TLC (ethyl acetate/hexane/acetic acid, 4:4:0.1) $R_f=0.19$.

Anal. calc'd. for $C_{18}H_{24}N_2O_4S \cdot 0.02\ C_4H_{10}O$: C, 59.34; H, 6.67; N, 7.66; S, 8.76 Found: C, 58.97; H, 6.72; N, 7.52; S, 8.67.

EXAMPLE 60

[R-(R*,S*)]-2,3,4,5-Tetrahydro-3-[(2-mercapto-2-methyl-1-oxo-3-phenylpropyl)amino]-2-oxo-1H-benzazepine-1-acetic acid a) S,S'-Bis(4-methoxy-α-toluenethiol)

A solution of 4-methoxy-α-toluenethiol (25 g., 0.16 mol.) in benzene (200 ml) was added to a solution of potassium carbonate (44.8 g., 0.32 mol.) in water (200 ml.) and the resulting mixture was treated portionwise, with rapid stirring, with iodine (23.6 g.) until the color of iodine persisted. The reaction mixture was stirred for 15 minutes after which the excess iodine was destroyed by the addition of solid sodium sulfite (10 g.). The reaction mixture was diluted with benzene (200 ml.) and partitioned, reextracting the aqueous phase with more benzene (100 ml.). The combined organic extracts were washed with water (100 ml.), 5% sodium sulfite (100 ml.) and brine (50 ml.), dried (anhydrous magnesium sulfate), filtered, evaporated to dryness and dried in vacuo. The crude product was recrystallized from ethyl acetate (200 ml.) and filtered, washing the cream colored precipitates with ethyl acetate (25 ml.), to give 16.596 g. of title product; m.p. 99°–100° C. TLC (methylene chloride:methanol, 9:1) $R_f=0.57$.

b) α-Methyl-hydrocinnamic acid

A solution of α-methyl cinnamic acid (10.0 g., 61.7 mmol.) in dry methanol (250 ml.) was treated with 10% palladium on carbon and hydrogenated (balloon used) at room temperature for 16 hours. The reaction mixture was diluted with methanol (250 ml.), filtered through a Celite pad in a millipore unit, washing the pad well with methanol (2×100 ml.). The clear filtrate was evaporated to dryness to give 10.225 g. of title product as a thick syrup.

c) α-Methyl-α-[[(4-methoxyphenyl)methyl]thio]-hydrocinnamic acid

A solution of diisopropylamine (1.69 ml., 12.2 mmol.) in dry tetrahydrofuran (9.0 ml.) was cooled to −30° C. (acetonitrile-dry ice bath), treated with 2.5M butyllithium (4.84 ml., 12.1 mmol.) and stirred at −30° C. for 20 minutes. The resulting lithium diisopropylamide solution was then treated with a solution of α-methyl-hydrocinnamic acid (1.0 g., 6.1 mmol.) in dry tetrahydrofuran (1.0 ml.), warmed up to room temperature and stirred under argon for 1.5 hours. The reaction mixture was cooled to 0° C. (ice-salt bath), treated with a solution of S,S'-bis(4-methoxy-α-toluenethiol) (1.869 g., 6.1 mmol.) in dry tetrahydrofuran (6.0 ml) and stirred for 45 minutes at 0° C. under argon. The mixture was then added slowly to 1.0N hydrochloric acid (19.0 ml.) and the aqueous mixture was extracted with ethyl acetate (2×50 ml). The combined organic extracts were washed with water (15 ml.) and brine (15 ml.), dried (anhydrous magnesium sulfate), filtered, evaporated to dryness and dried in vacuo. The crude product mixture was chromatographed on a silica gel column (Merck), eluting the column with ethyl acetate:hexane mixtures (1:4; 1:2) followed by ethyl acetate:acetic acid (100:2) to give 1.45 g. of title product.

d) [R-(R*,S*)]-2,3,4,5-Tetrahydro-3-[[2-[[(4-methoxyphenyl)methyl]thio]-2-methyl-1-oxo-3-phenylpropyl]amino]-2-oxo-1H-benzazepine-1-acetic acid, 1,1-dimethylethyl ester and [S-(R*,R*)]-2,3,4,5-tetrahydro-3-[[2-[[(4-methoxyphenyl)methyl]thio]-2-methyl-1-oxo-3-phenylpropyl]amino]-2-oxo-1H-benzazepine-1-acetic acid, 1,1-dimethylethyl ester A solution of the product from part (c) (497 mg., 1.57 mmol., 1.09 eq.) was cooled to 0° C. (ice-salt bath), treated with a solution of (S)-2,3,4,5-tetrahydro-3-amino-2-oxo-1H-benzazepine-1-acetic acid, 1,1-dimethylethyl ester [prepared according to the procedure of Watthey et al., J. Med. Chem. 28, p. 1511–1516 (1985)] (417 mg., 1.44 mmol.) in dry methylene chloride (2.9 ml.) followed by triethylamine (0.2 ml., 1.45 mmol.) and benzotriazol-1-yloxytris(dimethylamino)phosphonium hexafluorophosphate (642 mg., 1.45 mmol.). The reaction mixture was stirred at 0° C. for 1.0 hour then at room temperature for 2.5 hours after which it was evaporated to dryness. The syrup obtained was redissolved in ethyl acetate (50 ml.) and the resulting solution washed with 0.5N hydrochloric acid (2×8.3 ml.), water (8.3 ml.) and brine (8.3 ml.), dried (anhydrous sodium sulfate), filtered, evaporated to dryness and dried in vacuo. The crude product was chromatographed on a silica gel column (Merck), eluting the column with ethyl acetate:hexane (1:4) to give 709 mg. of a mixture of isomeric products.

Rechromatography of the isomer mixture on a silica gel column and elution with ethyl acetate: methylene chloride (1:99, 2:98) gave 340 mg. of the [R-(R*,S*)] title product; $[\alpha]_D$=−72° (c=0.66, methanol); TLC (ethyl acetate:hexane, 1:1) $R_f$=0.70 and 316 mg. of the [S-(R*,R*)title product; $[\alpha]_D$=−142° (c=0.5, methanol); TLC (ethyl acetate:hexane, 1:1) $R_f$=0.87.

e) [R-(R*,S*)]-2,3,4,5-Tetrahydro-3-[(2-mercapto-2-methyl-1-oxo-3-phenylpropyl)amino]-2-oxo-1H-benzazepine-1-acetic acid A solution of the [R-(R*,S*)] product from part (d) (300 mg., 0.51 mmol.) in trifluoroacetic acid (2.5 ml.) was cooled to 0° C. (ice-salt bath), treated with anisole (0.25 ml., 2.3 mmol.) and trifluoromethanesulfonic acid (0.13 ml., 1.47 mmol.) and stirred at 0° C. for 2.5 hours under argon. The reaction mixture was stripped to dryness, evaporating the residual syrup from ethyl acetate (2×15 ml.) then dried in vacuo. The crude product mixture was chromatographed on a silica gel column (Merck), eluting the column with ethyl acetate and ethyl acetate:acetic acid (100:2). The first set of desired fractions were combined and partitioned between ethyl acetate and 1.0N hydrochloric acid to give 91.0 mg. of crude product. This was combined with a second set of fractions which were also rechromatographed separately on another silica gel column to give a total amount of 301 mg. which still had impurities. Rechromatography on a third silica gel column was done, eluting the column with toluene:acetic acid (6:1) to give 156 mg. of pure title product as a solid foam; $[\alpha]_D$=−248.3° (c=0.73, methanol). TLC (toluene:acetic acid, 5:1) $R_f$=0.28.

Anal. calc'd. for $C_{22}H_{24}N_2O_4S \cdot 0.21\ C_6H_{14} \cdot 0.54\ H_2O$: C, 63.82; H, 5.85; N, 6.40; S, 7.32 Found: C, 63.82; H, 6.14; N, 6.21; S, 7.16.

EXAMPLE 61

[S-(R*,R*)]-2,3,4,5-Tetrahydro-3-[(2-mercapto-2-methyl-1-oxo-3-phenylpropyl)amino]-2-oxo-1H-benzazepine-1-acetic acid A solution of the [S-(R*,R*)]product from Example 60 part (d) (316 mg., 0.54 mmol.) in trifluoroacetic acid (2.63 ml.) was cooled to 0° C. and treated with anisole (0.26 ml., 2.30 mmol.) and trifluoromethanesulfonic acid (0.14 ml., 1.58 mmol.) according to the procedure of Example 60 part (e) to give 209.8 mg. of title product; $[\alpha]_D$=−123° (c=0.48, methanol). TLC (toluene:acetic acid, 5:1) $R_f$=0.35.

Anal. calc'd. for $C_{22}H_{24}N_2O_4S \cdot 0.4\ C_6H_{14}$: C, 64.22; H, 5.95; N, 6.73; S, 7.70 Found: C, 64.38; H, 6.19; N, 6.27; S, 7.05.

EXAMPLE 62

[3R-[3α, 6α(S*),9αβ]]-Octahydro-6-[(2-mercapto-1-oxo-3-phenylpropyl)amino]-5-oxothiazolo[3,2-a]azepine-3-carboxylic acid, 1-oxide a) [3R-[3α,6β(S*),9α,β]]-Octahydro-6-[[2-(acetylthio)-1-oxo-3-phenylpropyl]amino]-5-oxothiazolo[3,2-a]azepine-3-carboxylic acid, 1-oxide, methyl ester A solution of the product from Example 11 part (f) (301 mg., 0.67 mmol.) in chloroform (9.5 ml.) was cooled to 0°–5° C. To this solution was added a solution of meta-chloroperoxybenzoic acid (137 mg., 0.79 mmol.) in chloroform (7 ml.). The reaction mixture was stirred at 0° C. under nitrogen. After 1 hour, TLC showed the absence of starting material. The reaction mixture was diluted with chloroform (66 ml.), washed with dilute sodium bicarbonate (2×13 ml.) (pH=10), water (27 ml.) and dried over sodium sulfate. It was filtered and concentrated in vacuo to a foamy solid. The foamy solid was flash chromatographed over Merck silica gel (30 ml.) with ethyl acetate:acetonitrile (95:5) (400 ml.) to give 263 mg. of title product as a 55:45 mixture of diastereomers (R,S mixture of sulfoxide). TLC (ethyl acetate:acetonitrile, 95:5) $R_f$=0.23.

b) [3R-[3α,6α(S*)9αβ]]-Octahydro-6-[(2-mercapto-1-oxo-3-phenylpropyl)amino]-5-oxothiazolo[3,2-a]azepine-3-carboxylic acid, 1-oxide.

A solution of the product from part (a) (263 mg., 0.56 mmol.) in methanol (3.4 ml., deoxygenated via argon bubbling) was treated with 1N sodium hydroxide (2.8 ml., 2.8 mmol., deoxygenated via argon bubbling) and the clear solution was stirred under argon at room temperature. After 2 hours, TLC showed the absence of starting material. The solution was acidified with 10% potassium bisulfate (12.5 ml.), diluted with water (17 ml.), and extracted with ethyl acetate (3×60 ml.). The ethyl acetate extract was washed with water (25 ml.), brine (50 ml.) and dried over sodium sulfate. It was filtered and concentrated to an oily residue. Treatment of this residue with hexane and ethyl ether gave a solid (230 mg.). The solid was flash chromatographed over Merck silica gel (50 ml.), using ethyl acetate/acetonitrile/ acetic acid (50:50:6to7) (600 ml.) to give (142 mg.) of solid. The solid (142 mg.) was dissolved in methanol (2 ml.) and diluted with ethyl acetate (25 ml.). It was washed with 10% potassium bisulfate (3 ml.) (pH=2), diluted with water (8 ml.). The organic layer was separated. The aqueous layer was extracted with ethyl acetate (3×10 ml.). The combined ethyl acetate extract was washed with water (5 ml.), brine (5 ml.), dried over sodium sulfate, filtered and concentrated to an oily residue. Trituration of this residue with ethyl acetate/ ethyl ether gave 102 mg. of title product as a single isomer; m.p. 129°–132° C. (foaming); $[\alpha]_D=-89.3°$ (c=0.3, dimethylformamide). TLC (ethyl acetate/acetonitrile/acetic acid) $R_f=0.26$.

Anal. calc'd. for $C_{18}H_{22}N_2O_5S_2 \cdot 0.12\ C_4H_8O_2 \cdot 0.56\ H_2O$: C, 51.48; H, 5.62; N, 6.49; S,14.87 Found: C, 51.32; H, 5.34; N,6.74; S,14.50.

EXAMPLE 63

[3S-[3α(R*),7α]]-Hexahydro-3-[(2-mercapto-1-oxo-3-phenylpropyl)amino]-2-oxo-7-propyl-1H-azepine-1-acetic acid a) (S)-2-Phthalimido-6-hydroxyhexanoic acid, phenylmethyl ester A slurry of cesium carbonate (3.819 g, 11.7 mmol.) and (S)-2-phthalimido-6-hydroxyhexanoic acid (6.00 g, 21.6 mmol.) in dimethylformamide (60 ml.) was treated with benzyl bromide (3.30 ml., 4.75 g., 27.7 mmol.). After stirring at room temperature for 2 hours, the mixture was partitioned between ethyl acetate and water. The organic extract was washed with water (twice) and brine, then dried (sodium sulfate), filtered and stripped to give an oil. The oil was flash chromatographed (Merck silica gel, 6/4-ethyl acetate/hexane) to give essentially pure product as a solid. Recrystallization from ethyl acetate/hexane gave 7.173 g. (1st crop) and 394 mg. (2nd crop) for a total of 7.567 g. of pure title product; m.p. 106°–108.5° C.; $[\alpha]_D=-27.5°$ (c=1.5, methanol). TLC (75/25 ethyl acetate/hexanes) $R_f=0.43$.

b) (S)-2-Phthalimido-6-oxohexanoic acid, phenylmethyl ester

A –78° C. solution of oxalyl chloride (2.0 ml., 2.91 g., 22.9 mmol.) in dry methylene chloride (180 ml.) was treated dropwise with a solution of dry dimethylsulfoxide (3.20 ml., 3.52 g., 45.1 mmol.) in methylene chloride (3 ml.). After 15 minutes, a solution of the product from part (a) (6.874 g., 18.7 mmol.) in methylene chloride (20 ml.) was added. After an additional 15 minutes, triethylamine (15.0 ml.) was added and the mixture was stirred at –78° C. for 5 minutes, then allowed to warm to 0° C. The mixture was diluted with ethyl ether and was subsequently washed with water, 1N hydrochloric acid, and brine, then dried (sodium sulfate), filtered and stripped. The residue was flash chromatographed (Merck silica gel, 4/6-ethyl acetate/hexanes) to give 6.87 g. of title product as a colorless oil. TLC (1:1, ethyl acetate:hexanes) $R_f=0.43$.

c) (2S)-2-Phthalimido-6-hydroxy-8-nonenoic acid, phenylmethyl ester

A cold (0° C.) solution of the product from part (b) (6.249 g., 17.1 mmol.) and allyl trimethylsilane (3.40 ml., 2.44 g., 21.4 mmol.) in dry methylene chloride (120 ml.) was treated with titanium tetrachloride (1.0M in methylene chloride, 18.8 ml., 18.8 mmol.) over a 2 minute period. After 30 minutes, the bright yellow solution was quenched with water and partitioned between ethyl acetate and saturated ammonium chloride. The ethyl acetate extract was washed with water and brine, dried (sodium sulfate), filtered and stripped to give a cloudy oil. The residue was flash chromatographed (Merck silica gel, 15/85-ethyl acetate/methylene chloride) to afford 6.40 g., of title product as a 1:1 mixture of diastereomers. TLC (1:4, ethyl acetate:methylene chloride) $R_f=0.52$.

d) (2S)-2-Phthalimido-6-azido-8-nonenoic acid, phenylmethyl ester

A solution of the product from part (c) (6.365 g., 15.6 mmol.) in dimethylformamide (120 ml.) at room temperature was treated with lithium azide (4.620 g., 94.4 mmol.) and bromotrichloromethane (4.60 ml., 9.26 g., 46.7 mmol.). The bright yellow solution was then treated with triphenylphosphine (10.242 g., 39.0 mmol.). The mixture became dark orange and a water bath was necessary in order to cool the slightly exothermic reaction. After 2 hours at room temperature, the reaction was quenched with saturated sodium bicarbonate and extracted with ethyl acetate/ethyl ether. The organic layer was washed with water (3 times) and brine, dried (sodium sulfate), filtered and stripped. The residue was flash chromatographed (Merck silica gel, 5/95-ethyl acetate/methylene chloride) to afford partially purified product. This material was rechromatographed (Merck silica gel, 1/9-hexanes/methylene chloride) to give essentially pure title product as a yellow oil. TLC (5:95, ethyl acetate:methylene chloride) $R_f=0.63$.

e) (3S-trans)-Hexahydro-3-phthalimido-7-propyl-2H-azepin-2-one and (3S-cis)-hexahydro-3-phthalimido-7-propyl-2H-azepin-2-one The product from part (d) (4.27 g., 9.87 mmol.) was hydrogenated (balloon) in dimethylformamide (100 ml.) over palladium (10% on carbon, 1.8 g.) for 42 hours. The solution was filtered through Celite® and the filtrate was treated with hydroxybenzotriazole (1.366 g., 10.1 mmol.) followed by ethyl-3-(dimethylamino)propyl carbodiimide, (1.987 g., 10.4 mmol.). After stirring at room temperature for 5 hours, the mixture was partitioned between ethyl acetate and 0.5N hydrochloric acid, and the organic layer was washed successively with water, 50% saturated sodium bicarbonate, and brine, then dried (sodium sulfate), filtered and stripped to give an orange oil. Initial purification of the oil (flash chromatography, Merck silica gel, 6/4-ethyl acetate/hexanes) yielded a partially separated mixture of the (3S-trans) and (3S-cis) products (1.519 g. total of both). Repeated flash chromatography (Merck silica gel, 6/4-ethyl acetate/hexanes) and recrystallization permitted the quantitative isolation of 774 mg. of (3S-cis)hexahydro-3-phthalimido-7-propyl-2H-azepin-2-one, m.p. 155°–175° C. (very broad); $[\alpha]_D=+55.7°$ (c=0.7, chloroform). TLC (75/25, ethyl acetate/hexane) $R_f=0.48$.

An analytical sample of (3S-trans)-hexahydro-3-phthalimido-7-propyl-2H-azepin-2-one was also obtained; m.p. 146°–151° C. TLC (75/25 ethyl acetate/hexanes) $R_f=0.38$.

f) (3S-cis)-Hexahydro-3-[[(1,1-dimethylethoxy)carbonyl] amino]-7-propyl-2H-azepin-2-one A solution of the (3S-cis)product from part (e) (758 mg., 2.52 mmol.) in methylene chloride (4 ml.) and methanol (8 ml.) was treated with hydrazine monohydrate (147 μl., 152 mg., 3.0 mmol.). After 1 hour additional hydrazine monohydrate (50 μl.) was added and stirring continued for 4 days. The resulting thick slurry was diluted with additional methanol and methylene chloride and was subsequently filtered. The filtrate was stripped, slurried in methylene chloride, filtered and stripped again to afford the crude amine as an oil. The oil was dissolved in chloroform (5 ml.) and treated in succession with triethylamine (350 μl., 254 mg., 2.5 mmol.) and di-tert-butyl dicarbonate (660 mg., 3.0 mmol.). After stirring at room temperature for 2 hours, the solvent was stripped and the residue was flash chromatographed (Merck silica gel, 2/8-ethyl acetate/methylene chloride) to give 609 mg. of title product as a solid; m.p. 114.4°–115.5° C.; $[\alpha]_D=28.7°$ (c=0.5, chloroform). TLC (25/75 ethyl acetate/methylene chloride) $R_f=0.37$.

g) (3S-cis)-Hexahydro-3-[[(1,1-dimethylethoxy)carbonyl]amino]-7-propyl-1H-azepine-1-acetic acid, ethyl ester A room temperature solution of the product from part (f) (539 mg., 1.99 mmol.) in dry tetrahydrofuran (20 ml.) was treated dropwise with lithium hexamethyldisilazide (1.0M in tetrahydrofuran, 2.60 ml., 2.60 mmol.) followed 30 seconds later with ethyl bromoacetate (450 µL, 678 mg., 4.06 mmol.). The mixture was stirred at room temperature for 45 minutes, then quenched with saturated ammonium chloride, diluted with water, and extracted with ethyl acetate. The ethyl acetate extract was washed with brine, dried (sodium sulfate), filtered and stripped to give an oil. Flash chromatography (Merck silica gel, 35/65-ethyl acetate/hexane) afforded 620 mg. of pure title product as an oil. TLC (1:1 ethyl acetate/hexane) $R_f=0.55$.

h) [3S-{3α(R*),7α}]-Hexahydro-3-[[2-(acetylthio)-1-oxo-3-phenylpropyl]amino]-2-oxo-7-propyl-1H-azepine-1-acetic acid, ethyl ester A solution of the product from part (g) (700 mg., 1.96 mmol.) in p-dioxane (3 ml.) was treated with hydrochloric acid (4.0M in p-dioxane, 6.3 ml.). The mixture was stirred at room temperature for 2 hours. The solvent was stripped and the residue was partitioned between ethyl ether and 0.2 N sodium hydroxide (13 ml.). The layers were separated and the aqueous layer was extracted with ethyl acetate. The pooled organic extracts were dried (sodium sulfate), filtered and stripped to give 462 mg. of the crude free amine as a pale yellow oil.

A solution of (S)-(acetylthio)benzenepropanoic acid (obtained from the dicyclohexylamine salt as described previously, 485 mg., 2.16 mmol.) and the above crude amine in methylene chloride (15 ml.) was treated with triethylamine (300 µL, 218 mg., 2.15 mmol.) and the mixture was cooled to 0° C. Benzotriazol-1-yloxy-tris(dimethylamino)phosphonium hexafluorophosphate (956 mg., 2.16 mmol.) was then added as a solid. The solution was stirred at 0° C. for 1 hour and then at room temperature for 1.5 hours. The solvent was stripped and the residue was partitioned between ethyl acetate and 0.5N hydrochloric acid. The organic layer was washed successively with water, 50% saturated sodium bicarbonate and brine, then dried (sodium sulfate), filtered and stripped. The residue was flash chromatographed (Merck silica gel, 4:6-ethyl acetate:hexanes) to give 685 mg. of title product as an oil. TLC (1:1, ethyl acetate:hexanes) $R_f=0.37$.

i) [3S-[3α(R*),7α]]-Hexahydro-3-[(2-mercapto-1-oxo-3-phenylpropyl)amino]-2-oxo-7-propyl-1H-azepine-1-acetic acid A room temperature solution of the product from part (h) (679 mg., 1.47 mmol.) in methanol (10 ml., deoxygenated via argon bubbling) was treated with 1N sodium hydroxide (10 ml., deoxygenated via argon bubbling). After stirring for 30 minutes, the solution was acidified with 10% hydrochloric acid and extracted with ethyl acetate. The ethyl acetate extract was washed with water and brine, then dried (sodium sulfate), filtered and stripped. The residue was flash chromatographed (Merck silica gel, ethyl acetate followed by 1.5% acetic acid in ethyl acetate). The fractions containing pure product were pooled, stripped, and azeotroped twice with ethyl acetate. The mixture was dissolved in a small amount of ethyl acetate and triturated with hexane to give a foam. The volatiles were stripped, the residue was slurried in hexane, stripped to dryness again, and dried in vacuo to give 573 mg. of title product as a relatively hard white foam; $[\alpha]_D=+7.6$ (c=0.8, chloroform). TLC (2% acetic acid in ethyl acetate) $R_f=0.47$.

Anal. calc'd. for $C_{20}H_{28}N_2O_4S \cdot 0.26\ H_2O$: C, 60.47; H, 7.24; N, 7.05; S, 8.07; Found: C, 60.73; H, 7.38; N, 6.79; S, 7.76.

EXAMPLE 64

[3S-[3α(R*),7β]]-Hexahydro-3-[(2-mercapto-1-oxo-3-phenylpropyl)amino]-7-methyl-2-oxo-1H-azepine-1-acetic acid a) (S)-2-Phthalimido-6-hydroxyhexanoic acid, methyl ester A slurry of (S)-2-phthalimido-6-hydroxyhexanoic acid (3.752 g., 13.5 mmol.) and cesium carbonate (2.178 g., 6.7 mmol.) in dimethylformamide (44 ml.) was treated with methyl iodide (3.0 ml., 6.84 g., 48.2 mmol.). After stirring at room temperature for 2 hours, the mixture was diluted with ethyl acetate and washed successively with water containing a small amount of sodium bisulfite, water, 50% saturated sodium bicarbonate, and brine, then dried (sodium sulfate), filtered and stripped to give the title product as a colorless oil (3.825 g.). The oil was homogeneous by TLC (1:1-acetone:hexanes) $R_f=0.37$.

b) (S)-2-Phthalimido-6-oxohexanoic acid, methyl ester

A solution of oxalyl chloride (2.76 ml.) in methylene chloride (150 ml.) at –78° C. under argon was treated with the dropwise addition of dimethylsulfoxide (4.41 ml.) in methylene chloride (18 ml.). After 15 minutes, a solution of the product from part (a) (7.77 g., 25.1 mmol.) in methylene chloride (20 ml.) was added and the resulting mixture was stirred for 15 minutes. Following the addition of triethylamine (18.7 ml.), the mixture was stirred for 10 minutes then warmed to room temperature. The mixture was diluted with ethyl acetate then partitioned with water. The organic layer was washed with 1N hydrochloric acid and brine, dried over sodium sulfate, filtered and concentrated. The yellow residue was flash chromatographed (E Merck silica gel) eluting with 2:3 ethyl acetate/hexanes to give 6.47 g. of title product as as a yellow oil. TLC (1:1 ethyl acetate:hexane) $R_f=0.47$.

c) (2S)-2-Phthalimido-6-hydroxyheptanoic acid, methyl ester

A solution of the product from part (b) (6.4 g., 22.15 mmol.) in methylene chloride (150 ml.) at room temperature under argon was cooled to 0° C. and treated with 14.4 ml. of 2M trimethylaluminum in hexanes (28.8 mmol.). After stirring for 1 hour, the mixture was carefully quenched with saturated aqueous ammonium chloride and partitioned between ethyl acetate and 1 N hydrochloric acid. The organic layer was washed with brine, dried (sodium sulfate), filtered and concentrated to give 7.4 g. of title product as a light yellow oil. TLC (1:1 ethyl acetate:hexane) Rf=0.30.

d) (2S)-2-Phthalimido-6-azidoheptanoic acid, methyl ester

To a solution of the product from part (c) (7.1 g., 21 mmol.) in dimethylformamide (45 ml.) at room temperature under argon was added sodium azide (4.93 g., 75.8 mmol.) followed by trichlorobromomethane (6.3 ml., 63.0 mmol.) and then triphenylphosphine (13.77 g., 52.5 mmol.). The resulting mixture was stirred 2.5 hours then partitioned between ethyl acetate and saturated aqueous sodium bicarbonate. The organic layer was washed with water and brine, dried (sodium sulfate), filtered and concentrated. The residue was flash chromatographed (E Merck silica gel) eluting with 20% ethyl acetate in methylene chloride to give 10 g. of product contaminated with other impurities. This was resubjected to flash chromatography eluting with 4:1 hexane/ethyl acetate to give 6.7 g. of title compound as a yellow oil. TLC (1:1 ethyl acetate:hexane) Rf=0.60.

e) (2S)-2-[[(1,1-Dimethylethoxy)carbonyl]amino]-6-azidoheptanoic acid, methyl ester Hydrazine monohydrate (1.05 ml., 21.74 mmol.) was added to a solution of the product from part (d) (6.7 g., 19.8 mmol.) in methanol (50 ml.) at room temperature under argon. The resulting mixture was stirred for 96 hours then filtered to remove the formed white precipitate. The volatiles were evaporated and the residue was dissolved in methylene chloride and filtered to remove additional precipitate. The volatiles were evaporated and the residue was partitioned between ethyl ether and 0.5M aqueous hydrochloric acid. The aqueous layer was basified with aqueous sodium bicarbonate and extracted eight times with methylene chloride. The combined organic layers were dried (sodium sulfate), filtered, and concentrated to give 2.9 g. of the free amine as a yellow oil. This amine intermediate (2.9 g., 14.5 mmol.) was dissolved in methylene chloride (10 ml.), treated with triethylamine (2.02 ml., 14.5 mmol.), and stirred for 5 minutes. Di-tert-butyl dicarbonate (3.8 g., 17.44 mmol.) was added and the resulting mixture was stirred for 45 minutes. Additional di-tert-butyl dicarbonate (0.63 g.) was added and the mixture was stirred for 30 minutes. The mixture was diluted with methylene chloride and washed twice with water, dried (sodium sulfate), filtered and concentrated to a yellow oil. The oil was flash chromatographed (E Merck silica gel) eluting with 4:1 hexanes/ethyl acetate to give 3.34 g. of title compound as a yellow oil. TLC (4:1 hexanes:ethyl acetate) Rf=0.60.

f) (3S-trans)-Hexahydro-3-[[(1,1-dimethylethoxy)carbonyl]amino]-7-methyl-2H-azepinn-2-one and (3S-cis)-hexahydro-3-[[(1,1-dimethylethoxy)carbonyl]amino]-7-methyl-2H-azepin-2-one To a solution of the product from part (e) (2.8 g., 9.3 mmol.) in methanol (125 ml.) was added 1.0 g. of 10% palladium on carbon at room temperature. The resulting mixture was hydrogenated (balloon) for 28 hours and then filtered through Celite® to remove the catalyst. The volatiles were evaporated and the residue was azeotroped twice with chloroform to ensure the complete removal of methanol. The free amine was dissolved in methylene chloride (125 ml.) then treated with 2M trimethylaluminum in hexanes (8.8 ml., 17.52 mmol.). The resulting mixture was stirred at room temperature under argon for 27 hours. The mixture was quenched with saturated aqueous ammonium chloride and extracted with ethyl acetate. The organic layer was washed with brine, dried (sodium sulfate), filtered and concentrated. The residue was flash chromatographed (E Merck silica gel) eluting with 1:1 ethyl acetate/hexanes to give a clean separation of 452 mg. of the more polar isomer (3S-trans) hexahydro-3-[[(1,1-dimethylethoxy)carbonyl]amino]-7-methyl-2H-azepine-2-one; m.p. 137°–138° C.; [α]$_D$=–2.8° (c=0.82, methylene chloride); TLC (1:1 ethyl acetate:hexane) R$_f$=0.23 and 550 mg. of the less polar isomer (3S-cis)-hexahydro-3-[[(1,1-dimethylethoxy)carbonly]amino]-7-methyl-2H-azepin-2-one; m. p. 108°–109° C.; [α]$_D$=+18.1° (c=0.27, methylene chloride); TCL (1:1 ethyl acetate:hexane) R$_f$=0.39.

g) (3S-trans)-Hexahydro-3-[[(1,1-dimethylethoxy)carbonyl]amino]-7-methyl-2-oxo-1H-azepine-1-acetic acid, ethyl ester.

A solution of (3S-trans)-hexahydro-3-[[(1,1-dimethylethoxy)carbonyl]aminio]-7-methyl-2H-azepin-2-one (313 mg., 1.3 mmol.) in tetrahydrofuran (8 ml.) at room temperature under argon was treated with the dropwise addition of 1.0M lithium bis(trimethylsilyl)amide in tetrahydrofuran (1.7 ml., 1.7 mmol.) immediately followed by the dropwise addition of ethyl bromoacetate (0.30 ml., 2.65 mmol.). The resulting mixture was stirred for 15 minutes, quenched with aqueous ammonium chloride, diluted with water and extracted twice with ethyl acetate. The combined organic layers were washed with brine, dried (sodium sulfate), filtered and concentrated to a yellow oil. Following flash chromatography (E Merck silica gel) eluting with 2:1 hexane/ethyl acetate, 360 mg. of title compound was obtained as a light yellow oil; TLC (1:1 ethyl acetate:hexane) R$_f$=0.56.

h) [3S-[3α (R*),7β]]-Hexahydro-3-[[2-(acetylthio)-1-oxo-3-phenylpropyl]amino]-7-methyl-2-oxo-1H-azepine-1-acetic acid, ethyl ester A solution of the product from part (g) (296 mg., 0.90 mmol.) in p-dioxane (2 ml.) was treated with 4.0 M hydrochloric acid in dioxane (2.9 ml.) at room temperature under argon. After stirring for 6 hours, the volatiles were evaporated and the residue was partitioned between ethyl acetate and half saturated aqueous sodium bicarbonate. The aqueous layer was back-extracted with ethyl acetate and the combined organic layers were washed with brine, dried (sodium sulfate), filtered, and concentrated to give the deprotected amine as a yellow oil.

(S)-(Acetylthio)benzenepropanoic acid, dicyclohexylamine salt (405.6 mg., 1.0 mmol.) was partitioned between ethyl acetate and 10% potassium bisulfate. The organic layer was washed with brine, dried (sodium sulfate), filtered, and concentrated to give the free acid (S)-(acetylthio) benzenepropanoic acid as an oil. This oil was dissolved in methylene chloride (15 ml.) at room temperature under argon. Following the addition of the above deprotected amine, the mixture was cooled to 0° C. and triethylamine (0.12 ml.) was added. The resulting mixture was stirred for 5 minutes then benzotriazol-1-yloxy-tris(dimethylamino) phosphonium hexafluorophosphate (442 mg., 1.0 mmol.) was added. After stirring at 0° C. for 1 hour, the reaction mixture was warmed to room temperature and was stirred for 16 hours. The volatiles were evaporated and the residue was dissolved in ethyl acetate and washed successively with 1N hydrochloric acid, water, 50% saturated sodium bicarbonate, and brine. The organic layer was dried (sodium sulfate), filtered, and concentrated and the residue was flash chromatographed (E Merck silica gel ) eluting with 2:1 hexane/ethyl acetate to give 260 mg. of title product as a pale yellow oil; TLC (2:1 hexane:ethyl acetate) Rf=0.43.

i) [3S-[3α(R*),7β]]-Hexahydro-3-[(2-mercapto-1-oxo-3-phenylpropyl)amino]-7-methyl-2-oxo-1H-azepine-1-acetic acid A solution of the product from part (h) (255 mg., 0.63 mmol) in methanol (8 ml., deoxygenated via argon bubbling) was cooled to 0° C. and treated with 1N sodium hydroxide (6 ml., deoxygenated via argon bubbling). After stirring under argon at 0° C. for 30 minutes, the resulting mixture was warmed to room temperature and stirred an additional hour. The mixture was acidified with 10% potassium bisulfate and extracted with ethyl acetate. The organic layer was washed successively with water and brine, dried (sodium sulfate), filtered and concentrated to give a yellow oil. This residue was flash chromatographed (E Merck silica gel) eluting with 1% acetic acid in 1:2 hexane/ethyl acetate. The fractions containing clean desired product were combined, stripped, azeotroped with ethyl acetate, and washed with water to remove any acetic acid. The organic layer was dried (sodium sulfate), filtered and concentrated. The residue was taken up in ethyl acetate and triturated with hexane. The solvent was removed and the residue was slurried in hexane, stripped, and dried in vacuo to give 120 mg. of title product as a white powdery foam; $[\alpha]_D=-28.7°$ (c=0.30, methanol). TLC (1% acetic acid in 2:1 ethyl acetate/hexane) $R_f=0.40$.

Anal. calc'd. for $C_{18}H_{24}N_2O_4S$: C, 59.32; H, 6.64; N, 7.69; S, 8.80 Found: C, 59.03; H, 6.76; N, 7.36; S, 8.58.

EXAMPLE 65

[3S-[3α(R*),7α]]-Hexahydro-3-[(2-mercapto-1-oxo-3-phenylpropyl)amino]-7-methyl-2-oxo-1H-azepine-1-acetic acid a) (3S-cis)-Hexahydro-3-[[(1,1-dimethylethoxy)carbonyl]amino]-7-methyl-2-oxo-1H-azepine-1-acetic acid, ethyl ester A solution of (3S-cis)-hexahydro-3-[[(1,1-dimethylethoxy)carbonyl]amino]-7-methyl-2H-azepin-2-one [prepared as described in Example 64(f), 500 mg., 2.06 mmol.] in tetrahydrofuran (13 ml.) at room temperature under argon was treated dropwise with 1.0M lithium bis(trimethylsilyl)amide in tetrahydrofuran (2.7 ml., 2.7 mmol.) immediately followed by the dropwise addition of ethyl bromoacetate (0.47 ml., 4.21 mmol.). The resulting mixture was stirred for 30 minutes, quenched with aqueous ammonium chloride, diluted with water and extracted twice with ethyl acetate. The combined organic layers were washed with brine, dried (sodium sulfate), filtered and concentrated to a yellow oil. Following flash chromatography (E Merck silica gel) eluting with 2:1 hexane/ethyl acetate, 750 mg. of title product was obtained as a light yellow oil; TLC (1:1 ethyl acetate:hexane) $R_f=0.52$.

b) [3S-[3α(R*),7α]]-Hexahydro-3-[[2-(acetylthio)-1-oxo-3-phenylpropyl]amino]-7-methyl-2-oxo-1H-azepine-1-acetic acid, ethyl ester A solution of the product from part (a) (351 mg., 1.07 mmol.) in p-dioxane (3 ml.) was treated with 4.0M hydrochloric acid in dioxane (3.45 ml.) at room temperature under argon. After stirring for 2 hours, the volatiles were evaporated and the residue was partitioned between ethyl acetate and 50% saturated aqueous sodium bicarbonate. The aqueous layer was back-extracted with ethyl acetate and the combined organic layers were washed with brine, dried (sodium sulfate), filtered, and concentrated to give the deprotected amine as a yellow oil.

(S)-(Acetylthio)benzenepropanoic acid, dicyclohexylamine salt (477 mg., 1.18 mmol.) was partitioned between ethyl acetate and 10% potassium bisulfate. The organic layer was washed with brine, dried (sodium sulfate), filtered, and concentrated to give (S)-(acetylthio)benzenepropanoic acid as an oil. This oil was dissolved in methylene chloride (15 ml.) at room temperature under argon. Following the addition of the above deprotected amine, the mixture was cooled to 0° C. and triethylamine (0.14 ml.) was added. The resulting mixture was stirred for 5 minutes, then benzotriazol-1-yloxy-tris(dimethylamino)phosphonium hexafluorophosphate (522 mg., 1.8 mmol.) was added. After stirring at 0° C. for 1 hour, the reaction mixture was warmed to room temperature and was stirred for 16 hours. The volatiles were evaporated and the residue was dissolved in ethyl acetate and washed successively with 1N hydrochloric acid, water, 50% saturated sodium bicarbonate, and brine. The organic layer was dried (sodium sulfate), filtered, and concentrated and the residue was flash chromatographed (Merck silica gel) eluting with 1:1 hexane/ethyl acetate to give 135 mg. of title product as a yellow oil. TLC (2:1 hexane:ethyl acetate) $R_f=0.41$.

c) [3S-[3α(R*),7α]]-Hexahydro-3-[(2-mercapto-1-oxo-3-phenylpropyl)amino]-7-methyl-2-oxo-1H-azepine-1-acetic acid A solution of the product from part (b) (130 mg., 0.32 mmol.) in methanol (4 ml., deoxygenated via argon bubbling) was cooled to 0° C. and treated with 1N sodium hydroxide (3 ml., deoxygenated via argon bubbling). After being stirred under argon at 0° C. for 45 minutes, the resulting mixture was warmed to room temperature and stirred an additional hour. The mixture was acidified with 10% potassium bisulfate and extracted with ethyl acetate. The organic layer was washed successively with water and brine, dried (sodium sulfate), filtered and concentrated to give a yellow oil. This residue was flash chromatographed (Merck silica gel) eluting with ethyl acetate and 1% acetic acid in 1:2 hexane/ethyl acetate. The fractions containing clean desired product were combined, stripped, azeotroped with ethyl acetate, and washed with water to remove any acetic acid. The organic layer was dried (sodium sulfate), filtered and concentrated. The residue was taken up in ethyl acetate and triturated with hexane. The solvent was removed and the residue was slurried in hexane, stripped, and dried in vacuo to give 103 mg. of title product as a white powdery foam; $[\alpha]_D=+16.8°$ (c=0.28, methanol). TLC (1% acetic acid in 2:1 ethyl acetate/hexane) $R_f=0.38$.

Anal. calc'd. for $C_{18}H_{24}N_2O_4S$.0.31 $H_2O$: C, 58.44; H, 6.70; N, 7.57; S, 8.67 Found: C, 58.65; H, 6.75; N, 7.36; S, 8.37.

EXAMPLE 66

[S-(R*,R*)]-Hexahydro-6-[(2-mercapto-1-oxo-3-phenylpropyl)amino]-2,2-dimethyl-7-oxo-1H-azepine-1-acetic acid a) (2S)-2-Phthalimido-6-hydroxyheptanoic acid, phenylmethyl ester A −78° C. solution of oxalyl chloride (3.0 ml., 4.36 g., 34.4 mmol.) in methylene chloride (100 ml.) was treated dropwise with a solution of dry dimethylsulfoxide (4.8 ml., 5.28 g., 67.6 mmol.) in methylene chloride (2.0 ml.). After 10 minutes, a solution of (S)-2-phthalimido-6-hydroxyhexanoic acid, phenylmethyl ester [prepared as described in Example 63(a) 10.365 g., 28.2 mmol.] in methylene chloride (20 ml.) was added over a 7 minute period. After an additional 15 minutes, dry triethylamine (17 ml.) was added and the mixture was stirred at −78° C. for 5 minutes, then allowed to gradually warm to 0° C. The mixture was partitioned between ethyl ether and water. The organic layer was washed with 1N hydrochloric acid and brine, dried (sodium sulfate), filtered and stripped to give the desired aldehyde as an oil. TLC (6:4 ethyl acetate:hexanes) $R_f=0.56$.

The oil was re-dissolved in dry methylene chloride (170 ml.), cooled in an ice bath, and treated dropwise with trimethylaluminum (2.0M in hexanes, 20.0 ml.). After 20 minutes, additional trimethylaluminum solution (5.0 ml.) was added and stirring continued for 10 minutes. The mixture was cautiously quenched by the addition of saturated ammonium chloride and then partitioned between ethyl ether and water. The aqueous layer was back-extracted with ethyl acetate and the pooled organic layers were washed with brine, dried (sodium sulfate), filtered and stripped to give a near colorless oil. Flash chromatography (Merck silica gel, 6/4-ethyl acetate/hexanes) afforded 9.836 g. of pure title product as a colorless oil. TLC (6:4 ethyl acetate:hexanes) $R_f=0.41$.

b) (S)-2-Phthalimido-6-oxoheptanoic acid, phenylmethyl ester

A −78° C. solution of oxalyl chloride (1.52 ml., 2.21 g., 17.4 mmol.) in methylene chloride (120 ml.) was treated dropwise with a solution of dry dimethylsulfoxide (2.50 ml., 2.75 g., 35.2 mmol.) in methylene chloride (2.0 ml.). After 10 minutes, a solution of the product from part (a) (5.078 g., 13.3 mmol.) in methylene chloride (30 ml.) was added. After an additional 15 minutes, dry triethylamine (10 ml.) was added and the mixture was stirred at −78° C. for 5 minutes, then allowed to gradually warm to 0° C. The mixture was partitioned between ethyl acetate and 1N hydrochloric acid. The aqueous layer was back-extracted with ethyl acetate and the pooled organic layers were washed with brine, dried (sodium sulfate), filtered and stripped. Flash chromatography (Merck silica gel, 1/1-ethyl acetate/hexanes) afforded 4.892 g., of title product as a colorless oil. TLC (1:1 ethyl acetate:hexanes) $R_f$=0.32; $[\alpha]_D$=−10.7° (c=0.9, chloroform).

c) (S)-2-Phthalimido-6-methyl-6-hydroxyheptanoic acid, phenylmethyl ester

Neat titanium tetrachloride (2.48 ml., 4.28 g., 22.5 mmol.) was added dropwise to dry ethyl ether (150 ml.) at −78° C., resulting in a bright yellow suspension. The addition of methyl lithium (1.4M in ethyl ether, 16.1 ml., 22.5 mmol.) over a 5 minute period afforded a dark-brown non-homogeneous mixture. Gradual warming to −35° C. resulted in a deep brown-purple near-homogeneous solution. The product from part (b) (5.682 g., 15.00 mmol.) in ethyl ether (30 ml.) was added dropwise to the above solution, affording a gummy intractable reaction mixture. The reaction was warmed to 0° C. and occasionally agitated with a spatula in order to effect magnetic stirring. After 4 hours at 0° C., the mixture was quenched with saturated ammonium chloride, diluted with water, and extracted with ethyl acetate. The organic layer was washed with water and brine, dried (sodium sulfate), filtered and stripped. The residue was flash chromatographed (Merck silica gel, 1/1-ethyl acetate/hexane) to afford 5.165 g., of title product as an oil; $[\alpha]_D$=−3.4° (c=0.7, chloroform). TLC (1:1 ethyl acetate:hexanes) $R_f$=0.25.

d) (S)-2-Phthalimido-6-methyl-6-azidoheptanoic acid, phenylmethyl ester

A solution of the product from part (c) (5.152 g., 13.0 mmol.) in methylene chloride (120 ml.) was treated first with trimethylsilylazide (2.25 ml., 1.95 g., 17.0 mmol.) followed by boron trifluoride etherate (2.1 ml., 2.42 g., 17.1 mmol.). After stirring for 40 hours at room temperature, the mixture was quenched with water and extracted with ethyl ether. The organic layer was washed with 50% saturated sodium bicarbonate and brine, dried (sodium sulfate), filtered and stripped. The residue was flash chromatographed twice (Merck silica gel, 25/75-ethyl acetate/hexanes) to give 4.165 g. of the desired product as a colorless oil; $[\alpha]_D$=−9.2° (c=0.6, chloroform). TLC (35:65 ethyl acetate:hexanes) $R_f$=0.34.

e) (S)-Hexahydro-6-phthalimido-2,2-dimethyl-2H-azepin-7-one

A solution of the product from part (d) (5.550 g., 13.2 mmol.) in dimethylformamide (90 ml.) was hydrogenated (balloon) over 10% palladium on carbon (1.41 g.) at room temperature for 27 hours. The resulting thick mixture was evacuated, purged with nitrogen, and treated with dimethyl sulfide (100 μl., catalyst poison). The mixture was subsequently treated with hydroxybenzotriazole (1.834 g.) followed by ethyl-3-(dimethylamino)propyl carbodiimide (3.057 g., 16.0 mmol.) and the viscous solution quickly became free flowing. After stirring for 16 hours, the mixture was diluted with ethyl acetate and filtered through Celite®. The filtrate was washed with 0.5N hydrochloric acid and water and the pooled aqueous layers were back-extracted with ethyl acetate. The pooled organic layers were washed with 50% saturated sodium bicarbonate and brine, then dried (sodium sulfate), filtered, and stripped to give a white solid. The solid was dissolved in hot ethyl acetate/hexanes and cooled to give the product (2.652 g.) as fine white needles. An additional 730 mg. of product was isolated from the mother liquor affording a total of 3.382 g. of the desired product; m.p. 193°–194° C.; $[\alpha]_D$=+58.5° (c=1.2, chloroform). TLC (3:7 ethyl acetate:methylene chloride) $R_f$=0.38.

Anal. calc'd. for $C_{16}H_{18}N_2O_3$: C, 67.12; H, 6.34; N, 9.78 Found: C, 66.83; H, 6.31; N, 9.74.

f) (S)-Hexahydro-6-[[(1,1-dimethylethoxy)carbonyl]amino]-2,2-dimethyl-2H-azepin-7-one A solution of the product from part (e) (3.342 g., 11.7 mmol.) in methylene chloride (10 ml.) and methanol (40 ml.) was treated with hydrazine monohydrate (775 μl., 800 mg., 16.0 mmol.). After stirring at room temperature for 66 hours, the mixture was filtered and the solid was washed with methanol. The filtrate was stripped, triturated with methylene chloride and filtered again. Removal of the solvent afforded the crude amine which was re-dissolved in methylene chloride (50 ml.) and subsequently treated with di-tert-butyl dicarbonate (3.502 g., 16.0 mmol.) and triethylamine (1.70 ml., 1.23 g., 12.2 mmol.). After 2.5 hours at room temperature, the solvent was stripped and the residue was flash chromatographed (Merck silica gel, 25/75-ethyl acetate/methylene chloride) to give 2.923 g. of title product as a white solid; m.p. 118°–120° C.; $[\alpha]_D$=+38.4° (c=0.7, chloroform). TLC (25:75 ethyl acetate:methylene chloride) $R_f$=0.33.

Anal. calc'd. for $C_{13}H_{24}N_2O_3$: C, 60.91; H, 9.44; N, 10.93 Found: C, 61.27; H, 9.60; N, 10.86.

g) (S)-Hexahydro-6-[[(1,1-dimethylethoxy)carbonyl]amino]-2,2-dimethyl-7-oxo-1H-azepine-1-acetic acid, ethyl ester A room temperature solution of the product from part (f) (2.945 g., 11.5 mmol.) in dry tetrahydrofuran (100 ml.) was treated with lithium hexamethyldisilazide (1.0M in tetrahydrofuran, 17.0 ml.). After 4 minutes, ethyl bromoacetate (1.90 ml., 2.86 g, 17.1 mmol.) was added to the mixture. Additional lithium hexamethyl disilazane solution (17.0 ml.) and ethyl bromoacetate (1.90 ml.) were added at both 20 and 40 minutes after the first addition. One hour after the reaction was initiated, the mixture was quenched with saturated ammonium chloride and extracted with ethyl acetate. The ethyl acetate extract was washed with brine, dried (sodium sulfate), filtered and stripped to give a brown liquid. Flash chromatography (Merck silica gel, 30 to 50% ethyl acetate in hexane) afforded 1.447 g. of title product as a pale yellow oil; $[\alpha]_D$=+10.6° (c=1.0, chloroform). TLC (1:1 ethyl acetate:hexanes) $R_f$=0.42.

h) [S-(R*,R*)]-Hexahydro-6-[[2-(acetylthio)-1-oxo-3-phenylpropyl]amino]-2,2-dimethyl-7-oxo-1H-azepine-1-acetic acid, ethyl ester A solution of the product from part (g) (764 mg., 2.23 mmol.) in p-dioxane (3.5 ml.) was treated with hydrochloric acid (4.0M in p-dioxane, 6.0 ml.). The mixture was stirred at room temperature for 2 hours. The solvent was stripped and the residue was partitioned between hexane and water. The hexane layer was extracted again with 0.5N hydrochloric acid and the pooled aqueous layers were made basic with saturated sodium bicarbonate. The aqueous layer was extracted with methylene chloride (4 times) and the pooled methylene chloride extracts were dried (sodium sulfate), filtered, and stripped to give the free amine as a yellow oil.

A solution of (S)-(acetylthio)benzenepropanoic acid (obtained from the dicyclohexylamine salt as previously described, 603 mg., 2.69 mmol.) and the above crude amine in methylene chloride (20 ml.) was treated with triethylamine (357 μL., 259 mg., 2.56 mmol.) and the mixture was cooled to 0° C. Benzotriazol-1-yloxy-tris(dimethylamino) phosphonium hexafluorophosphate (1.138 g., 25.7 mmol.) was then added as a solid. The solution was stirred at 0° C. for 1 hour and then at room temperature for 1 hour. The solvent was stripped and the residue was partitioned between ethyl acetate and 0.5N hydrochloric acid. The organic layer was washed successively with water, 50% saturated sodium bicarbonate and brine, then dried (sodium sulfate), filtered and stripped. The residue was flash chromatographed (Merck silica gel, 1:1-ethyl acetate:hexanes) to give 804 mg. of the title product as an oil/foam. HPLC showed the product to be in 96.5% diastereomeric purity. TLC (1:1 ethyl acetate:hexanes) $R_f$=0.29.

i) [S-(R*,R*)]-Hexahydro-6-[(2-mercapto-1-oxo-3-phenylpropyl)amino]-2,2-dimethyl-7-oxo-1H-azepine-1-acetic acid A room temperature solution of the product from part (h) (792 mg., 1.76 mmol.) in methanol (6 ml., deoxygenated via argon bubbling) was treated with 1N sodium hydroxide (10 ml., deoxygenated via argon bubbling). After stirring under argon bubbling for 3 hours, the solution was acidified with 10% hydrochloric acid and extracted with ethyl acetate. The ethyl acetate extract was washed with brine, then dried (sodium sulfate), filtered and stripped to afford an oil. This material was flash chromatographed (Merck silica gel, ethyl acetate followed by 1.5% acetic acid in ethyl acetate). The fractions containing the product were pooled, stripped, and azeotroped three times with ethyl acetate. The mixture was dissolved in a small amount of ethyl acetate and triturated with hexane to give a foam. The volatiles were stripped, the residue was slurried in hexane for 1 hour, and the resulting precipitate was collected by filtration and dried in vacuo to give 601 mg. of title product as a hard white foam. NMR analysis shows the product to be comprised of a 95:5 mixture of diastereomers; $[\alpha]_D$=–18.4° (c=0.5, chloroform). TLC (2% acetic acid in ethyl acetate) $R_f$=0.36.

Anal. calc'd. for $C_{19}H_{26}N_2O_4S$: C. 60.30; H, 6.92; N, 7.40; S, 8.47 Found: C. 60.16; H, 7.06; N, 7.06; S, 8.10.

EXAMPLE 67

[3S-[3α,6α(R*),9αβ]-Octahydro-6-[(2-mercapto-1-oxo-3-phenylpropyl)amino]-5-oxo-1H-pyrrolo[1,2-a]azepine-3-carboxylic acid a) (S)-2-Phthalimido-5-oxo-5-(phenylmethoxy)pentanoic acid To a solution of γ-benzyl-L-glutamate (17.49 g., 73.70 mmol.) in aqueous (180 ml.) sodium carbonate (7.81 g., 73.70 mmol.) and dioxane (120 ml.) was added N-carbethoxyphthalimide (16.50 g., 75.27 mmol., 1.02 eq.). After stirring at room temperature for 4.5 hours, The reaction mixture was acidified with 6N hydrochloric acid (30 ml.) and extracted into ethyl acetate (2×400 ml.). The combined ethyl acetate extracts were washed with 50% brine (200 ml.), and brine (200 ml.), dried over sodium sulfate, filtered, concentrated and dried in vacuo to yield a crude oil (41.4 g.). To a solution of the crude residue in ethyl ether (100 ml.) was added dicyclohexylamine (14 ml.). After standing in the refrigerator overnight, the ethyl ether was removed by rotary evaporation and the oily residue was crystallized from ethyl acetate/hexane. The resulting precipitate was collected by filtration, washed with hexane and dried in vacuo to yield 21.21 g. of the title product as the dicyclohexyl amine salt. A suspension of this dicyclohexylamine salt in ethyl acetate (200. ml.) was washed with 5% potassium bisulfate (3×50 ml.), brine (50 ml.) and dried over magnesium sulfate, filtered and concentrated to yield 13.5 g. of the title product as a white foam. TLC: (3% acetic acid in 9:1 ethyl acetate:heptane) $R_f$=0.30.

b) (S)-2-Phthalimido-5-oxo-5-(phenylmethoxy)pentanoic acid, methyl ester

To a solution of the product from part (a) (13.22 g., 36.0 mmol.) and cesium carbonate (5.86 g., 18.0 mmol.) in dimethylformamide (100 ml.) was added iodomethane (8.1 ml., 129.6 mmol., 3.6 eq.). The yellow solution was stirred for 2.5 hours, and was then partitioned between ethyl acetate (300 ml.) and water (250 ml.). The ethyl acetate extract was washed with 5% sodium bicarbonate (200 ml.) and brine, dried over magnesium sulfate, filtered and concentrated to yield 13.68 g. a yellow oil. The residue was purified by chromatography on a 5×20 cm. silica gel column eluting with 30% ethyl acetate/hexane. The desired fractions were combined and concentrated to yield 10.0 g of the title product. TLC (1:1, ethyl acetate:hexane) $R_f$=0.45.

c) (S)-2-Phthalimido-4-(carboxy)butanoic acid, methyl ester

To a solution of the product from part (b) (10.0 g., 26.22 mmol.) in ethyl acetate (115 ml.) was added 20% palladium hydroxide on carbon catalyst (1.90 g.) and the resulting suspension was stirred under hydrogen atmosphere (balloon) for 2.5 hours. The mixture was filtered through a millipore filter washing thoroughly with ethyl acetate, concentrated and dried in vacuo to yield 7.29 g. of crude title product as a white solid; m.p. 137°–138° C. TLC (10% methanol/methylene chloride) $R_f$=0.43.

d) (S)-2-Phthalimido-5-oxo-5-(ethylthio)pentanoic acid, methyl ester

To a solution of the product from part (c) (7.27 g., 24.95 mmol.) in methylene chloride (125 ml.) at 0° C. under argon was added ethanethiol (4.81 ml., 64.92 mmol., 2.6 eq), 4-dimethylaminopyridine (609 mg., 4.99 mmol., 0.2 eq.) and ethyl-3-(3-dimethylamino)propyl carbodiimide, hydrochloride salt (5.27 g., 27.47 mmol., 1.1 eq.). After stirring at 0° C. for 2 hours and at room temperature for 1 hour the reaction was concentrated, diluted with ethyl acetate (400 ml.) and washed with 5% potassium bisulfate (200 ml.), saturated sodium bicarbonate (200 ml.), and brine (200 ml.), dried over sodium sulfate, filtered, concentrated and dried in vacuo to yield 8.30 g. of title product as a crude oil. TLC (1:1, ethyl acetate:hexane) $R_f$=0.47.

e) (S)-2-Phthalimido-5-oxopentanoic acid, methyl ester

A suspension of the product from part (d) (8.30 g., 24.75 mmol.) and 10% palladium on carbon (1.24 g.) in acetonitrile (150 ml.) under argon was treated dropwise with triethylsilane (7.91 ml., 49.5 mmol., 2 eq.). After stirring at room temperature for 45 minutes, the mixture was filtered through a millipore unit, concentrated and dried in vacuo. The crude residue was purified by chromatography on a 5×25 cm silica gel column eluting with 25% ethyl acetate/hexane (4 l.) followed by 35% ethyl acetate/hexane (2 l.). The desired fractions were combined to yield 5.60 g. of title product. TLC (1:1, ethyl acetate:hexane) $R_f$=0.32.

f) (S)-2-Phthalimido-5,5-dimethoxyoentanoic acid, methyl ester

A solution of the product from part (e) (5.60 g., 20.34 mmol.) in methanol (60 ml.) and methylene chloride (40 ml.) was treated with trimethylorthoformate (3.8 ml., 34.59 mmol., 1.7 eq.) and p-toluenesulfonic acid monohydrate (280 mg.). After stirring at room temperature for 1.5 hours the reaction was quenched with 2 ml. of saturated sodium bicarbonate, concentrated, and partitioned between ethyl acetate (400 ml.) and water (100 ml.). The ethyl acetate extract was washed with saturated sodium bicarbonate (100 ml.), brine (100 ml.), dried over magnesium sulfate, filtered and concentrated to a crude oil. The crude residue was purified by chromatography on a 5×20 cm silica gel column eluting with 30% ethyl aceatate/hexane (2 l.). The desired fractions were combined, concentrated and dried in vacuo to yield 6.20 g. of title product. TLC (1:1, ethyl acetate:hexane) $R_f$=0.40.

g) [S-(R*,R*)]-2-[(2-Phthalimido-1-oxo-4-pentenyl)amino]-5,5-dimethoxypentanoic acid, ethyl ester A solution of the product from part (f) (5.315 g., 16.5 mmol.) in methanol (90 ml.) was treated with hydrazine monohydrate (870 μl., 898 mg., 17.9 mmol.). After stirring at room temperature for 6 days, the solution was filtered and evaporated, triturated with methylene chloride, filtered and evaporated again to give the crude free amine as a near colorless oil.

A solution of (S)-2-phthalimido-4-pentenoic acid [prepared as described in Example 35(b), 4.451 g., 18.1 mmol.] in methylene chloride (120 ml.) was treated with triethylamine (2.40 ml., 1.74 g., 17.2 mmol.) followed by the above primary amine in methylene chloride (20 ml.). The solution was cooled to 0° C. and subsequently treated with benzotriazol-1-yloxy-tris(dimethylamino)phosphonium hexafluorophosphate (7.663 g., 17.3 mmol.) as a solid. The solution was stirred at 0° C. for 1 hour and then at room temperature for 2.5 hours. The solvent was stripped and the residue was partitioned between ethyl acetate and water. The organic layer was washed successively with 50% saturated sodium bicarbonate and brine, then dried (sodium sulfate), filtered and stripped. The residue was flash chromatographed (Merck silica gel, 6:4-ethyl acetate:hexanes followed by 8:2-ethyl acetate:hexanes) to give the desired product as a solid. Recrystallization from ethyl ether/ethyl acetate afforded 4.466 g. of the title product; m.p. 83.5°–85.5° C.; $[\alpha]_D$=+15.3° (c=0.6, chloroform). TLC (6:4 ethyl acetate:hexanes) $R_f$=0.28.

Anal. calc'd. for $C_{21}H_{26}N_2O_7$: C, 60.28; H, 6.26; N, 6.69 Found: C, 60.04; H, 6.22; N, 6.75.

h) [S-(R*,R*)]-1-(2-Phthalimido-1-oxo-4-pentenyl)-1H-pyrrole-2-carboxylic acid, methyl ester A solution of the product from part (g) (3.801 g., 9.08 mmol.) and trifluoroacetic acid (1.0 ml.) in 1,1,1-trichloroethane (100 ml.) was heated at 60° C. under argon for 18 hours and then at reflux for an additional 24 hours. The cooled mixture was quenched with saturated sodium bicarbonate and water then extracted with ethyl acetate/ethyl ether. The organic layer was washed with brine, dried (sodium sulfate), filtered and stripped. The residue was flash chromatographed (Merck silica gel, 50–60% ethyl acetate:hexanes) to afford the desired product as a solid. Recrystallization from methylene chloride/ethyl ether provided 2.068 g. of analytically pure title product; m.p. 147°–148° C.; $[\alpha]_D$=–273.2° (c=0.4, chloroform). TLC (6:4 ethyl acetate:hexanes) $R_f$=0.43.

Anal. calc'd. for $C_{19}H_{18}N_2O_5$: C, 64.40; H, 5.12; N, 7.91 Found: C, 64.13; H, 4.95; N, 7.62.

i) [3S-(3α,6α,9αβ)]-Octahydro-8-iodo-5-oxo-6-phthalimido-1H-pyrrolo[1,2-a]azepine-3-carboxylic acid, methyl ester A cold (0° C.) solution of the product from part (h) (1.004 g., 2.83 mmol.) in methylene chloride (10 ml.) was added dropwise to a mixture of trifluoromethanesulfonic acid (1.5 ml.) and trifluoromethanesulfonic anhydride (150 μl.) at 0° C. The colorless solution was allowed to warm to room temperature. After 2.75 hours, the now bright yellow solution was poured into ice water and extracted with ethyl acetate. The ethyl acetate extract was washed with brine, dried (sodium sulfate), filtered and stripped. The crude residue was dissolved in methyl ethyl ketone (15 ml.) and treated with sodium iodide (1.98 g.). After stirring at room temperature for 1.5 hours, the mixture was partitioned between ethyl acetate and water which contained a small amount of sodium bisulfite. The organic layer was washed with brine, dried (sodium sulfate), filtered and stripped. The residue was flash chromatographed twice (Merck silica gel, 6:4 ethyl acetate:hexanes) to give 799 mg. of title product as a white foam; TLC (6:4 ethyl acetate:hexanes) $R_f$=0.31. In addition, 232 mg. of [3S-(3α,6α,8α,9αβ)]-octahydro-8-chloro-5-oxo-6-phthalimido-1H-pyrrolo[1,2-a]azepine-3-carboxylic acid, methyl ester was also obtained as a white foam. TLC (6:4 ethyl acetate:hexanes) $R_f$=0.25.

j) [3S-(3α,6α,9αβ)]-Octahydro-5-oxo-6-phthalimido-1H-pyrrolo[1,2-a]azepine-3-carboxylic acid, methyl ester A solution of the 8-iodo product from part (i) (705 mg., 1.46 mmol.) and tris(trimethylsilyl)silane (860 μl., 693 mg., 2.8 mmol.) in dry toluene (11 ml.) was heated to 55° C. and treated every 30 minutes with a catalytic amount (2–3 mg.) of 2,2'-azobisisobutyronitrile. After 2 hours, the solution was cooled to room temperature and concentrated. The residue was flash chromatographed (Merck silica gel, 6:4 ethyl acetate:hexanes) to give 470 mg. of title product as a white foam; $[\alpha]_D$=–36.4° (c=0.5, chloroform). TLC (6:4 ethyl acetate:hexanes) $R_f$=0.27.

k) [3S-[3α,6α(R*),9αβ]]-Octahydro-6-[[2-(acetylthio)-1-oxo-3-phenylpropyl]amino]-5-oxo-1H-pyrrolo[1,2-a]azepine-3-carboxylic acid, methyl ester The product from part (j) (448 mg., 1.26 mmol.) in methanol (7 ml.) was treated with hydrazine monohydrate (73 μl., 75 mg., 1.51 mmol.) and the solution was stirred at room temperature for 42 hours. The mixture was filtered and the solid was washed with methanol. The filtrate was stripped, triturated with methylene chloride, filtered again and evaporated to afford the crude amine as a pale yellow oil (277 mg.).

A cold (0° C.) solution of (S)-(acetylthio)benzenepropanoic acid (obtained from the dicyclohexylamine salt as described previously, 339 mg., 1.51 mmol.) and the above amine in methylene chloride (10 ml.) was cooled to 0° C., then treated with triethylamine (193 μl., 140 mg., 1.38 mmol.) followed by benzotriazol-1-yloxy-tris(dimethylamino)phosphonium hexafluorophosphate (641 mg., 1.45 mmol.). The solution was stirred at 0° C. for 50 minutes and then at room temperature for 2 hours. The solvent was stripped and the residue was partitioned between ethyl acetate and 0.5N hydrochloric acid. The organic layer was washed successively with water, 50% saturated sodium bicarbonate and brine, then dried (sodium sulfate), filtered and stripped. The residue was flash chromatographed (Merck silica gel, 6:4 ethyl acetate:hexanes) to give 461 mg. of pure title product as an oil/foam. TLC (75:25 ethyl acetate:hexanes) $R_f$=0.36.

l) [3S-[3α,6α(R*),9αβ]]-Octahydro-6-[(2-mercapto-1-oxo-3-phenylpropyl)amino]-5-oxo-1H-pyrrolo[1,2-a]azepine-3-carboxylic acid A room temperature solution of the product from part (k) (456 mg., 1.05 mmol.) in methanol (8 ml., deoxygenated via argon bubbling) was treated with 1N sodium hydroxide (9 ml., deoxygenated via argon bubbling). After stirring for 2.5 hours, the mixture was acidified with 10% hydrochloric acid, diluted with water and extracted with ethyl acetate. The ethyl acetate extract was washed with brine, then dried (sodium sulfate), filtered and stripped. The residue was flash chromatographed (Merck silica gel, ethyl acetate followed by 1% acetic acid in ethyl acetate). The desired product fractions were stripped, azeotroped three times with ethyl acetate, taken up in a small amount of ethyl acetate and triturated with hexanes. The solids were collected by filtration, washed with hexane and dried in vacuo to afford 351 mg. of title product as a white amorphous powder; $[\alpha]_D=-107.9°$ (c=0.6, chloroform). TLC (2% acetic acid in ethyl acetate) $R_f=0.35$.

Anal. calc'd. for $C_{19}H_{24}N_2O_4S$: C, 60.62; H, 6.43; N, 7.44; S, 8.52 Found: C, 60.49; H, 6.42; N, 7.21; S, 8.39.

EXAMPLE 68

(2S)-8-[(2-Mercapto-1-oxo-3-phenylpropyl)amino]-7-oxo-6-azaspiro[4,6]undecane-6-carboxylic acid a) 1-(4-Chlorobutyl)cyclopentanecarboxylic acid A solution of lithium diisopropylamide was prepared under nitrogen from diisopropylamine (31.0 ml., 220 mmol.) and n-butyl lithium (1.5M in hexane, 88.0 ml., 220 mmol.) in tetrahydrofuran (80 ml.), maintaining the temperature between -3° C.-1° C. After stirring 15 minutes, cyclopentanecarboxylic acid (11.4 g., 100 mmol.) in tetrahydrofuran (10 ml.) was added at 0° C.-3° C. over 25 minutes. After an additional 15 minutes at 0° C, the bath was removed and the reaction stirred 15 minutes more, causing the temperature to rise to 11° C. The milky white solution was cooled to -74° C. and 1-bromo-4-chlorobutane (23 ml., 200 mmol.) in tetrahydrofuran was added quickly, the temperature rising to -66° C. After 16 hours, the reaction was allowed to warm to room temperature in situ. The reaction was quenched with methanol (10 ml.) and concentrated in vacuo. The residue was partitioned between water (200 ml.) and ethyl ether (200 ml.). The aqueous layer was acidified to pH 1 with 12M hydrochloric acid and extracted with methylene chloride (3×150 ml.), dried (magnesium sulfate), filtered and evaporated to give 20.0 g. of the title product as a yellow oil.

b) 1-(4-Chlorobutyl)cyclopentanecarboxylic acid, methyl ester

To a solution of the product from part (a) (19.8 g., 96.5 mmol.) in methylene chloride (100 ml.) was added diazomethane [prepared from N-methyl-N'-nitro-N-nitrosoguanidine (22.8 g., 155 mmol.) in 40% potassium hydroxide (85 ml.) and ethyl ether (100 ml.)] until a yellow color was maintained. When all of the starting material had been consumed (monitored by TLC), nitrogen was bubbled through the reaction for approximately 20 minutes. The solution was dried (magnesium sulfate) and the reaction stirred an additional 10 minutes before being filtered and concentrated in vacuo. The crude product was adsorbed onto silica gel, then purified by flash chromatography, eluting with 2:3 methylene chloride/hexane to give 17.1 g. of title product as as a clear oil.

c) 1-(4-Iodobutyl)cyclopentanecarboxylic acid, methyl ester

To a solution of the product from part (b) (15.0 g., 68.6 mmol.) in acetone (343 ml.) was added sodium iodide (51.4 g., 343 mmol.). The solution was stirred in the dark under nitrogen at 60° C. for 64 hours. The reaction was cooled to room temperature, diluted with ether and washed with a saturated solution of sodium bicarbonate. The aqueous phase was extracted with ether (5×200 ml.). The ether extracts were combined, washed with brine, dried (magnesium sulfate), filtered and concentrated in vacuo to a clear oil (20.0 g). Purification by flash chromatography, eluting with 7:15 methylene chloride/hexane, gave 18.2 g. of title product as a clear oil.

d) Spiro[4,6]undecan-6-one t-Butyl lithium (1.7M in pentane, 20.0 ml., 34 mmol.) was slowly added to ether (38 ml.) at -20° C. as the reaction was further cooled to -100° C. in a methanol/dry ice/liquid nitrogen bath. To this -100° C. solution was added the product from part (c) (5.0 g., 16.1 mmol.) in 2:1 ether/pentane (3 ml.) over 35 minutes, maintaining the temperature below -97° C. The reaction was warmed to -50° C. over two hours then quenched with a saturated solution of ammonium chloride, extracted with ethyl acetate (4×100 ml.), washed with brine, dried (magnesium sulfate), filtered and concentrated to give a clear oil (mixture of desired product and the iodo starting material).

e) Spiro[4,6]undecan-6-oxime

A solution of the crude mixture from part (d) (4.4 g., 29 mmol.), hydroxylamine·hydrochloride (4.7 g., 67 mmol.) and sodium acetate (5.7 g., 70 mmol.) in isopropanol (30 ml.) was heated to 85° C. for two hours. The reaction was partitioned between ethyl ether and water. The ether extract was washed with 1N hydrochloric acid, brine, dried (sodium sulfate) and concentrated to a clear oil. Purification by flash chromatography, eluting with 7:3 methylene chloride/hexane, gave 1.76 g. of title product as a white solid, m.p. 62°-63° C.

f) 8,8-Dichloro-6-azaspiro[4,6]undecan-7-one

A cold slurry of phosphorus pentoxide (6.57 g., 31.6 mmol.) in methylene chloride (7 ml.) was treated with a solution of the product from part (e) (1.76 g., 10.5 mmol.) in methylene chloride (10 ml.) over a three minute period. The mixture was warmed to room temperature and chlorine gas was bubbled through the solution at 0.5 and 1.5 hours after the addition of the oxime. After a total of three hours, the mixture was quenched with crushed ice and brought to pH 8 with saturated sodium bicarbonate solution. The biphasic mixture was stirred vigorously for 19 hours. The layers were separated, washed with saturated sodium bicarbonate solution, brine, dried (sodium sulfate), filtered and concentrated in vacuo. Purification by flash chromatography, eluting with 2:98 ether/methylene chloride, gave 952 mg. of title product as a white solid; m.p. 114°-120° C.

g) 8-Chloro-6-azaspiro[4,6]undecan-7-one

To a solution of the product from part (f) (1.85 g., 7.83 mmol.) in glacial acetic acid (34 ml.) was added 10% palladium on carbon (0.55 g.). The reaction was stirred under hydrogen at atmospheric pressure. After two hours, the reaction was purged with nitrogen, filtered through Celite® and washed with ether. The oily solid was purified by flash chromatography, eluting with 4:96 ethyl acetate/methylene chloride to give 1.35 g. of the title product as a white solid; m.p. 109°-111° C.

h) 8-Azido-6-azaspiro[4,6]undecan-7-one

The product from part (g) (1.20 g., 5.95 mmol.), sodium azide (2.32 g., 35.7 mmol.) and sodium iodide (50 mg.) were combined in dimethylsulfoxide (22 ml.) and heated to 80° C. under nitrogen. After 16 hours, the solution was diluted with water and extracted with ether (4×50 ml.). The ether extracts were combined, washed with brine, dried (sodium sulfate), filtered and concentrated to a white solid. Purification by flash chromatography, eluting with 3:7 ethyl acetate/hexane, gave 1.13 g. of title product as a white solid; m.p. 96°-99° C.

i) 8-[[(1,1-Dimethylethoxy)carbonyl]amino]-6-azaspiro[4,6]undecan-7-one

To a solution of the product from part (h) (873 mg., 4.21 mmol.) in methanol (17.5 ml.) was added 10% palladium on carbon catalyst (188 mg.) and the reaction was rapidly stirred under hydrogen at atmospheric pressure. After 90 minutes, the reaction was purged with nitrogen, filtered through Celite®, washed with methylene chloride and the filtrate was concentrated in vacuo. The resulting white solid was dissolved in chloroform (15 ml.), treated with triethylamine (0.59 ml., 4.21 mmol.) and then a solution of di-tert-butyl dicarbonate (1.1 g., 5.1 mmol.) in chloroform (2.5 ml.). After two hours at room temperature, the reaction was concentrated in vacuo. Purification by flash chromatography, eluting with 4:6 ethyl acetate/methylene chloride, gave a white solid which was repurified by flash chromatography, eluting first with methylene chloride (500 ml.) followed by 4:6 ethyl acetate/methylene chloride, to give 1.00 g. of title product as a white solid; m.p. 180°–181° C.

j) 8-[[(1,1-Dimethylethoxy)carbonyl]amino]-7-oxo-6-azaspiro[4,6]undecane-6-acetic acid, ethyl ester To a solution of the product from part (i) (0.97 g., 3.4 mmol.) in tetrahydrofuran (27 ml.) at room temperature was added lithium bis(trimethylsilyl)amide (5.1 ml., 5.1 mmol., 1M in tetrahydrofuran) followed by ethyl bromoacetate (0.78 ml., 6.8 mmol.). After stirring twenty minutes at room temperature, another portion of lithium bis(trimethylsilyl)amide (5.1 ml.) and ethyl bromoacetate (0.39 ml.) were added. The reaction was stirred for thirty minutes at room temperature and then treated with a third portion of lithium bis(trimethylsilyl)amide and ethyl bromoacetate. One hour after the third addition was complete, the reaction was quenched with a saturated solution of ammonium chloride, diluted with water (50 ml.), and extracted with ethyl acetate (3×50 ml.). The organic extracts were dried (sodium sulfate), filtered and concentrated to an orange oil. Purification by flash chromatography, eluting first with 3:7 ethyl acetate/hexane followed by 50% ethyl acetate/hexane, gave 508 mg. of title product as a colorless oil.

k) 8-Amino-7-oxo-6-azaspiro[4,6]undecane-6-acetic acid ethyl ester, hydrochloride A solution of the product from part (j) (507 mg., 1.38 mmol.; previously evaporated three times from toluene) in dioxane (1.0 ml.) at 0° C. was treated with hydrochloric acid (4.0M in dioxane, 4.15 ml.). The reaction was stirred 10 minutes at 0° C. and then warmed to room temperature. After 2.75 hours, the reaction was concentrated in vacuo to give 455 mg. of the title product as a white gummy solid.

l) (2S)-8-[[2-(Acetylthio)-1-oxo-3-phenylpropyl]-amino]-7-oxo-6-azaspiro[4,6]undecane-6-acetic acid, ethyl ester (S)-(Acetylthio)benzenepropanoic acid, dicyclohexylamine salt (280 mg., 0.69 mmol.) was suspended in ethyl acetate, washed (3×) with 5% potassium bisulfate, dried (magnesium sulfate), filtered and evaporated twice from hexanes. To this was added the product from part (k) (200 mg., 0.66 mmol.) in methylene chloride (6.6 ml.) at 0° C. followed by triethylamine (137 mg., 1.4 mmol.). The reaction was stirred for ten minutes at 0° C. Benzotriazol-1-yloxytris(dimethylamino)phosphonium hexafluorophosphate (305 mg., 0.69 mmol.) was then added as a solid. The solution was stirred at 0° C. for 1.75 hours and then at room temperature for 10 minutes. The reaction was concentrated in vacuo and the residue partitioned between ethyl acetate (50 ml.) and 5% potassium bisulfate. The organic layer was washed with brine, a saturated solution of sodium bicarbonate and brine, dried (magnesium sulfate), filtered and concentrated to a yellow oil. Purification by flash chromatography eluting with 2:3 ethyl acetate/hexane gave 241 mg. of title product as a clear oil.

m) (2S)-8-[(2-Mercapto-1-oxo-3-phenylpropyl)amino]-7-oxo-6-azaspiro[4,6]undecane-6-acetic acid A solution of the product from part (l) (232 mg., 0.43 mmol.) in methanol (5 ml., deoxygenated via nitrogen bubbling) was cooled to 0° C. and treated with 1N sodium hydroxide (5 ml., deoxygenated via nitrogen bubbling). After stirring for one hour at 0° C. while purging continuously with nitrogen, the reaction was warmed to room temperature. After a total of three hours, the reaction was acidified to pH 1 with 5% potassium bisulfate and extracted with ethyl acetate. The organic layers were combined, washed with water (50 ml.), brine, dried (sodium sulfate), filtered, concentrated in vacuo, and reevaporated from hexanes to give 204 mg. of title product as a white foam. HPLC indicates the product to be a 47:53 mixture of diastereomers. TLC (2:3 ethyl acetate:hexanes) $R_f$=0.22.

Anal. calc'd. for $C_{21}H_{28}N_2O_4S \cdot 1.0\ C_4H_8O_2 \cdot 0.03\ C_6H_{14}$: C, 61.07; H, 7.41; N, 5.66; S, 6.47 Found: C, 60.61; H, 7.45; N, 5.97; S, 6.69.

EXAMPLE 69

(2S)-7-[(2-Mercapto-1-oxo-3-phenylpropyl)amino]-6-oxo-5-azaspiro[3,6]decane-5-acetic acid a) 1-(4-Pentenyl)cyclobutanecarboxylic acid, phenylmethyl ester To a solution of lithium diisopropylamide prepared from 31.0 ml. (221 mmol.) of diisopropyl amine and 87.0 ml. (218 mmol., 2.5M in hexanes) of n-butyllithium at 0° C. was added a solution of 10.01 g. (100.0 mmol.) of cyclobutanecarboxylic acid in 10 ml. of tetrahydrofuran over 5 minutes. The temperature was not allowed to rise above 11° C. during the addition. The resulting yellow, turbid solution was stirred for 30 minutes, whereupon 14.0 ml. (118 mmol.) of 5-bromo-1-pentene was added over the course of 5 minutes. The temperature rose autogenously to 50° C. over 10 minutes and then slowly subsided. When the temperature returned to 20° C., the reaction was quenched with 4 ml. of methanol and then 20 ml. of water. The solution was concentrated under reduced pressure below 30° C. To the oily residue was added 100 ml. of water and the mixture was extracted twice with 100 ml. portions of ether. The aqueous layer was then acidified with cold 50% sulfuric acid to pH 2 and then extracted three times with methylene chloride The methylene chloride extracts were combined, dried (magnesium sulfate) and evaporated to give 17.61 g. of 1-(4-pentenyl)cyclobutanecarboxylic acid as a yellow oil.

To a stirred solution of this oil in 75 ml. of dimethylformamide at room temperature under nitrogen was added 32.8 g. (100 mmol.) of cesium carbonate and then 12.6 ml. (105 mmol.) of benzyl bromide. After 3 hours, the reaction mixture was diluted with 200 ml. of water and extracted three times with ether. The combined extracts were washed once with water and once with brine, dried (magnesium sulfate) and evaporated onto 40 g. of silica gel. Purification by flash chromatography (10×30 cm column, 1:2 methylene chloride:hexanes) provided 22.65 g. of title product as a colorless oil.

b) 1-(5-Hydroxypentyl)cyclobutanecarboxylic acid, phenylmethyl ester

To a solution of 20.0 g. (77.4 mmol.) of the product from part (a) in 75 ml. of tetrahydrofuran under nitrogen at 0°–5° C. was added a solution of 170 ml. (85.0 ml., 0.5M in tetrahydrofuran) of 9-borabicyclononane over 20 minutes. The reaction was then warmed to room temperature and stirred for 45 minutes. To this solution was added 26 ml. (78 mmol.) of ice-cold 3M sodium hydroxide and then 26 ml. of 30% hydrogen peroxide was added at a rate to keep the temperature below 48° C. After an additional 30 minutes, the reaction was quenched with 100 ml. of saturated sodium sulfite solution. The reaction mixture was extracted three times with ether, the extracts were combined, dried (magnesium sulfate) and evaporated. Purification by flash chromatography (10×30 cm column, 7:93 ether:methylene chloride) gave 19.15 g. of title product as a colorless oil.

c) 1-[(Phenylmethoxy)carbonyl]cyclobutanepentanoic acid, methyl ester

To a stirred solution of 6.8 ml. (78 mmol.) of oxalyl chloride in 180 ml. of methylene at −72° C. under nitrogen was added 12.2 ml. (172 mmol.) of dimethylsulfoxide in 40 ml. of methylene chloride dropwise over 10 minutes. The temperature was not allowed to rise above −60° C. After an additional 5 minutes, a solution of 18.66 g. (67.5 mmol.) of the product from part (b) in 30 ml. of methylene chloride was added over 5 minutes. The resulting cloudy solution was stirred 15 minutes and then treated with 30.8 ml. (186 mmol.) of diisopropylethylamine. The clear yellow solution was warmed to room temperature and treated with 100 ml of water. The aqueous layer was extracted once with 100 ml. of methylene chloride and the combined organic extracts were evaporated to leave a foul-smelling yellow oil.

The oil was dissolved in 140 ml. of 9:1 methanol/water and treated with 120 g (1.4 mol) of solid sodium bicarbonate. The thick slurry was rapidly stirred at room temperature while 142 ml. (0.28 mol.) of 2M bromine in 9:1 methanol/water was added over 15 minutes. After 3 hours, the reaction was quenched with 20 ml. of saturated sodium thiosulfate solution and evaporated below 30° C. to remove methanol. The pasty residue was partitioned between water and ether. The aqueous layer was extracted twice with ether, the organic layers were combined, dried (magnesium sulfate) and evaporated. Purification by flash chromatography (10× 30 cm column, 1:9 hexanes/methylene chloride) gave 16.35 g. of title product as a faintly yellow oil.

d) 1-Carboxycyclobutanepentanoic acid, methyl ester

20% Palladium hydroxide on carbon catalyst (1.3 g.) was added to the product from part (c) (16.30 g., 53.5 mmol.) in 100 ml. of nitrogen-purged 3:1 ethyl acetate/ethanol in a 500 ml. Parr hydrogenation vessel. The reaction vessel was agitated on a Parr Hydrogenator for 6 hours (hydrogen uptake was 5.9 psi). The reaction was purged with nitrogen and filtered through Celite®. Additional hydrogenation with fresh catalyst (2.0 g. of palladium hydroxide on carbon) for 14 hours resulted in a total hydrogen uptake of 48 psi. The reaction was repurged with nitrogen, filtered through Celite® and evaporated. Re-evaporation from toluene gave 11.40 g. of title product as a colorless oil.

e) 1-Aminocyclobutanepentanoic acid, methyl ester

To the product from part (d) (11.35 g., 53.0 mmol.) in tetrahydrofuran (5 ml.) at 0° C. under nitrogen was added 7.8 ml. (56 mmol.) of triethylamine and then 5.2 ml. (54.3 mmol.) of ethyl chloroformate, dropwise, over 15 minutes. The temperature was not allowed to rise above 6° C. The resulting thick slurry was stirred for 10 minutes and then treated rapidly with a slurry of 7.34 g. (113 mmol.) of sodium azide in 40 ml. of 1:1 acetone/water. The solution thus formed was stirred for 15 minutes, diluted with 100 ml. of ice water and extracted twice with 125 ml. portions of toluene. The organic extracts were combined, washed once with 5% potassium bisulfate, once with brine, dried (magnesium sulfate) and filtered.

The filtrate was set to reflux with the aid of a Dean-Stark trap: 175 ml. of solvent was removed from the reaction. After 30 minutes, the residue was cooled to room temperature. The solution was diluted with methylene chloride (50 ml.) under nitrogen at room temperature and treated with 8.2 ml. (78 mmol.) of benzyl alcohol and 0.4 ml. (4.5 mmol.) of chlorotrimethylsilane. After 40 minutes, the reaction was quenched with 5 ml. of saturated sodium bicarbonate solution, partitioned, dried (magnesium sulfate) and evaporated.

The resulting oil was dissolved in 100 ml. of nitrogen-purged methanol, treated with 1.7 g. of 20% palladium hydroxide on carbon catalyst and hydrogenated on a Parr Hydrogenator for 16 hours (total hydrogen uptake of 33.8 psi.). The reaction mixture was purged with nitrogen and evaporated. The residue was diluted with ether and washed three times with 10% hydrochloric acid. The acidic extracts were combined and washed three times with ether. The aqueous layer was made basic with potassium hydroxide pellets to pH 8.5 and extracted twice with methylene chloride. The organic extracts were dried (sodium sulfate) and evaporated to provide essentially pure title product as a colorless oil.

f) 5-Azaspiro[3.6]decan-6-one

To a stirred solution of of the product from part (e) (4.16 g., 22.5 mmol.) in methylene chloride (50 ml.) under nitrogen at room temperature was added 20 ml. (40 mmol.) of 2M trimethylaluminum in heptane over 5 minutes. The reaction was stirred for 15 hours and then quenched with saturated ammonium chloride solution and extracted twice with methylene chloride. The extracts were combined, dried (magnesium sulfate) and evaporated. Recrystallization from ethyl acetate/hexane gave 3.32 g. of title product as a white solid.

a) 5-(2-Propenyl)-5-azaspiro[3.6]undecan-6-one

To a stirred solution of 3.26 g. (21.3 mmol.) of the product from part (f) in 25 ml. of dimethylsulfoxide under nitrogen at room temperature was added 2.86 g. (25.5 mmol.) of potassium t-butoxide. The slurry was heated to 50° C. for 1 hour and then 2.5 ml. (28.9 mmol.) of allyl bromide was added. A white precipitate formed instantly. After 3 hours, an additional 2.86 g. of potassium t-butoxide was added. A brown slurry formed. After 30 minutes, an additional 2.5 ml. of allyl bromide was added and the color faded at once. After 16 hours, a third batch of 2.5 ml. of allyl bromide was added and the reaction stirred for 2 hours. The reaction was then cooled, quenched with 5% potassium bisulfate and extracted four times with 100 ml. of ether. The combined extracts were washed once with water, once with brine, dried (magnesium sulfate) and evaporated. Purification by flash chromatography (5×25 cm column, 55:45 ethyl acetate/hexanes) gave 2.80 g. of title product as a light yellow oil., h) 5-(2,2-Dimethoxyethyl)-5-azaspiro[3.6]undecan-6-one To a solution of 2.75 g. (14.2 mmol.) of the product from part (g) in 50 ml. of methylene chloride at −78° C. in a flask protected by a calcium chloride drying tube was bubbled 8% ozone in oxygen gas until a blue color persists in the reaction mixture (about 2 hours). The reaction was briefly purged with oxygen and then nitrogen for 30 minutes. To this solution was added 10 ml. of dimethylsulfide and the cold bath was removed. Upon warming to room temperature, the reaction mixture was evaporated and the oily residue was dissolved in 20 ml. of methylene chloride, 30 ml. of methanol and 5 ml. of trimethylorthoformate. To this stirred solution under nitrogen at room temperature was added 75 mg. (0.4 mmol.) of p-toluenesulfonic acid hydrate. The reaction was stirred 16 hours, 1 g. (12 mmol.) of solid sodium bicarbonate was added, and stirred an additional 30 minutes. The reaction was partitioned between ethyl acetate and saturated sodium bicarbonate solution and extracted again with ethyl acetate. The organic extracts were combined, washed once with brine, dried (sodium sulfate)

and evaporated. Purification by flash chromatography (5×25 cm column, 4:1 ethyl acetate/hexane) provided 1.60 g. of title product as a colorless oil.

i) 7-Bromo-5-(2,2-dimethoxyethyl)-5-azaspiro[3.6]undecan-6-one

To a solution of lithium diisopropylamide prepared from 0.56 ml. (4.0 mmol.) of diisopropyl amine and 1.60 ml. (4.0 mmol., 2.5M in hexanes) of n-butyl lithium at 0° C. was added a solution of 908 mg. (3.76 mmol.) of the product from part (h) in 4 ml. of tetrahydrofuran over 2 minutes. The reaction was warmed to –45° C. and stirred 45 minutes. To this pale yellow solution was added a solution of 1.37 g. (4.11 mmol.) of carbon tetrabromide in 5 ml. of tetrahydrofuran over 15 minutes. The resulting deep red-brown solution was stirred for 20 minutes, quenched cold with saturated ammonium chloride solution and extracted twice with ethyl acetate. The extracts were combined, washed once with brine, dried (sodium sulfate) and evaporated. Purification by flash chromatography (5×15 cm column, 3:7 ethyl acetate/hexane) provided 1.012 g. of title product as white solid, m.p. 62°–64° C.

j) 7-Azido-6-oxo-5-azaspiro[3.6]decane-5-acetaldehyde

To a stirred solution of 810 mg. (2.53 mmol.) of the product from part (i) in 10 ml. of dimethylsulfoxide at room temperature under nitrogen was added 1.6 g. (25 mmol.) of sodium azide. The reaction was heated to 45°–55° C. and stirred 16 hours After cooling to room temperature, the slurry was diluted with 25 ml. of water and extracted three times with ether. The extracts were combined, washed once with water, once with brine, dried (sodium sulfate) and evaporated to give 680 mg. of the azido-acetal as a brown oil.

To a solution of this azide in 5 ml. of methylene chloride at room temperature under nitrogen was added 2.5 ml. of water and then 2.5 ml. of trifluoroacetic acid. After 1 hour, the reaction mixture was poured into a slurry of 8 g. of sodium bicarbonate in 15 ml. of water (considerable foaming). The mixture was extracted twice with ethyl acetate. The extracts were combined, washed once with saturated sodium bicarbonate, once with brine, dried (magnesium sulfate) and evaporated to give 466 mg. of title product as an orange oil.

k) 7-Azido-6-oxo-5-azaspiro[3.6]decane-5-acetic acid, methyl ester

To a stirred slurry of 465 mg. (1.97 mmol.) of the product from part (j) and 8 g. (95 mmol.) of sodium bicarbonate in 8 ml. of 9:1 methanol/water at room temperature was added 8 ml. (16 mmol.) of 2M bromine in 9:1 methanol/water. The reaction was stirred for 4 hours, then quenched with saturated sodium thiosulfate solution and extracted twice with ethyl acetate. The extracts were combined, washed once with brine, dried (magnesium sulfate) and evaporated. Purification by flash chromatography (2.5×20 cm column, 1:2 ethyl acetate/hexanes) gave 275 mg. of title product as a colorless oil.

l) 7-Amino-6-oxo-5-azaspiro[3.6]decane-5-acetic acid, methyl ester

To a stirred solution of 250 mg. (0.94 mmol.) of the product from part (k) in 15 ml. of dry, nitrogen-purged methanol at room temperature was added 320 mg. of 10% palladium on carbon. A hydrogen-filled balloon was attached to the reaction flask and the reaction mixture was stirred rapidly. After 2 hours, the reaction was purged with nitrogen, filtered through Celite® and evaporated to give 215 mg. of title product as a colorless oil.

m) (2S)-7-[[2-(Acetylthio)-1-oxo-3-phenylpropyl]amino]-6-oxo-5-azaspiro[3.6]decane-5-acetic acid, methyl ester A stirred suspension of (S)-(acetylthio)benzenepropanoic acid prepared from the dicyclohexylamine salt as described previously (324 mg., 0.80 mmol.) in ethyl acetate (15 ml.) was washed twice with 5% potassium bisulfate (5 ml.). The organic extract was dried (magnesium sulfate), filtered and evaporated twice from methylene chloride. The resulting oil was dissolved methylene chloride (15 ml.) and stirred under argon at –5° C. To this solution was added a solution of the product from part (l) (174 mg., 0.724 mmol.) in methylene chloride (4 ml.), then triethylamine (100 µl., 0.74 mmol.) and finally benzotriazol-1-yloxytris (dimethylamino) phosphonium hexafluorophosphate (325 mg., 0.733 mmol.). After 1 hour, the reaction was warmed to room temperature and stirred 3 hours. The resulting colorless solution was evaporated at less than 30° C. and the oily residue redissolved in ethyl acetate. The solution was washed once with 1M hydrochloric acid, once with water and once with brine. The organic layer was dried (magnesium sulfate), filtered and evaporated. Purification by flash chromatography (2.5× 20 cm column, eluting with 47:53 ethyl acetate/hexanes) provided 240 mg. of title product as a white foam.

n) (2S)-7-[(2-Mercapto-1-oxo-3-phenylpropyl)amino]-6-oxo-5-azaspiro[3.6]decane-5-acetic acid A solution of the product from part (m) (145 mg., 0.32 mmol.) in 3 ml. of methanol was purged with nitrogen for 10 minutes and cooled to 0° C. To this solution was added dropwise 3 ml. of nitrogen-purged 1M sodium hydroxide. Nitrogen was slowly bubbled through the solution during the reaction. After 30 minutes, the reaction was warmed to room temperature and stirred 3 hours. The reaction was acidified with 1 ml. of 6M hydrochloric acid, extracted twice with ethyl acetate and the extracts combined, dried (magnesium sulfate) and evaporated. Purification by flash chromatography (2.5×15 cm column, 1:79:20 acetic acid/ethyl acetate/hexanes) gave, after reevaporation from toluene, 118 mg. of title product as a white foam. TLC (79:20:1, ethyl acetate:hexane:acetic acid) $R_f$=0.20.

Anal. calc'd. for $C_{20}H_{25}N_2O_4S.0.33\ C_7H_8.0.04\ C_6H_{14}$: C, 63.83; H, 6.94; N, 6.60; S, 7.56 Found: C, 63.72; H, 6.90; N, 6.29; S, 7.42.

EXAMPLE 70

[S-(R*,R*)]-Hexahydro-6-[(2-mercapto-1-oxo-3-phenylpropyl)amino]-2,2-dimethyl-7-oxo-1H-azepine-1-acetic acid The product of Example 66 was also prepared as follows:

a) (S)-Hexahydro-6-[(triphenylmethyl)amino]-2,2-dimethyl-2H-azepine-7-one

Hydrazine monohydrate (4.59 ml., 94.6 mmol.) was added to a solution of (S)-hexahydro-6-phthalimido-2,2-dimethyl-2H-azepine-7-one [preparred as described in Example 66(e), 19.98 g., 68.76 mmol.] in methanol (250 ml.) at room temperature under argon. The resulting mixture was stirred for 72 hours then filtered to remove the white precipitate. The volatiles were evaporated and the residue was dissolved in methylene chloride (560 ml.) and filtered to remove additional precipitate. To this filtrate was added triethylamine (13.3 ml., 96.21 mmol.) followed by triphenylchloromethane (20.65 g., 74.07 mmol.) and the resulting mixture was stirred for 1.5 hours. Additional triphenylchloromethane (958 mg., 3.44 mmol.) was added and the solvent was removed. The residue was partitioned between ethyl acetate and water. The organic layer was washed with brine, dried, filtered and concentrated to give a pale yellow foam. Following a crystallization from ethyl acetate and hexanes, 7.47 g. of title product was obtained as off-white crystals.

The mother liquor was concentrated and crystallized from ethyl acetate and pentane to give a second crop (8.02 g.) of title product. The mother liquor was concentrated and the residue was flash chromatographed (E Merck silica gel) eluting with 4.5:5.5 ethyl acetate/hexanes to give 6.0 g of title compound as a white foam. The combined yield of title product was 21.49 g.; m.p. 139°–140° C.; $[\alpha]_D$=+43.4° (c=0.37, methylene chloride). TLC (2:3 hexane:ethyl acetate) $R_f$=0.63.

b) (S)-Hexahydro-6-[(triphenylmethyl)amino]-2,2-dimethyl-7-oxo-1H-azepine-1-acetic acid, ethyl ester Lithium bis(trimethylsilyl)amide (1.0M in tetrahydrofuran; 212.8 ml., 212.8 mmol.) and ethyl bromoacetate (23.6 ml., 212.8 mmol., in 190 ml. tetrahydrofuran) were simultaneously added to a solution of the product from part (a) (21.0 g., 53.19 mmol.) in tetrahydrofuran (210 ml.) at room temperature under argon over 1 hour. Additional lithium bis(trimethylsilyl)amide (1.0M in tetrahydrofuran; 53.2 ml., 53.2 mmol.) and ethyl bromoacetate (59.0 ml., 53.2 mmol., in 47.3 ml. tetrahydrofuran) were simultaneously added over 40 minutes then the reaction mixture was quenched with saturated aqueous ammonium chloride and extracted with ethyl acetate. The organic layer was washed with saturated aqueous sodium bicarbonate and brine, dried (sodium sulfate), filtered and concentrated to give a yellow oil. The residue was flash chromatographed twice (E Merck silica gel) eluting with 1:1 hexanes/ethyl acetate and 3:1 hexanes/ ethyl acetate to give 25.93 g. of impure title product. TLC (3:2 hexane:ethyl acetate) $R_f$=0.55.

c) [S-(R*,R*)]-Hexahydro-6-[[2-(acetylthio)-1-oxo-3-phenylpropyl]amino]-2,2-dimethyl-7-oxo-1H-azepine-1-acetic acid, ethyl ester A solution of the product from part (b) (25.92 g.) in methylene chloride (450 ml.) was treated with trifluoroacetic acid (14.82 ml., 192.4 mmol.) at room temperature under argon. After stirring for one hour, the volatiles were evaporated and the residue was partitioned between ethyl ether and 1N hydrochloric acid. The organic layer was extracted with 1N hydrochloric acid and water, the combined aqueous layers were cooled to 0° C., and the pH was made basic with solid sodium bicarbonate. Following three extractions with methylene chloride, the combined organic layers were dried (sodium sulfate), filtered, and concentrated to give 7.0 g. of the pure amine as a yellow oil.

(S)-(Acetylthio)benzenepropanoic acid, dicyclohexylamine salt (7.55 g., 18.61 mmol.) was partitioned between ethyl acetate and 10% potassium bisulfate. The organic layer was washed with 10% potassium bisulfate and brine, dried (sodium sulfate), filtered, and concentrated to give (S)-(acetylthio)benzenepropanoic acid as an oil. This residue was dissoved in methylene chloride (185 ml.) at room temperature under argon. Following the addition of the above amine (4.1 g., 16.92 mmol.), the mixture was cooled to 0° C. and triethylamine (2.59 ml.) was added. The resulting mixture was stirred for 5 minutes then benzotriazol-1-yloxytris(dimethylamino)phosphonium hexafluorophosphate reagent (8.31 g., 18.79 mmol.) was added. After stirring at 0° C. for 1 hour, the reaction mixture was warmed to room temperature and was stirred for 16 hours. The volatiles were evaporated and the residue was dissolved in ethyl acetate and washed successively with 0.5N hydrochloric acid, water, saturated aqueous sodium bicarbonate, and brine. The organic layer was dried (sodium sulfate), filtered, and concentrated, and the residue was flash chromatographed (E Merck silica gel) eluting with 1:1 hexane/ethyl acetate to give 6.94 g. of title product as a yellow foam. TLC (1:1 hexane:ethyl acetate) $R_f$=0.36.

d) [S-(R,R*)]-Hexahydro-6-[(2-mercapto-1-oxo-3-phenylpropyl)amino]-2,2-dimethyl-7-oxo-1H-azepine-1-acetic acid A solution of the product from part (c) (6.94 g., 15.47 mmol.) in methanol (55 ml., deoxygenated via argon bubbling) was treated with 1N sodium hydroxide (90.3 ml., deoxygenated via argon bubbling). After stirring under argon for 4 hours, the mixture was acidified with 10% hydrochloric acid and extracted with ethyl acetate. The organic layer was washed successively with water and brine, dried (sodium sulfate), filtered and concentrated to give a yellow residue. The residue was flash chromatographed (E Merck silica gel) eluting with ethyl acetate and 2% acetic acid in ethyl acetate. The fractions containing clean desired product were combined, concentrated, azeotroped with ethyl acetate and washed with water to remove any acetic acid to give 2.2 g. of title product as white heavy crystals. Impure fractions were combined, then concentrated to a white solid, and finally triturated with ethyl acetate to obtain 2.3 g. of title product for a total yield of 4.5 g. of title product; m.p. 173°–176° C.; $[\alpha]_D$=−21.9° (c=0.29, chloroform). TLC (2% acetic acid in ethyl acetate) $R_f$=0.38.

Anal. calc'd. for $C_{19}H_{26}N_2O_4S \cdot 0.2\ C_4H_8O_2$: C, 60.04; H, 7.02; N, 7.07; S, 8.09 Found C, 59.79; H, 6.97; N, 7.33; S, 8.35.

EXAMPLE 71

1000 tablets each containing the following ingredients:

| | |
|---|---|
| [S-(R*,R*)-2,3,4,5-Tetrtahydro-3-[(2-mercapto-1-oxo-3-phenylpropyl)-amino]-2-oxo-1H-benzazepine-2-acetic acid | 200 mg. |
| Cornstarch | 100 mg. |
| Gelatin | 20 mg. |
| Avicel (microcrystalline cellulose) | 50 mg. |
| Magnesium stearate | 5 mg. |
| | 375 mg. | are prepared from sufficient bulk quantities by mixing the product of Example 6 and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 200 mg. of active ingredient.

In a similar manner, tablets containing 200 mg. of the product of any of Examples 1 to 5 and 7 to 70 can be prepared.

Similar procedures can be employed to form tablets or capsules containing from 50 mg. to 500 mg. of active ingredient.

What is claimed is:

1. A compound of the formula

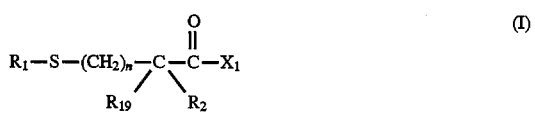

and pharmaceutically acceptable salts thereof wherein:

$R_1$ is hydrogen,

or $R_{18}-S-$;

$R_2$ and $R_{19}$ are independently selected from the group consisting of hydrogen, alkyl, cycloalkyl-$(CH_2)_m-$, substituted alkyl, aryl-$(CH_2)_m-$, substituted aryl-$(CH_2)_m-$, and heteroaryl-$(CH_2)_m-$ or $R_2$ and $R_{19}$ taken together with the carbon atom to which they are attached complete a cycloalkyl ring or a benzofused cycloalkyl ring;

n is zero or one;

m is zero or an integer from 1 to 6;

$R_3$ is alkyl, substituted alkyl, cycloalkyl-$(CH_2)_m-$, aryl-$(CH_2)_m-$, substituted aryl-$(CH_2)_m-$, or heteroaryl-$(CH_2)_m-$;

$R_{18}$ is alkyl, substituted alkyl, cycloalkyl-$(CH_2)_m-$, aryl-$(CH_2)_m-$, substituted aryl-$(CH_2)_m-$, heteroaryl-$(CH_2)_m-$ or $-S-R_{18}$ completes a symmetrical disulfide wherein $R_{18}$ is of the formula

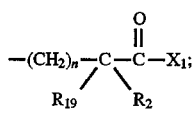 (II)

$X_1$ is of the formula

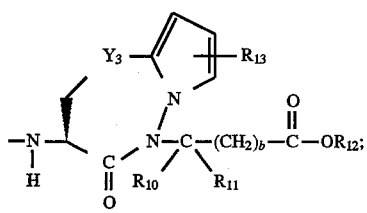 (XIII)

$Y_3$ is $-CH_2-$ or

s is zero, one, or two;

$R_{10}$ and $R_{11}$ are independently selected from the group consisting of hydrogen, alkyl, substituted alkyl, alkenyl, substituted alkenyl, cycloalkyl $-(CH_2)_m-$, aryl-$(CH_2)_m-$, substituted aryl-$(CH_2)_m-$, and heteroaryl-$(CH_2)_m-$;

b is zero or one;

$R_{12}$ is hydrogen, alkyl, substituted alkyl, aryl-$(CH_2)_m-$, substituted aryl-$(CH_2)_m-$, heteroaryl-$(CH_2)_m-$;

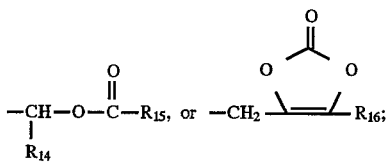

$R_{13}$ is hydrogen, lower alkyl, or substituted lower alkyl;
$R_{14}$ is hydrogen, lower alkyl, cycloalkyl, or phenyl;
$R_{15}$ is hydrogen, lower alkyl, lower alkoxy or phenyl;

$R_{16}$ is lower alkyl or aryl-$(CH_2)_m-$;

the term "alkyl" refers to straight and branched chain radicals having one to seven carbon atoms;

the term "substituted alkyl" refers to such straight or branched chain radicals of 1 to 7 carbons wherein one or more hydrogens have been replaced by a hydroxy, amino, halo, trifluoromethyl, cyano, —NH(lower alkyl), —N(lower alkyl)$_2$, lower alkoxy, lower alkylthio or carboxy;

the term "alkenyl" refers to straight or branched chain radicals of 3 to 7 carbon atoms having one or two double bonds;

the term "substituted alkenyl" refers to such straight or branched radicals of 3 to 7 carbons having one or two double bonds wherein a hydrogen has been replaced by a hydroxy, amino, halo, trifluoromethyl, cyano, —NH (lower alkyl), —N(lower alkyl)$_2$, lower alkoxy, lower alkylthio, or carboxy;

the term "cycloalkyl" refers to saturated rings of 3 to 7 carbon atoms;

the term "aryl" refers to phenyl, 1-naphthyl, and 2-naphthyl;

the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), and —N(lower alkyl)$_2$, di- and tri-substituted phenyl, 1-naphthyl, or 2-naphthyl wherein said substituents are selected from methyl, methoxy, methylthio, halo, hydroxy, and amino;

the term "heteroaryl" refers to unsaturated monocyclic rings of 5 or 6 atoms containing one or two O and S atoms and/or one to four N atoms provided that the total number of hetero atoms is four or less and bicyclic rings wherein the five or six membered ring as defined above is fused to a phenyl or pyridyl ring, said heteroaryl ring is attached by way of an available carbon or nitrogen atom; and said monocyclic or bicyclic ring can be substituted at an available carbon atom by lower alkyl of 1 to 4 carbons, halo, hydroxy, benzyl, or cyclohexylmethyl, or can be substituted at an available nitrogen atom by benzyloxymethyl, p-toluene sulfonyl, 2,4-dinitrophenyl, lower alkyl of 1 to 4 carbons, benzyl or benzhydryl;

the term "lower alkyl" refers to straight or branched chain radicals having one to four carbons;

the term "substituted lower alkyl" refers to such straight or branched chain radicals having one to four carbons wherein one hydrogen has been replaced by a hydroxy, amino, halo, trifluoromethyl, cyano, —NH(lower alkyl), —N(lower alkyl)$_2$, lower alkoxy, lower alkylthio, or carboxy;

the terms "lower alkoxy" and "lower alkylthio" refer to such lower alkyl groups as defined above attached to an oxygen or sulfur; and the term "halo" refers to chloro, bromo, fluoro, and iodo.

2. A compound of claim 1 wherein:

$R_1$ is hydrogen,

or $R_{18}-S-$;

$R_3$ is lower alkyl of 1 to 4 carbons or phenyl;

$R_{18}$ is lower alkyl of 1 to 4 carbons;

n is zero or one;

$R_2$ is aryl-CH$_2$—, substituted aryl-CH$_2$—, heteroaryl-CH$_2$—, or straight or branched chain alkyl of 1 to 7 carbons; and $R_{19}$ is hydrogen.

3. A compound of claim 2 wherein:

$Y_3$ is CH$_2$ or S;

$R_{13}$ is hydrogen;

$R_{10}$ and $R_{11}$ are both hydrogen or one is hydrogen and the other is lower alkyl of 1 to 4 carbons;

b is zero; and $R_{12}$ is hydrogen or lower alkyl of 1 to 4 carbons.

4. A compound of claim 3 wherein:

$R_1$ is hydrogen;

n is zero;

$R_2$ is benzyl, (2-thienyl)methyl, or straight or branched chain alkyl of 1 to 5 carbons.

5. A compound of claim 4 wherein:

$Y_3$ is CH$_2$;

$R_{10}$, $R_{11}$, $R_{12}$ and $R_{13}$ are all hydrogen.

6. The compound of claim 5, [S-(R*,R*)]-2,3,4,5-tetrahydro-3-[(2-mercapto-1-oxo-3-phenylpropyl)amino]-2-oxo-1H-pyrrolo[1,2-b][1,2]diazepine-1-acetic acid.

7. A pharmaceutical composition comprising a pharmaceutically acceptable carrier and a compound of the formula

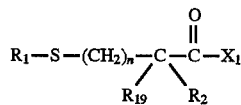

or a pharmaceutically acceptable salt thereof wherein $R_1$, $R_2$, $R_{19}$, n, and $X_1$ are as defined in claim 1.

8. A compound of the formula

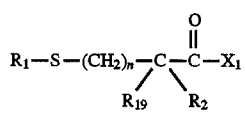  (I)

and pharmaceutically acceptable salts thereof wherein:

$R_1$ is hydrogen,

or $R_{18}$—S—;

$R_2$ and $R_{19}$ are independently selected from the group consisting of hydrogen, alkyl, cycloalkyl-(CH$_2$)$_m$—, substituted alkyl, aryl-(CH$_2$)$_m$—, substituted aryl-(CH$_2$)$_m$—, and heteroaryl-(CH$_2$)$_m$—;

n is zero or one provided that n must be zero when $R_2$ and $R_{19}$ are both other than hydrogen;

m is zero or an integer from 1 to 6;

$R_3$ is alkyl, substituted alkyl, cycloalkyl-(CH$_2$)$_m$—, aryl-(CH$_2$)$_m$—, substituted aryl-(CH$_2$)$_m$—, or heteroaryl-(CH$_2$)$_m$—;

$R_{18}$ is alkyl, substituted alkyl, cycloalkyl-(CH$_2$)$_m$—, aryl-(CH$_2$)$_m$—, substituted aryl-(CH$_2$)$_m$—, heteroaryl-(CH$_2$)$_m$— or —S—$R_{18}$ completes a symmetrical disulfide wherein $R_{18}$ is of the formula

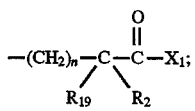 (II)

$X_1$ is of the formula

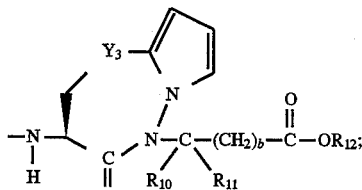 (XIII)

$Y_3$ is —CH$_2$— or

s is zero, one, or two;

b is zero or one;

$R_{10}$ and $R_{11}$ are independently selected from the group consisting of hydrogen, alkyl, substituted alkyl, alkenyl, substituted alkenyl, cycloalkyl —(CH$_2$)$_m$—, aryl-(CH$_2$)$_m$—, substituted aryl-(CH$_2$)$_m$—, and heteroaryl-(CH$_2$)$_m$—;

$R_{12}$ is hydrogen, alkyl, substituted alkyl, aryl-(CH$_2$)$_m$—, substituted aryl-(CH$_2$)$_m$—, heteroaryl-(CH$_2$)$_m$—,

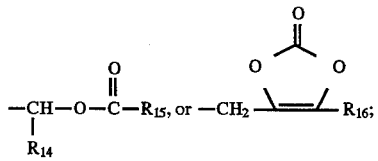

$R_{13}$ is hydrogen, lower alkyl, or substituted lower alkyl;

$R_{14}$ is hydrogen, lower alkyl, cycloalkyl, or phenyl;

$R_{15}$ is hydrogen, lower alkyl, lower alkoxy or phenyl;

$R_{16}$ is lower alkyl or aryl-(CH$_2$)$_m$—;

the term "alkyl" refers to straight and branched chain radicals having one to seven carbon atoms;

the term "substituted alkyl" refers to such straight or branched chain radicals of 1 to 7 carbons wherein one or more hydrogens have been replaced by a hydroxy, amino, halo, trifluoromethyl, cyano, —NH(lower alkyl), —N(lower alkyl)$_2$, lower alkoxy, lower alkylthio or carboxy;

the term "alkenyl" refers to straight or branched chain radicals of 3 to 7 carbon atoms having one or two double bonds;

the term "substituted alkenyl" refers to such straight or branched radicals of 3 to 7 carbons having one or two double bonds wherein a hydrogen has been replaced by a hydroxy, amino, halo, trifluoromethyl, cyano, —NH (lower alkyl), —N(lower alkyl)$_2$, lower alkoxy, lower alkylthio, or carboxy;

the term "cycloalkyl" refers to saturated rings of 3 to 7 carbon atoms;

the term "aryl" refers to phenyl, 1-naphthyl, and 2-naphthyl;

the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), and —N(lower alkyl)$_2$, di- and tri-substituted phenyl, 1-naphthyl, or 2-naphthyl wherein said substituents are selected from methyl, methoxy, methylthio, halo, hydroxy, and amino;

the term "heteroaryl" refers to unsaturated monocyclic rings of 5 or 6 atoms containing one or two O and S atoms and/or one to four N atoms provided that the total number of hetero atoms is four or less and bicyclic rings wherein the five or six membered ring as defined above is fused to a phenyl or pyridyl ring, said heteroaryl ring is attached by way of an available carbon or nitrogen atom; and said monocyclic or bicyclic ring can be substituted at an available carbon atom by lower alkyl of 1 to 4 carbons, halo, hydroxy, benzyl, or cyclohexylmethyl, or can be substituted at an available nitrogen atom by benzyloxymethyl, p-toluene sulfonyl, 2,4-dinitrophenyl, lower alkyl of 1 to 4 carbons, benzyl or benzhydryl;

the term "lower alkyl" refers to straight or branched chain radicals having one to four carbons;

the term "substituted lower alkyl" refers to such straight or branched chain radicals having one to four carbons wherein one hydrogen has been replaced by a hydroxy, amino, halo, trifluoromethyl, cyano, —NH(lower alkyl), —N(lower alkyl)$_2$, lower alkoxy, lower alkylthio, or carboxy;

the terms "lower alkoxy" and "lower alkylthio" refer to such lower alkyl groups as defined above attached to an oxygen or sulfur; and the term "halo" refers to chloro, bromo, fluoro, and iodo.

* * * * *